United States Patent
Chang et al.

(10) Patent No.: US 12,384,847 B2
(45) Date of Patent: Aug. 12, 2025

(54) CANCER THERAPY INVOLVING AN ANTI-PD1 ANTIBODY AND A MULTI-SPECIFIC BINDING PROTEIN THAT BINDS NKG2D, CD16, AND A TUMOR-ASSOCIATED ANTIGEN

(71) Applicant: Dragonfly Therapeutics, Inc., Waltham, MA (US)

(72) Inventors: Gregory P. Chang, Medford, MA (US); Ann F. Cheung, Lincoln, MA (US); Asya Grinberg, Lexington, MA (US); Eva Gutierrez, Waltham, MA (US); William Haney, Wayland, MA (US); Nicolai Wagtmann, Concord, MA (US); Bradley M. Lunde, Lebanon, NH (US); Blanka Prinz, Lebanon, NH (US)

(73) Assignee: Dragonfly Therapeutics, Inc., Waltham, MA (US)

( * ) Notice: Subject to any disclaimer, the term of this patent is extended or adjusted under 35 U.S.C. 154(b) by 590 days.

(21) Appl. No.: 16/967,218

(22) PCT Filed: Feb. 8, 2019

(86) PCT No.: PCT/US2019/017284
§ 371 (c)(1),
(2) Date: Aug. 4, 2020

(87) PCT Pub. No.: WO2019/157332
PCT Pub. Date: Aug. 15, 2019

(65) Prior Publication Data
US 2021/0079102 A1 Mar. 18, 2021

Related U.S. Application Data

(60) Provisional application No. 62/628,178, filed on Feb. 8, 2018.

(51) Int. Cl.
*A61K 39/395* (2006.01)
*A61K 39/00* (2006.01)
(Continued)

(52) U.S. Cl.
CPC ...... *C07K 16/2851* (2013.01); *A61K 39/0011* (2013.01); *A61K 39/3955* (2013.01);
(Continued)

(58) Field of Classification Search
None
See application file for complete search history.

(56) References Cited

U.S. PATENT DOCUMENTS 5,776,427 A   7/1998  Thorpe et al.
5,807,706 A   9/1998  Carter et al.
(Continued)

FOREIGN PATENT DOCUMENTS

CA    2990511 A1    12/2016
CN    102378768 A    3/2012
(Continued)

OTHER PUBLICATIONS

Stagg et al., Anti-ErbB-2 mAb therapy requires type I and II interferons and synergizes with anti-PD-1 or anti-CD137 mAb therapy, Proc. Natl. Acad. Sci. USA, 108(17):7142-7147, Apr. 26, 2011.*
(Continued)

*Primary Examiner* — Claire Kaufman

(57) ABSTRACT

Combination therapy of a cancer with a multi-specific binding protein that bind a tumor associated antigen, the NKG2D receptor, and CD16, in combination with a second anti-cancer agent are described. Also described are pharmaceutical compositions of the multi-specific binding protein,
(Continued)

and therapeutic methods useful for the treatment of cancer in combination with a second anti-cancer agent.

20 Claims, 69 Drawing Sheets

Specification includes a Sequence Listing.

(51) Int. Cl.

| | | |
|---|---|---|
| A61K 40/15 | (2025.01) | |
| A61K 40/31 | (2025.01) | |
| A61K 40/42 | (2025.01) | |
| A61P 35/00 | (2006.01) | |
| C07K 16/28 | (2006.01) | |
| C07K 16/32 | (2006.01) | |
| C07K 14/55 | (2006.01) | |

(52) U.S. Cl.
CPC ........ *A61K 39/39558* (2013.01); *A61K 40/15* (2025.01); *A61K 40/31* (2025.01); *A61K 40/4205* (2025.01); *A61K 40/421* (2025.01); *A61K 40/4215* (2025.01); *A61K 40/4221* (2025.01); *A61K 40/4224* (2025.01); *A61P 35/00* (2018.01); *C07K 16/2803* (2013.01); *C07K 16/2818* (2013.01); *C07K 16/283* (2013.01); *C07K 16/2878* (2013.01); *C07K 16/32* (2013.01); *A61K 2039/505* (2013.01); *A61K 2239/57* (2023.05); *C07K 14/55* (2013.01); *C07K 2317/31* (2013.01); *C07K 2317/52* (2013.01); *C07K 2317/524* (2013.01); *C07K 2317/53* (2013.01); *C07K 2317/565* (2013.01); *C07K 2317/569* (2013.01); *C07K 2317/732* (2013.01); *C07K 2317/734* (2013.01)

(56) References Cited

U.S. PATENT DOCUMENTS

| | | | |
|---|---|---|---|
| 5,863,538 | A | 1/1999 | Thorpe et al. |
| 5,959,084 | A | 9/1999 | Ring et al. |
| 6,036,955 | A | 3/2000 | Thorpe et al. |
| 6,129,914 | A | 10/2000 | Weiner et al. |
| 6,210,670 | B1 | 4/2001 | Berg |
| 6,294,167 | B1 | 9/2001 | Lindhofer et al. |
| 6,572,856 | B1 | 6/2003 | Taylor et al. |
| 6,737,056 | B1 | 5/2004 | Presta |
| 7,112,324 | B1 | 9/2006 | Dorken et al. |
| 7,235,641 | B2 | 6/2007 | Kufer et al. |
| 7,575,923 | B2 | 8/2009 | Dorken et al. |
| 7,635,472 | B2 | 12/2009 | Kufer et al. |
| 7,642,228 | B2 | 1/2010 | Carter et al. |
| 7,695,936 | B2 | 4/2010 | Carter et al. |
| 7,820,166 | B2 | 10/2010 | Lanzavecchia |
| 7,879,985 | B2 | 2/2011 | Urso et al. |
| 7,951,917 | B1 | 5/2011 | Arathoon et al. |
| 8,007,796 | B2 | 8/2011 | Baeuerle et al. |
| 8,076,459 | B2 | 12/2011 | Hofmeister et al. |
| 8,101,722 | B2 | 1/2012 | Kufer et al. |
| 8,236,308 | B2 | 8/2012 | Kischel et al. |
| 8,409,577 | B2 | 4/2013 | Thompson et al. |
| 8,518,403 | B2 | 8/2013 | Hoffmann et al. |
| 8,592,562 | B2 | 11/2013 | Kannan et al. |
| 8,658,765 | B2 | 2/2014 | Martin, Jr. et al. |
| 8,679,785 | B2 | 3/2014 | Carter et al. |
| 8,759,494 | B2 | 6/2014 | Bachmann et al. |
| 8,784,821 | B1 | 7/2014 | Kufer et al. |
| 8,796,420 | B2 | 8/2014 | Martin, Jr. et al. |
| 8,840,888 | B2 | 9/2014 | Nagorsen et al. |
| 9,079,969 | B2 | 7/2015 | Martin, Jr. et al. |
| 9,095,527 | B2 * | 8/2015 | Bui .......... A61Q 1/02 |
| 9,102,736 | B2 | 8/2015 | Hofmeister et al. |
| 9,127,064 | B2 | 9/2015 | Urso et al. |
| 9,150,656 | B2 | 10/2015 | Johnson et al. |
| 9,150,663 | B2 | 10/2015 | Labrijn et al. |
| 9,200,078 | B2 | 12/2015 | Bachmann |
| 9,248,181 | B2 | 2/2016 | De Kruif et al. |
| 9,248,182 | B2 | 2/2016 | De Kruif et al. |
| 9,273,136 | B2 | 3/2016 | Rader et al. |
| 9,334,331 | B2 | 5/2016 | Igawa et al. |
| 9,447,185 | B2 | 9/2016 | Romagne et al. |
| 9,493,578 | B2 | 11/2016 | Lazar et al. |
| 9,562,109 | B2 | 2/2017 | Von Kreudenstein et al. |
| 9,587,036 | B2 | 3/2017 | Kufer et al. |
| 9,637,557 | B2 | 5/2017 | Scheer et al. |
| 9,683,053 | B2 | 6/2017 | Blein et al. |
| 9,690,969 | B2 | 6/2017 | Okamoto |
| 9,718,893 | B2 | 8/2017 | Jung et al. |
| 9,907,854 | B2 * | 3/2018 | Huang .......... A61K 47/6809 |
| 9,951,145 | B2 | 4/2018 | Kim et al. |
| 9,963,513 | B2 | 5/2018 | Vu et al. |
| 10,040,853 | B2 | 8/2018 | Spies et al. |
| 10,047,167 | B2 | 8/2018 | Demarest et al. |
| 10,059,765 | B2 | 8/2018 | Velardi et al. |
| 10,377,827 | B2 | 8/2019 | Swanson et al. |
| 10,421,807 | B2 | 9/2019 | Gonzales et al. |
| 10,526,409 | B2 | 1/2020 | Urso et al. |
| 10,767,760 | B2 | 9/2020 | Ando |
| 11,084,880 | B2 | 8/2021 | Brogdon et al. |
| 11,124,582 | B2 | 9/2021 | Ambrogelly et al. |
| 11,787,864 | B2 | 10/2023 | Cheung et al. |
| 11,834,506 | B2 | 12/2023 | Chang et al. |
| 11,939,384 | B1 | 3/2024 | Chang et al. |
| 2002/0103345 | A1 | 8/2002 | Zhu |
| 2002/0193569 | A1 | 12/2002 | Hanna |
| 2003/0095965 | A1 | 5/2003 | Van Beneden et al. |
| 2004/0038339 | A1 | 2/2004 | Kufer et al. |
| 2004/0052783 | A1 | 3/2004 | Weiner et al. |
| 2004/0115198 | A1 | 6/2004 | Spies et al. |
| 2005/0037002 | A1 | 2/2005 | Velardi et al. |
| 2005/0054019 | A1 | 3/2005 | Michaud et al. |
| 2005/0058639 | A1 | 3/2005 | Gudas et al. |
| 2005/0158307 | A1 | 7/2005 | Spies et al. |
| 2005/0244416 | A1 | 11/2005 | Jung |
| 2006/0018899 | A1 | 1/2006 | Kao et al. |
| 2006/0235201 | A1 | 10/2006 | Kischel |
| 2006/0246004 | A1 | 11/2006 | Adams et al. |
| 2007/0004909 | A1 | 1/2007 | Johnson et al. |
| 2007/0071759 | A1 | 3/2007 | Shin et al. |
| 2007/0179086 | A1 | 8/2007 | Gliniak et al. |
| 2007/0190063 | A1 | 8/2007 | Bahjat et al. |
| 2008/0025975 | A1 | 1/2008 | Weiner et al. |
| 2008/0299137 | A1 | 12/2008 | Svendsen et al. |
| 2008/0305105 | A1 | 12/2008 | Kufer et al. |
| 2009/0142352 | A1 | 6/2009 | Jackson et al. |
| 2009/0175867 | A1 | 7/2009 | Thompson et al. |
| 2009/0226442 | A1 | 9/2009 | Huet et al. |
| 2009/0226466 | A1 | 9/2009 | Fong et al. |
| 2009/0252729 | A1 | 10/2009 | Farrington et al. |
| 2009/0304693 | A1 | 12/2009 | Ghayur et al. |
| 2009/0304696 | A1 | 12/2009 | Lawson et al. |
| 2010/0009866 | A1 | 1/2010 | Prinz et al. |
| 2010/0055034 | A1 | 3/2010 | Martin et al. |
| 2010/0056764 | A1 | 3/2010 | Urso et al. |
| 2010/0124764 | A1 | 5/2010 | Hufton et al. |
| 2010/0174053 | A1 | 7/2010 | Johnson et al. |
| 2010/0178298 | A1 | 7/2010 | Lindhofer |
| 2010/0260765 | A1 | 10/2010 | Barry et al. |
| 2010/0272718 | A1 | 10/2010 | Urso et al. |
| 2010/0286374 | A1 | 11/2010 | Kannan et al. |
| 2010/0291112 | A1 | 11/2010 | Kellner et al. |
| 2010/0310463 | A1 | 12/2010 | Cicortas Gunnarsson et al. |
| 2011/0008335 | A1 | 1/2011 | Velardi et al. |
| 2011/0020273 | A1 | 1/2011 | Chang et al. |
| 2011/0044980 | A1 | 2/2011 | Ghayur et al. |
| 2011/0054151 | A1 | 3/2011 | Lazar et al. |
| 2011/0150870 | A1 | 6/2011 | Rader et al. |
| 2011/0311535 | A1 | 12/2011 | Dranoff et al. |
| 2012/0014957 | A1 | 1/2012 | Ghayur et al. |
| 2012/0058082 | A1 | 3/2012 | Kaplan et al. |
| 2012/0058906 | A1 | 3/2012 | Smider et al. |
| 2012/0093823 | A1 | 4/2012 | Van Den Brink et al. |

(56) References Cited

U.S. PATENT DOCUMENTS

| | | |
|---|---|---|
| 2012/0149876 A1 | 6/2012 | Von Kreudenstein et al. |
| 2012/0171173 A1 | 7/2012 | Ideno et al. |
| 2012/0195900 A1 | 8/2012 | Ghayur et al. |
| 2012/0263722 A1 | 10/2012 | Ghayur et al. |
| 2012/0269723 A1 | 10/2012 | Brinkmann et al. |
| 2012/0294796 A1 | 11/2012 | Johnson et al. |
| 2012/0294857 A1 | 11/2012 | Sentman et al. |
| 2012/0321626 A1 | 12/2012 | Zhou |
| 2012/0328619 A1 | 12/2012 | Fey et al. |
| 2013/0115208 A1 | 5/2013 | Ho et al. |
| 2013/0177555 A1 | 7/2013 | Wilkinson et al. |
| 2013/0209514 A1 | 8/2013 | Gilboa et al. |
| 2013/0216528 A1 | 8/2013 | Cheung et al. |
| 2013/0216544 A1 | 8/2013 | Bachmann |
| 2013/0230525 A1 | 9/2013 | Li et al. |
| 2013/0336977 A1 | 12/2013 | Thompson et al. |
| 2014/0044739 A1 | 2/2014 | Teng et al. |
| 2014/0072579 A1 | 3/2014 | De Kruif et al. |
| 2014/0072581 A1 | 3/2014 | Dixit et al. |
| 2014/0105889 A1 | 4/2014 | Igawa et al. |
| 2014/0112926 A1 | 4/2014 | Liu et al. |
| 2014/0120096 A1 | 5/2014 | Bakker et al. |
| 2014/0127203 A1 | 5/2014 | Thompson et al. |
| 2014/0140999 A1 | 5/2014 | De Kruif et al. |
| 2014/0141022 A1 | 5/2014 | Thompson et al. |
| 2014/0154250 A1 | 6/2014 | Thompson et al. |
| 2014/0154252 A1 | 6/2014 | Thompson et al. |
| 2014/0199294 A1 | 7/2014 | Mimoto et al. |
| 2014/0234342 A1 | 8/2014 | Narni-Mancinelli et al. |
| 2014/0242077 A1 | 8/2014 | Choi et al. |
| 2014/0271617 A1 | 9/2014 | Igawa et al. |
| 2014/0288275 A1 | 9/2014 | Moore et al. |
| 2014/0294827 A1 | 10/2014 | Gastwirt et al. |
| 2014/0302064 A1 | 10/2014 | Moore |
| 2014/0363426 A1 | 12/2014 | Moore et al. |
| 2014/0364340 A1 | 12/2014 | Vasquez et al. |
| 2014/0377269 A1 | 12/2014 | Mabry et al. |
| 2015/0050269 A1 | 2/2015 | Igawa et al. |
| 2015/0056206 A1 | 2/2015 | Zhou |
| 2015/0079088 A1 | 3/2015 | Lowman et al. |
| 2015/0119555 A1 | 4/2015 | Jung et al. |
| 2015/0166636 A1 | 6/2015 | Igawa et al. |
| 2015/0166654 A1 | 6/2015 | Igawa et al. |
| 2015/0175697 A1 | 6/2015 | Bonvini et al. |
| 2015/0175700 A1 | 6/2015 | Lum et al. |
| 2015/0203591 A1 | 7/2015 | Yancopoulos et al. |
| 2015/0210765 A1 | 7/2015 | Roschke et al. |
| 2015/0259431 A1 | 9/2015 | Stemmer et al. |
| 2015/0259434 A1 | 9/2015 | Johnson et al. |
| 2015/0274838 A1 | 10/2015 | Johnson et al. |
| 2015/0299319 A1 | 10/2015 | Velardi et al. |
| 2015/0307617 A1 | 10/2015 | Du et al. |
| 2015/0307628 A1 | 10/2015 | Kim et al. |
| 2015/0329637 A1 | 11/2015 | Urech et al. |
| 2015/0353636 A1 | 12/2015 | Parren et al. |
| 2016/0017038 A1 | 1/2016 | Koenig |
| 2016/0024214 A1 | 1/2016 | Urso et al. |
| 2016/0032009 A1 | 2/2016 | Cheung et al. |
| 2016/0039942 A1 | 2/2016 | Cobbold et al. |
| 2016/0046727 A1 | 2/2016 | Labrijn et al. |
| 2016/0046730 A1 | 2/2016 | Ghayur et al. |
| 2016/0077105 A1 | 3/2016 | Bobrowicz et al. |
| 2016/0090426 A1 | 3/2016 | Zhou et al. |
| 2016/0096892 A1 | 4/2016 | Brogdon et al. |
| 2016/0122432 A1 | 5/2016 | Baty et al. |
| 2016/0159882 A1 | 6/2016 | Landgraf et al. |
| 2016/0159924 A1 | 6/2016 | Padkjaer et al. |
| 2016/0176968 A1 | 6/2016 | Chang et al. |
| 2016/0289341 A1 | 10/2016 | Wu |
| 2016/0326249 A1 | 11/2016 | Ng et al. |
| 2016/0347849 A1 | 12/2016 | Cai et al. |
| 2016/0369002 A1 | 12/2016 | Gauthier et al. |
| 2017/0022291 A1 | 1/2017 | Baruah et al. |
| 2017/0029529 A1 | 2/2017 | Croasdale et al. |
| 2017/0066827 A1 | 3/2017 | Pule et al. |
| 2017/0114141 A1 | 4/2017 | Amann et al. |
| 2017/0233472 A1 | 8/2017 | Barat et al. |
| 2017/0291955 A1 | 10/2017 | Li et al. |
| 2017/0362321 A1 | 12/2017 | Campbell et al. |
| 2017/0368169 A1 | 12/2017 | Loew et al. |
| 2017/0369595 A1 | 12/2017 | Brinkmann et al. |
| 2018/0044415 A1 | 2/2018 | Escarpe et al. |
| 2018/0057608 A1 | 3/2018 | Jung et al. |
| 2018/0105594 A1 | 4/2018 | Urso et al. |
| 2018/0105599 A1 | 4/2018 | Cobbold et al. |
| 2018/0118851 A1 | 5/2018 | Comeau et al. |
| 2018/0237519 A1 | 8/2018 | Caligiuri et al. |
| 2018/0237541 A1 | 8/2018 | Kim et al. |
| 2018/0273633 A1 | 9/2018 | Jiang et al. |
| 2018/0312592 A1 | 11/2018 | Junutula et al. |
| 2018/0327499 A1* | 11/2018 | Baty ..................... C07K 16/32 |
| 2018/0346600 A1 | 12/2018 | Kim et al. |
| 2019/0048079 A1 | 2/2019 | Spies et al. |
| 2019/0225702 A1 | 7/2019 | Baeuerle et al. |
| 2019/0359716 A1 | 11/2019 | Chang et al. |
| 2019/0375838 A1 | 12/2019 | Chang et al. |
| 2020/0002436 A1 | 1/2020 | Chang et al. |
| 2020/0024353 A1 | 1/2020 | Chang et al. |
| 2020/0048347 A1 | 2/2020 | Miao et al. |
| 2020/0055939 A1 | 2/2020 | Lombana et al. |
| 2020/0095327 A1 | 3/2020 | Chang et al. |
| 2020/0157174 A1 | 5/2020 | Chang et al. |
| 2020/0157226 A1 | 5/2020 | Chang et al. |
| 2020/0157227 A1 | 5/2020 | Chang et al. |
| 2020/0165344 A1 | 5/2020 | Chang et al. |
| 2020/0216544 A1 | 7/2020 | Chang et al. |
| 2020/0231678 A1 | 7/2020 | Chang et al. |
| 2020/0231679 A1 | 7/2020 | Chang et al. |
| 2020/0231700 A1 | 7/2020 | Cheung et al. |
| 2020/0277383 A1 | 9/2020 | Chang et al. |
| 2020/0277384 A1 | 9/2020 | Chang et al. |
| 2020/0376034 A1 | 12/2020 | Chang et al. |
| 2021/0009718 A1 | 1/2021 | Ambrogelly et al. |
| 2021/0032349 A1 | 2/2021 | Dengl et al. |
| 2021/0054082 A1 | 2/2021 | Chang et al. |
| 2021/0070887 A1 | 3/2021 | Ambrogelly et al. |
| 2021/0079102 A1 | 3/2021 | Chang et al. |
| 2021/0101976 A1 | 4/2021 | Chang et al. |
| 2021/0130471 A1 | 5/2021 | Chang et al. |
| 2021/0130474 A1 | 5/2021 | Chang et al. |
| 2021/0130496 A1 | 5/2021 | Chang et al. |
| 2021/0198369 A1 | 7/2021 | Chang et al. |
| 2021/0206859 A1 | 7/2021 | Chang et al. |
| 2021/0214436 A1 | 7/2021 | Chang et al. |
| 2021/0221894 A1 | 7/2021 | Bigelow et al. |
| 2021/0238290 A1 | 8/2021 | Chang et al. |
| 2021/0261668 A1 | 8/2021 | Chang et al. |
| 2021/0292420 A1 | 9/2021 | Chang et al. |
| 2021/0363261 A1 | 11/2021 | Chang et al. |
| 2022/0025037 A1 | 1/2022 | Baruah et al. |
| 2022/0089760 A1 | 3/2022 | Bigelow et al. |
| 2022/0119533 A1 | 4/2022 | Cheung et al. |
| 2022/0119534 A1 | 4/2022 | Baruah et al. |
| 2022/0153848 A1 | 5/2022 | Chang et al. |
| 2022/0195065 A1 | 6/2022 | Chang et al. |
| 2022/0380459 A1 | 12/2022 | Chang et al. |
| 2023/0034186 A1 | 2/2023 | Cuillerot et al. |
| 2023/0203202 A1 | 6/2023 | Bigelow et al. |
| 2023/0227562 A1 | 7/2023 | Chang et al. |
| 2023/0250176 A1 | 8/2023 | Cheung et al. |
| 2023/0257467 A1 | 8/2023 | Cheung et al. |
| 2023/0272041 A1 | 8/2023 | Bigelow et al. |
| 2023/0303702 A1 | 9/2023 | Chang et al. |
| 2023/0357409 A1 | 11/2023 | Chang et al. |
| 2023/0391877 A1 | 12/2023 | Chang et al. |
| 2023/0416402 A1 | 12/2023 | Cuillerot et al. |

FOREIGN PATENT DOCUMENTS

| | | |
|---|---|---|
| CN | 105814084 A | 7/2016 |
| CN | 105906722 A | 8/2016 |
| DE | 102013019352 A1 | 9/2015 |
| EP | 627940 A1 | 12/1994 |
| EP | 845998 A1 | 6/1998 |

(56) References Cited

FOREIGN PATENT DOCUMENTS

| | | |
|---|---|---|
| EP | 871673 A1 | 10/1998 |
| EP | 1124568 A1 | 8/2001 |
| EP | 1769000 B1 | 4/2007 |
| EP | 2185595 A1 | 5/2010 |
| EP | 2222706 B2 | 9/2010 |
| EP | 2927321 A1 | 10/2015 |
| EP | 2930188 A1 | 10/2015 |
| EP | 2942629 A1 | 11/2015 |
| EP | 2982380 A1 | 2/2016 |
| EP | 2990416 A1 | 3/2016 |
| KR | 10-2013-0103325 A | 9/2013 |
| KR | 10-2014-0067944 A | 6/2014 |
| RU | 2588668 C2 | 7/2016 |
| RU | 2593720 C2 | 8/2016 |
| WO | WO-1988008854 A1 | 11/1988 |
| WO | WO-1989006544 A1 | 7/1989 |
| WO | WO-1996/027011 A1 | 9/1996 |
| WO | WO-2001071005 A2 | 9/2001 |
| WO | WO-2004056873 A1 | 7/2004 |
| WO | WO-2005/003172 A2 | 1/2005 |
| WO | WO-2005/009465 A1 | 2/2005 |
| WO | WO-2005/105849 A1 | 11/2005 |
| WO | WO-2006037960 A2 | 4/2006 |
| WO | WO-2007002905 A1 | 1/2007 |
| WO | WO-2007042573 A2 | 4/2007 |
| WO | WO-2007055926 A1 | 5/2007 |
| WO | WO-2007097812 A2 | 8/2007 |
| WO | WO-2009007124 A1 | 1/2009 |
| WO | WO-2009077483 A1 | 6/2009 |
| WO | WO-2009/089004 A1 | 7/2009 |
| WO | WO-2010017103 A2 | 2/2010 |
| WO | WO-2010080124 A2 | 7/2010 |
| WO | WO-2011014659 A2 | 2/2011 |
| WO | WO-2011075636 A2 | 6/2011 |
| WO | WO-2011109400 A2 | 9/2011 |
| WO | WO-2011/131746 A2 | 10/2011 |
| WO | WO-2011143545 A1 | 11/2011 |
| WO | WO-2012006490 A2 | 1/2012 |
| WO | WO-2012/025530 A1 | 3/2012 |
| WO | WO-2012/032080 A1 | 3/2012 |
| WO | WO-2012034039 A2 | 3/2012 |
| WO | WO-2012/045752 A1 | 4/2012 |
| WO | WO-2012058768 A1 | 5/2012 |
| WO | WO-2012/115241 A1 | 8/2012 |
| WO | WO-2012125850 A1 | 9/2012 |
| WO | WO-2012/131555 A2 | 10/2012 |
| WO | WO-2012158818 A2 | 11/2012 |
| WO | WO-2012162482 A1 | 11/2012 |
| WO | WO-2013013700 A1 | 1/2013 |
| WO | WO-2013036799 A2 | 3/2013 |
| WO | WO-2013092001 A1 | 6/2013 |
| WO | WO-2013192594 A2 | 12/2013 |
| WO | WO-2014001324 A1 | 1/2014 |
| WO | WO-2014012085 A2 | 1/2014 |
| WO | WO-2014079000 A1 | 5/2014 |
| WO | WO-2014/084607 A1 | 6/2014 |
| WO | WO-2014110601 A1 | 7/2014 |
| WO | WO-2014124326 A1 | 8/2014 |
| WO | WO-2014131712 A1 | 9/2014 |
| WO | WO-2014144763 A2 | 9/2014 |
| WO | WO-2014145806 A2 | 9/2014 |
| WO | WO-2014/165818 A2 | 10/2014 |
| WO | WO-2014159562 A1 * 10/2014 ......... A61K 39/3955 | |
| WO | WO-2014159940 A1 | 10/2014 |
| WO | WO-2014198748 A1 | 12/2014 |
| WO | WO-2015009856 A2 | 1/2015 |
| WO | WO-2015036582 A2 | 3/2015 |
| WO | WO-2015036606 A1 | 3/2015 |
| WO | WO-2015063187 A1 | 5/2015 |
| WO | WO-2015070061 A1 | 5/2015 |
| WO | WO-2015089344 A1 | 6/2015 |
| WO | WO-2015095412 A1 | 6/2015 |
| WO | WO-2015095539 A1 | 6/2015 |
| WO | WO-2015095972 A1 | 7/2015 |
| WO | WO-2015/150447 A1 | 10/2015 |
| WO | WO-2015153765 A1 | 10/2015 |
| WO | WO-2015153912 A1 | 10/2015 |
| WO | WO-2015158636 A1 | 10/2015 |
| WO | WO-2015169781 A1 | 11/2015 |
| WO | WO-2015181282 A1 | 12/2015 |
| WO | WO-2015184203 A1 | 12/2015 |
| WO | WO-2015184207 A1 | 12/2015 |
| WO | WO-2015197582 A1 | 12/2015 |
| WO | WO-2015197593 A1 | 12/2015 |
| WO | WO-2015197598 A2 | 12/2015 |
| WO | WO-2016001810 A1 | 1/2016 |
| WO | WO-2016011571 A1 | 1/2016 |
| WO | WO-2016023909 A1 | 2/2016 |
| WO | WO-2016025880 A1 | 2/2016 |
| WO | WO-2016028672 A1 | 2/2016 |
| WO | WO-2016032334 A1 | 3/2016 |
| WO | WO-2016070959 A1 | 5/2016 |
| WO | WO-2016090278 A2 | 6/2016 |
| WO | WO-2016097408 A1 | 6/2016 |
| WO | WO-2016100533 A2 | 6/2016 |
| WO | WO-2016109774 A1 | 7/2016 |
| WO | WO-2016115274 A1 | 7/2016 |
| WO | WO-2016122701 A1 | 8/2016 |
| WO | WO-2016134371 A2 | 8/2016 |
| WO | WO-2016135041 A1 | 9/2016 |
| WO | WO-2016135066 A1 | 9/2016 |
| WO | WO-2016142768 A1 | 9/2016 |
| WO | WO-2016146702 A1 | 9/2016 |
| WO | WO-2016161390 A1 | 10/2016 |
| WO | WO-2016164369 A2 | 10/2016 |
| WO | WO-2016164637 A1 | 10/2016 |
| WO | WO-2016166139 A1 | 10/2016 |
| WO | WO-2016184592 A1 | 11/2016 |
| WO | WO-2016187220 A2 | 11/2016 |
| WO | WO-2016191305 A1 | 12/2016 |
| WO | WO-2016196237 A1 | 12/2016 |
| WO | WO-2016201300 A1 | 12/2016 |
| WO | WO-2016201389 A2 | 12/2016 |
| WO | WO-2016207273 A2 | 12/2016 |
| WO | WO-2016207278 A1 | 12/2016 |
| WO | WO-2017005732 A1 | 1/2017 |
| WO | WO-2017008169 A1 | 1/2017 |
| WO | WO-2017011342 A1 | 1/2017 |
| WO | WO-2017021349 A1 | 2/2017 |
| WO | WO-2017048824 A1 | 3/2017 |
| WO | WO-2017075432 A2 | 5/2017 |
| WO | WO-2017079694 A2 | 5/2017 |
| WO | WO-2017081190 A1 | 5/2017 |
| WO | WO-2017083545 A1 | 5/2017 |
| WO | WO-2017114694 A1 | 7/2017 |
| WO | WO-2017124002 A1 | 7/2017 |
| WO | WO-2017125897 A1 | 7/2017 |
| WO | WO-2017143406 A1 | 8/2017 |
| WO | WO-2017143449 A1 | 8/2017 |
| WO | WO-2017165464 A1 | 9/2017 |
| WO | WO-2017165683 A1 | 9/2017 |
| WO | WO-2017177337 A1 | 10/2017 |
| WO | WO-2017180813 A1 | 10/2017 |
| WO | WO-2017211873 A1 | 12/2017 |
| WO | WO-2017218707 A2 | 12/2017 |
| WO | WO-2017220990 A1 | 12/2017 |
| WO | WO-2018045090 A1 | 3/2018 |
| WO | WO-2018098365 A2 | 5/2018 |
| WO | WO-2018119171 A1 | 6/2018 |
| WO | WO-2018148445 A1 | 8/2018 |
| WO | WO-2018148447 A1 | 8/2018 |
| WO | WO-2018148566 A1 | 8/2018 |
| WO | WO-2018148610 A1 | 8/2018 |
| WO | WO-2018152516 A1 | 8/2018 |
| WO | WO-2018152518 A1 | 8/2018 |
| WO | WO-2018152530 A1 | 8/2018 |
| WO | WO-2018152547 A1 | 8/2018 |
| WO | WO-2018157147 A1 | 8/2018 |
| WO | WO-2018201051 A1 | 11/2018 |
| WO | WO-2018217799 A1 | 11/2018 |
| WO | WO-2018217945 A1 | 11/2018 |
| WO | WO-2018217947 A1 | 11/2018 |
| WO | WO-2019028027 A1 | 2/2019 |
| WO | WO-2019035939 A1 | 2/2019 |

(56) References Cited

FOREIGN PATENT DOCUMENTS

| | | |
|---|---|---|
| WO | WO-2019040727 A1 | 2/2019 |
| WO | WO-2019051308 A1 | 3/2019 |
| WO | WO-2019055677 A1 | 3/2019 |
| WO | WO-2019/157332 A1 | 8/2019 |
| WO | WO-2019/157366 A1 | 8/2019 |
| WO | WO-2019/164929 A1 | 8/2019 |
| WO | WO-2019/164930 A1 | 8/2019 |
| WO | WO-2019/195408 A1 | 10/2019 |
| WO | WO-2019/195409 A1 | 10/2019 |
| WO | WO-2019/217332 A1 | 11/2019 |
| WO | WO-2019/222449 A1 | 11/2019 |
| WO | WO-2019/231920 A1 | 12/2019 |
| WO | WO-2020/033587 A1 | 2/2020 |
| WO | WO-2020/033630 A1 | 2/2020 |
| WO | WO-2020/033664 A1 | 2/2020 |
| WO | WO-2020/033702 A1 | 2/2020 |
| WO | WO-2020/086758 A1 | 4/2020 |
| WO | WO-2020172189 A1 | 8/2020 |
| WO | PCT/US2020/055497 | 10/2020 |
| WO | WO-2021041878 A1 | 3/2021 |
| WO | WO-2021/076554 A1 | 4/2021 |
| WO | WO-2021/076564 A1 | 4/2021 |
| WO | PCT/US2021/044737 | 8/2021 |
| WO | WO-2021/216916 A1 | 10/2021 |
| WO | WO-2021/226163 A2 | 11/2021 |
| WO | WO-2021/226193 A1 | 11/2021 |
| WO | WO-2022/031935 A1 | 2/2022 |
| WO | WO-2022/031965 A1 | 2/2022 |
| WO | WO-2022/187539 A1 | 9/2022 |
| WO | WO-2023/056243 A1 | 4/2023 |
| WO | WO-2023/056252 A1 | 4/2023 |
| WO | WO-2023/107954 A1 | 6/2023 |
| WO | WO-2023/107956 A1 | 6/2023 |
| WO | WO-2023/154796 A2 | 8/2023 |
| WO | WO-2023/168384 A2 | 9/2023 |

OTHER PUBLICATIONS

Muntasell et al., Interplay between Natural Killer Cells and Anti-HER2 Antibodies: Perspectives for Breast Cancer Immunotherapy, Front. Immunol. 8:1544, doi: 10.3389/fimmu.2017.01544, Nov. 2017.*

(ClinicalTrial.Gov Identifier: NCT02129556 v7, Retrieved online: <URL: https://clinicaltrials.gov/ct2/history/NCT02129556?V_7=View#StudyPageTop> [retrieved on Jul. 8, 2022], Dec. 12, 2017.*

Merck, Merck Announces Generic Name for MK-3475, Merck's Investigational anti-PD-1Antibody: Pembrolizumab, Company Statement, Retrieved online: <URL: https://www.merck.com/news/merck-announces-generic-name-for-mk-3475-mercks-investigational-anti-pd-1-antibody-pembrolizumab/> [retrieved on Jul. 8, 2022], May 30, 2014.*

Affimed, Affimed Enters Into Collaboration With Merck To Evaluate AFM13 in Combination With . . . Retreived <URL:https://www.affimed.com/affimed-enters-into-collaboration-with-merck-to-evaluate-afm13-in-combination-with-keytruda-pembrolizumab-for-patients-with-hodgkin-lymphoma/>[retrieved on Feb. 1, 2023] Jan. 25, 2016.*

Muller et al. Trastuzumab emtansine (T-DM1) renders HER2+ breast cancer highly susceptible to CTLA-4/PD-1 blockade, Sci. Transl. Med. 7(315):1-14, doi: 10.1126/scitranslamed.aac4925, 2015.*

Bezman et al.,PD-1 blockade enhances elotuzumab efficacy in mouse tumor models, Blood Adv. 1(12):753-765, doi.org/10.1182/bloodadvances.2017004382, May 2017.*

Yang et al., Enhancing NK cell-mediated cytotoxicity to cisplatin-resistant lung cancer cells via MEK/Erk signaling inhibition, Nature Scientific Reports, 7: 7958, 13 pages, 2017.*

Jilani et al., CAR-T cell therapy targeting surface expression of TYRP1 to treat cutaneous and rare melanoma subtypes, Nat. Comm. 15:1244, 19 pages, 2024.*

Juneja et al., PD-L1 on tumor cells is sufficient for immune evasion in immunogenic tumors and inhibits CD8 T cell cytotoxicity, J. Exp. Med., 214(4):895-904, 2017.*

Ahmad et al. (2012) "scFv antibody: principles and clinical application," *Clinical and Developmental Immunology* 2012:1-16.

Averdam et al. (2009) "A Novel System of Polymorphic and Diverse NK Cell Receptors in Primates," *PLoS Genetics* 5(10):e1000688.

Busfield et al. (2014) "Targeting of acute myeloid leukemia in vitro and in vivo with an anti-CD123 mAb engineered for optimal ADCC," *Leukemia* 28(11): 2213-2221.

Cai et al. (2014) "Autonomous Stimulation of Cancer Cell Plasticity by the Human NKG2D Lymphocyte Receptor Coexpressed with Its Ligands on Cancer Cells," *Plos One* 9(10):e108942.

Cho et al. (2010) "Delivery of NKG2D Ligand Using an Anti-HER2 Antibody-NKG2D Ligand Fusion Protein Results in an Enhanced Innate and Adaptive Antitumor Response," *Cancer Research* 70(24):10121-10130.

Chu, S. et al. (2014) "Immunotherapy with Long-Lived Anti-CD123 x Anti-CD3 Bispecific Antibodies Stimulates Potent T Cell-Mediated Killing of Human AML Cell Lines and of CD123+ Cells in Monkeys: A Potential Therapy for Acute Myelogenous Leukemia 11," *Blood* 124(21):2316.

Ding et al. (2018) "Fusion Proteins of NKG2D/NKG2DL in Cancer Immunotherapy," *International Journal of Molecular Sciences* 19(1):177.

Germain et al. (2005) "MHC Class I-Related Chain a Conjugated to Antitumor antibodies Can Sensitize Tumor Cells to Specific Lysis by Natural Killer Cell," *Clinical Cancer Research* US 11(20):7516-7522.

Glas et al. (1997) "Analysis of rearranged immunoglobulin heavy chain variable region genes obtained from a bone marrow transplant (BMT) recipient," *Clinical & Experimental Immunology* 107(2):372-380.

Gleason et al. (2012) "Bispecific and Trispecific Killer Cell Engagers Directly Activate Human NK Cells through CD16 Signaling and Induce Cytotoxicity and Cytokine Production," *Molecular Cancer Therapeutics* 11(12):2674-2684.

Gleason et al. (2014) "CD16xCD33 bispecific killer cell engager (BiKE) activates NK cells against primary MDS and MDSC CD33+ targets," *Blood* 123(19):3016-3026.

Hezareh et al. (2001) "Effector Function Activities of a Panel of Mutants of a Broadly Neutralizing Antibody against Human Immunodeficiency Virus Type 1," *Journal of Virology* 75(24):12161-12168.

Jachimowicz et al. (2011) "Induction of In Vitro and In Vivo NK Cell Cytotoxicity Using High-Avidity Immunoligands Targeting Prostate-Specific Membrane Antigen in Prostate Carcinoma," *Mol Cancer Thera*, 10(6):1036-1045.

Kellner et al. (2012) "Fusion proteins between ligands for NKG2D and CD20-directed single-chain variable fragments sensitize lymphoma cells for natural killer cell-mediated lysis and enhance antibody-dependent cellular cytotoxicity," *Leukemia* 26:830-834.

Kellner et al. (2013) "Promoting natural killer cell functions by recombinant immunoligands mimicking an induced self phenotype," *Oncoimmunology* 2(6):e24481.

Kellner et al. (2016) "Enhancing natural killer cell-mediated lysis of lymphoma cells by combining therapeutic antibodies with CD20-specific immunoligands engaging NKG2D or NKp30," *OncoImmunology* 5(1):e1058459-1-e1058459-12.

Kwong et al. (2008) "Generation, affinity maturation, and characterization of a human anti-human NKG2D monoclonal antibody with dual antagonistic and agonistic activity," *Journal of Molecular Biology* 384(5):1143-1156.

Lin et al. (2013) "CD4+ NKG2D+ T cells induce NKG2D down-regulation in natural killer cells in CD86-RAE-1 E transgenic mice," *Immunology* 141(3):401-415.

Liu et al. (2017) "Fc engineering for Developing Therapeutic Bispecific Antibodies and Novel Scaffolds," *Frontiers in Immunology* 8(38):1-15.

Madlener et al. (2010) "A Bispecific Protein Targeting the NKG2D Receptor on Natural Killer Cells: In Vitro and In Vivo activity of ULBP2-CEA," *Blood* 116(21):2095.

Morvan et al. (2016)."NK cells and cancer: you can teach innate cells new tricks" *Nat Rev Cancer* 16(1):7-19.

(56) References Cited

OTHER PUBLICATIONS

Nagasaki et al. (2014) "Interleukin-6 released by colon cancer-associated fibroblasts is critical for tumour angiogenesis: anti-interleukin-6 receptor antibody suppressed angiogenesis and inhibited tumour-stroma interaction," *British Journal of Cancer* 110(2):469-478.

Petricevic et al. (2013) "Trastuzumab mediates antibody-dependent cell-mediated cytotoxicity and phagocytosis to the same extent in both adjuvant and metastatic HER2/neu breast cancer patients," *Journal of Translational Medicine* 11(307).

Raab et al. (2014) "Fc-Optimized NKG2D-Fc Constructs Induce NK Cell Antibody-Dependent Cellular Cytotoxicity Against Breast Cancer Cells Independently of HER2/neu Expession Status," *Journal of Immunology* 193(8):4261-72.

Romee et al. (2013) "NK cell CD16 surface expression and function is regulated by a disintegrin and metalloprotease-17 (ADAM17)," *Blood* 121(18):3599-608.

Rothe et al. (2013) "The Bispecific Immunoligand ULBP2-aCEA Redirects Natural Killer Cells to Tumor Cells and Reveals Potent Anti-Tumor Activity Against Colon Carcinoma," *Int. J. Cancer* 134(12):2829-2840.

Schuster et al. (2015) "Immunotherapy with the trifunctional anti-CD20 x anti-CD3 antibody FBTA05 (Lymphomun) in paediatric high-risk patients with recurrent CD20-positive B cell malignancies," *British Journal of Haematology* 169(1):90-102.

Smits et al. (2016) "Designing multivalent proteins based on natural killer cell receptors and their ligands as immunotherapy for cancer," *Expert Opinion on Biological Therapy* 16(9):1105-1112.

Spear et al. (2013) "NKG2D ligands as therapeutic targets," *Cancer Immunology* 13:8.

Steigerwald et al. (2009) "Human IgG1 antibodies antagonizing activating receptor NKG2D on natural killer cells," *mAbs* 1(2):115-127.

Steinbacher et al. (2015) "An Fc-optimized NKG2D-immunoglobulin G fusion protein for induction of natural killer cell reactivity against leukemia," *International Journal of Cancer* 136(5):1073-1084.

Strong (2002) "Asymmetric ligand recognition by the activating natural killer cell receptor NKG2D, a symmetric homodimer," *Molecular Immunology* 38(14):1029-1037.

Tay et al. (2016) "TriKEs and BiKEs join CARs on the cancer immunotherapy highway," *Human Vaccines & Immunotherapeutics* 12(11):2790-2796.

Vaks et al. (2018) "Design Principles for Bispecific IgGs, Opportunities and Pitfalls of Artificial Disulfide Bonds," *Antibodies* 7(27):1-28.

Von Strandmann et al. (2006) "A novel bispecific protein (ULBP2-BB4) targeting the NKG2D receptor on natural killer (NK) cells and CD138 activates NK cells and has potent antitumor activity against human multiple myeloma in vitro and in vivo," *Blood* 107(5):1955-1962.

Wang et al. (2016) "A bispecific protein rG7S-MICA recruits natural killer cells and enhances NKG2D-mediated immunosurveillance against hepatocellular carcinoma," *Cancer Letters* 372(2):166-178.

Weiss-Steider et al. (2011) "Expression of MICA, MICB and NKG2D in human leukemic myelomonocytic and cervical cancer cells," *Journal of Experimental & Clinical Cancer Research* 30(1):37.

Written Opinion for International Application No. PCT/US2019/017284 dated Jun. 7, 2019.

Xu et al. (2019) "A VEGFR2-MICA bispecific antibody activates tumor-infiltrating lymphocytes and exhibits potent anti-tumor efficacy in mice," *Cancer Immunology Immunotherapy* 68(9):1429-1441.

Yeap et al. (2016) "CD16 is indispensable for antibody dependent cellular cytotoxicity by human monocytes," *Scientific Reports* 6:34310.

Young et al. (1995) "Thermal stabilization of a single-chain Fv antibody fragment by introduction of a disulphide bond," *FEBS Letters* 377(2):135-139.

Felices et al. (2016) "Generation of BiKEs and TriKEs to Improve NK cell-Mediated Targeting of Tumor Cells," Natural Killer Cells: Methods and Protocols, *Methods in Molecular Biology* 1441:333-346.

Gantke et al. (2016) "Trispecific Antibodies for Selective CD16A-Directed NK-Cell Engagement in Multiple Myeloma," *Blood* 128(22):4513.

Gantke et al. (2017) "Trispecific antibodies for CD16A-directed NK cell engagement and dual-targeting of tumor cells," *Protein Engineering, Design & Selection* 38(9):673-684.

Gauthier et al. (2019) "Multifunctional Natural Killer Cell Engagers Targeting NKp46 Trigger Protective Tumor Immunity," *Cell* 177(7):1701-1713.

Gooden et al. (2012) "Infiltrating CTLs are bothered by HLA-E on tumors," *OncoImmunology*, 1(1):92-93.

Kluge et al. (2017) "EGFR/CD16A TandAbs are efficacious NK-cell engagers with favorable biological properties which potently kill EGFR(+) tumors with and without Ras mutation," *Cancer Research* 77(13 Suppl.):Abstract 3641.

McWilliams, et al. (2016) "Targeting the Tumor Evasion Interaction of NKG2A and Its Ligand HLA-E Increases Natural-Killer Cell Activity in Chronic Lymphocytic Leukemia," *Blood* 1289-1291.

Myers et al. (2021) "Exploring the NK cell platform for cancer immunotherapy," *Nature Reviews Clinical Oncology* 18(2):85-100.

Nie et al. (2020) "Biology drives the discovery of bispecific antibodies as innovative therapeutics," *Antibody Therapeutics* 3(1):18-62.

Vyas et al. (2016) "Mono- and dual-targeting triplebodies activate natural killer cells and have anti-tumor activity in vitro and in vivo against chronic lymphocytic leukemia," *Oncoimmunology* 5(9):p.e1211220.

Bendayan et al. (1995) "Possibilities of False Immunocytochemical Results Generated by The Use of Monoclonal Antibodies: The Example of the Anti-proinsulin Antibody," *J. Histochem. Cytochem.* 43:881-886.

Bost et al. (1988) "Antibodies Against a Peptide Sequence Within the HIV Envelope Protein Crossreacts with Human Interleukin-2," *Immunological Investigations* 17(6&7):577-586.

Bostrom, et al. (2009) "Improving Antibody Binding Affinity and Specificity for Therapeutic Development," *Methods and Protocols* 525:353-376.

Brinkmann et al. (2017) "The making of bispecific antibodies," *MABS* 9(2)182-212.

Bryceson et al. (2006) "Synergy among receptors on resting NK cells for the activation of natural cytotoxicity and cytokine secretion," *Blood* 107(1):159-166.

Casset et al. (2003) "A peptide mimetic of an anti-CD4 monoclonal antibody by rational design," *Biochemical and Biophysical Research Communications* 307:198-205.

Chen et al. (1995) "Enhancement and destruction of antibody function by somatic mutation: unequal occurrence is controlled by V gene combinatorial associations," *The EMBO Journal* 14(12):2784-2794.

Chen et al. (1999) "Selection and Analysis of an Optimized Anti-VEGF Antibody: Crystal Structure of an Affinity-matured Fab in Complex with Antigen," *J. Mol. Biol.* 293:865-881.

Chen X. et al. (2013) "Fusion protein linkers: property, design and functionality" *Advanced drug delivery reviews*, 65(10):1357-1369.

Choi et al. (2013) "A Heterodimeric Fc-Based Bispecific Antibody Simultaneously Targeting VEGFR-2 and Met Exhibits Potent Antitumor Activity," *Mol Cancer Ther*, 12(12):2748-2759.

Colman P. M. (1994) "Effects of amino acid sequence changes on antibody-antigen interactions" *Research in Immunology* 145(1):33-36.

De Pascalis et al. (2002) "Grafting of "Abbreviated" Complementarity-Determining Regions Containing Specificity-Determining Residues Essential for Ligand Contact to Engineer a Less Immunogenic Humanized Monoclonal Antibody," *The Journal of Immunology* 169:3076-3084.

Dickopf et al. (2020) "Format and geometries matter: Structure-based design defines the functionality of bispecific antibodies," *Computational and Structural Biotechnology Journal* 18:1221-1227.

(56) References Cited

OTHER PUBLICATIONS

Edwards et al. (2003) "The Remarkable Flexibility of the Human Antibody Repertoire; Isolation of Over One Thousand Different Antibodies to a Single Protein, BLyS," *J. Mol. Biol.* 334:103-118.
Goel et al. (2004) "Plasticity within the Antigen-Combining Site May Manifest as Molecular Mimicry in the Humoral Immune Response," *The Journal of Immunology* 173(12):7358-7367.
Gonzales, et al. (2005) "Minimizing the Immunogenicity of Antibodies for Clinical Application," *Tumor Biol.* 26(1):31-43.
Henry et al. (2017) "Stability-Diversity Tradeoffs Impose Fundamental Constraints on Selection of Synthetic Human VH/VL Single-Domain Antibodies from In Vitro Display Libraries," *Frontiers in Immunology*, 8:1-15.
Hoseini et al. (2017) "Acute myeloid leukemia targets for bispecific antibodies," *Blood Cancer Journal* 7(2):e522 (12 pages).
Janeway et al. (1997) Chapter 3, Structure of the Antibody Molecule and Immunoglobulin Genes, *Immunology Third Edition, Garland Publishing Inc.*, 3:1-3:11.
Junttila et al. (2014) "Antitumor Efficacy of a Bispecific Antibody That Targets HER2 and Activates T Cells," *Cancer Research* 74(19):5561-5571.
Kanyavuz et al. (2019) "Breaking the law: unconventional strategies for antibody diversification," *Nature Reviews Immunology* 19(6):355-368.
Kijanka et al. (2013) "Rapid optical imaging of human breast tumour xenografts using anti-HER2 VHHs site-directly conjugated to IRDye 800CW for image-guided surgery," *Eur J Nucl Med Mol Imaging* 40:1718-1729.
Kim et al. (2014) "Mutational approaches to improve the biophysical properties of human single-domain antibodies," *Biochimica et Biophysica Acta*, 1844:1983-2001.
Koerner et al. (2015) "Induction of NK and T Cell Immune Responses Against Leukemia Cells By Bispecific NKG2D-CD16 and -CD3 Fusion Proteins," *Blood* 126(23):2558, Abstract 606 (2 pages).
Kranz et al. (1981) "Restricted reassociation of heavy and light chains from hapten-specific monoclonal antibodies," *Pro. Natl. Acad. Sci. USA* 78(9):5807-5811.
Krieg et al. (2005) "Functional Analysis of B and T Lymphocyte Attenuator Engagement on CD4+ and CD8+ T Cells," *The Journal of Immunology* 175(10):6420-6427.
Lamminmäki et al. (2001) "Crystal Structure of a Recombinant Anti-estradiol Fab Fragment in Complex with 17β-Estradiol," *The Journal of Biological Chemistry* 276(39):36687-36694.
Lin et al. (2011) "Improved affinity of a chicken single-chain antibody to avian infectious bronchitis virus by site-directed mutagenesis of complementarity-determining region H3," *African Journal of Biotechnology* 10(79):18294-18303.
Lloyd et al. (2009) "Modelling the human immune response: performance of a 1011 human antibody repertoire against a broad panel of therapeutically relevant antigens," *Protein Engineering, Design and Selection* 22(3):159-168.
Lund et al. (1996) "Multiple interactions of IgG with its core oligosaccharide can modulate recognition by complement and human Fc gamma receptor I and influence the synthesis of its oligosaccharide chains," *J. Immunol* 157:4963-4969.
MacCallum et al. (1996) "Antibody-antigen Interactions: Contact Analysis and Binding Site Topography," *J. Mol. Biol.* 262:732-745.
Maeda et al. (2015) "New antibody modification technology and its application to antibody drugs," Farumashia 51(5):424-428.
Maeda Y. et al. (1997) "Engineering of Functional Chimeric Protein G-Vargula Luciferase" Analytical biochemistry, 249(2):147-152.
Mariuzza et al. (1987) "The Structural Basis of Antigen-Antibody Recognition," *Ann. Rev. Biophys. Chem.* 16:139:59.
McCarthy et al. (2001) "Altering the fine specificity of an anti-Legionella single chain antibody by a single amino acid insertion," *Journal of Immunological Methods* 251:137-149.
Morris "Epitope Mapping of Protein Antigens by Competition ELISA," The Protein Protocols Handbook, Totowa, NJ, Humana Press, (Jan. 1, 1996):595-600.
Padlan et al. (1989) "Structure of an antibody-antigen complex: Crystal structure of the HyHEL-10 Fab-lysozyme complex," *Pro. Natl. Acad. Sci. USA* 86:5938-5942.
Pakula et al. (1989) "Genetic Analysis of Protein Stability and Function," *Annu. Rev. Genet.* 23:289-310.
Paul et al. (1993) "Fundamental Immunology," (textbook) 292-295.
Piche-Nicholas et al. (2018) "Changes in complementarity-determining regions significantly alter IgG binding to the neonatal Fc receptor (FcRn) and pharmacokinetics," *MABS* 10(1)81-94.
Portolano et al. (1993) "Lack of promiscuity in autoantigen-specific H and L chain combinations as revealed by human H and L chain roulette," *J. Immunol.* 15(30):880-887.
Powers et al. (2016) "Abstract 1407: FPA 144, a therapeutic monoclonal antibody targeting the FGFR2b receptor, promotes antibody dependent cell-mediated cytotoxicity and stimulates sensitivity to PD-1 in the 4T1 syngeneic tumor model," *Cancer Research* (4 pages).
Roda-Navarro et al. (2020) "Understanding the Spatial Topology of Artificial Immunological Synapses Assembled in T Cell-Redirecting Strategies: A Major Issue in Cancer Immunotherapy," *Frontiers in Cell and Developmental Biology* 7:1-5.
Rudikoff et al. (1982) "Single amino acid substitution altering antigen-binding specificity," *Pro. Natl. Acad. Sci USA* 79:1979-1983.
Safdari Y. et al. (2013) "Antibody humanization methods—a review and update" Biotechnology and Genetic Engineering Reviews, 29(2):175-186.
Schroeder et al. (2010) "Structure and Function of Immunoglobulins," *J Allergy Clin Immunol* 125:S41-S52 (24 pages).
Shen J. et al. (2006) "Single variable domain-IgG fusion: a novel recombinant approach to Fc domain-containing bispecific antibodies" Journal of Biological Chemistry, 281(16):10706-10714.
Shum et al. (2002) "Conservation and Variation in Human and Common Chimpanzee CD94 and NKG2 Genes," *The Journal of Immunology* 168:240-252.
Stamova et al. (2011) "Simultaneous engagement of the activatory receptors NKG2D and CD3 for retargeting of effector cells to CD33-positive malignant cells," *Leukemia* 25:1053-1056.
Stein et al. (2012) "Natural Killer (NK)- and T-Cell Engaging Antibody-Derived Therapeutics," *Antibodies* 1:88-123.
Teplyakov A. et al. (2014) "Antibody modeling assessment II. Structures and models" Proteins: Structure, Function, and Bioinformatics, 82(8):1563-1582.
Torres M. et al. (2008) "The immunoglobulin constant region contributes to affinity and specificity" Trends in immunology, 29(2):91-97.
Vajdos et al. (2002) "Comprehensive Functional Maps of the Antigen-binding Site of an Anti-ErbB2 Antibody Obtained with Shotgun Scanning Mutagenesis," *J. Mol. Biol.* 320:415-428.
Vallera et al. (2016) "IL 15 Trispecific Killer Engagers (TriKE) Make Natural Killer Cells Specific to CD33+ Targets While Also Inducing Persistence, In Vivo Expansion, and Enhanced Function," *Clin Cancer Res*, 22(14):3440-50.
Wang et al. (2018) "IgG Fc engineering to modulate antibody effector functions," *Protein Cell* 9(1):63-73.
Wensveen et al. (2018) "NKG2D: A Master Regulator of Immune Cell Responsiveness," *Frontiers in Immunology* 9(Article 411):8 pages.
Wu et al. (1999) "Humanization of a Murine Monoclonal Antibody by Simultaneous Optimization of Framework and CDR Residues," *J. Mol. Biol.* 294:151-162.
Xu et al. (2014) "Production of bispecific antibodies in "knobs-into-holes" using a cell-free expression system," mAbs 7(1)231-242.
Yan et al. (2014) "Construction of a synthetic phage-displayed Nanobody library with CDR3 regions randomized by trinucleotide cassettes for diagnostic applications," *Journal of Translational Medicine* 12:343 (12 pages).
Zhang et al. (2021) "Bispecific antibody-mediated redirection of NKG2D-CAR natural killer cells facilitates dual targeting and enhances antitumor activity," *Journal for ImmunoTherapy of Cancer*; 9:e002980 (24 pages). doi:10.1136/jitc-2021-002980.

(56) References Cited

OTHER PUBLICATIONS

Akbar et al. (2021) "A compact vocabulary of paratope-epitope interactions enables predictability of antibody-antigen binding," *Cell Reports* 34:108856 21 pages.
Altshuler et al. (2010) "Generation of Recombinant Antibodies and Means for Increasing Their Affinity," *Biochemistry* (Moscow) 75(13):1584-1605.
Berenbaum (1977) "Synergy, additivism and antagonism in immunosuppression," Clin. Exp. Immunol. 28:1-18.
Berenbaum (1989) "What is Synergy?" Pharmacological Reviews 41:93-141.
Boltz (2011) "Bi-specific Aptamers mediating Tumour Cell Lysis," Dissertation, M.Sc. Molekulare Biotechnologie, Technische Universität Darmstadt, pp. 1-133.
Bowen et al. (2016) "Revisiting the Immunoglobulin Intramolecular Signaling Hypothesis," *Trends Immunol.* 37(11):721-723.
Branca et al. (2018) "Nature Biotechnology's academic spinouts of 2017," Nature Biotechnology 36(4):297-306.
Bruhns et al. (2009) "Specificity and affinity of human FCγ receptors and their polymorphic variants for human IgG subclasses," *Blood* 113(16):3716-3724.
Dahlberg et al. (2015) "Natural Killer Cell-Based Therapies Targeting Cancer: Possible Strategies to Gain and sustain Anti-Tumor Activity" Frontiers In Immunology 6(Article 605):19 pages.
El-Amine et al. (2002) "In vivo induction of tolerance by an Ig peptide is not affected by the deletion of FcR or a mutated IgG Fc fragment," *International Immunology* 14(7):761-766.
Germain et al. (2008) "Redirecting NK cells mediated tumor cell lysis by a new recombinant bifunctional protein," *Protein Engineering, Design & Selection* 21(11):665-672.
Hasegawa et al. (2017) "Single amino acid substitution in LC-CDR1 induces Russell body phenotype that attenuates cellular protein synthesis through eIF2α phosphorylation and thereby downregulates IgG secretion despite operational secretory pathway traffic," *MABS* 9(5):854-873.
Hlavacek et al. 1999 "Steric Effects on Multivalent Ligand-Receptor Binding: Exclusion of Ligand Sites by Bound Cell Surface Receptors," *Biophysical Journal* 76:3031-3043.
Jonnalagadda et al. (2015) "Chimeric Antigen Receptors With Mutated IgG4 Fc Spacer Avoid Fc Receptor Binding and Improve T Cell Persistence and Antitumor Efficacy," *Molecular Therapy* 23(4):757-768.
Kaur et al. (2015) "Applications of In Vitro-In Vivo Correlations in Generic Drug Development: Case Studies," *The AAPS Journal* 17(4):1035-1039; doi: 10.1208/s12248-015-9765-1.
Kjellev et al. (2007) "Inhibition of NKG2D receptor function by antibody therapy attenuates transfer-induced colitis in SCID mice," *Eur. J. Immunol.* 37:1397-1406.
Kunik, et al. (2012) "Structural consensus among antibodies defines the antigen binding site," *PLoS Comput Biol.* 8(2):e1002388.
Lippow et al. (2007) "Computational design of antibody-affinity improvement beyond in vivo maturation," *Nature Biotechnology* 25(10):1171-1176.
Lo et al. (2021) "Conformational epitope matching and prediction based on protein surface spiral features," *BMC Genomics* 22(Suppl 2):116 16 pages.
Mandelboim et al. (1999) "Human CD16 as a lysis receptor mediating direct natural killer cell cytotoxicity," *PNAS USA* 96(10):5640-5644; doi: 10.1073/pnas.96.10.5640.
Marks et al. (2020) "How repertoire data are changing antibody science," *J. Biol. Chem.* 295(29):9823-9837.
Rabia et al. (2018) "Understanding and overcoming trade-offs between antibody affinity, specificity, stability and solubility" Biochem Eng J. 137:365-374.
Raulet (2003) "Roles of the NKG2D immunoreceptor and its ligands," *Nature: Reviews Immunology* 3:781-790; doi: 10.1038/nri1199.
Roell et al. (2017) "An Introduction to Terminology and Methoodology of Chemical Synergy—Perspectives from Across Disciplines," *Frontiers in Pharmacology: Cancer Molecular Targets and Therapeutics* 8:1-11.
Rosano et al. (2014) "Recombinant protein expression in *Escherichia coli*: advances and challenges" Frontiers in Microbiology 5(172):17 pages.
Sazinsky et al. (2008) "Aglycosylated immunoglobulin $G_1$ variants productively engage activating Fc receptors," *Proceedings of the National Academy of Sciences* 105(51)20167-20172.
Singer et al. (1998) "Genes and Genomes," Moscow, "Mir" 1:63-64. Concise description of relevance attached (1 page).
Sulea et al. (2018) "Application of Assisted Design of Antibody and Protein Therapeutics (ADAPT) improves efficacy of a *Clostridium difficile* toxin A single-domain antibody," 8:2260 11 pages.
Tallarida (2000) "Drug Synergism and Dose Effect Analysis," Ed. Chapman & Hall pp. 1-71.
Thakur et al. (2018) "Bispecific antibody based therapeutics: Strengths and challenges," Blood Review 32:339-347.
Vajda et al. (2021) "Progress toward improved understanding of antibody maturation," *Current Opinion in Structural Biology* 67:226-231.
Ward et al. (1989) "Binding activities of a epertoire of single immunoglobulin variable domains secreted from *Escherichia coli*," Nature 341:544-546.
Wark et al. (2006) "Latest technologies for the enhancement of antibody affinity", *Advanced Drug Delivery Reviews* 58(5-6):657-670.
U.S. Appl. No. 16/483,330, filed Aug. 2, 2019.
U.S. Appl. No. 16/483,572, filed Aug. 5, 2019.
U.S. Appl. No. 16/483,788, filed Aug. 6, 2019.
U.S. Appl. No. 16/486,569, filed Aug. 16, 2019.
U.S. Appl. No. 16/486,570, filed Aug. 16, 2019.
U.S. Appl. No. 16/488,395, filed Aug. 23, 2019.
U.S. Appl. No. 16/615,203, filed Nov. 20, 2019.
U.S. Appl. No. 16/615,231, filed Nov. 20, 2019.
U.S. Appl. No. 16/638,559, filed Feb. 12, 2020.
U.S. Appl. No. 17/188,978, filed Mar. 1, 2021.
U.S. Appl. No. 16/644,585, filed Mar. 5, 2020.
U.S. Appl. No. 17/190,155, filed Mar. 2, 2021.
U.S. Appl. No. 16/967,216, filed Aug. 4, 2020.
U.S. Appl. No. 17/045,016, filed Oct. 2, 2020.
U.S. Appl. No. 17/053,558, filed Nov. 6, 2020.
Atwell et al. (1989) "Stable Heterodimers from Remodeling the Domain Interface of a Homodimer using a Phage Display Library," J Mol Biol 270:26-35.
Baek et al. (2014) "Construction of a Large Synthetic Human Fab Antibody Library on Yeast Cell Surface by Optimized Yeast Mating," J Microbial Biotechnol 24(3):408-420.
Brown et al. (1996) "Tolerance of single, but not multiple, amino acid replacements in antibody Vh Cdr 2: a means of minimizing B cell wastage from somatic hypermutation?," Journal of Immunology, 156: 3285-3291.
Chan et al. (2010) "Therapeutic antibodies for autoimmunity and inflammation," Nature Reviews 10:301-316.
Choi et al. (2015) "Crystal structures of immunoglobulin Fc heterodimers reveal the molecular basis for heterodimer formation," Molecular Immunology 65(2):377-83.
Choi et al. (2015) "Engineering of Immunoglobulin Fc Heterodimers Using Yeast Surface-Displayed Combinatorial Fc Library Screening," PloS One. Dec. 16, 2015; 10(12);e0145349; pp. 1-20.
Cunningham et al. (1969) "Subgroups of Amino Acid Sequences in the Variable Regions of Immunoglobulin Heavy Chains," Proc Natl Acad Sci USA 64(3):997-1003.
Davis et al. (2010) "SEEDbodies: Fusion Proteins Based on Strand-Exchange Engineered Domain (Seed) CH3 Heterodimers in an Fc Analogue Platform for Asymmetric Binders or Immunofusions and Bispecific Antibodies," Protein Eng Des Sel 23(4):195-202.
Elliott et al. (2014) "Antiparallel conformation of knob and hole aglycosylated half-antibody homodimers is mediated by a CH2-CH3 hydrophobic interaction", J. Mol. Biol., 426(9):1947-57.

(56) References Cited

OTHER PUBLICATIONS

Feng et al. (2011) "Design, Expression and Characterization of a Soluble Single-Chain Functional Human Neonatal Fe Receptor," Protein Expr Purif 79(1):66-71.

Feng et al., (2020) "NKG2D-Fc fusion protein promotes antitumor immunity through the depletion of immunosuppressive cells," Cancer Immunol. Immunother. 69(10):2147-2155.

Gunasekaran et al. (2010) "Enhancing Antibody Fe Heterodimer Formation through Electrostatic Steering Effects: Applications to Bispecific Molecules and Monovalent IgG," J Biol Chem 285(25):19637-46.

Ha et al. (2016) "Immunoglobulin Fc Heterodimer Platform Technology: From Design to Applications in Therapeutic Antibodies and Proteins," Front Immunol. 7:394, 16 pages.

Henry et al. (2004) "A Prostate-Specific Membrane Antigen-Targeted Monoclonal Antibody- Chemotherapeutic Conjugate Designed for the Treatment of Prostate Cancer," *Cancer Research* 64:7995-8001.

Herold et al. (2017) "Determinants of the assembly and function of antibody variable domains," Scientific Reports, 7:12276.

Holliger et al. (2005) "Engineered antibody fragments and the rise of single domains," Nat Biotechnol 23(9): 1126-36.

Klein et al. (2012) "Progress in overcoming the chain association issue in bispecific; heterodimeric IgG antibodies," mAbs 4(6):653-663.

Lewis et al. (2014) "Generation of bispecific lgG antibodies by structure-based design of an orthogonal Fab interface," Nat Biotechnol 32(2):191-98.

Long et al. (2013) "Controlling NK Cell Responses: Integration of Signals for Activation and Inhibition," Annu Rev Immunol. 2013 ; 31: 10.1146/annurev-immunol-020711-075005.

Maelig et al. (2016) "NK cells and cancer: you can teach innate cells new tricks", Nature Reviews Cancer, 16(1):7-19.

Merchant et al. (1998), "An efficient route to human bispecific lgG," Nature Biotechnology 16, 677-681 doi : 10.1038/nbt0798-677.

Miller et al. (2003) "Design, Construction, and in Vitro Analyses of Multivalent Antibodies," J Immunol 170(9):4854-61.

Mimoto et al. (2014) "Crystal structure of a novel asymmetrically engineered Fe variant with improved affinity for FcyRs," Mo/ Immunol 58(1):132-38.

Moore et al. (2011) "A novel bispecific antibody format enables simultaneous bivalent and monovalent co-engagement of distinct target antigens," mAbs 3:6, 546-557; Nov./Dec. 2011, Landes Bioscience, DOI: 10.4161/mabs.3.6.18123.

Muda et al. (2011) "Therapeutic assessment of SEED: a new engineered antibody platform designed to generate mono- and bispecific antibodies," Protein Eng Des Se/ 24(5):447-54.

Muntasell et al. (2017) "Targeting NK-cell checkpoints for cancer immunotherapy," Current Opinion in Immunology 45:73-81.

Parsons et al. (2016) "NKG2D Acts as a Co-Receptor for Natural Killer Cell-Mediated Anti-HIV-1 Antibody-Dependent Cellular Cytotoxicity," AIDS Research and Human Retroviruses 32(10-11) 1089-1096.

Ridgway et al. (1996) "Knobs-into-Holes' engineering of antibody Ch3 domains for heavy chain heterodimerization," Protein Engineering 9(7):617-21.

Singer et al. (1998) "Genes and Genomes," Moscow, "Mir" 1:63-64.

Sondermann et al. (2000) "The 3.2-Å crystal structure of the human IgG1 Fc fragment-Fc[gamma]RIII complex," Nature 406(6793):267-273.

Strop et al. (2012) "Generating Bispecific Human IgG1 and IgG2 Antibodies from Any Antibody Pair," J Mol Biol 420:204-19.

Trivedi et al. (2017) "Clinical pharmacology and translational aspects of bispecific antibodies," Clin. Transl. Sci., 10:147-162.

Van de Winkel et al. (1993) "Human IgG Fc receptor heterogeneity: molecular aspects and clinical implications," Immunology Today 14(5):215-221.

Vidarsson et al. (2014) "IgG subclasses and allotypes: from structure to effector functions," Front. Immunol. 5:520, 17 pages.

Von Kreudenstein et al. (2013) "Improving Biophysical Properties of a Bispecific Antibody Scaffold to Aid Developability: Quality by Molecular Design," mAbs 5(5):646-54.

Von Kreudenstein et al. (2014), "Protein Engineering and the Use of Molecular Modeling and Simulation: The Case of Heterodimeric Fe Engineering," Methods 65(1):77-94.

Wikipedia: "Trifunctional antibody Feb. 1, 2018",, Jan. 2, 2018 (Jan. 2, 2018), pp. 1-4, XP093016568, Retrieved from the Internet: URL:https://en.wikipedia.org/w/index.php?title=Trifunctional antibody8 oldid=818265015.

Wranik et al. (2012) "LUZ-Y, a novel platform for the mammalian cell production of full-length IgG-bispecific antibodies," J Biol Chem 287(52):43331-9.

Xie et al. (2005) "A new format of bispecific antibody: highly efficient heterodimerization, expression and tumor cell lysis," J Immunol Methods 296(1):95-101.

Xie et al. (2015) "VEGFR2 targeted antibody fused with MICA stimultes NKG2D mediated immunosurveillance and exhibits potent anti-tumor activity against breast cancer," Oncotarget 7(13):16455-16471.

Zhou et al. (1995) "Characterization of human homologue of 4-1BB and its ligand," Immunology Letters 45:67-73.

U.S. Appl. No. 16/483,330, filed Aug. 2, 2019, U.S. Pat. No. 11,834,506, Dec. 5, 2023.
U.S. Appl. No. 18/482,629, filed Oct. 6, 2023.
U.S. Appl. No. 16/484,936, filed Aug. 9, 2019.
U.S. Appl. No. 16/486,921, filed Aug. 19, 2019.
U.S. Appl. No. 16/486,569, filed Aug. 16, 2019, U.S. Pat. No. 11,884,732, Jan. 30, 2024.
U.S. Appl. No. 18/541,475, filed Dec. 15, 2023.
U.S. Appl. No. 18/304,652, filed Apr. 21, 2023.
U.S. Appl. No. 17/095,238, filed Nov. 11, 2020.
U.S. Appl. No. 18/107,292, filed Feb. 8, 2023.
U.S. Appl. No. 16/615,261, filed Nov. 20, 2019.
U.S. Appl. No. 16/635,079, filed Jan. 29, 2020.
U.S. Appl. No. 16/639,150, filed Feb. 14, 2020.
U.S. Appl. No. 18/108,961, filed Feb. 13, 2023.
U.S. Appl. No. 16/645,613, filed Mar. 9, 2020.
U.S. Appl. No. 16/967,216, filed Aug. 4, 2020, U.S. Pat. No. 11,884,733, Jan. 30, 2024.
U.S. Appl. No. 18/501,413, filed Nov. 3, 2023.
U.S. Appl. No. 18/501,419, filed Nov. 3, 2023.
U.S. Appl. No. 18/501,427, filed Nov. 3, 2023.
U.S. Appl. No. 17/058,335, filed Nov. 24, 2020.
U.S. Appl. No. 16/971,098, filed Aug. 19, 2020.
U.S. Appl. No. 18/149,965, filed Jan. 4, 2023.
U.S. Appl. No. 18/150,040, filed Jan. 4, 2023.
U.S. Appl. No. 17/045,015, filed Oct. 2, 2020.
U.S. Appl. No. 17/055,792, filed Nov. 16, 2020.
U.S. Appl. No. 17/265,876, filed Feb. 4, 2021.
U.S. Appl. No. 17/543,628, filed Dec. 6, 2021.
U.S. Appl. No. 17/266,349, filed Feb. 5, 2021.
U.S. Appl. No. 17/265,879, filed Feb. 4, 2021.
U.S. Appl. No. 17/266,966, filed Feb. 8, 2021.
U.S. Appl. No. 17/929,282, filed Sep. 1, 2022.
U.S. Appl. No. 17/287,849, filed Apr. 22, 2021.
U.S. Appl. No. 16/971,104, filed Aug. 19, 2020.
U.S. Appl. No. 17/682,367, filed Feb. 28, 2022.
U.S. Appl. No. 17/769,160, filed Apr. 14, 2022.
U.S. Appl. No. 18/003,308, filed Dec. 23, 2022.
U.S. Appl. No. 17/920,174, filed Oct. 20, 2022.
U.S. Appl. No. 17/308,691, filed May 5, 2021.
U.S. Appl. No. 17/686,238, filed Mar. 3, 2022.
U.S. Appl. No. 18/062,453, filed Dec. 6, 2022.
U.S. Appl. No. 18/166,769, filed Feb. 9, 2023.
U.S. Appl. No. 18/177,847, filed Mar. 3, 2023.
U.S. Appl. No. 18/366,876, filed Aug. 8, 2023.

Bartlett et al. (2007) "Lenalidomide and pomalidomide strongly enhance tumor cell killing in vitro during antibody-dependent cellular cytotoxicity (ADCC) mediated by trastuzumab, cetuximab and rituximab," American Society of Clinical Oncology, 25(18S) (19 pages).

(56) References Cited

OTHER PUBLICATIONS

Bogen et al. (2021) "Design of a Trispecific Checkpoint Inhibitor and Natural Killer Cell Engager Based on a 2 + 1 Common Light Chain Antibody Architecture," Frontiers in Immunology 12:16 pages.
Briney et al. (2019) "Commonality despite exceptional diversity in the baseline human antibody repertoire," Nature 566:393 (19 pages).
Dasgupta et al. (2005) "Inhibition of NK Cell Activity through TGF-β1 by Down-Regulation of NKG2D in a Murine Model of Head and Neck Cancer," J Immunol 175(8):5541-5550.
Demaria et al. (2021) "Natural killer cell engagers in cancer immunotherapy: Next generation of immuno-oncology treatments," Eur. J. Immunol. 51:1934-1942.
Giuliani et al. (2017) "Activation of NK cells and disruption of PD-L1/PD-1 axis: two different ways for lenalidomide to block myeloma progression," Oncotarget 8(14):24031-24044.
Hilpert et al. (2012) "Comprehensive analysis of NKG2D ligand expression and release in leukemia: implications for NKG2D-mediated NK cell responses," J Immunol. 189(3):1360-71.
Jorge Flavio Mendoza Rincón (2014) "El receptor NKG2D en la frontera de la inmunovigilancia y la carcinogénesis," Publicación Científica en Ciencias Biomédicas 2(21):237-43.
Katano et al. (2015) "Predominant Development of Mature and Functional Human NK Cells in a Novel Human IL-2-Producing Transgenic NOG Mouse" J. Immunol. 194(7):3513-3525.
Khan et al. (2014) "Adjustable Locks and Flexible Keys: Plasticity of Epitope-Paratope Interactions in Germline Antibodies," J. Immunol 192:5398-5405.
Kim et al. (1995) "Evidence That the Hinge Region Plays a Role in Maintaining Serum Levels of the Murine IgG1 Molecule," Molecular Immunology 32(7):467-475.
Miller et al. (2018) "Annual Review of Cancer Biology Natural Killer Cells in Cancer Immunotherapy," *Annu. Rev. Cancer Biol.* 8(3):77-103.
Miller et al. 2019 "Natural Killer Cells in Cancer Immunotherapy," Ann. Rev. Cancer Biol. 3:77-103.
Novus Biologicals, 2015, "CD-16: Find me on macrophages, neutrophils and NK cells," https://www.novusbio.com/antibody-news/antibodies/cd16-find-me-on-macrophages-neutrophils-and-nk-cells.
Poosaria et al. (2017) "Computational de novo Design of Antibodies binding to a Peptide with High Affinity," 114(6):1331-1342.
Spiess et al. (2015) "Alternative molecular formats and therapeutic applications for bispecific antibodies," Molecular Immunology 67:95-106.
Watanabe et al. (2014) NKG2D functions as an activating receptor on natural killer cells in the common marmoset (*Callithrix jacchus*) International Immunology 26(11):597-606.
Watzl et al. (2010) "Signal Transduction During Activation and Inhibition of Natural Killer Cells", Curr Protoc Immunol., 90(1):11.9B1-11.9B.17.
Whalen et al. (2023) "Engaging natural killer cells for cancer therapy via NKG2D, CD16A and other receptors," 15(1) 15 pages.
Wu et al. (2011), "Lenalidomide enhances antibody-dependent cellular cytotoxicity of solid tumor cells in vitro: influence of host immune and tumor markers," Cancer Immunology, Immunotherapy, Springer, 60(1):61-73.
Yang et al. (2017) "Bispecific Antibodies as a Development Platform for New Concepts and Treatment Strategies" Int. J. Mol. Sci. 18(48) 21 pages.
Absolute Antibody, 2023, Anti-NKG2D [ADI-27749 (A49)] Standard Size Ab03079-3.0, 1 page.
Bryceson et al. (2006) "Activation, coactivation, and costimulation of resting human natural killer cells Immunological Reviews," 214:73-91.
Chen et al. (2017) "Targeting FLT3 by Chimeric Antigen Receptor T Cells for the Treatment of Acute Myeloid Leukemia," Leukemia 31(8):1830-1834.
Davis et al. (2017) "Natural killer cells unleashed: Checkpoint receptor blockade and BiKE/TriKE utilization in NK-mediated anti-tumor immunotherapy," Seminars in Immunology 31:64-75.
Epling-Burnette et al. (2004) "Dysregulated NK receptor expression in patients with lymphoproliferative disease of granular lymphocytes," Blood 13(9):3431-3439.
Eruslanov et al. (2013) "Expansion of CCR8+ Inflammatory Myeloid Cells in Cancer Patients with Urothelial and Renal Carcinomas," *Clinical Cancer Research* 19(7):1670-1680.
Kontermann et al. (2015) "Bispecific antibodies," Drug Discovery Today 20(7):838-847 (12 pages).
Liu et al. (2020) "Fc-Engineering for Modulated Effector Functions-Improving Antibodies for Cancer Treatment," Antibodies 9(64):34 pages.
Nersesian et al (2020) "N K cell infiltration is associated with improved overall survival in solid cancers: A systematic review and meta-analysis," Translational Oncology 14 (20 pages).
Plitas et al. (2016) "Regulatory T Cells Exhibit Distinct Features in Human Breast Cancer," *Immunity* 45(5):1122-1134.
Raynaud et al. (2021) "Anti-NKG2D single domain-based antibodies for the modulation of anti-tumor immune response," Oncoimmunology 10(1):e1854529-1-e1854529-14.
Stallard (2016) "New Approach Could Boost Immunotherapy for Breast Cancer," Memorial Sloan Kettering Cancer Center 1-5.
Weatherill et al. (2012) "Towards a universal disulphide stabilised single chain Fv format: importance of interchain disulphide bond location and vL-vH orientation," Protein Engineering, Design, and Selection, 25(7):321-329.
Ho et al. (2002) "Costimulation of multiple NK cell activation receptors by NKG2D," Journal of Immunology 169(7):3667-3675.
Kawakami et al. (2016) Combinational Cancer Immunotherapy, Jikken Igaku [Experimental Medicine] 34(12):2038-2042, and a concise explanation of relevance as set forth in an English Translation of the Penultimate Official Action dated Dec. 4, 2024 for Japanese Patent Application No. 2023-90959 (5 pages) that cites the Kawakami et al. (2016) reference.

\* cited by examiner

Fluorescence measured by flow cytometry

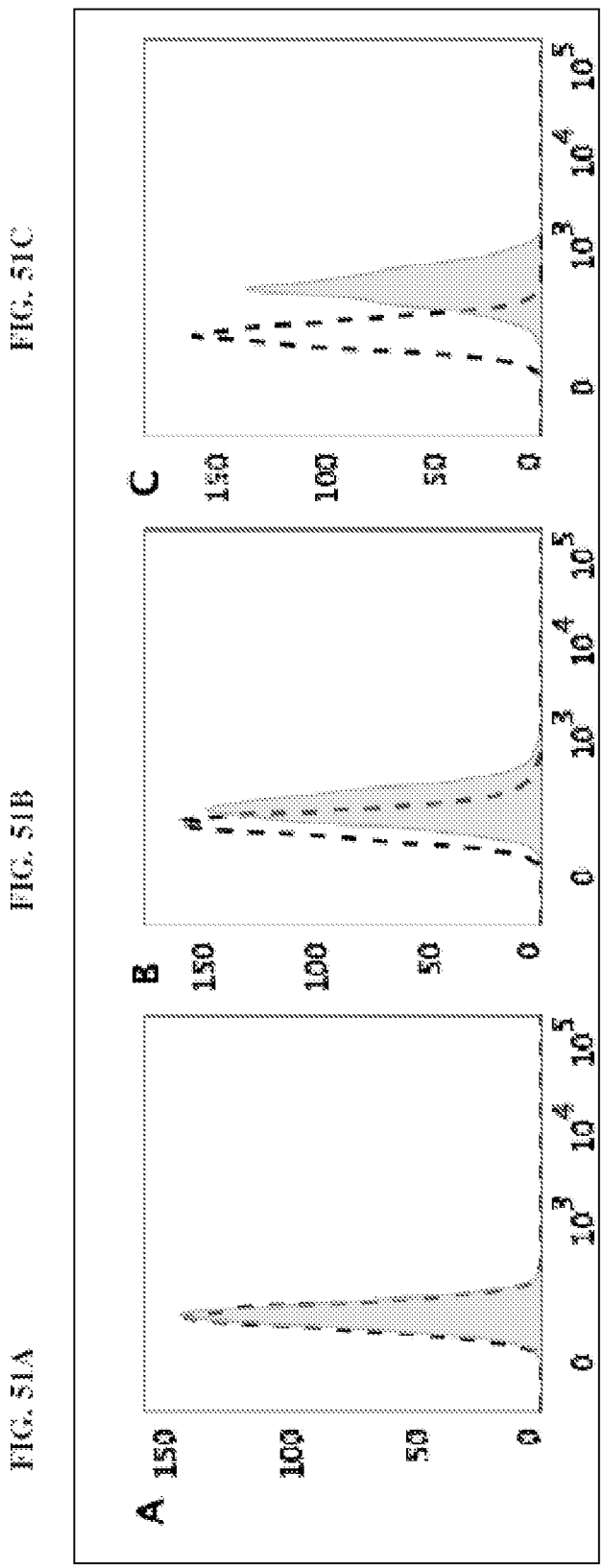

FIG. 80B
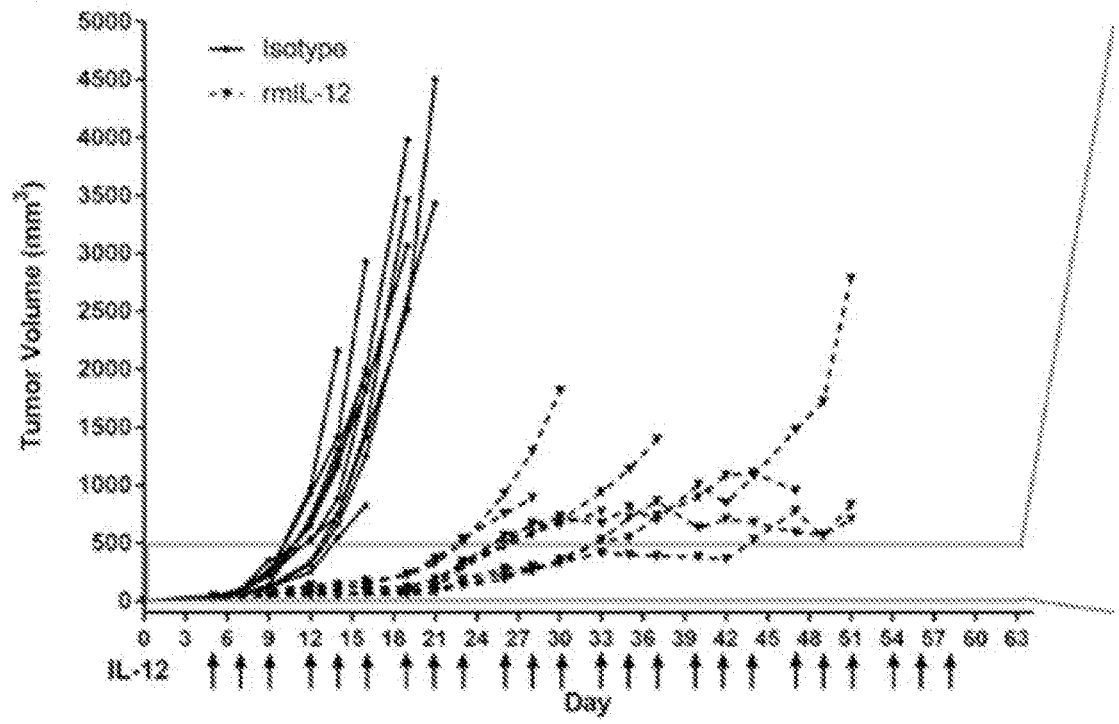
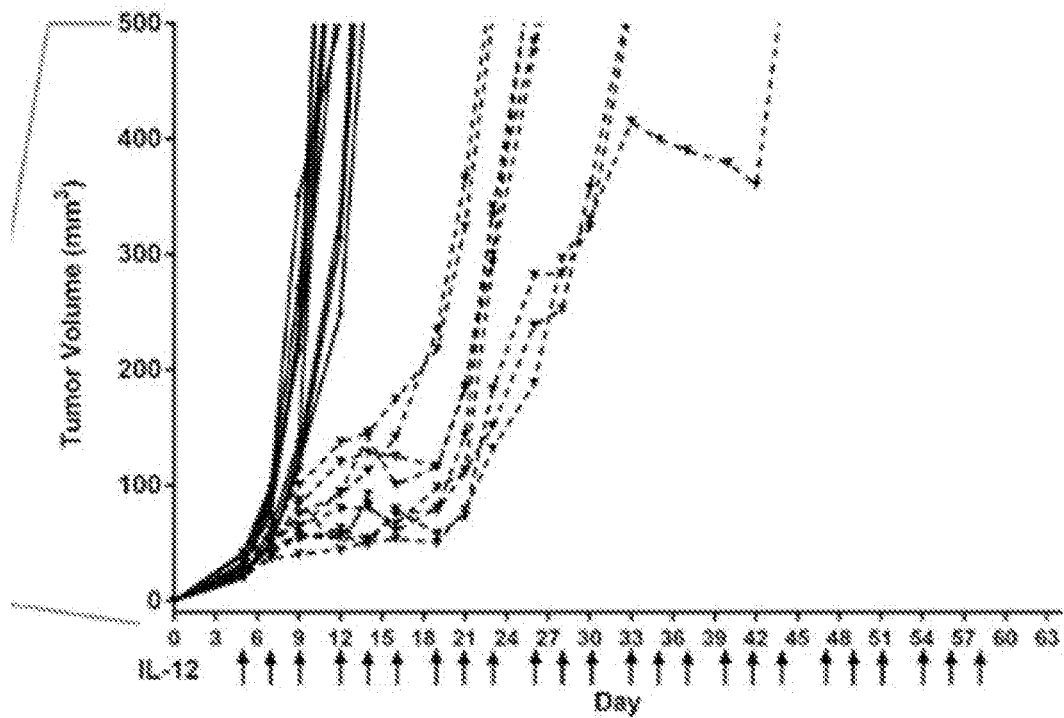

FIG. 80C
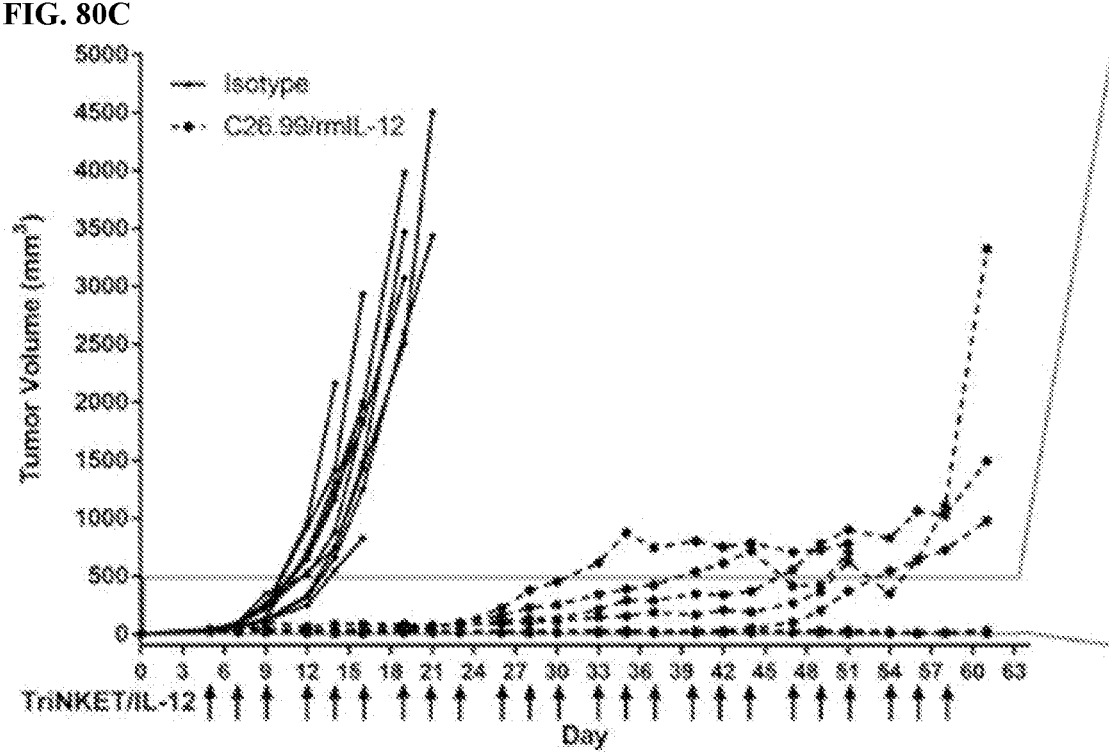
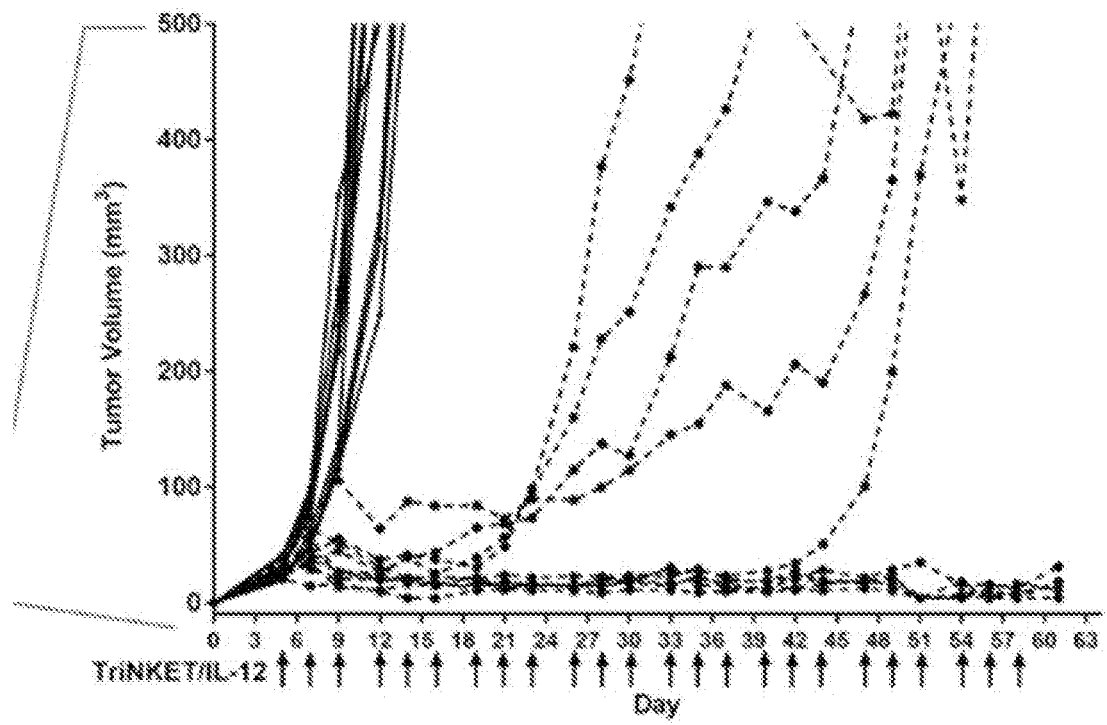

CANCER THERAPY INVOLVING AN ANTI-PD1 ANTIBODY AND A MULTI-SPECIFIC BINDING PROTEIN THAT BINDS NKG2D, CD16, AND A TUMOR-ASSOCIATED ANTIGEN

CROSS-REFERENCE TO RELATED APPLICATIONS

This application is a U.S. national stage application, filed under 35 U.S.C. § 371, of International Application No. PCT/US2019/017284, filed on Feb. 8, 2019, which claims the benefit of and priority to U.S. Provisional Patent Application No. 62/628,178, filed on Feb. 8, 2018, the disclosure of which is incorporated by reference herein in its entirety for all purposes.

SEQUENCE LISTING

This application contains a Sequence Listing which has been submitted electronically in ASCII format and is hereby incorporated by reference in its entirety. Said ASCII file, created on Feb. 8, 2019, is named DFY_051WO_sequence_listing_as_filed.txt and is 112,334 bytes in size.

FIELD OF THE INVENTION

Combination therapy of a cancer with a multi-specific binding protein that bind a tumor associated antigen, the NKG2D receptor, and CD16, in combination with a second anti-cancer agent are described. Also described are pharmaceutical compositions of the multi-specific binding protein, and therapeutic methods useful for the treatment of cancer in combination with a second anti-cancer agent.

BACKGROUND

Cancer continues to be a significant health problem despite the substantial research efforts and scientific advances reported in the literature for treating this disease. Some of the most frequently diagnosed cancers include prostate cancer, breast cancer, and lung cancer. Prostate cancer is the most common form of cancer in men. Breast cancer remains a leading cause of death in women. Current treatment options for these cancers are not effective for all patients and/or can have substantial adverse side effects. Other types of cancer also remain challenging to treat using existing therapeutic options.

Cancer immunotherapies are desirable because they are highly specific and can facilitate destruction of cancer cells using the patient's own immune system. Fusion proteins such as bi-specific T-cell engagers are cancer immunotherapies described in the literature that bind to tumor cells and T-cells to facilitate destruction of tumor cells. Antibodies that bind to certain tumor-associated antigens and to certain immune cells have been described in the literature. See, for example WO 2016/134371 and WO 2015/095412.

Natural killer (NK) cells are a component of the innate immune system and make up approximately 15% of circulating lymphocytes. NK cells infiltrate virtually all tissues and were originally characterized by their ability to kill tumor cells effectively without the need for prior sensitization. Activated NK cells kill target cells by means similar to cytotoxic T cells—i.e. via cytolytic granules that contain perforin and granzymes as well as via death receptor pathways. Activated NK cells also secrete inflammatory cytokines such as IFN-gamma and chemokines that promote the recruitment of other leukocytes to the target tissue.

NK cells respond to signals through a variety of activating and inhibitory receptors on their surface. For example, when NK cells encounter healthy self-cells, their activity is inhibited through activation of the killer-cell immunoglobulin-like receptors (KIRs). Alternatively, when NK cells encounter foreign cells or cancer cells, they are activated via their activating receptors (e.g. NKG2D, NCRs, DNAM1). NK cells are also activated by the constant region of some immunoglobulins through CD16 receptors on their surface. The overall sensitivity of NK cells to activation depends on the sum of stimulatory and inhibitory signals.

SUMMARY

In one aspect, the invention provides a method of enhancing tumor cell death directly or indirectly, the method includes exposing a tumor and natural killer cells to a protein comprising: (a) a first antigen-binding site that binds NKG2D; (b) a second antigen-binding site that binds a tumor-associated antigen; and (c) an antibody Fc domain or a portion thereof sufficient to bind CD16, or a third antigen-binding site that binds CD16; in combination with a second therapeutic agent selected from: a checkpoint blocker; a cytokine; a TLR agonist; a STING agonist; a chemotherapeutic agent; a cancer target agent that interferes with specific molecules in cancer cells that are involved in cancer cell growth or survival, including, for example, kinase inhibitors such as Ibrutinib, Vemurafenib, or Gleevec; an oncolytic virus; a vaccine; radiation; an adoptive NK therapy which involves infusion of ex vivo expanded NK cells, an adoptive T cell therapy which involves infusion of ex vivo expanded T cells, including cell that have been modified in vitro to express a chimeric antigen receptor (e.g., CAR-T cells); a stem cell transplant (SCT) therapy, and an agent that induces cellular senescence.

In one aspect, the invention provides a method of treating cancer in a subject in need thereof, the method comprising administering to the subject a protein comprising: (a) a first antigen-binding site that binds NKG2D; (b) a second antigen-binding site that binds a tumor-associated antigen; and (c) an antibody Fc domain or a portion thereof sufficient to bind CD16, or a third antigen-binding site that binds CD16; or a formulation comprising the protein; in combination with a second therapeutic agent selected from: a checkpoint blocker, a cytokine, a TLR agonist, a STING agonist, a chemotherapeutic agent, a cancer target agent, an oncolytic virus, a vaccine, radiation, an adoptive NK therapy which involves infusion of ex vivo expanded NK cells, an adoptive T cell therapy which involves infusion of ex vivo expanded T cells, including cell that have been modified in vitro to express a chimeric antigen receptor (e.g., CAR-T cells), a stem cell transplant (SCT) therapy, and an agent that induces cellular senescence.

The present disclosure provides a method of enhancing tumor cell death directly or indirectly and/or a method of treating cancer with a protein comprising: (a) a first antigen-binding site that binds NKG2D; (b) a second antigen-binding site that binds a tumor-associated antigen; and (c) an antibody Fc domain or a portion thereof sufficient to bind CD16, or a third antigen-binding site that binds CD16, in combination with a checkpoint blocker selected from: an anti-PD1 antibody, an anti-PD-L1 antibody, an anti-CTLA4 antibody, an anti-KIR antibody, an anti-NKG2A antibody, an anti-LAG3 antibody, and an anti-TIM3 antibody.

The present disclosure provides a method of enhancing tumor cell death directly or indirectly and/or a method of treating cancer with a protein comprising: (a) a first antigen-binding site that binds NKG2D; (b) a second antigen-binding site that binds a tumor-associated antigen; and (c) an antibody Fc domain or a portion thereof sufficient to bind CD16, or a third antigen-binding site that binds CD16, in combination with a cytokine including interferons and interleukins, such as IL-2, IL-15, IL-12, INFα, IL-21, PEG-IL-2 (polyethylene glycol-modified interleukin-2), and IL15/IL15R heterodimers.

The present disclosure provides a method of enhancing tumor cell death directly or indirectly and/or a method of treating cancer with a protein comprising: (a) a first antigen-binding site that binds NKG2D; (b) a second antigen-binding site that binds a tumor-associated antigen; and (c) an antibody Fc domain or a portion thereof sufficient to bind CD16, or a third antigen-binding site that binds CD16, in combination with a TLR agonist selected from a TLR7 agonist, a TLR8 agonist, a TLR7/8 agonist, a TLR9 agonist, a TLR4 agonist, and a TLR3 agonist.

The present disclosure provides a method of enhancing tumor cell death directly or indirectly and/or a method of treating cancer with a protein comprising: (a) a first antigen-binding site that binds NKG2D; (b) a second antigen-binding site that binds a tumor-associated antigen; and (c) an antibody Fc domain or a portion thereof sufficient to bind CD16, or a third antigen-binding site that binds CD16, in combination with a STING agonist ADU-S100.

The present disclosure provides a method of enhancing tumor cell death directly or indirectly and/or a method of treating cancer with a protein comprising: (a) a first antigen-binding site that binds NKG2D; (b) a second antigen-binding site that binds a tumor-associated antigen; and (c) an antibody Fc domain or a portion thereof sufficient to bind CD16, or a third antigen-binding site that binds CD16, in combination with a chemotherapeutic agent including alkylating agents such as cyclophosphamide, mechlorethamine, chlorambucil, melphalan, dacarbazine (DTIC), nitrosoureas, temozolomide (Oral dacarbazine); anthracyclines, such as daunorubicin, doxorubicin, epirubicin, idarubicin, mitoxantrone, and valrubicin; cytoskeletal disruptors, such as paclitaxel, nab-paclitaxel, docetaxel, abraxane, and taxotere; epothilones; histone deacetylase inhibitors such as vorinostat and romidepsin; inhibitors of topoisomerase I such as irinotecan and topotecan; inhibitors of topoisomerase II such as etoposide, teniposide and tafluposide; kinase inhibitors such as bortezomib, erlotinib, gefitinib, imatinib, vemurafenib and vismodegib; nucleotide analogs and precursor analogs such as azacitidine, azathioprine, capecitabine; peptide antibiotics such as bleomycin and actinomycin; platinum-based agents, such as carboplatin, cisplatin and oxaliplatin; retinoids such as tretinoin and alitretinoin; and *vinca* alkaloids and derivatives such as vinblastine, vincristine, vindesine and vinorelbine.

The present disclosure provides a method of enhancing tumor cell death directly or indirectly and/or a method of treating cancer with a protein comprising: (a) a first antigen-binding site that binds NKG2D; (b) a second antigen-binding site that binds a tumor-associated antigen; and (c) an antibody Fc domain or a portion thereof sufficient to bind CD16, or a third antigen-binding site that binds CD16, in combination with a checkpoint blocker selected from: nivolumab, pembrolizumab, atezolizumab, durvalumab, avelumab, ipilimumab, tremelimumab, lirilumab, and monalizumab.

The present disclosure provides a method of enhancing tumor cell death directly or indirectly and/or a method of treating cancer with a protein comprising: (a) a first antigen-binding site that binds NKG2D; (b) a second antigen-binding site that binds a tumor-associated antigen; and (c) an antibody Fc domain or a portion thereof sufficient to bind CD16, or a third antigen-binding site that binds CD16, in combination with a TLR agonist selected from: R848/resiquimod, VTX-2337, imiquimod, and CpG oligodeoxynucleotide.

The invention provides multi-specific binding proteins that bind to a tumor-associated antigen on a cancer cell and the NKG2D receptor and CD16 receptor on natural killer cells to activate the natural killer cells, pharmaceutical compositions comprising such multi-specific binding proteins, and therapeutic methods using such multi-specific proteins and pharmaceutical compositions, including for the treatment of cancer. Such proteins can engage more than one kind of NK activating receptor, and may block the binding of natural ligands to NKG2D. In certain embodiments, the protein can agonize NK cells in humans, and in other species such as rodents and/or cynomolgus monkeys. Various aspects and embodiments of the invention are described in further detail below.

In some embodiments, the multi-specific binding protein can incorporate a first antigen-binding site that binds NKG2D; a second antigen-binding site that binds a tumor-associated antigen; and an antibody Fc domain, a portion thereof sufficient to bind CD16, or a third antigen-binding site that binds CD16.

In some embodiments, the multi-specific binding protein is trivalent, which includes a first and a second antigen binding site that both bind the same tumor-associated antigen; a third antigen binding site that binds NKG2D; and an antibody Fc domain, a portion thereof sufficient to bind CD16.

In some embodiments, the multi-specific binding protein is tetravalent, which includes a first and a second antigen binding site that both bind the same tumor-associated antigen; a third and fourth antigen binding site that both bind NKG2D; and an antibody Fc domain, a portion thereof sufficient to bind CD16.

The antigen-binding sites may each incorporate an antibody heavy chain variable domain and an antibody light chain variable domain (e.g. arranged as in an antibody, or fused together to from an scFv), or one or more of the antigen-binding sites may be a single domain antibody, such as a $V_HH$ antibody like a camelid antibody or a $V_{NAR}$ antibody like those found in cartilaginous fish. In some instances, the tumor-associated antigen can be selected from the group consisting of HER2, CD20, CD33, B-cell maturation antigen (BCMA), EpCAM, CD2, CD19, CD25, CD30, CD38, CD40, CD52, CD70, CLL1/CLEC12A, FLT3, EGFR/ERBB1, IGF1R, HER3/ERBB3, HER4/ERBB4, MUC1, cMET, SLAMF7, PSCA, MICA, MICB, TRAILR1, TRAILR2, MAGE-A3, B7.1, B7.2, CTLA4, HLA-E, and PD-L1.

In some embodiments, the antigen binding site that binds NKG2D comprises a heavy chain variable domain and a light chain variable domain, the heavy chain variable domain and the light chain variable domain each comprising an amino acid sequence at least 90% (e.g., 91%, 92%, 93%, 94%, 95%, 96%, 97%, 98%, 99%, or 100%) identical to the amino acid sequences of the heavy chain variable region and the light chain variable region of an antigen binding site disclosed in Table 1. In some embodiments, the heavy chain variable domain comprises the heavy chain complementarity-determining region 1 (CDR1), complementarity-determining region 2 (CDR2), and complementarity-determining region 3 (CDR3) sequences and the light chain CDR1, CDR2, and CDR3 sequences as disclosed in Table 1 of the antigen binding site.

For example, in some embodiments, the antigen binding site that binds NKG2D comprises a heavy chain variable domain and a light chain variable domain, the heavy chain variable domain comprising an amino acid sequence at least 90% (e.g., 91%, 92%, 93%, 94%, 95%, 96%, 97%, 98%, 99%, or 100%) identical to the amino acid sequence of SEQ ID NO:47 and the light chain variable domain comprising an amino acid sequence at least 90% (e.g., 91%, 92%, 93%, 94%, 95%, 96%, 97%, 98%, 99%, or 100%) identical to the amino acid sequence of SEQ ID NO:48. In some embodiments, the heavy chain variable domain comprises a CDR1 sequence represented by the amino acid sequence of SEQ ID NO:92, a CDR2 sequence represented by the amino acid sequence of SEQ ID NO:58, and a CDR3 sequence represented by the amino acid sequence of SEQ ID NO:113; and the light chain variable domain comprises a CDR1 sequence represented by the amino acid sequence of SEQ ID NO:60, a CDR2 sequence represented by the amino acid sequence of SEQ ID NO:61, and a CDR3 sequence represented by the amino acid sequence of SEQ ID NO:62.

In some embodiments, the antigen binding site that binds NKG2D comprises a heavy chain variable domain and a light chain variable domain, the heavy chain variable domain comprising an amino acid sequence at least 90% (e.g., 91%, 92%, 93%, 94%, 95%, 96%, 97%, 98%, 99%, or 100%) identical to the amino acid sequence of SEQ ID NO:47 and the light chain variable domain comprising an amino acid sequence at least 90% (e.g., 91%, 92%, 93%, 94%, 95%, 96%, 97%, 98%, 99%, or 100%) identical to the amino acid sequence of SEQ ID NO:48. In some embodiments, the heavy chain variable domain comprises a CDR1 sequence represented by the amino acid sequence of SEQ ID NO:92, a CDR2 sequence represented by the amino acid sequence of SEQ ID NO:58, and a CDR3 sequence represented by the amino acid sequence of SEQ ID NO:93; and the light chain variable domain comprises a CDR1 sequence represented by the amino acid sequence of SEQ ID NO:60, a CDR2 sequence represented by the amino acid sequence of SEQ ID NO:61, and a CDR3 sequence represented by the amino acid sequence of SEQ ID NO:62. In some embodiments, the heavy chain variable domain comprises a CDR1 sequence represented by the amino acid sequence of SEQ ID NO:57, a CDR2 sequence represented by the amino acid sequence of SEQ ID NO:58, and a CDR3 sequence represented by the amino acid sequence of SEQ ID NO:59; and the light chain variable domain comprises a CDR1 sequence represented by the amino acid sequence of SEQ ID NO:60, a CDR2 sequence represented by the amino acid sequence of SEQ ID NO:61, and a CDR3 sequence represented by the amino acid sequence of SEQ ID NO:62.

In some embodiments, the antigen binding site that binds NKG2D comprises a heavy chain variable domain and a light chain variable domain, the heavy chain variable domain comprising an amino acid sequence at least 90% (e.g., 91%, 92%, 93%, 94%, 95%, 96%, 97%, 98%, 99%, or 100%) identical to the amino acid sequence of SEQ ID NO:47 and the light chain variable domain comprising an amino acid sequence at least 90% (e.g., 91%, 92%, 93%, 94%, 95%, 96%, 97%, 98%, 99%, or 100%) identical to the amino acid sequence of SEQ ID NO:48. In some embodiments, the heavy chain variable domain comprises a CDR1 sequence represented by the amino acid sequence of SEQ ID NO:92, a CDR2 sequence represented by the amino acid sequence of SEQ ID NO:58, and a CDR3 sequence represented by the amino acid sequence of SEQ ID NO:104; and the light chain variable domain comprises a CDR1 sequence represented by the amino acid sequence of SEQ ID NO:60, a CDR2 sequence represented by the amino acid sequence of SEQ ID NO:61, and a CDR3 sequence represented by the amino acid sequence of SEQ ID NO:62. In some embodiments, the heavy chain variable domain comprises a CDR1 sequence represented by the amino acid sequence of SEQ ID NO:57, a CDR2 sequence represented by the amino acid sequence of SEQ ID NO:58, and a CDR3 sequence represented by the amino acid sequence of SEQ ID NO:103; and the light chain variable domain comprises a CDR1 sequence represented by the amino acid sequence of SEQ ID NO:60, a CDR2 sequence represented by the amino acid sequence of SEQ ID NO:61, and a CDR3 sequence represented by the amino acid sequence of SEQ ID NO:62.

In some embodiments, the antigen binding site that binds NKG2D comprises a heavy chain variable domain and a light chain variable domain, the heavy chain variable domain comprising an amino acid sequence at least 90% (e.g., 91%, 92%, 93%, 94%, 95%, 96%, 97%, 98%, 99%, or 100%) identical to the amino acid sequence of SEQ ID NO:45 and the light chain variable domain comprising an amino acid sequence at least 90% (e.g., 91%, 92%, 93%, 94%, 95%, 96%, 97%, 98%, 99%, or 100%) identical to the amino acid sequence of SEQ ID NO:46. In some embodiments, the heavy chain variable domain comprises a CDR1 sequence represented by the amino acid sequence of SEQ ID NO:90, a CDR2 sequence represented by the amino acid sequence of SEQ ID NO:52, and a CDR3 sequence represented by the amino acid sequence of SEQ ID NO:91; and the light chain variable domain comprises a CDR1 sequence represented by the amino acid sequence of SEQ ID NO:54, a CDR2 sequence represented by the amino acid sequence of SEQ ID NO:55, and a CDR3 sequence represented by the amino acid sequence of SEQ ID NO:56. In some embodiments, the heavy chain variable domain comprises a CDR1 sequence represented by the amino acid sequence of SEQ ID NO:51, a CDR2 sequence represented by the amino acid sequence of SEQ ID NO:52, and a CDR3 sequence represented by the amino acid sequence of SEQ ID NO:53; and the light chain variable domain comprises a CDR1 sequence represented by the amino acid sequence of SEQ ID NO:54, a CDR2 sequence represented by the amino acid sequence of SEQ ID NO:55, and a CDR3 sequence represented by the amino acid sequence of SEQ ID NO:56.

In some embodiments, the antigen binding site that binds NKG2D comprises a heavy chain variable domain and a light chain variable domain, the heavy chain variable domain comprising an amino acid sequence at least 90% (e.g., 91%, 92%, 93%, 94%, 95%, 96%, 97%, 98%, 99%, or 100%) identical to the amino acid sequence of SEQ ID NO:49 and the light chain variable domain comprising an amino acid sequence at least 90% (e.g., 91%, 92%, 93%, 94%, 95%, 96%, 97%, 98%, 99%, or 100%) identical to the amino acid sequence of SEQ ID NO:50. In some embodiments, the heavy chain variable domain comprises a CDR1 sequence represented by the amino acid sequence of SEQ ID NO:94, a CDR2 sequence represented by the amino acid sequence of SEQ ID NO:64, and a CDR3 sequence represented by the amino acid sequence of SEQ ID NO:95; and the light chain variable domain comprises a CDR1 sequence represented by the amino acid sequence of SEQ ID NO:66, a CDR2 sequence represented by the amino acid sequence of SEQ ID NO:67, and a CDR3 sequence represented by the amino acid sequence of SEQ ID NO:68. In some embodiments, the heavy chain variable domain comprises a CDR1 sequence represented by the amino acid sequence of SEQ ID NO:63, a CDR2 sequence represented by the amino acid sequence of SEQ ID NO:64, and a CDR3 sequence represented by the amino acid sequence of SEQ ID NO:65; and the light chain variable domain comprises a CDR1 sequence represented by the amino acid sequence of SEQ ID NO:66, a CDR2 sequence represented by the amino acid sequence of SEQ ID NO:67, and a CDR3 sequence represented by the amino acid sequence of SEQ ID NO:68.

In some embodiments, the antigen binding site that binds NKG2D comprises a heavy chain variable domain and a light chain variable domain, the heavy chain variable domain comprising an amino acid sequence at least 90% (e.g., 91%, 92%, 93%, 94%, 95%, 96%, 97%, 98%, 99%, or 100%) identical to the amino acid sequence of SEQ ID NO:114 and the light chain variable domain comprising an amino acid sequence at least 90% (e.g., 91%, 92%, 93%, 94%, 95%, 96%, 97%, 98%, 99%, or 100%) identical to the amino acid sequence of SEQ ID NO:115. In some embodiments, the heavy chain variable domain comprises a CDR1 sequence represented by the amino acid sequence of SEQ ID NO:122, a CDR2 sequence represented by the amino acid sequence of SEQ ID NO:117, and a CDR3 sequence represented by the amino acid sequence of SEQ ID NO:123; and the light chain variable domain comprises a CDR1 sequence represented by the amino acid sequence of SEQ ID NO:119, a CDR2 sequence represented by the amino acid sequence of SEQ ID NO:120, and a CDR3 sequence represented by the amino acid sequence of SEQ ID NO:121. In some embodiments, the heavy chain variable domain comprises a CDR1 sequence represented by the amino acid sequence of SEQ ID NO:116, a CDR2 sequence represented by the amino acid sequence of SEQ ID NO:117, and a CDR3 sequence represented by the amino acid sequence of SEQ ID NO:118; and the light chain variable domain comprises a CDR1 sequence represented by the amino acid sequence of SEQ ID NO:119, a CDR2 sequence represented by the amino acid sequence of SEQ ID NO:120, and a CDR3 sequence represented by the amino acid sequence of SEQ ID NO:121.

In some embodiments, the antigen binding site that binds NKG2D comprises a heavy chain variable domain and a light chain variable domain, the heavy chain variable domain comprising an amino acid sequence at least 90% (e.g., 91%, 92%, 93%, 94%, 95%, 96%, 97%, 98%, 99%, or 100%) identical to the amino acid sequence of SEQ ID NO:124 and the light chain variable domain comprising an amino acid sequence at least 90% (e.g., 91%, 92%, 93%, 94%, 95%, 96%, 97%, 98%, 99%, or 100%) identical to the amino acid sequence of SEQ ID NO:125. In some embodiments, the heavy chain variable domain comprises a CDR1 sequence represented by the amino acid sequence of SEQ ID NO:122, a CDR2 sequence represented by the amino acid sequence of SEQ ID NO:117, and a CDR3 sequence represented by the amino acid sequence of SEQ ID NO:130; and the light chain variable domain comprises a CDR1 sequence represented by the amino acid sequence of SEQ ID NO:127, a CDR2 sequence represented by the amino acid sequence of SEQ ID NO:128, and a CDR3 sequence represented by the amino acid sequence of SEQ ID NO:129. In some embodiments, the heavy chain variable domain comprises a CDR1 sequence represented by the amino acid sequence of SEQ ID NO:116, a CDR2 sequence represented by the amino acid sequence of SEQ ID NO:117, and a CDR3 sequence represented by the amino acid sequence of SEQ ID NO:126; and the light chain variable domain comprises a CDR1 sequence represented by the amino acid sequence of SEQ ID NO:127, a CDR2 sequence represented by the amino acid sequence of SEQ ID NO:128, and a CDR3 sequence represented by the amino acid sequence of SEQ ID NO:129.

In some embodiments, the antigen binding site that binds NKG2D comprises a heavy chain variable domain comprising an amino acid sequence at least 90% (e.g., 91%, 92%, 93%, 94%, 95%, 96%, 97%, 98%, 99%, or 100%) identical to the amino acid sequence of SEQ ID NO:1.

In some embodiments, the antigen binding site that binds NKG2D comprises a heavy chain variable domain and a light chain variable domain, the heavy chain variable domain comprising an amino acid sequence at least 90% (e.g., 91%, 92%, 93%, 94%, 95%, 96%, 97%, 98%, 99%, or 100%) identical to the amino acid sequence of SEQ ID NO:41 and the light chain variable domain comprising an amino acid sequence at least 90% (e.g., 91%, 92%, 93%, 94%, 95%, 96%, 97%, 98%, 99%, or 100%) identical to the amino acid sequence of SEQ ID NO:42.

In some embodiments, the antigen binding site that binds NKG2D comprises a heavy chain variable domain and a light chain variable domain, the heavy chain variable domain comprising an amino acid sequence at least 90% (e.g., 91%, 92%, 93%, 94%, 95%, 96%, 97%, 98%, 99%, or 100%) identical to the amino acid sequence of SEQ ID NO:43 and the light chain variable domain comprising an amino acid sequence at least 90% (e.g., 91%, 92%, 93%, 94%, 95%, 96%, 97%, 98%, 99%, or 100%) identical to the amino acid sequence of SEQ ID NO:44.

In some embodiments, the antigen binding site that binds NKG2D comprises a heavy chain variable domain and a light chain variable domain, the heavy chain variable domain comprising an amino acid sequence at least 90% (e.g., 91%, 92%, 93%, 94%, 95%, 96%, 97%, 98%, 99%, or 100%) identical to the amino acid sequence of SEQ ID NO:69 and the light chain variable domain comprising an amino acid sequence at least 90% (e.g., 91%, 92%, 93%, 94%, 95%, 96%, 97%, 98%, 99%, or 100%) identical to the amino acid sequence of SEQ ID NO:70.

In some embodiments, the antigen binding site that binds NKG2D comprises a heavy chain variable domain and a light chain variable domain, the heavy chain variable domain comprising an amino acid sequence at least 90% (e.g., 91%, 92%, 93%, 94%, 95%, 96%, 97%, 98%, 99%, or 100%) identical to the amino acid sequence of SEQ ID NO:71 and the light chain variable domain comprising an amino acid sequence at least 90% (e.g., 91%, 92%, 93%, 94%, 95%, 96%, 97%, 98%, 99%, or 100%) identical to the amino acid sequence of SEQ ID NO:72.

Another aspect of the invention provides a method of treating cancer in a patient. The method comprises administering to a patient in need thereof a therapeutically effective amount of a multi-specific binding protein described herein to treat the cancer. Exemplary cancers for treatment using the multi-specific binding proteins include, for example, a carcinoma that expresses HER2.

BRIEF DESCRIPTION OF THE DRAWINGS

FIG. 13A is an exemplary representation of one form of a κλ-Body; FIG. 13B is an exemplary representation of another κλ-Body.

FIG. 37 shows binding of the two TriNKETs when a CD33-binding domain is used as the second targeting arm.

FIG. 38 shows the same two NKG2D-binding domains now paired with a HER2 second targeting arm.

FIG. 45A demonstrates levels of CD107a; FIG. 45B demonstrates levels of IFNγ.

FIG. 47A shows that human NK cells are activated by TriNKETs when cultured with SkBr-3 cells. FIG. 47B shows that human NK cells are activated by TriNKETs when cultured with Colo201 cells. FIG. 47C shows that human NK cell are activated by TriNKETs when cultured with HCC1954 cells.

FIG. 48A shows TriNKET-mediated activation of resting human NK cells. FIG. 48B shows TriNKET-mediated activation of IL-2-activated human NK cells from the same donor.

FIG. 49A shows percent specific lysis of SkBr-3 tumor cells by rested human NK cells. FIG. 49B shows percent specific lysis of SkBr-3 tumor cells by IL-2-activated human NK cells.

FIG. 50A shows activated human NK cell killing of HER2 high-SkBr-3 tumor cells. FIG. 50B shows human NK cell killing of HER2 low-786-O tumor cells. TriNKETs provide a greater advantage compared to trastuzumab against cancer cells with low HER2 expression.

FIGS. 51A-51C are histograms showing that the expression of the high-affinity FcRγI (CD64) on three human AML cells lines, Molm-13 cell line (FIG. 51A), Mv4-11 cell line (FIG. 51B), and THP-1 cell line (FIG. 51C).

FIG. 53A shows that Mv4-11 cells, which express CD64, but at a lower level than THP-1, showed reduced efficacy with the monoclonal anti-CD33. FIG. 53B demonstrates that a monoclonal antibody against CD33 shows good efficacy against Molm-13 cells, which do not express CD64. FIG. 53C demonstrates that THP-1 cells showed no effect with monoclonal anti-CD33 alone. The identities of the line graphs noted in FIG. 53C are also applicable to the line graphs in FIGS. 53A-53B.

FIG. 61A represents tumor burden when antibodies were administered at a 150-µg dose (days 4, 6, 8, 11, 13, 15). FIG. 61B represents tumor burden when antibodies were administered at a 150-µg dose (days 7, 9, 11, 13, 15). 18 days after tumor challenge, mice were euthanized and surface lung metastases were scored.

FIG. 66A are line graphs showing tumor size (mm³) in mice treated intraperitoneally with isotype controls mouse IgG2a monoclonal antibody C1.18.4 with rat IgG2a monoclonal antibody 2A3, or with mcFAE-C26.99. FIG. 66B are line graphs showing tumor size (mm³) in mice treated intraperitoneally with isotype controls or anti-PD-1 monoclonal antibody clone RPM1-14. FIG. 66C are line graphs showing tumor size (mm³) in mice treated intraperitoneally with combination of mcFAE-C26.99 and anti-PD-1 monoclonal antibody. Tumor growth was assessed for 30 days. Graphs show tumor growth curves of individual mice.

FIG. 67A are line graphs showing tumor size (mm³) in mice treated intraperitoneally with isotype control mouse IgG2a monoclonal antibody C1.18.4 or with mcFAE-C26.99. FIG. 67B are line graphs showing tumor size (mm³) in mice treated intraperitoneally with isotype control or with IL-2. FIG. 67C are line graphs showing tumor size (mm³) in mice treated intraperitoneally with a combination of mcFAE-C26.99 and IL-2. Tumor growth was assessed for 40 days with 3 mice from the combination group remaining tumor-free. Graphs show tumor growth curves of individual mice.

FIGS. 80A-80C are line graphs showing tumor growth curves of individual mice inoculated with B16F10 tumor cells and treated with 7.5 mg/kg mcFAE-C26.99 TriNKET or 7.5 mg/kg isotype control mouse IgG2a monoclonal antibody C1.18.4 (FIG. 80A), 1 µg recombinant murine IL-12 (rmIL-12) or 7.5 mg/kg isotype control mouse IgG2a monoclonal antibody C1.18.4 (FIG. 80B), or a combination of 7.5 mg/kg mcFAE-C26.99 TriNKET and 1 µg rmIL-12 (FIG. 80C). In FIGS. 80B and 80C, the lower panels represent plotting on a small scale of the y-axis.

DETAILED DESCRIPTION

Figure 1:
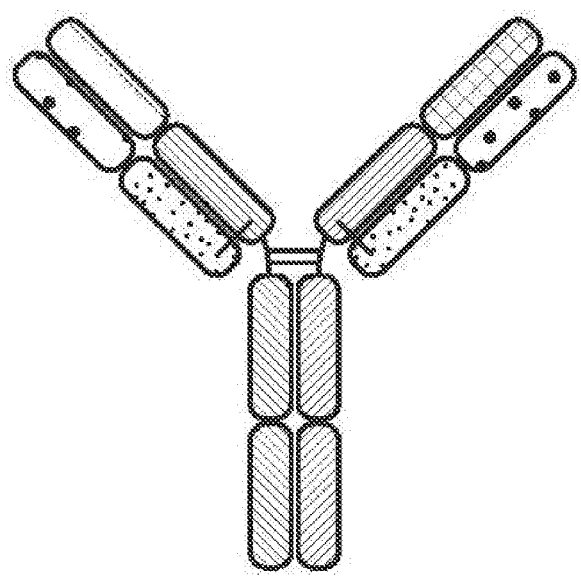
FIG. 1 is a representation of a multi-specific binding protein that contains an NKG2D-binding domain (right arm), a tumor associated antigen-binding domain (left arm) and an Fc domain or a portion thereof that binds to CD16.

The invention provides multi-specific binding proteins that bind a tumor-associated antigen on a cancer cell and the NKG2D receptor and CD16 receptor on natural killer cells to activate the natural killer cell, pharmaceutical compositions comprising such multi-specific binding proteins, and therapeutic methods using such multi-specific proteins and pharmaceutical compositions, including for the treatment of cancer. Various aspects of the invention are set forth below in sections; however, aspects of the invention described in one particular section are not to be limited to any particular section.

To facilitate an understanding of the present invention, a number of terms and phrases are defined below.

The terms "a" and "an" as used herein mean "one or more" and include the plural unless the context is inappropriate.

As used herein, the term "antigen-binding site" refers to the part of the immunoglobulin molecule that participates in antigen binding. In human antibodies, the antigen binding site is formed by amino acid residues of the N-terminal variable ("V") regions of the heavy ("H") and light ("L") chains. Three highly divergent stretches within the V regions of the heavy and light chains are referred to as "hypervariable regions" which are interposed between more conserved flanking stretches known as "framework regions," or "FRs". Thus the term "FR" refers to amino acid sequences which are naturally found between and adjacent to hypervariable regions in immunoglobulins. In a human antibody molecule, the three hypervariable regions of a light chain and the three hypervariable regions of a heavy chain are disposed relative to each other in three dimensional space to form an antigen-binding surface. The antigen-binding surface is complementary to the three-dimensional surface of a bound antigen, and the three hypervariable regions of each of the heavy and light chains are referred to as "complementarity-determining regions," or "CDRs." In certain animals, such as camels and cartilaginous fish, the antigen-binding site is formed by a single antibody chain providing a "single domain antibody." Antigen-binding sites can exist in an intact antibody, in an antigen-binding fragment of an antibody that retains the antigen-binding surface, or in a recombinant polypeptide such as an scFv, using a peptide linker to connect the heavy chain variable domain to the light chain variable domain in a single polypeptide.

The term "tumor associated antigen" as used herein means any antigen including but not limited to a protein, glycoprotein, ganglioside, carbohydrate, lipid that is associated with cancer. Such antigen can be expressed on malignant cells or in the tumor microenvironment such as on tumor-associated blood vessels, extracellular matrix, mesenchymal stroma, or immune infiltrates.

As used herein, the terms "subject" and "patient" refer to an organism to be treated by the methods and compositions described herein. Such organisms preferably include, but are not limited to, mammals (e.g., murines, simians, equines, bovines, porcines, canines, felines, and the like), and more preferably include humans.

As used herein, the term "effective amount" refers to the amount of a compound (e.g., a compound of the present invention) sufficient to effect beneficial or desired results. An effective amount can be administered in one or more administrations, applications or dosages and is not intended to be limited to a particular formulation or administration route. As used herein, the term "treating" includes any effect, e.g., lessening, reducing, modulating, ameliorating or eliminating, that results in the improvement of the condition, disease, disorder, and the like, or ameliorating a symptom thereof.

As used herein, the term "pharmaceutical composition" refers to the combination of an active agent with a carrier, inert or active, making the composition especially suitable for diagnostic or therapeutic use in vivo or ex vivo.

As used herein, the term "pharmaceutically acceptable carrier" refers to any of the standard pharmaceutical carriers, such as a phosphate buffered saline solution, water, emulsions (e.g., such as an oil/water or water/oil emulsions), and various types of wetting agents. The compositions also can include stabilizers and preservatives. For examples of carriers, stabilizers and adjuvants, see e.g., Martin, Remington's Pharmaceutical Sciences, 15th Ed., Mack Publ. Co., Easton, PA [1975].

As used herein, the term "pharmaceutically acceptable salt" refers to any pharmaceutically acceptable salt (e.g., acid or base) of a compound of the present invention which, upon administration to a subject, is capable of providing a compound of this invention or an active metabolite or residue thereof. As is known to those of skill in the art, "salts" of the compounds of the present invention may be derived from inorganic or organic acids and bases. Exemplary acids include, but are not limited to, hydrochloric, hydrobromic, sulfuric, nitric, perchloric, fumaric, maleic, phosphoric, glycolic, lactic, salicylic, succinic, toluene-p-sulfonic, tartaric, acetic, citric, methanesulfonic, ethane-sulfonic, formic, benzoic, malonic, naphthalene-2-sulfonic, benzenesulfonic acid, and the like. Other acids, such as oxalic, while not in themselves pharmaceutically acceptable, may be employed in the preparation of salts useful as intermediates in obtaining the compounds of the invention and their pharmaceutically acceptable acid addition salts.

Exemplary bases include, but are not limited to, alkali metal (e.g., sodium) hydroxides, alkaline earth metal (e.g., magnesium) hydroxides, ammonia, and compounds of formula $NW_4^+$, wherein W is $C_{1-4}$ alkyl, and the like.

Exemplary salts include, but are not limited to: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, flucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, palmoate, pectinate, persulfate, phenylpropionate, picrate, pivalate, propionate, succinate, tartrate, thiocyanate, tosylate, undecanoate, and the like. Other examples of salts include anions of the compounds of the present invention compounded with a suitable cation such as $Na^+$, $NH_4^+$, and $NW_4^+$ (wherein W is a $C_{1-4}$ alkyl group), and the like.

For therapeutic use, salts of the compounds of the present invention are contemplated as being pharmaceutically acceptable. However, salts of acids and bases that are non-pharmaceutically acceptable may also find use, for example, in the preparation or purification of a pharmaceutically acceptable compound.

Throughout the description, where compositions are described as having, including, or comprising specific components, or where processes and methods are described as having, including, or comprising specific steps, it is contemplated that, additionally, there are compositions of the present invention that consist essentially of, or consist of, the recited components, and that there are processes and methods according to the present invention that consist essentially of, or consist of, the recited processing steps.

As a general matter, compositions specifying a percentage are by weight unless otherwise specified. Further, if a variable is not accompanied by a definition, then the previous definition of the variable controls.

I. Proteins

The invention provides multi-specific binding proteins that bind a tumor-associated antigen on a cancer cell and the NKG2D receptor and CD16 receptor on natural killer cells to activate the natural killer cell. The multi-specific binding proteins are useful in the pharmaceutical compositions and therapeutic methods described herein. Binding of the multi-specific binding protein to the NKG2D receptor and CD16 receptor on natural killer cell enhances the activity of the natural killer cell toward destruction of a cancer cell. Binding of the multi-specific binding protein to a tumor-associated antigen on a cancer cell brings the cancer cell into proximity to the natural killer cell, which facilitates direct and indirect destruction of the cancer cell by the natural killer cell. Further description of exemplary multi-specific binding proteins are provided below.

The first component of the multi-specific binding proteins binds to NKG2D receptor-expressing cells, which can include but are not limited to NK cells, γδ T cells and $CD8^+$ αβ T cells. In some embodiments, upon NKG2D-binding, the multi-specific binding proteins can block natural ligands, such as ULBP6 and MICA, from binding to NKG2D.

The second component of the multi-specific binding proteins binds to one or more tumor-associated antigens, which can include, but are not limited to HER2, CD20, CD33, BCMA, EpCAM, CD2, CD19, CD30, CD38, CD40, CD52, CD70, EGFR/ERBB1, IGF1R, HER3/ERBB3, HER4/ERBB4, MUC1, cMET, SLAMF7, PSCA, MICA, MICB, TRAILR1, TRAILR2, MAGE-A3, B7.1, B7.2, CTLA4, and PD-L1.

The third component for the multi-specific binding proteins binds to cells expressing CD16, a Fc receptor on the surface of leukocytes including natural killer cells, macrophages, neutrophils, eosinophils, mast cells, and follicular dendritic cells.

The multi-specific binding proteins can take several formats as shown in but not limited to the examples below. One format is a heterodimeric, multi-specific antibody that includes a first immunoglobulin heavy chain, a second immunoglobulin heavy chain and an immunoglobulin light chain. The first immunoglobulin heavy chain includes a first Fc (hinge-CH2-CH3) domain, a first variable heavy chain domain and an optional first CH1 heavy chain domain. The immunoglobulin light chain includes a variable light chain domain and a constant light chain domain; together with the first immunoglobulin heavy chain, the immunoglobulin light chain forms an antigen-binding site that binds NKG2D. The second immunoglobulin heavy chain comprises a second Fc (hinge-CH2-CH3) domain, a second variable heavy chain domain and a second optional CH1 heavy chain domain that may pair with an immunoglobulin light chain identical to the one that pairs with the first immunoglobulin heavy chain, except that when immunoglobulin light chain is paired with the second immunoglobulin heavy chain, the resulting antigen binding site binds to a tumor antigen. The first Fc domain and second Fc domain together are able to bind to CD16 (FIG. 1).

Figure 2:
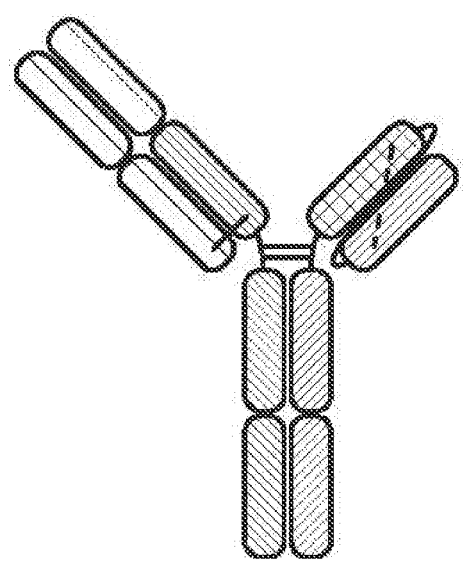
FIG. 2 is a representation of a multi-specific binding protein that contains an NKG2D-binding domain in a scFv format (right arm), a tumor associated antigen-binding domain (left arm) and an Fc domain or a portion thereof that binds to CD16.
Figure 3:
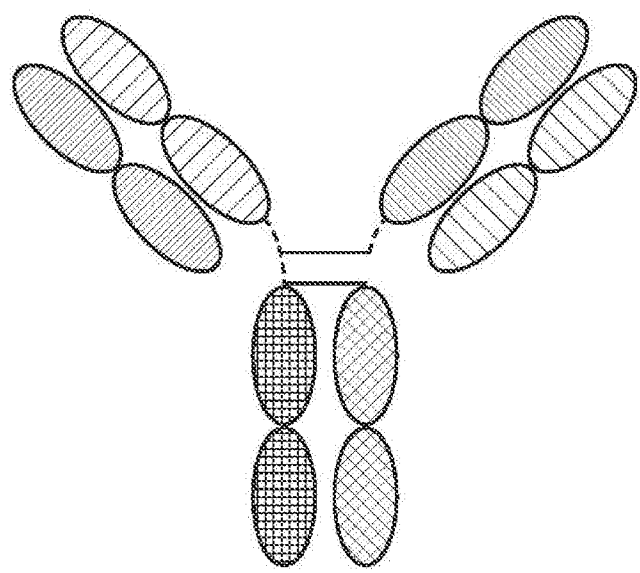
FIG. 3 is a representation of a TriNKET in the Triomab form, which is a trifunctional, bispecific antibody that maintains an IgG-like shape. This chimera consists of two half antibodies, each with one light and one heavy chain, that originate from two parental antibodies. Triomab form is an heterodimeric construct containing ½ of rat antibody and ½ of mouse antibody.
Figure 4:
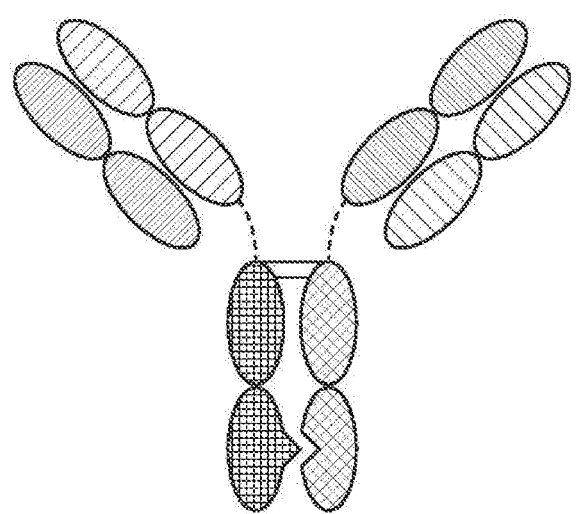
FIG. 4 is a representation of a TriNKET in the KiH Common Light Chain (LC) form, which involves the knobs-into-holes (KIHs) technology. KiH is a heterodimer containing 2 Fabs binding to target 1 and 2, and an $F_C$ stabilized by heterodimerization mutations. TriNKET in the KiH format may be an heterodimeric construct with 2 fabs binding to target 1 and target 2, containing 2 different heavy chains and a common light chain that pairs with both HC.
Figure 5:
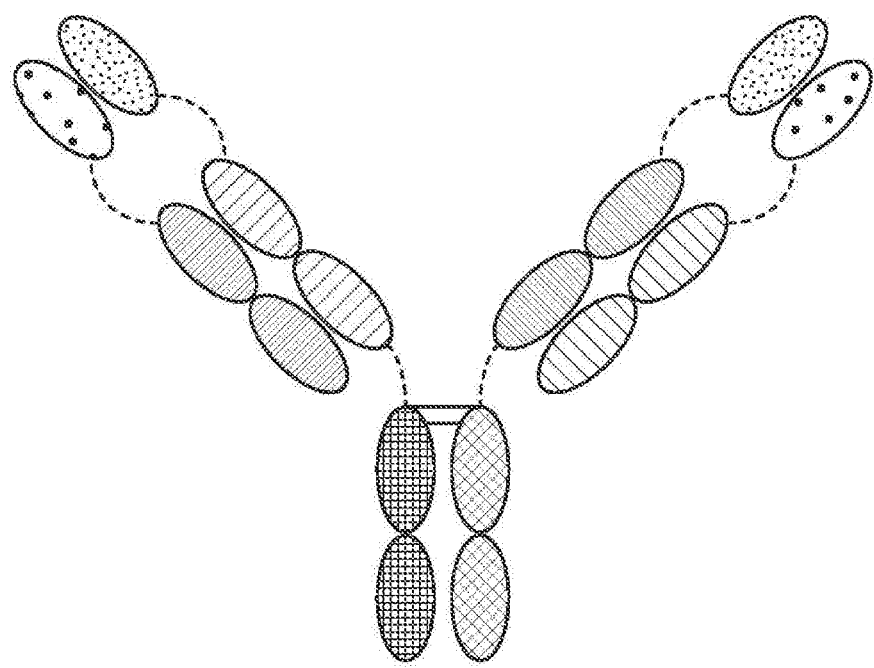
FIG. 5 is a representation of a TriNKET in the dual-variable domain immunoglobulin (DVD-Ig™) form, which combines the target binding domains of two monoclonal antibodies via flexible naturally occurring linkers, and yields a tetravalent IgG-like molecule. DVD-Ig™ is an homodimeric construct where variable domain targeting antigen 2 is fused to the N terminus of variable domain of Fab targeting antigen 1 Construct contains normal Fc.
Figure 6:
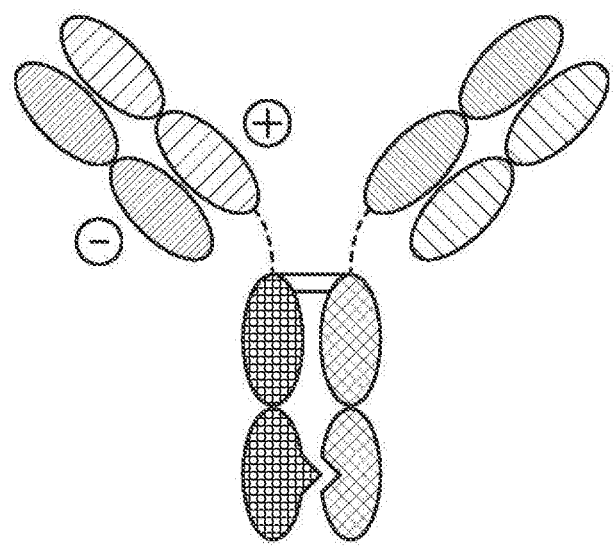
FIG. 6 is a representation of a TriNKET in the Orthogonal Fab interface (Ortho-Fab) form, which is an heterodimeric construct that contains 2 Fabs binding to target1 and target2 fused to Fc. LC-HC pairing is ensured by orthogonal interface. Heterodimerization is ensured by mutations in the $F_C$.
Figure 7:
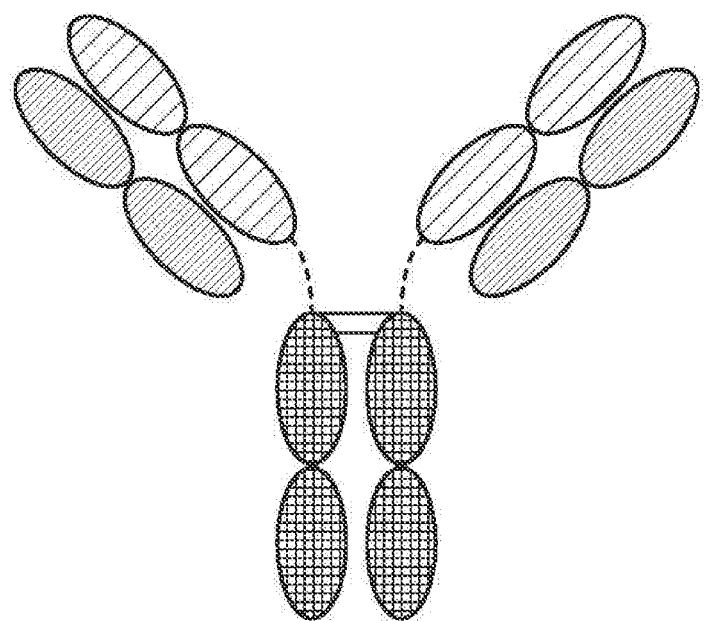
FIG. 7 is a representation of a TrinKET in the 2 in 1Ig format.
Figure 8:
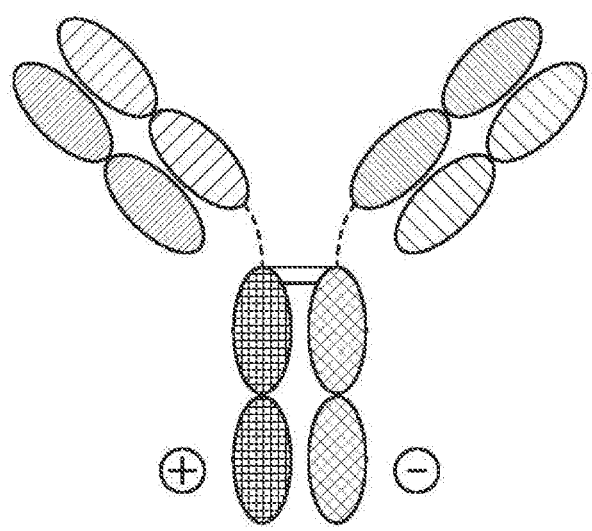
FIG. 8 is a representation of a TriNKET in the ES form, which is an heterodimeric construct containing 2 different Fabs binding to target 1 and target 2 fused to the $F_C$. Heterodimerization is ensured by electrostatic steering mutations in the Fc.
Figure 9:
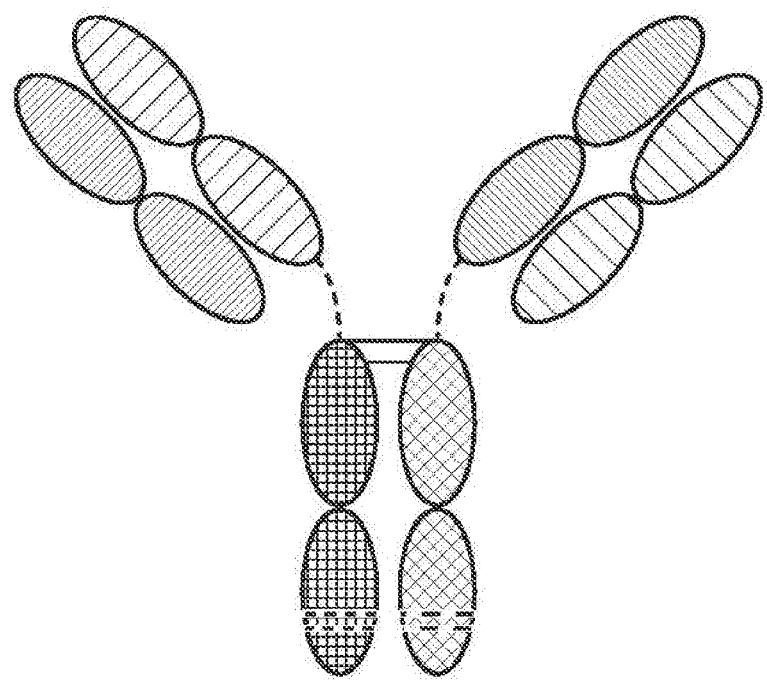
FIG. 9 is a representation of a TriNKET in the Fab Arm Exchange form: antibodies that exchange Fab arms by swapping a heavy chain and attached light chain (half-molecule) with a heavy-light chain pair from another molecule, resulting in bispecific antibodies. Fab Arm Exchange form (cFae) is a heterodimer containing 2 Fabs binding to target 1 and 2, and an $F_C$ stabilized by heterodimerization mutations.
Figure 10:
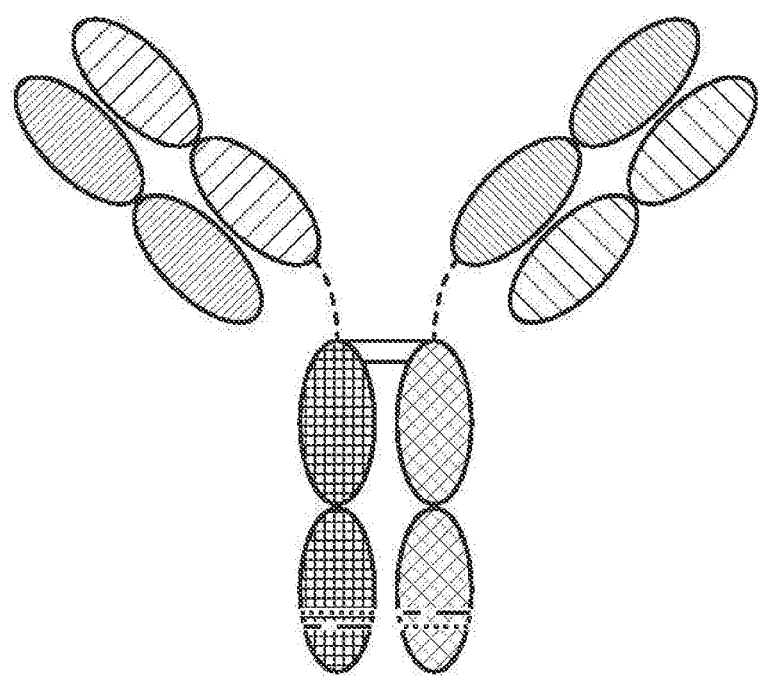
FIG. 10 is a representation of a TriNKET in the SEED Body form, which is an heterodimer containing 2 Fabs binding to target 1 and 2, and an $F_C$ stabilized by heterodimerization mutations.
Figure 11:
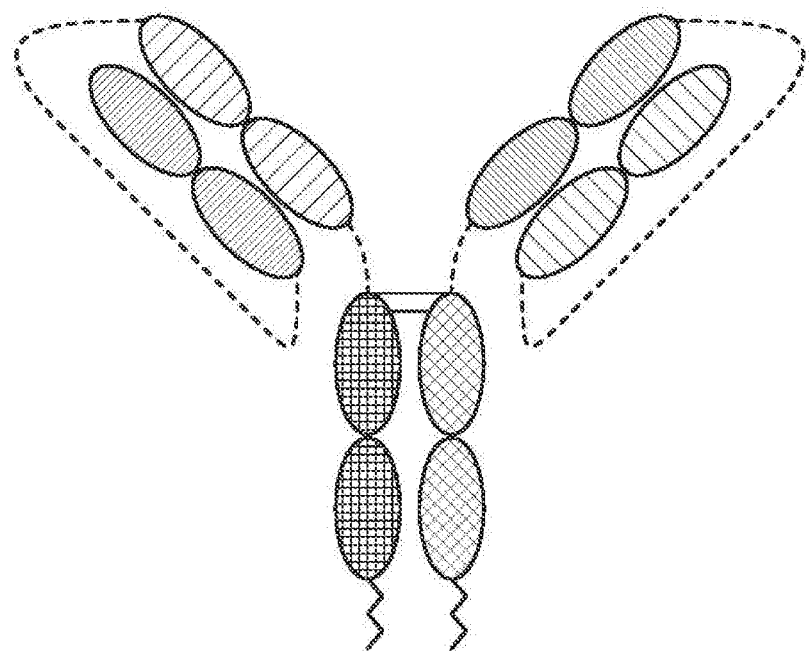
FIG. 11 is a representation of a TriNKET in the LuZ-Y form, in which leucine zipper is used to induce heterodimerization of two different HCs. LuZ-Y form is a heterodimer containing 2 different scFabs binding to target 1 and 2, fused to $F_C$. Heterodimerization is ensured through leucine zipper motifs fused to C-terminus of $F_C$.
Figure 12:
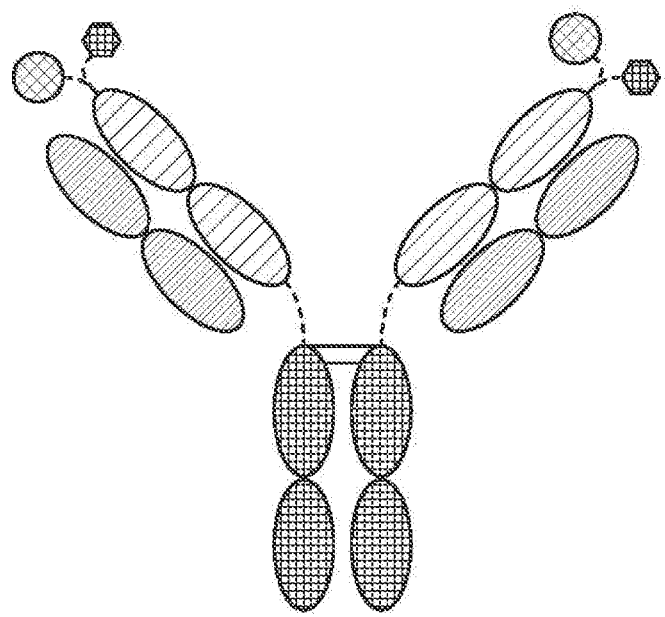
FIG. 12 is a representation of a TriNKET in the Cov-X-Body form.

Another exemplary format involves a heterodimeric, multi-specific antibody which includes a first immunoglobulin heavy chain, an immunoglobulin light chain and a second immunoglobulin heavy chain. The first immunoglobulin heavy chain includes a first Fc (hinge-CH2-CH3) domain fused via either a linker or an antibody hinge to a single chain Fv (scFv) that binds NKG2D. A variety of linkers could be used for linking the scFv to the first Fc domain or within the scFv itself. In addition, the scFv can incorporate mutations that enable the formation of a disulfide bond to stabilize the overall scFv structure. The scFv can also incorporate mutations to modify the isoelectric point of the overall first immunoglobulin heavy chain and/or to enable more facile downstream purification. The second immunoglobulin heavy chain includes a second Fc (hinge-CH2-CH3) domain and a second variable heavy chain domain and a second optional CH1 heavy chain domain. The immunoglobulin light chain includes a variable light chain domain and a constant light chain domain. The second immunoglobulin heavy chain pairs with the immunoglobulin light chain and binds to a tumor antigen. The first Fc domain and the second Fc domain together are able to bind to CD16 (FIG. 2).

An alternative format of the heterodimeric multi-specific proteins includes a first immunoglobulin heavy chain, a second immunoglobulin heavy chain, a first immunoglobulin light chain and a second immunoglobulin light chain. The first immunoglobulin heavy chain includes a first Fc (hinge-CH2-CH3) domain, a first variable heavy chain domain and an optional first CH1 heavy chain domain. The first immunoglobulin light chain includes a variable light chain domain and a constant light chain domain. Together with the first immunoglobulin heavy chain, the first immunoglobulin light chain forms an antigen-binding site that binds a tumor antigen. The second immunoglobulin heavy chain comprises a second Fc (hinge-CH2-CH3) domain, a second variable heavy chain domain and a second optional CH1 heavy chain domain. The second immunoglobulin light chain includes a variable light chain domain and a constant light chain domain. Together with the second immunoglobulin heavy chain, the immunoglobulin light chain forms an antigen-binding site that binds to the same tumor antigen. The second immunoglobulin heavy chain may pair with an immunoglobulin light chain, which may be identical to the immunoglobulin light chain that pairs with the first immunoglobulin heavy chain, except that when immunoglobulin light chain is paired with the second immunoglobulin heavy chain, the resulting antigen binding site is a second antigen-binding site that binds to a tumor antigen. In certain embodiments, the first Fc domain and second Fc domain together are able to bind to CD16 (FIG. 1).

One or more additional binding motifs may be fused to the C-terminus of the constant region CH3 domain, optionally via a linker sequence. In certain embodiments, the antigen-binding site could be a single-chain or disulfide-stabilized variable region (ScFv) or could form a tetravalent or trivalent molecule.

In some embodiments, the multi-specific binding protein is in the Triomab form, which is a trifunctional, bispecific antibody that maintains an IgG-like shape. This chimera consists of two half antibodies, each with one light and one heavy chain, that originate from two parental antibodies.

In some embodiments, the multi-specific binding protein is in the KiH Common Light Chain (LC) form, which involves the knobs-into-holes (KIHs) technology. The KIH involves engineering $C_H3$ domains to create either a "knob" or a "hole" in each heavy chain to promote heterodimerization. The concept behind the "Knobs-into-Holes (KiH)" Fc technology was to introduce a "knob" in one CH3 domain (CH3A) by substitution of a small residue with a bulky one (i.e., $T366W_{CH3A}$ in EU numbering). To accommodate the "knob," a complementary "hole" surface was created on the other CH3 domain (CH3B) by replacing the closest neighboring residues to the knob with smaller ones (i.e., T366S/L368A/$Y407V_{CH3B}$). The "hole" mutation was optimized by structured-guided phage library screening (Atwell S, Ridgway J B, Wells J A, Carter P. Stable heterodimers from remodeling the domain interface of a homodimer using a phage display library. J Mol Biol (1997) 270(1):26-35). X-ray crystal structures of KiH Fc variants (Elliott J M, Ultsch M, Lee J, Tong R, Takeda K, Spiess C, et al., Antiparallel conformation of knob and hole aglycosylated half-antibody homodimers is mediated by a CH2-CH3 hydrophobic interaction. J Mol Biol (2014) 426(9):1947-57; Mimoto F, Kadono S, Katada H, Igawa T, Kamikawa T, Hattori K. Crystal structure of a novel asymmetrically engineered Fc variant with improved affinity for FcgammaRs. Mol Immunol (2014) 58(1):132-8) demonstrated that heterodimerization is thermodynamically favored by hydrophobic interactions driven by steric complementarity at the inter-CH3 domain core interface, whereas the knob-knob and the hole-hole interfaces do not favor homodimerization owing to steric hindrance and disruption of the favorable interactions, respectively.

In some embodiments, the multi-specific binding protein is in the dual-variable domain immunoglobulin (DVD-Ig™) form, which combines the target binding domains of two monoclonal antibodies via flexible naturally occurring linkers, and yields a tetravalent IgG—like molecule.

In some embodiments, the multi-specific binding protein is in the Orthogonal Fab interface (Ortho-Fab) form. In ortho-Fab IgG approach (Lewis S M, Wu X, Pustilnik A, Sereno A, Huang F, Rick H L, et al. Generation of bispecific IgG antibodies by structure-based design of an orthogonal Fab interface. Nat. Biotechnol. (2014) 32(2):191-8), structure-based regional design introduces complementary mutations at the LC and $H_{VH-CH1}$ interface in only one Fab, without any changes being made to the other Fab.

Figure 13A:
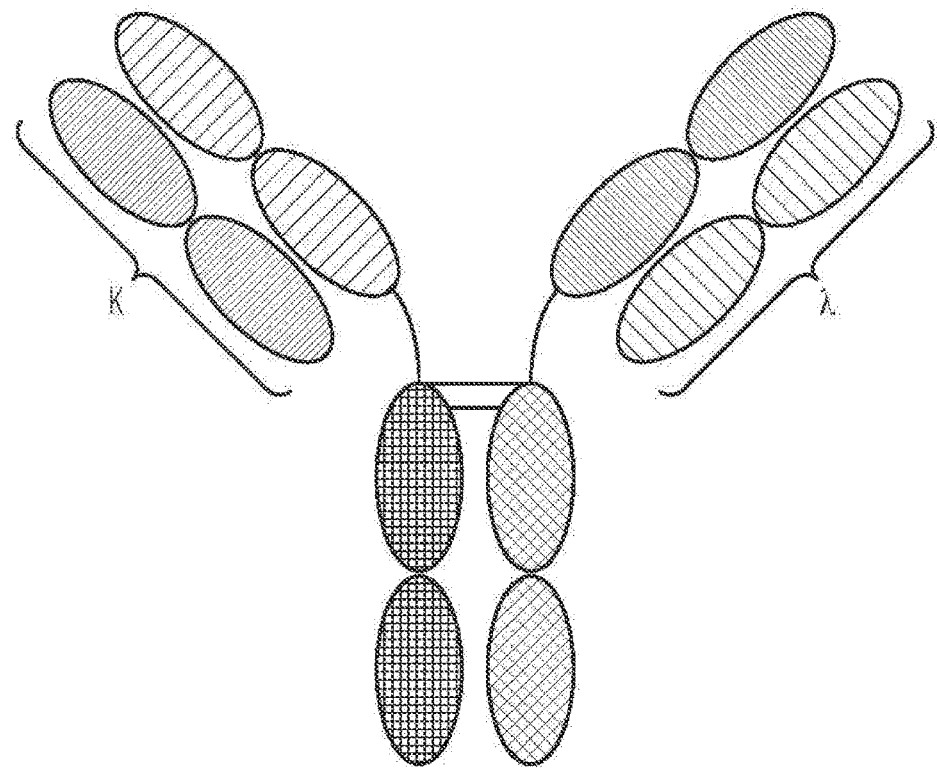
FIGS. 13A-13B are representations of TriNKETs in the κλ-Body forms, which are an heterodimeric constructs with 2 different Fabs fused to Fc stabilized by heterodimerization mutations: Fab1 targeting antigen 1 contains kappa LC, while second Fab targeting antigen 2 contains lambda LC.
Figure 13B:
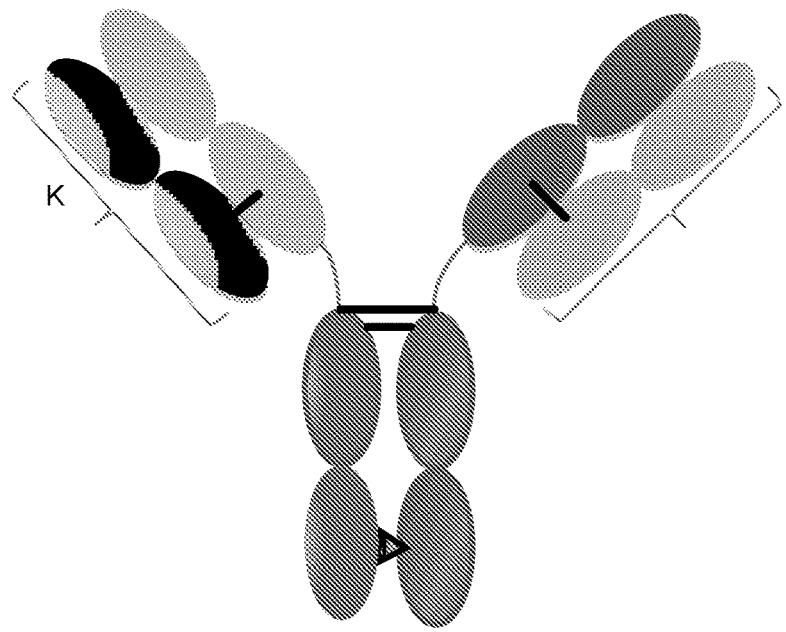

In some embodiments, the multi-specific binding protein is in the 2 in 1Ig format. In some embodiments, the multi-specific binding protein is in the ES form, which is an heterodimeric construct containing 2 different Fabs binding to target 1 and target 2 fused to the $F_C$. Heterodimerization is ensured by electrostatic steering mutations in the Fc. In some embodiments, the multi-specific binding protein is in the κλ-Body form, which is an heterodimeric constructs with 2 different Fabs fused to Fc stabilized by heterodimerization mutations: Fab 1 targeting antigen 1 contains kappa LC, while second Fab targeting antigen 2 contains lambda LC. FIG. 13A is an exemplary representation of one form of a κλ-Body; FIG. 13B is an exemplary representation of another κλ-Body.

In some embodiments, the multi-specific binding protein is in Fab Arm Exchange form (antibodies that exchange Fab arms by swapping a heavy chain and attached light chain (half-molecule) with a heavy-light chain pair from another molecule, which results in bispecific antibodies). In some embodiments, the multi-specific binding protein is in the SEED Body form (The strand-exchange engineered domain (SEED) platform was designed to generate asymmetric and bispecific antibody-like molecules, a capability that expands therapeutic applications of natural antibodies. This protein engineered platform is based on exchanging structurally related sequences of immunoglobulin within the conserved CH3 domains. The SEED design allows efficient generation of AG/GA heterodimers, while disfavoring homodimerization of AG and GA SEED CH3 domains. (Muda M. et al., Protein Eng. Des. Sel. (2011, 24(5):447-54)). In some embodiments, the multi-specific binding protein is in the LuZ-Y form, in which leucine zipper is used to induce heterodimerization of two different HCs. (Wranik, B J. et al., J. Biol. Chem. (2012), 287:43331-9).

In some embodiments, the multi-specific binding protein is in the Cov-X-Body form (In bispecific CovX-Bodies, two different peptides are joined together using a branched azetidinone linker and fused to the scaffold antibody under mild conditions in a site-specific manner. Whereas the pharmacophores are responsible for functional activities, the antibody scaffold imparts long half-life and Ig-like distribution. The pharmacophores can be chemically optimized or replaced with other pharmacophores to generate optimized or unique bispecific antibodies. (Doppalapudi V R et al., PNAS (2010), 107(52); 22611-22616).

In some embodiments, the multi-specific binding protein is in an Oasc-Fab heterodimeric form that includes Fab binding to target 1 and scFab binding to target 2 fused to Fc. Heterodimerization is ensured by mutations in the $F_C$.

In some embodiments, the multi-specific binding protein is in a DuetMab form, which is an heterodimeric construct containing 2 different Fabs binding to antigen 1 and 2 and $F_C$ stabilized by heterodimerization mutations. Fab 1 and 2 contain differential S-S bridges that ensure correct LC and HC pairing.

In some embodiments, the multi-specific binding protein is in a CrossmAb form, which is an heterodimeric construct with 2 different Fabs binding to Target 1 and 2 fused to Fc stabilized by heterodimerization. CL and CH1 domains and VH and VL domains are switched, e.g., CH1 is fused in-line with VL, while CL is fused in-line with VH.

In some embodiments, the multi-specific binding protein is in a Fit-Ig form, which is an homodimeric constructs where Fab binding to antigen 2 is fused to the N terminus of HC of Fab that binds to antigen 1. The construct contains wild-type Fc.

Table 1 lists peptide sequences of heavy chain variable domains and light chain variable domains that, in combination, can bind to NKG2D. Unless otherwise indicated, the CDR sequences provided in Table 1 are determined under Kabat.

TABLE 1

| Clones | Heavy chain variable region amino acid sequence | Light chain variable region amino acid sequence |
| --- | --- | --- |
| ADI-27705 | QVQLQQWGAGLLKPSETLSLTCAV YGGSFSGYYWSWIRQPPGKGLEWI GEIDHSGSTNYNPSLKSRVTISVDT SKNQFSLKLSSVTAADTAVYYCAR ARGPWSFDPWGQGTLVTSS (SEQ ID NO: 1) | DIQMTQSPSTLSASVGDRVTITC RASQSISSWLAWYQQKPGKAP KLLIYKASSLESGVPSRFSGSGS GTEFTLTISSLQPDDFATYYCQQ YNSYPITFGGGTKVEIK (SEQ ID NO: 2) |
| ADI-27724 | QVQLQQWGAGLLKPSETLSLTCAV YGGSFSGYYWSWIRQPPGKGLEWI GEIDHSGSTNYNPSLKSRVTISVDT SKNQFSLKLSSVTAADTAVYYCAR ARGPWSFDPWGQGTLVTSS (SEQ ID NO: 3) | EIVLTQSPGTLSLSPGERATLSC RASQSVSSSYLAWYQQKPGQA PRLLIYGASSRATGIPDRFSGSGS GTDFTLTISRLEPEDFAVYYCQQ YGSSPITFGGGTKVEIK (SEQ ID NO: 4) |
| ADI-27740 (A40) | QVQLQQWGAGLLKPSETLSLTCAV YGGSFSGYYWSWIRQPPGKGLEWI GEIDHSGSTNYNPSLKSRVTISVDT SKNQFSLKLSSVTAADTAVYYCAR ARGPWSFDPWGQGTLVTSS (SEQ ID NO: 5) | DIQMTQSPSTLSASVGDRVTITC RASQSIGSWLAWYQQKPGKAP KLLIYKASSLESGVPSRFSGSGS GTEFTLTISSLQPDDFATYYCQQ YHSFYTFGGGTKVEIK (SEQ ID NO: 6) |
| ADI-27741 | QVQLQQWGAGLLKPSETLSLTCAV YGGSFSGYYWSWIRQPPGKGLEWI GEIDHSGSTNYNPSLKSRVTISVDT SKNQFSLKLSSVTAADTAVYYCAR ARGPWSFDPWGQGTLVTSS (SEQ ID NO: 7) | DIQMTQSPSTLSASVGDRVTITC RASQSIGSWLAWYQQKPGKAP KLLIYKASSLESGVPSRFSGSGS GTEFTLTISSLQPDDFATYYCQQ SNSYYTFGGGTKVEIK (SEQ ID NO: 8) |

TABLE 1-continued

| Clones | Heavy chain variable region amino acid sequence | Light chain variable region amino acid sequence |
|---|---|---|
| ADI-27743 | QVQLQQWGAGLLKPSETLSLTCAV YGGSFSGYYWSWIRQPPKGLEWI GEIDHSGSTNYNPSLKSRVTISVDT SKNQFSLKLSSVTAADTAVYYCAR ARGPWSFDPWGQGTLVTVSS (SEQ ID NO: 9) | DIQMTQSPSTLSASVGDRVTITC RASQSISSWLAWYQQKPGKAP KLLIYKASSLESGVPSRFSGSGS GTEFTLTISSLQPDDFATYYCQQ YNSYPTFGGGTKVEIK (SEQ ID NO: 10) |
| ADI-28153 | QVQLQQWGAGLLKPSETLSLTCAV YGGSFSGYYWSWIRQPPKGLEWI GEIDHSGSTNYNPSLKSRVTISVDT SKNQFSLKLSSVTAADTAVYYCAR ARGPWGFDPWGQGTLVTVSS (SEQ ID NO: 11) | ELQMTQSPSSLSASVGDRVTITC RTSQSISSYLNWYQQKPGQPPK LLIYWASTRESGVPDRFSGSGSG TDFTLTISSLQPEDSATYYCQQS YDIPYTFGQGTKLEIK (SEQ ID NO: 12) |
| ADI-28226 (C26) | QVQLQQWGAGLLKPSETLSLTCAV YGGSFSGYYWSWIRQPPKGLEWI GEIDHSGSTNYNPSLKSRVTISVDT SKNQFSLKLSSVTAADTAVYYCAR ARGPWSFDPWGQGTLVTVSS (SEQ ID NO: 13) | DIQMTQSPSTLSASVGDRVTITC RASQSISSWLAWYQQKPGKAP KLLIYKASSLESGVPSRFSGSGS GTEFTLTISSLQPDDFATYYCQQ YGSFPITFGGGTKVEIK (SEQ ID NO: 14) |
| ADI-28154 | QVQLQQWGAGLLKPSETLSLTCAV YGGSFSGYYWSWIRQPPKGLEWI GEIDHSGSTNYNPSLKSRVTISVDT SKNQFSLKLSSVTAADTAVYYCAR ARGPWSFDPWGQGTLVTVSS (SEQ ID NO: 15) | DIQMTQSPSTLSASVGDRVTITC RASQSISSWLAWYQQKPGKAP KLLIYKASSLESGVPSRFSGSGS GTDFTLTISSLQPDDFATYYCQQ SKEVPWTFGQGTKVEIK (SEQ ID NO: 16) |
| ADI-29399 | QVQLQQWGAGLLKPSETLSLTCAV YGGSFSGYYWSWIRQPPKGLEWI GEIDHSGSTNYNPSLKSRVTISVDT SKNQFSLKLSSVTAADTAVYYCAR ARGPWSFDPWGQGTLVTVSS (SEQ ID NO: 17) | DIQMTQSPSTLSASVGDRVTITC RASQSISSWLAWYQQKPGKAP KLLIYKASSLESGVPSRFSGSGS GTEFTLTISSLQPDDFATYYCQQ YNSFPTFGGGTKVEIK (SEQ ID NO: 18) |
| ADI-29401 | QVQLQQWGAGLLKPSETLSLTCAV YGGSFSGYYWSWIRQPPKGLEWI GEIDHSGSTNYNPSLKSRVTISVDT SKNQFSLKLSSVTAADTAVYYCAR ARGPWSFDPWGQGTLVTVSS (SEQ ID NO: 19) | DIQMTQSPSTLSASVGDRVTITC RASQSIGSWLAWYQQKPGKAP KLLIYKASSLESGVPSRFSGSGS GTEFTLTISSLQPDDFATYYCQQ YDIYPTFGGGTKVEIK (SEQ ID NO: 20) |
| ADI-29403 | QVQLQQWGAGLLKPSETLSLTCAV YGGSFSGYYWSWIRQPPKGLEWI GEIDHSGSTNYNPSLKSRVTISVDT SKNQFSLKLSSVTAADTAVYYCAR ARGPWSFDPWGQGTLVTVSS (SEQ ID NO: 21) | DIQMTQSPSTLSASVGDRVTITC RASQSISSWLAWYQQKPGKAP KLLIYKASSLESGVPSRFSGSGS GTEFTLTISSLQPDDFATYYCQQ YDSYPTFGGGTKVEIK (SEQ ID NO: 22) |
| ADI-29405 | QVQLQQWGAGLLKPSETLSLTCAV YGGSFSGYYWSWIRQPPKGLEWI GEIDHSGSTNYNPSLKSRVTISVDT SKNQFSLKLSSVTAADTAVYYCAR ARGPWSFDPWGQGTLVTVSS (SEQ ID NO: 23) | DIQMTQSPSTLSASVGDRVTITC RASQSISSWLAWYQQKPGKAP KLLIYKASSLESGVPSRFSGSGS GTEFTLTISSLQPDDFATYYCQQ YGSFPTFGGGTKVEIK (SEQ ID NO: 24) |
| ADI-29407 | QVQLQQWGAGLLKPSETLSLTCAV YGGSFSGYYWSWIRQPPKGLEWI GEIDHSGSTNYNPSLKSRVTISVDT SKNQFSLKLSSVTAADTAVYYCAR ARGPWSFDPWGQGTLVTVSS (SEQ ID NO: 25) | DIQMTQSPSTLSASVGDRVTITC RASQSISSWLAWYQQKPGKAP KLLIYKASSLESGVPSRFSGSGS GTEFTLTISSLQPDDFATYYCQQ YQSFPTFGGGTKVEIK (SEQ ID NO: 26) |
| ADI-29419 | QVQLQQWGAGLLKPSETLSLTCAV YGGSFSGYYWSWIRQPPKGLEWI GEIDHSGSTNYNPSLKSRVTISVDT SKNQFSLKLSSVTAADTAVYYCAR ARGPWSFDPWGQGTLVTVSS (SEQ ID NO: 27) | DIQMTQSPSTLSASVGDRVTITC RASQSISSWLAWYQQKPGKAP KLLIYKASSLESGVPSRFSGSGS GTEFTLTISSLQPDDFATYYCQQ YSSFSTFGGGTKVEIK (SEQ ID NO: 28) |
| ADI-29421 | QVQLQQWGAGLLKPSETLSLTCAV YGGSFSGYYWSWIRQPPKGLEWI GEIDHSGSTNYNPSLKSRVTISVDT SKNQFSLKLSSVTAADTAVYYCAR ARGPWSFDPWGQGTLVTVSS (SEQ ID NO: 29) | DIQMTQSPSTLSASVGDRVTITC RASQSISSWLAWYQQKPGKAP KLLIYKASSLESGVPSRFSGSGS GTEFTLTISSLQPDDFATYYCQQ YESYSTFGGGTKVEIK (SEQ ID NO: 30) |

TABLE 1-continued

| Clones | Heavy chain variable region amino acid sequence | Light chain variable region amino acid sequence |
| --- | --- | --- |
| ADI-29424 | QVQLQQWGAGLLKPSETLSLTCAV YGGSFSGYYWSWIRQPPGKGLEWI GEIDHSGSTNYNPSLKSRVTISVDT SKNQFSLKLSSVTAADTAVYYCAR ARGPWSFDPWGQGTLVTVSS (SEQ ID NO: 31) | DIQMTQSPSTLSASVGDRVTITC RASQSISSWLAWYQQKPGKAP KLLIYKASSLESGVPSRFSGSGS GTEFTLTISSLQPDDFATYYCQQ YDSFITFGGGTKVEIK (SEQ ID NO: 32) |
| ADI-29425 | QVQLQQWGAGLLKPSETLSLTCAV YGGSFSGYYWSWIRQPPGKGLEWI GEIDHSGSTNYNPSLKSRVTISVDT SKNQFSLKLSSVTAADTAVYYCAR ARGPWSFDPWGQGTLVTVSS (SEQ ID NO: 33) | DIQMTQSPSTLSASVGDRVTITC RASQSISSWLAWYQQKPGKAP KLLIYKASSLESGVPSRFSGSGS GTEFTLTISSLQPDDFATYYCQQ YQSYPTFGGGTKVEIK (SEQ ID NO: 34) |
| ADI-29426 | QVQLQQWGAGLLKPSETLSLTCAV YGGSFSGYYWSWIRQPPGKGLEWI GEIDHSGSTNYNPSLKSRVTISVDT SKNQFSLKLSSVTAADTAVYYCAR ARGPWSFDPWGQGTLVTVSS (SEQ ID NO: 35) | DIQMTQSPSTLSASVGDRVTITC RASQSIGSWLAWYQQKPGKAP KLLIYKASSLESGVPSRFSGSGS GTEFTLTISSLQPDDFATYYCQQ YHSFPTFGGGTKVEIK (SEQ ID NO: 36) |
| ADI-29429 | QVQLQQWGAGLLKPSETLSLTCAV YGGSFSGYYWSWIRQPPGKGLEWI GEIDHSGSTNYNPSLKSRVTISVDT SKNQFSLKLSSVTAADTAVYYCAR ARGPWSFDPWGQGTLVTVSS (SEQ ID NO: 37) | DIQMTQSPSTLSASVGDRVTITC RASQSIGSWLAWYQQKPGKAP KLLIYKASSLESGVPSRFSGSGS GTEFTLTISSLQPDDFATYYCQQ YELYSYTFGGGTKVEIK (SEQ ID NO: 38) |
| ADI-29447 (F47) | QVQLQQWGAGLLKPSETLSLTCAV YGGSFSGYYWSWIRQPPGKGLEWI GEIDHSGSTNYNPSLKSRVTISVDT SKNQFSLKLSSVTAADTAVYYCAR ARGPWSFDPWGQGTLVTVSS (SEQ ID NO: 39) | DIQMTQSPSTLSASVGDRVTITC RASQSISSWLAWYQQKPGKAP KLLIYKASSLESGVPSRFSGSGS GTEFTLTISSLQPDDFATYYCQQ YDTFITFGGGTKVEIK (SEQ ID NO: 40) |
| ADI-27727 | QVQLVQSGAEVKKPGSSVKVSCK ASGGTFSSYAISWVRQAPGQGLEW MGGIIPIFGTANYAQKFQGRVTITA DESTSTAYMELSSLRSEDTAVYYC ARGDSSIRHAYYYYGMDVWGQGT TVTVSS (SEQ ID NO: 41) | DIVMTQSPDSLAVSLGERATINC KSSQSVLYSSNNKNYLAWYQQ KPGQPPKLLIYWASTRESGVPD RFSGSGSGTDFTLTISSLQAEDV AVYYCQQYYSTPITFGGGTKVE IK (SEQ ID NO: 42) |
| ADI-29443 (F43) | QLQLQESGPGLVKPSETLSLTCTVS GGSISSSSYYWGWIRQPPGKGLEWI GSIYYSGSTYYNPSLKSRVTISVDT SKNQFSLKLSSVTAADTAVYYCAR GSDRFHPYFDYWGQGTLVTVSS (SEQ ID NO: 43) | EIVLTQSPATLSLSPGERATLSC RASQSVSRYLAWYQQKPGQAP RLLIYDASNRATGIPARFSGSGS GTDFTLTISSLEPEDFAVYYCQQ FDTWPPTFGGGTKVEIK (SEQ ID NO: 44) |
| ADI-27744 (A44) | EVQLLESGGGLVQPGGSLRLSCAA SGFTFSSYAMSWVRQAPGKGLEW VSAISGSGGSTYYADSVKGRFTISR DNSKNTLYLQMNSLRAEDTAVYY CAKDGGYYDSGAGDYWGQGTLV TVSS (SEQ ID NO: 45) CDR1 non-Kabat (SEQ ID NO: 51) - FTFSSYAMS or CDR1 (SEQ ID NO: 90) - SYAMS CDR2 (SEQ ID NO: 52) - AISGSGGSTYYADSVKG CDR3 non-Kabat (SEQ ID NO: 53) - AKDGGYYDSGAGDY or CDR3 (SEQ ID NO: 91) - DGGYYDSGAGDY | DIQMTQSPSSVSASVGDRVTITC RASQGIDSWLAWYQQKPGKAP KLLIYAASSLQSGVPSRFSGSGS GTDFTLTISSLQPEDFATYYCQQ GVSYPRTFGGGTKVEIK (SEQ ID NO: 46) CDR1 (SEQ ID NO: 54) - RASQGIDSWLA CDR2 (SEQ ID NO: 55) - AASSLQS CDR3 (SEQ ID NO: 56) - QQGVSYPRT |

TABLE 1-continued

| Clones | Heavy chain variable region amino acid sequence | Light chain variable region amino acid sequence |
|---|---|---|
| ADI-27749 (A49) | EVQLVESGGGLVKPGGSLRLSCAA SGFTFSSYSMNWVRQAPGKGLEW VSSISSSSSYIYYADSVKGRFTISRD NAKNSLYLQMNSLRAEDTAVYYC ARGAPMGAAAGWFDPWGQGTLV TVSS (SEQ ID NO: 47) CDR1 non-Kabat (SEQ ID NO: 57) - FTFSSYSMN or CDR1 (SEQ ID NO: 92) - SYSMN CDR2 (SEQ ID NO: 58) - SIS SS S SYIYYADSVKG CDR3 non-Kabat (SEQ ID NO: 59) - ARGAPMGAAAGWFDP or CDR3 (SEQ ID NO: 93) - GAPMGAAAGWFDP | DIQMTQSPSSVSASVGDRVTITC RASQGISSWLAWYQQKPGKAP KLLIYAASSLQSGVPSRFSGSGS GTDFTLTISSLQPEDFATYYCQQ GVSFPRTFGGGTKVEIK (SEQ ID NO: 48) CDR1 (SEQ ID NO: 60) - RASQGISSWLA CDR2 (SEQ ID NO: 61) - AASSLQS CDR3 (SEQ ID NO: 62) - QQGVSFPRT |
| ADI-29463 (F63) | QVQLVQSGAEVKKPGASVKVSCK ASGYTFTGYYMHWVRQAPGQGLE WMGWINPNSGGTNYAQKFQGRVT MTRDTSISTAYMELSRLRSDDTAV YYCARDTGEYYDTDDHGMDVWG QGTTVTVSS (SEQ ID NO: 49) CDR1 non-Kabat (SEQ ID NO: 63) - YTFTGYYMH or CDR1 (SEQ ID NO: 94) - GYYMH CDR2 (SEQ ID NO: 64) - WINPNSGGTNYAQKFQG CDR3 non-Kabat (SEQ ID NO: 65) - ARDTGEYYDTDDHGMDV or CDR3 (SEQ ID NO: 95) - DTGEYYDTDDHGMDV | EIVLTQSPGTLSLSPGERATLSC RASQSVSSNLAWYQQKPGQAP RLLIYGASTRATGIPARFSGSGS GTEFTLTISSLQSEDFAVYYCQQ DDYWPPTFGGGTKVEIK (SEQ ID NO: 50) CDR1 (SEQ ID NO: 66) - RASQSVSSNLA CDR2 (SEQ ID NO: 67) - GASTRAT CDR3 (SEQ ID NO: 68) - QQDDYWPPT |
| ADI-29404 (F04) | QVQLQQWGAGLLKPSETLSLTCAV YGGSFSGYYWSWIRQPPGKGLEWI GEIDHSGSTNYNPSLKSRVTISVDT SKNQFSLKLSSVTAADTAVYYCAR ARGPWSFDPWGQGTLVTVSS (SEQ ID NO: 78) | DIQMTQSPSTLSASVGDRVTITC RASQSISSWLAWYQQKPGKAP KLLIYKASSLESGVPSRFSGSGS GTEFTLTISSLQPDDFATYYCEQ YDSYPTFGGGTKVEIK (SEQ ID NO: 79) |
| ADI-28200 | QVQLVQSGAEVKKPGSSVKVSCK ASGGTFSSYAISWVRQAPGQGLEW MGGIIPIFGTANYAQKFQGRVTITA DESTSTAYMELSSLRSEDTAVYYC ARRGRKASGSFYYYYGMDVWGQ GTTVTVSS (SEQ ID NO: 80) | DIVMTQSPDSLAVSLGERATINC ESSQSLLNSGNQKNYLTWYQQ KPGQPPKLIYWASTRESGVPD RFSGSGSGTDFTLTISSLQAEDV AVYYCQNDYSYPYTFGQGTKL EIK (SEQ ID NO: 81) |
| A49MQ | EVQLVESGGGLVKPGGSLRLSCAA SGFTFSSYSMNWVRQAPGKGLEW VSSISSSSSYIYYADSVKGRFTISRD NAKNSLYLQMNSLRAEDTAVYYC ARGAPQGAAAGWFDPWGQGTLV TVSS (SEQ ID NO: 96) CDR1 non-Kabat (SEQ ID NO: 57) - FTFSSYSMN or CDR1 (SEQ ID NO: 92) - SYSMN CDR2 (SEQ ID NO: 58) - SISSSSSYIYYADSVKG CDR3 non-Kabat (SEQ ID NO: 97) - ARGAPQGAAAGWFDP or CDR3 (SEQ ID NO: 98) - GAPQGAAAGWFDP | DIQMTQSPSSVSASVGDRVTITC RASQGISSWLAWYQQKPGKAP KLLIYAASSLQSGVPSRFSGSGS GTDFTLTISSLQPEDFATYYCQQ GVSFPRTFGGGTKVEIK (SEQ ID NO: 48) CDR1 (SEQ ID NO: 60) - RASQGISSWLA CDR2 (SEQ ID NO: 61) - AAS SLQ S CDR3 (SEQ ID NO: 62) - QQGVSFPRT |

TABLE 1-continued

| Clones | Heavy chain variable region amino acid sequence | Light chain variable region amino acid sequence |
| --- | --- | --- |
| A49ML | EVQLVESGGGLVKPGGSLRLSCAA SGFTFSSYSMNWVRQAPGKGLEW VSSISSSSSYIYYADSVKGRFTISRD NAKNSLYLQMNSLRAEDTAVYYC ARGAPLGAAAGWFDPWGQGTLVT VSS (SEQ ID NO: 99) CDR1 non-Kabat (SEQ ID NO: 57) - FTFSSYSMN or CDR1 (SEQ ID NO: 92) - SYSMN CDR2 (SEQ ID NO: 58) - SISSSSSYWYADSVKG CDR3 non-Kabat (SEQ ID NO: 100) - ARGAPLGAAAGWFDP or CDR3 (SEQ ID NO: 101) - GAPLGAAAGWFDP | DIQMTQSPSSVSASVGDRVTITC RASQGISSWLAWYQQKPGKAP KLLIYAASSLQSGVPSRFSGSGS GTDFTLTISSLQPEDFATYYCQQ GVSFPRTFGGGTKVEIK (SEQ ID NO: 48) CDR1 (SEQ ID NO: 60) - RASQGISSWLA CDR2 (SEQ ID NO: 61) - AASSLQS CDR3 (SEQ ID NO: 62) - QQGVSFPRT |
| A49MI | EVQLVESGGGLVKPGGSLRLSCAA SGFTFSSYSMNWVRQAPGKGLEW VSSISSSSSYIYYADSVKGRFTISRD NAKNSLYLQMNSLRAEDTAVYYC ARGAPIGAAAGWFDPWGQGTLVT VSS (SEQ ID NO: 102) CDR1 non-Kabat (SEQ ID NO: 57) - FTFSSYSMN or CDR1 (SEQ ID NO: 92) - SYSMN CDR2 (SEQ ID NO: 58) - SISSSSSYWYADSVKG CDR3 non-Kabat (SEQ ID NO: 103) - ARGAPIGAAAGWFDP or CDR3 (SEQ ID NO: 104) - GAPIGAAAGWFDP | DIQMTQSPSSVSASVGDRVTITC RASQGISSWLAWYQQKPGKAP KLLIYAASSLQSGVPSRFSGSGS GTDFTLTISSLQPEDFATYYCQQ GVSFPRTFGGGTKVEIK (SEQ ID NO: 48) CDR1 (SEQ ID NO: 60) - RASQGISSWLA CDR2 (SEQ ID NO: 61) - AASSLQS CDR3 (SEQ ID NO: 62) - QQGVSFPRT |
| A49MF | EVQLVESGGGLVKPGGSLRLSCAA SGFTFSSYSMNWVRQAPGKGLEW VSSISSSSSYIYYADSVKGRFTISRD NAKNSLYLQMNSLRAEDTAVYYC ARGAPFGAAAGWFDPWGQGTLVT VSS (SEQ ID NO: 105) CDR1 non-Kabat (SEQ ID NO: 57) - FTFSSYSMN or CDR1 (SEQ ID NO: 92) - SYSMN CDR2 (SEQ ID NO: 58) - SISSSSSYWYADSVKG CDR3 non-Kabat (SEQ ID NO: 106) - ARGAPFGAAAGWFDP or CDR3 (SEQ ID NO: 107) - GAPFGAAAGWFDP | DIQMTQSPSSVSASVGDRVTITC RASQGISSWLAWYQQKPGKAP KLLIYAASSLQSGVPSRFSGSGS GTDFTLTISSLQPEDFATYYCQQ GVSFPRTFGGGTKVEIK (SEQ ID NO: 48) CDR1 (SEQ ID NO: 60) - RASQGISSWLA CDR2 (SEQ ID NO: 61) - AASSLQS CDR3 (SEQ ID NO: 62) - QQGVSFPRT |
| A49MV | EVQLVESGGGLVKPGGSLRLSCAA SGFTFSSYSMNWVRQAPGKGLEW VSSISSSSSYIYYADSVKGRFTISRD NAKNSLYLQMNSLRAEDTAVYYC ARGAPVGAAAGWFDPWGQGTLVT VSS (SEQ ID NO: 108) CDR1 non-Kabat (SEQ ID NO: 57) - FTFSSYSMN or CDR1 (SEQ ID NO: 92) - SYSMN CDR2 (SEQ ID NO: 58) - SISSSSSYIYYADSVKG CDR3 non-Kabat (SEQ ID NO: 109) - ARGAPVGAAAGWFDP or CDR3 (SEQ ID NO: 110) - GAPVGAAAGWFDP | DIQMTQSPSSVSASVGDRVTITC RASQGISSWLAWYQQKPGKAP KLLIYAASSLQSGVPSRFSGSGS GTDFTLTISSLQPEDFATYYCQQ GVSFPRTFGGGTKVEIK (SEQ ID NO: 48) CDR1 (SEQ ID NO: 60) - RASQGISSWLA CDR2 (SEQ ID NO: 61) - AASSLQS CDR3 (SEQ ID NO: 62) - QQGVSFPRT |

TABLE 1-continued

| Clones | Heavy chain variable region amino acid sequence | Light chain variable region amino acid sequence |
|---|---|---|
| A49-consensus | EVQLVESGGGLVKPGGSLRLSCAA SGFTFSSYSMNWVRQAPGKGLEW VSSISSSSSYIYYADSVKGRFTISRD NAKNSLYLQMNSLRAEDTAVYYC ARGAPXGAAAGWFDPWGQGTLVT VSS, wherein X is M, L, I, V, Q, or F (SEQ ID NO: 111) CDR1 non-Kabat (SEQ ID NO: 57) - FTFSSYSMN or CDR1 (SEQ ID NO: 92) - SYSMN CDR2 (SEQ ID NO: 58) - SISSSSSYIYYADSVKG CDR3 non-Kabat (SEQ ID NO: 112) - ARGAPXGAAAGWFDP or CDR3 (SEQ ID NO: 113) - GAPXGAAAGWFDP, wherein X is M, L, I, V, Q, or F | DIQMTQSPSSVSASVGDRVTITC RASQGISSWLAWYQQKPGKAP KLLIYAASSLQSGVPSRFSGSGS GTDFTLTISSLQPEDFATYYCQQ GVSFPRTFGGGTKVEIK (SEQ ID NO: 48) CDR1 (SEQ ID NO: 60) - RASQGISSWLA CDR2 (SEQ ID NO: 61) - AASSLQS CDR3 (SEQ ID NO: 62) - QQGVSFPRT |
| ADI-29378 (E78) | QVQLVQSGAEVKKPGASVKVSCK ASGYTFTSYYMHWVRQAPGQGLE WMGIINPSGGSTSYAQKFQGRVTM TRDTSTSTVMELSSLRSEDTAVY YCAREGAGFAYGMDYYYMDVWG KGTTVTVSS (SEQ ID NO: 114) CDR1 non-Kabat (SEQ ID NO: 116) - YTFTSYYMH or CDR1 (SEQ ID NO: 122) - SYYMH CDR2 (SEQ ID NO: 117) - IINPSGGSTSYAQKFQG CDR3 non-Kabat (SEQ ID NO: 118) - AREGAGFAYGMDYYYMDV or CDR3 (SEQ ID NO: 123) - EGAGFAYGMDYYYMDV | EIVLTQSPATLSLSPGERATLSC RASQSVSSYLAWYQQKPGQAP RLLIYDASNRATGIPARFSGSGS GTDFTLTISSLEPEDFAVYYCQQ SDNWPFTFGGGTKVEIK (SEQ ID NO: 115) CDR1 (SEQ ID NO: 119) - RASQSVSSYLA CDR2 (SEQ ID NO: 120) - DASNRAT CDR3 (SEQ ID NO: 121) - QQSDNWPFT |
| ADI-29379 (E79) | QVQLVQSGAEVKKPGASVKVSCK ASGYTFTSYYMHWVRQAPGQGLE WMGIINPSGGSTSYAQKFQGRVTM TRDTSTSTVMELSSLRSEDTAVY YCARGAPNYGDTTHDYYYMDVW GKGTTVTVSS (SEQ ID NO: 124) CDR1 non-Kabat (SEQ ID NO: 116) - YTFTSYYMH or CDR1 (SEQ ID NO: 122) - SYYMH CDR2 (SEQ ID NO: 117) - IINPSGGSTSYAQKFQG CDR3 non-Kabat (SEQ ID NO: 126) - ARGAPNYGDTTHDYYYMDV or CDR3 (SEQ ID NO: 130) - GAPNYGDTTHDYYYMDV | EIVMTQSPATLSVSPGERATLSC RASQSVSSNLAWYQQKPGQAP RLLIYGASTRATGIPARFSGSGS GTEFTLTISSLQSEDFAVYYCQQ YDDWPFTFGGGTKVEIK (SEQ ID NO: 125) CDR1 (SEQ ID NO: 127) - RASQSVSSNLA CDR2 (SEQ ID NO: 128) - GASTRAT CDR3 (SEQ ID NO: 129) - QQYDDWPFT |

Alternatively, a heavy chain variable domain defined by SEQ ID NO:69 can be paired with a light chain variable domain defined by SEQ ID NO:70 to form an antigen-binding site that can bind to NKG2D, as illustrated in U.S. Pat. No. 9,273,136.

SEQ ID NO: 69
QVQLVESGGGLVKPGGSLRLSCAASGFTFSSYGMHWVRQAPGKGLEWVAF

IRYDGSNKYYADSVKGRFTISRDNSKNTLYLQMNSLRAEDTAVYYCAKDR

GLGDGTYFDYWGQGTTVTVSS

SEQ ID NO: 70
QSALTQPASVSGSPGQSITISCSGSSSNIGNNAVNWYQQLPGKAPKLLIY

YDDLLPSGVSDRFSGSKSGTSAFLAISGLOSEDEADYYCAAWDDSLNGPV

FGGGTKLTVL

Alternatively, heavy chain variable domain defined by SEQ ID NO:71 can be paired with light chain variable domain defined by SEQ ID NO:72 to form an antigen-binding site that can bind to NKG2D, as illustrated in U.S. Pat. No. 7,879,985.

SEQ ID NO: 71
QVHLQESGPGLVKPSETLSLTCTVSDDSISSYYWSWIRQPPGKGLEWIGH

ISYSGSANYNPSLKSRVTISVDTSKNQFSLKLSSVTAADTAVYYCANWDD

AFNIWGQGTMVTVSS

SEQ ID NO: 72
EIVLTQSPGTLSLSPGERATLSCRASQSVSSSYLAWYQQKPGQAPRLLIY

GASSRATGIPDRFSGSGSGTDFTLTISRLEPEDFAVYYCQQYGSSPWTFG

QGTKVEIK

Within the Fc domain, CD16 binding is mediated by the hinge region and the CH2 domain. For example, within human IgG1, the interaction with CD16 is primarily focused on amino acid residues Asp 265-Glu 269, Asn 297-Thr 299, Ala 327-Ile 332, Leu 234-Ser 239, and carbohydrate residue N-acetyl-D-glucosamine in the CH2 domain (see, Sondermann et al, Nature, 406(6793):267-273). Based on the known domains, mutations can be selected to enhance or reduce the binding affinity to CD16, such as by using phage-displayed libraries or yeast surface-displayed cDNA libraries, or can be designed based on the known three-dimensional structure of the interaction.

The assembly of heterodimeric antibody heavy chains can be accomplished by expressing two different antibody heavy chain sequences in the same cell, which may lead to the assembly of homodimers of each antibody heavy chain as well as assembly of heterodimers. Promoting the preferential assembly of heterodimers can be accomplished by incorporating different mutations in the CH3 domain of each antibody heavy chain constant region as shown in U.S. Ser. No. 13/494,870, U.S. Ser. No. 16/028,850, U.S. Ser. No. 11/533,709, U.S. Ser. No. 12/875,015, U.S. Ser. No. 13/289,934, U.S. Ser. No. 14/773,418, U.S. Ser. No. 12/811,207, U.S. Ser. No. 13/866,756, U.S. Ser. No. 14/647,480, U.S. Ser. No. 14/830,336. For example, mutations can be made in the CH3 domain based on human IgG1 and incorporating distinct pairs of amino acid substitutions within a first polypeptide and a second polypeptide that allow these two chains to selectively heterodimerize with each other. The positions of amino acid substitutions illustrated below are all numbered according to the EU index as in Kabat.

In one scenario, an amino acid substitution in the first polypeptide replaces the original amino acid with a larger amino acid, selected from arginine (R), phenylalanine (F), tyrosine (Y) or tryptophan (W), and at least one amino acid substitution in the second polypeptide replaces the original amino acid(s) with a smaller amino acid(s), chosen from alanine (A), serine (S), threonine (T), or valine (V), such that the larger amino acid substitution (a protuberance) fits into the surface of the smaller amino acid substitutions (a cavity). For example, one polypeptide can incorporate a T366W substitution, and the other can incorporate three substitutions including T366S, L368A, and Y407V.

An antibody heavy chain variable domain of the invention can optionally be coupled to an amino acid sequence at least 90% identical to an antibody constant region, such as an IgG constant region including hinge, CH2 and CH3 domains with or without CH1 domain. In some embodiments, the amino acid sequence of the constant region is at least 90% identical to a human antibody constant region, such as an human IgG1 constant region, an IgG2 constant region, IgG3 constant region, or IgG4 constant region. In some other embodiments, the amino acid sequence of the constant region is at least 90% identical to an antibody constant region from another mammal, such as rabbit, dog, cat, mouse, or horse. One or more mutations can be incorporated into the constant region as compared to human IgG1 constant region, for example at Q347, Y349, L351, S354, E356, E357, K360, Q362, S364, T366, L368, K370, N390, K392, T394, D399, S400, D401, F405, Y407, K409, T411 and/or K439. Exemplary substitutions include, for example, Q347E, Q347R, Y349S, Y349K, Y349T, Y349D, Y349E, Y349C, T350V, L351K, L351D, L351Y, S354C, E356K, E357Q, E357L, E357W, K360E, K360W, Q362E, S364K, S364E, S364H, S364D, T366V, T366I, T366L, T366M, T366K, T366W, T366S, L368E, L368A, L368D, K370S, N390D, N390E, K392L, K392M, K392V, K392F, K392D, K392E, T394F, T394W, D399R, D399K, D399V, S400K, S400R, D401K, F405A, F405T, Y407A, Y407I, Y407V, K409F, K409W, K409D, T411D, T411E, K439D, and K439E.

In certain embodiments, mutations that can be incorporated into the CH1 of a human IgG1 constant region may be at amino acid V125, F126, P127, T135, T139, A140, F170, P171, and/or V173. In certain embodiments, mutations that can be incorporated into the CK of a human IgG1 constant region may be at amino acid E123, F116, S176, V163, S174, and/or T164.

Alternatively, amino acid substitutions could be selected from the following sets of substitutions shown in Table 2.

TABLE 2

|  | First Polypeptide | Second Polypeptide |
| --- | --- | --- |
| Set 1 | S364E/F405A | Y349K/T394F |
| Set 2 | S364H/D401K | Y349T/T411E |
| Set 3 | S364H/T394F | Y349T/F405A |
| Set 4 | S364E/T394F | Y349K/F405A |
| Set 5 | S364E/T411E | Y349K/D401K |
| Set 6 | S364D/T394F | Y349K/F405A |
| Set 7 | S364H/F405A | Y349T/T394F |
| Set 8 | S364K/E357Q | L368D/K370S |
| Set 9 | L368D/K370S | S364K |
| Set 10 | L368E/K370S | S364K |
| Set 11 | K360E/Q362E | D401K |
| Set 12 | L368D/K370S | S364K/E357L |
| Set 13 | K370S | S364K/E357Q |
| Set 14 | F405L | K409R |
| Set 15 | K409R | F405L |

Alternatively, amino acid substitutions could be selected from the following sets of substitutions shown in Table 3.

TABLE 3

|  | First Polypeptide | Second Polypeptide |
| --- | --- | --- |
| Set 1 | K409W | D399V/F405T |
| Set 2 | Y349S | E357W |
| Set 3 | K360E | Q347R |
| Set 4 | K360E/K409W | Q347R/D399V/F405T |
| Set 5 | Q347E/K360E/K409W | Q347R/D399V/F405T |
| Set 6 | Y349S/K409W | E357W/D399V/F405T |

Alternatively, amino acid substitutions could be selected from the following set of substitutions shown in Table 4.

TABLE 4

|  | First Polypeptide | Second Polypeptide |
| --- | --- | --- |
| Set 1 | T366K/L351K | L351D/L368E |
| Set 2 | T366K/L351K | L351D/Y349E |
| Set 3 | T366K/L351K | L351D/Y349D |
| Set 4 | T366K/L351K | L351D/Y349E/L368E |
| Set 5 | T366K/L351K | L351D/Y349D/L368E |
| Set 6 | E356K/D399K | K392D/K409D |

Alternatively, at least one amino acid substitution in each polypeptide chain could be selected from Table 5.

TABLE 5

| First Polypeptide | Second Polypeptide |
|---|---|
| L351Y, D399R, D399K, S400K, S400R, Y407A, Y407I, Y407V | T366V, T366I, T366L, T366M, N390D, N390E, K392L, K392M, K392V, K392F K392D, K392E, K409F, K409W, T411D and T411E |

Alternatively, at least one amino acid substitutions could be selected from the following set of substitutions in Table 6, where the position(s) indicated in the First Polypeptide column is replaced by any known negatively-charged amino acid, and the position(s) indicated in the Second Polypeptide Column is replaced by any known positively-charged amino acid.

TABLE 6

| First Polypeptide | Second Polypeptide |
|---|---|
| K392, K370, K409, or K439 | D399, E356, or E357 |

Alternatively, at least one amino acid substitutions could be selected from the following set of in Table 7, where the position(s) indicated in the First Polypeptide column is replaced by any known positively-charged amino acid, and the position(s) indicated in the Second Polypeptide Column is replaced by any known negatively-charged amino acid.

TABLE 7

| First Polypeptide | Second Polypeptide |
|---|---|
| D399, E356, or E357 | K409, K439, K370, or K392 |

Alternatively, or in addition, the structural stability of a heteromultimer protein may be increased by introducing S354C on either of the first or second polypeptide chain, and Y349C on the opposing polypeptide chain, which forms an artificial disulfide bridge within the interface of the two polypeptides.

The multi-specific proteins described above can be made using recombinant DNA technology well known to a skilled person in the art. For example, a first nucleic acid sequence encoding the first immunoglobulin heavy chain can be cloned into a first expression vector; a second nucleic acid sequence encoding the second immunoglobulin heavy chain can be cloned into a second expression vector; a third nucleic acid sequence encoding the immunoglobulin light chain can be cloned into a third expression vector; the first, second, and third expression vectors can be stably transfected together into host cells to produce the multimeric proteins To achieve the highest yield of the multi-specific protein, different ratios of the first, second, and third expression vector can be explored to determine the optimal ratio for transfection into the host cells. After transfection, single clones can be isolated for cell bank generation using methods known in the art, such as limited dilution, ELISA, FACS, microscopy, or Clonepix.

Clones can be cultured under conditions suitable for bio-reactor scale-up and maintained expression of the multi-specific protein. The multi-specific proteins can be isolated and purified using methods known in the art including centrifugation, depth filtration, cell lysis, homogenization, freeze-thawing, affinity purification, gel filtration, ion exchange chromatography, hydrophobic interaction exchange chromatography, and mixed-mode chromatography.

II. Characteristics of TriNKETs

In certain embodiments, TriNKETs described herein, which include an NKG2D-binding domain and a binding domain for a tumor associated antigen, bind to cells expressing human NKG2D. In certain embodiments, TriNKETs, which include an NKG2D-binding domain and a binding domain for a tumor associated antigen, bind to the tumor associated antigen at a comparable level to that of a monoclonal antibody having the same tumor associated antigen-binding domain. For example, TriNKETs that include an NKG2D-binding domain and a HER2-binding domain from Trastuzumab can bind to HER2 expressed on cells at a level comparable to that of Trastuzumab.

However, the TriNKETs described herein are more effective in reducing tumor growth and killing cancer cells. For example, a TriNKET of the present disclosure that targets HER2 expressing tumor/cancer cells is more effective than SC2.2—a single chain bispecific molecule built from an scFv derived from trastuzumab linked to ULBP-6, a ligand for NKG2D. SC2.2 binds HER2+ cancer cells and NKG2D+ NK cells simultaneously. Therefore, effectiveness of SC2.2 in reducing HER2+ cancer cell number was investigated. In vitro activation and cytotoxity assays demonstrated that SC2.2 was effective in activating and killing NK cells. However, SC2.2 failed to demonstrate efficacy in the RMA/S-HER2 subcutaneous tumor model. The efficacy of SC2.2 was also tested in vivo using an RMA/S-HER2 overexpressing syngeneic mouse model. In this mouse model, SC2.2 failed to demonstrate control of tumor growth compared to vehicle control. Thus, although SC2.2 was able to activate and kill NK cells, and binds to HER2+ cancer cells, these properties were insufficient to effectively control HER2+ tumor growth.

In certain embodiments, TriNKETs described herein, which include an NKG2D-binding domain and a binding domain for tumor associated antigen, activate primary human NK cells when culturing with tumor cells expressing the antigen. NK cell activation is marked by the increase in CD107a degranulation and IFNγ cytokine production. Furthermore, compared to a monoclonal antibody that includes the tumor associated antigen-binding domain, TriNKETs show superior activation of human NK cells in the presence of tumor cells expressing the antigen. For example, compared to the monoclonal antibody trastuzumab, TriNKETs of the present disclosure having a HER2-binding domain, have a superior activation of human NK cells in the presence of HER2-expressing cancer cells.

In certain embodiments, TriNKETs described herein, which include an NKG2D-binding domain and a binding domain for a tumor associated antigen, enhance the activity of rested and IL-2-activated human NK cells in the presence of tumor cells expressing the antigen. Rested NK cells showed less background IFNγ production and CD107a degranulation than IL-2-activated NK cells. In certain embodiments, IL-2-activated NK cells show a greater percentage of cells becoming IFNγ+; CD107a+ after stimulation with TriNKETs.

In certain embodiments, TriNKETs described herein, which include an NKG2D-binding domain and a binding domain for a tumor associated antigen (non-limiting examples of tumor associated antigens including CD20, BCMA, and HER2), enhance the cytotoxic activity of rested and IL-2-activated human NK cells in the presence of tumor cells expressing the antigen. Furthermore, TriNKETs (e.g., A40-TriNKET, A44-TriNKET, A49-TriNKET, C26-TriNKET, F04-TriNKET, F43-TriNKET, F47-TriNKET, and F63-TriNKET), which include a binding domain for a tumor associated antigen (non-limiting examples of tumor associated antigens including CD20, BCMA, and HER2) more potently direct activated and rested NK cell responses against the tumor cells, compared to a monoclonal antibody that includes the same tumor associated antigen binding site. In certain embodiments, TriNKETs offer advantage against tumor cells expressing medium and low tumor antigens compared to monoclonal antibodies that include the same tumor antigen binding site. Therefore, a therapy including TriNKETs can be superior to a monoclonal antibody therapy. In all these settings, TriNKETs induced greater activation of NK cells, and greater tumor cell killing, when NK cells were incubated with IL-2 compared to NK cells without IL-2, demonstrating synergy between TriNKETs and IL-2.

In certain embodiments, compared to monoclonal antibodies, TriNKETs described herein (e.g., A40-TriNKET, A44-TriNKET, A49-TriNKET, C26-TriNKET, F04-TriNKET, F43-TriNKET, F47-TriNKET, and F63-TriNKET), which include a binding domain for a tumor associated antigen (non-limiting examples of tumor associated antigens including CD20, BCMA, and HER2) are advantageous in treating cancers with high expression of Fc receptor (FcR), or cancers residing in a tumor microenvironment with high levels of FcR. Monoclonal antibodies exert their effects on tumor growth through multiple mechanisms including ADCC, CDC, phagocytosis, and signal blockade amongst others. Amongst FcγRs, CD16 has the lowest affinity for IgG Fc; FcγRI (CD64) is the high-affinity FcR, which binds about 1000 times more strongly to IgG Fc than CD16. CD64 is normally expressed on many hematopoietic lineages such as the myeloid lineage, and can be expressed on tumors derived from these cell types, such as acute myeloid leukemia (AML). Immune cells infiltrating into the tumor, such as MDSCs and monocytes, also express CD64 and are known to infiltrate the tumor microenvironment. Expression of CD64 by the tumor or in the tumor microenvironment can have a detrimental effect on monoclonal antibody therapy. Expression of CD64 in the tumor microenvironment makes it difficult for these antibodies to engage CD16 on the surface of NK cells, as the antibodies prefer to bind the high-affinity receptor. TriNKETs, through targeting two activating receptors on the surface of NK cells, can overcome the detrimental effect of CD64 expression (either on tumor or tumor microenvironment) on monoclonal antibody therapy. Regardless of CD64 expression on the tumor cells, TriNKETs are able to mediate human NK cell responses against all tumor cells, because dual targeting of two activating receptors on NK cells provides stronger specific binding to NK cells.

In some embodiments, TriNKETs described herein (e.g., A40-TriNKET, A44-TriNKET, A49-TriNKET, C26-TriNKET, F04-TriNKET, F43-TriNKET, F47-TriNKET, and F63-TriNKET), which include a binding domain for a tumor associated antigen (non-limiting examples of tumor associated antigens including CD20, BCMA, and HER2) provide a better safety profile through reduced on-target off-tumor side effects. Natural killer cells and CD8 T cells are both able to directly lyse tumor cells, although the mechanisms through which NK cells and CD8 T cell recognize normal self from tumor cells differ. The activity of NK cells is regulated by the balance of signals from activating (NCRs, NKG2D, CD16, etc.) and inhibitory (KIRs, NKG2A, etc.) receptors. The balance of these activating and inhibitory signals allow NK cells to determine healthy self-cells from stressed, virally infected, or transformed self-cells. This 'built-in' mechanism of self-tolerance will help protect normal heathy tissue from NK cell responses. To extend this principle, the self-tolerance of NK cells will allow TriNKETs to target antigens expressed both on self and tumor without off tumor side effects, or with an increased therapeutic window. Unlike natural killer cells, T cells require recognition of a specific peptide presented by MHC molecules for activation and effector functions. T cells have been the primary target of immunotherapy, and many strategies have been developed to redirect T cell responses against the tumor. T cell bispecifics, checkpoint inhibitors, and CAR-T cells have all been approved by the FDA, but often suffer from dose-limiting toxicities. T cell bispecifics and CAR-T cells work around the TCR-MHC recognition system by using binding domains to target antigens on the surface of tumor cells, and using engineered signaling domains to transduce the activation signals into the effector cell. Although effective at eliciting an anti-tumor immune response these therapies are often coupled with cytokine release syndrome (CRS), and on-target off-tumor side effects. TriNKETs are unique in this context as they will not override the natural systems of NK cell activation and inhibition. Instead, TriNKETs are designed to sway the balance, and provide additional activation signals to the NK cells, while maintaining NK tolerance to healthy self.

In some embodiments, TriNKETs described herein including an NKG2D-binding domain (e.g., A40-TriNKET, A44-TriNKET, A49-TriNKET, C26-TriNKET, F04-TriNKET, F43-TriNKET, F47-TriNKET, and F63-TriNKET), which include a binding domain for a tumor associated antigen (non-limiting examples of tumor associated antigens including CD20, BCMA, and HER2) delay progression of the tumor more effectively than monoclonal antibodies that include the same tumor antigen-binding domain. In some embodiments, TriNKETs including an NKG2D-binding domain and a tumor antigen-binding domain are more effective against cancer metastases than monoclonal antibodies that include the same tumor antigen-binding domain.

The description above describes multiple aspects and embodiments of the invention. The patent application specifically contemplates all combinations and permutations of the aspects and embodiments.

III. Therapeutic Applications

The invention provides methods for treating cancer using a multi-specific binding protein described herein (e.g., A40-TriNKET, A44-TriNKET, A49-TriNKET, C26-TriNKET, F04-TriNKET, F43-TriNKET, F47-TriNKET, and F63-TriNKET), which include a binding domain for a tumor associated antigen (non-limiting examples of tumor associated antigens including CD20, BCMA, and HER2) and/or a pharmaceutical composition described herein. The methods may be used to treat a variety of cancers, including a solid tumor, a lymphoma, and a leukemia. The type of cancer to be treated is desirably matched with the type of cancer cell to which the multi-specific binding protein binds. For example, treatment of a cancer expressing epithelial cell adhesion molecule (EpCAM), such as a colon cancer expressing EpCAM, is desirably treated using a multi-specific binding protein described herein that binds to NKG2D, CD16 and EpCAM. Additional aspects and embodiments of the therapeutic methods are described below.

Accordingly, one aspect of the invention provides a method of treating cancer in a patient, wherein the method comprises administering to a patient in need thereof a therapeutically effective amount of a multi-specific binding protein described herein (e.g., A40-TriNKET, A44-TriNKET, A49-TriNKET, C26-TriNKET, F04-TriNKET, F43-TriNKET, F47-TriNKET, and F63-TriNKET), which include a binding domain for a tumor associated antigen (non-limiting examples of tumor associated antigens including CD20, BCMA, and HER2) to treat the cancer. Exemplary cancers for treatment include a solid tumor, leukemia, and lymphoma.

The therapeutic method can be characterized according to the cancer to be treated. For example, in certain embodiments, the cancer is a solid tumor. In certain other embodiments, the cancer is brain cancer, head and neck cancer, bladder cancer, breast cancer, cervical cancer, colon cancer, colorectal cancer, endometrial cancer, esophageal cancer, leukemia, lung cancer, liver cancer, melanoma, ovarian cancer, pancreatic cancer, prostate cancer, rectal cancer, renal cancer, stomach cancer, testicular cancer, or uterine cancer. In yet other embodiments, the cancer is a vascularized tumor, squamous cell carcinoma, adenocarcinoma, small cell carcinoma, melanoma, glioma, neuroblastoma, sarcoma (e.g., an angiosarcoma or chondrosarcoma), larynx cancer, parotid cancer, bilary tract cancer, thyroid cancer, acral lentiginous melanoma, actinic keratoses, acute lymphocytic leukemia, acute myeloid leukemia, adenoid cycstic carcinoma, adenomas, adenosarcoma, adenosquamous carcinoma, anal canal cancer, anal cancer, anorectum cancer, astrocytic tumor, bartholin gland carcinoma, basal cell carcinoma, biliary cancer, bone cancer, bone marrow cancer, bronchial cancer, bronchial gland carcinoma, carcinoid, cholangiocarcinoma, chondosarcoma, choriod plexus papilloma/carcinoma, chronic lymphocytic leukemia, chronic myeloid leukemia, clear cell carcinoma, connective tissue cancer, cystadenoma, digestive system cancer, duodenum cancer, endocrine system cancer, endodermal sinus tumor, endometrial hyperplasia, endometrial stromal sarcoma, endometrioid adenocarcinoma, endothelial cell cancer, ependymal cancer, epithelial cell cancer, Ewing's sarcoma, eye and orbit cancer, female genital cancer, focal nodular hyperplasia, gallbladder cancer, gastric antrum cancer, gastric fundus cancer, gastrinoma, glioblastoma, glucagonoma, heart cancer, hemangiblastomas, hemangioendothelioma, hemangiomas, hepatic adenoma, hepatic adenomatosis, hepatobiliary cancer, hepatocellular carcinoma, Hodgkin's disease, ileum cancer, insulinoma, intaepithelial neoplasia, interepithelial squamous cell neoplasia, intrahepatic bile duct cancer, invasive squamous cell carcinoma, jejunum cancer, joint cancer, Kaposi's sarcoma, pelvic cancer, large cell carcinoma, large intestine cancer, leiomyosarcoma, lentigo maligna melanomas, lymphoma, male genital cancer, malignant melanoma, malignant mesothelial tumors, medulloblastoma, medulloepithelioma, meningeal cancer, mesothelial cancer, metastatic carcinoma, mouth cancer, mucoepidermoid carcinoma, multiple myeloma, muscle cancer, nasal tract cancer, nervous system cancer, neuroepithelial adenocarcinoma nodular melanoma, non-epithelial skin cancer, non-Hodgkin's lymphoma, oat cell carcinoma, oligodendroglial cancer, oral cavity cancer, osteosarcoma, papillary serous adenocarcinoma, penile cancer, pharynx cancer, pituitary tumors, plasmacytoma, pseudosarcoma, pulmonary blastoma, rectal cancer, renal cell carcinoma, respiratory system cancer, retinoblastoma, rhabdomyosarcoma, sarcoma, serous carcinoma, sinus cancer, skin cancer, small cell carcinoma, small intestine cancer, smooth muscle cancer, soft tissue cancer, somatostatin-secreting tumor, spine cancer, squamous cell carcinoma, striated muscle cancer, submesothelial cancer, superficial spreading melanoma, T cell leukemia, tongue cancer, undifferentiated carcinoma, ureter cancer, urethra cancer, urinary bladder cancer, urinary system cancer, uterine cervix cancer, uterine corpus cancer, uveal melanoma, vaginal cancer, verrucous carcinoma, VIPoma, vulva cancer, well differentiated carcinoma, or Wilms tumor.

In certain other embodiments, the cancer is non-Hodgkin's lymphoma, such as a B-cell lymphoma or a T-cell lymphoma. In certain embodiments, the non-Hodgkin's lymphoma is a B-cell lymphoma, such as a diffuse large B-cell lymphoma, primary mediastinal B-cell lymphoma, follicular lymphoma, small lymphocytic lymphoma, mantle cell lymphoma, marginal zone B-cell lymphoma, extranodal marginal zone B-cell lymphoma, nodal marginal zone B-cell lymphoma, splenic marginal zone B-cell lymphoma, Burkitt lymphoma, lymphoplasmacytic lymphoma, hairy cell leukemia, or primary central nervous system (CNS) lymphoma. In certain other embodiments, the non-Hodgkin's lymphoma is a T-cell lymphoma, such as a precursor T-lymphoblastic lymphoma, peripheral T-cell lymphoma, cutaneous T-cell lymphoma, angioimmunoblastic T-cell lymphoma, extranodal natural killer/T-cell lymphoma, enteropathy type T-cell lymphoma, subcutaneous panniculitis-like T-cell lymphoma, anaplastic large cell lymphoma, or peripheral T-cell lymphoma.

The cancer to be treated can be characterized according to the presence of a particular antigen expressed on the surface of the cancer cell. In certain embodiments, the cancer cell expresses one or more of the following: HER2, CD20, CD33, BCMA, EpCAM, CD2, CD19, CD30, CD38, CD40, CD52, CD70, EGFR/ERBB1, IGF1R, HER3/ERBB3, HER4/ERBB4, MUC1, cMET, SLAMF7, PSCA, MICA, MICB, TRAILR1, TRAILR2, MAGE-A3, B7.1, B7.2, CTLA4, and PD-L1.

In certain embodiments, a protein of the present disclosure is used in a method of enhancing tumor cell death (synonymous with lysis, killing, ablation, reducing survival or cell proliferation, and the like) directly or indirectly, or manufacture of a medicament for use in a method of enhancing tumor cell death (synonymous with lysis, killing, ablation, reducing survival or cell proliferation, and the like) directly or indirectly, by exposing a tumor or cancer cell and natural killer cells to a protein of the present disclosure (e.g., A40-TriNKET, A44-TriNKET, A49-TriNKET, C26-TriNKET, F04-TriNKET, F43-TriNKET, F47-TriNKET, and F63-TriNKET), which include a binding domain for a tumor associated antigen (non-limiting examples of tumor associated antigens including CD20, BCMA, and HER2). The tumor cell that is responsive to a protein, as described above, expresses the tumor-associated antigen to which the second antigen-binding site of the protein binds. For example, in an exemplary embodiment the C26-TriNKET-CD20 is used to target a CD20-expressing tumor or cancer cell (either rested or activated); in another exemplary embodiment, C26-TriNKET-BMCA is used to target a BMCA-expressing tumor or cancer cell (either rested or activated).

In certain embodiments, a protein of the present disclosure is used in a method of treating a cancer in a subject in need thereof, or manufacture of a medicament for use in a method of treating a cancer in a subject in need thereof, which involves administration to the subject a protein or a formulation including the protein of the present disclosure (e.g., A40-TriNKET, A44-TriNKET, A49-TriNKET, C26-TriNKET, F04-TriNKET, F43-TriNKET, F47-TriNKET, and F63-TriNKET), which include a binding domain for a tumor associated antigen (non-limiting examples of tumor associated antigens including CD20, BCMA, and HER2). The cancer cell responsive to a protein, as described above, expresses the tumor-associated antigen to which the second antigen-binding site of the protein binds. For example, in an exemplary embodiment the C26-TriNKET-CD20 is used to target a CD20-expressing cancer cell (either rested or activated); in another exemplary embodiment, C26-TriNKET-BMCA is used to target a BMCA-expressing tumor or cancer cell (either rested or activated).

IV. Combination Therapy

Another aspect of the invention provides for combination therapy. Multi-specific binding proteins described herein be used in combination with additional therapeutic agents to treat the cancer.

In one aspect, the invention provides a method of enhancing tumor cell death directly or indirectly, the method includes exposing a tumor and natural killer cells to a protein comprising: (a) a first antigen-binding site that binds NKG2D; (b) a second antigen-binding site that binds a tumor-associated antigen; and (c) an antibody Fc domain or a portion thereof sufficient to bind CD16, or a third antigen-binding site that binds CD16; in combination with a second therapeutic agent selected from: a checkpoint blocker; a cytokine; a TLR agonist; a STING agonist; a chemotherapeutic agent; a cancer target agent that interferes with specific molecules in cancer cells that are involved in cancer cell growth or survival, including, for example, kinase inhibitors such as Ibrutinib, Vemurafenib, or Gleevec; an oncolytic virus; a vaccine; radiation; an adoptive NK therapy which involves infusion of ex vivo expanded NK cells or T cells, including cell that have been modified in vitro to express a chimeric antigen receptor (e.g., CAR-T cells); and stem cell transplant (SCT).

In certain embodiments, the second therapeutic agent comprises a CAR-T cell. The CAR-T technology is known in the art and is described in U.S. Pat. No. 10,174,095, U.S. Patent Application Publication No. 2015/0283178, and reviewed in Guedan et al., Mol Ther Methods Clin Dev. (2018) 12:145-156. CARs may target a variety of antigens. For example, in certain embodiments, the CAR-T cell expresses or is capable of expressing a CAR that specifically binds a tumor-associated antigen, e.g., CD19, CD22, BCMA, PSMA, mesothelin (MSLN), ROR1, WT1, L1 CAM, MUC16, or LeY. In certain embodiments, the tumor-associated antigen bound by the CAR is the same antigen bound by the second antigen-binding site of the multi-specific binding protein. In certain embodiments, the CAR comprises an antigen-binding site that is the same or substantially the same as the second antigen-binding site of the multi-specific binding protein.

In one aspect, the invention provides a method of treating cancer in a subject in need thereof, the method comprising administering to the subject a protein comprising: (a) a first antigen-binding site that binds NKG2D; (b) a second antigen-binding site that binds a tumor-associated antigen; and (c) an antibody Fc domain or a portion thereof sufficient to bind CD16, or a third antigen-binding site that binds CD16; or a formulation comprising the protein; in combination with a second therapeutic agent selected from: a checkpoint blocker; a cytokine; a TLR agonist; a STING agonist; a chemotherapeutic agent; a cancer target agent that interferes with specific molecules in cancer cells that are involved in cancer cell growth or survival, including, for example, kinase inhibitors such as Ibrutinib, Vemurafenib, or Gleevec; an oncolytic virus; a vaccine; radiation; an adoptive NK therapy which involves infusion of ex vivo expanded NK cells or T cells, including cell that have been modified in vitro to express a chimeric antigen receptor (e.g., CAR-T cells); and stem cell transplant (SCT).

The present disclosure provides a method of enhancing tumor cell death directly or indirectly and/or a method of treating cancer with a protein comprising: (a) a first antigen-binding site that binds NKG2D; (b) a second antigen-binding site that binds a tumor-associated antigen; and (c) an antibody Fc domain or a portion thereof sufficient to bind CD16, or a third antigen-binding site that binds CD16, in combination with a checkpoint blocker selected from: an anti-PD1 antibody, an anti-PD-L1 antibody, an anti-CTLA4 antibody, an anti-KIR antibody, an anti-NKG2A antibody, an anti-LAG3 antibody, and an anti-TIM3 antibody.

The present disclosure provides a method of enhancing tumor cell death directly or indirectly and/or a method of treating cancer with a protein comprising: (a) a first antigen-binding site that binds NKG2D; (b) a second antigen-binding site that binds a tumor-associated antigen; and (c) an antibody Fc domain or a portion thereof sufficient to bind CD16, or a third antigen-binding site that binds CD16, in combination with a cytokine including interferons and interleukins, such as IL-2, IL-15, IL-12, INFα, IL-21, PEG-IL-2 (polyethylene glycol-modified interleukin-2), and IL15/IL15R heterodimers.

The present disclosure provides a method of enhancing tumor cell death directly or indirectly and/or a method of treating cancer with a protein comprising: (a) a first antigen-binding site that binds NKG2D; (b) a second antigen-binding site that binds a tumor-associated antigen; and (c) an antibody Fc domain or a portion thereof sufficient to bind CD16, or a third antigen-binding site that binds CD16, in combination with a TLR agonist selected from a TLR7 agonist, a TLR8 agonist, a TLR7/8 agonist, a TLR9 agonist, a TLR4 agonist, and a TLR3 agonist.

The present disclosure provides a method of enhancing tumor cell death directly or indirectly and/or a method of treating cancer with a protein comprising: (a) a first antigen-binding site that binds NKG2D; (b) a second antigen-binding site that binds a tumor-associated antigen; and (c) an antibody Fc domain or a portion thereof sufficient to bind CD16, or a third antigen-binding site that binds CD16, in combination with a STING agonist ADU-S100.

The present disclosure provides a method of enhancing tumor cell death directly or indirectly and/or a method of treating cancer with a protein comprising: (a) a first antigen-binding site that binds NKG2D; (b) a second antigen-binding site that binds a tumor-associated antigen; and (c) an antibody Fc domain or a portion thereof sufficient to bind CD16, or a third antigen-binding site that binds CD16, in combination with a chemotherapeutic agent including alkylating agents such as cyclophosphamide, mechlorethamine, chlorambucil, melphalan, dacarbazine (DTIC), nitrosoureas, temozolomide (Oral dacarbazine); anthracyclines, such as daunorubicin, doxorubicin, epirubicin, idarubicin, mitoxantrone, and valrubicin; cytoskeletal disruptors, such as paclitaxel, nab-paclitaxel, docetaxel, abraxane, and taxotere; epothilones; histone deacetylase inhibitors such as vorinostat and romidepsin; inhibitors of topoisomerase I such as irinotecan and topotecan; inhibitors of topoisomerase II such as etoposide, teniposide and tafluposide; kinase inhibitors such as bortezomib, erlotinib, gefitinib, imatinib, vemurafenib and vismodegib; nucleotide analogs and precursor analogs such as azacitidine, azathioprine, capecitabine; peptide antibiotics such as bleomycin and actinomycin; platinum-based agents, such as carboplatin, cisplatin and oxaliplatin; retinoids such as tretinoin and alitretinoin; and *vinca* alkaloids and derivatives such as vinblastine, vincristine, vindesine and vinorelbine.

The present disclosure provides a method of enhancing tumor cell death directly or indirectly and/or a method of treating cancer with a protein comprising: (a) a first antigen-binding site that binds NKG2D; (b) a second antigen-binding site that binds a tumor-associated antigen; and (c) an antibody Fc domain or a portion thereof sufficient to bind CD16, or a third antigen-binding site that binds CD16, in combination with a checkpoint blocker selected from: nivolumab, pembrolizumab, atezolizumab, durvalumab, avelumab, ipilimumab, tremelimumab, lirilumab, and monalizumab.

The present disclosure provides a method of enhancing tumor cell death directly or indirectly and/or a method of treating cancer with a protein comprising: (a) a first antigen-binding site that binds NKG2D; (b) a second antigen-binding site that binds a tumor-associated antigen; and (c) an antibody Fc domain or a portion thereof sufficient to bind CD16, or a third antigen-binding site that binds CD16, in combination with a TLR agonist selected from: R848/resiquimod, VTX-2337, imiquimod, and CpG oligodeoxynucleotide.

The present disclosure provides a method of enhancing tumor cell death directly or indirectly and/or a method of treating cancer with a protein comprising: (a) a first antigen-binding site that binds NKG2D; (b) a second antigen-binding site that binds a tumor-associated antigen; and (c) an antibody Fc domain or a portion thereof sufficient to bind CD16, or a third antigen-binding site that binds CD16, in combination with an agent that induces cellular senescence. The agent that induces cancer cells into senescence, thereby sensitizing the cells to killing and/or clearance by immune cells (e.g., NK cells). Cellular senescence can be induced by a number of cellular events, such as cell cycle arrest, DNA damage, and inhibition of the mitogen-activated protein kinase (MAPK) cascade. Agents that induce cellular senescence are known in the art and are described in, for example, Ruscetti et al., Science (2018) 362, 1416-22; and Herranz et al., J. Clin. Invest. (2018) 128(4):1238-1246. In certain embodiments, the agent that induces cellular senescence comprises a combination of an agent that induces cell cycle arrest, such as an inhibitor to a cyclin-dependent kinase (CDK), and an inhibitor of a MAPK kinase (MEK). In certain embodiments, the agent that induces cellular senescence comprises a combination of a CDK4/6 inhibitor (e.g., palbociclib, abemaciclib, or ribociclib) and an MEK1/2 inhibitor (e.g., trametinib, cobimetinib, refametinib, or selumetinib).

Proteins of the invention can also be used as an adjunct to surgical removal of the primary lesion.

The amount of multi-specific binding protein and additional therapeutic agent and the relative timing of administration may be selected in order to achieve a desired combined therapeutic effect. For example, when administering a combination therapy to a patient in need of such administration, the therapeutic agents in the combination, or a pharmaceutical composition or compositions comprising the therapeutic agents, may be administered in any order such as, for example, sequentially, concurrently, together, simultaneously and the like. Further, for example, a multi-specific binding protein may be administered during a time when the additional therapeutic agent(s) exerts its prophylactic or therapeutic effect, or vice versa.

V. Pharmaceutical Compositions

The present disclosure also features pharmaceutical compositions that contain a therapeutically effective amount of a protein described herein (e.g., A40-TriNKET, A44-TriNKET, A49-TriNKET, C26-TriNKET, F04-TriNKET, F43-TriNKET, F47-TriNKET, and F63-TriNKET), which include a binding domain for a tumor associated antigen (non-limiting examples of tumor associated antigens including CD20, BCMA, and HER2). The composition can be formulated for use in a variety of drug delivery systems. One or more physiologically acceptable excipients or carriers can also be included in the composition for proper formulation. Suitable formulations for use in the present disclosure are found in Remington's Pharmaceutical Sciences, Mack Publishing Company, Philadelphia, Pa., 17th ed., 1985. For a brief review of methods for drug delivery, see, e.g., Langer (Science 249:1527-1533, 1990).

The intravenous drug delivery formulation of the present disclosure may be contained in a bag, a pen, or a syringe. In certain embodiments, the bag may be connected to a channel comprising a tube and/or a needle. In certain embodiments, the formulation may be a lyophilized formulation or a liquid formulation. In certain embodiments, the formulation may freeze-dried (lyophilized) and contained in about 12-60 vials. In certain embodiments, the formulation may be freeze-dried and 45 mg of the freeze-dried formulation may be contained in one vial. In certain embodiments, the about 40 mg—about 100 mg of freeze-dried formulation may be contained in one vial. In certain embodiments, freeze dried formulation from 12, 27, or 45 vials are combined to obtained a therapeutic dose of the protein in the intravenous drug formulation. In certain embodiments, the formulation may be a liquid formulation and stored as about 250 mg/vial to about 1000 mg/vial. In certain embodiments, the formulation may be a liquid formulation and stored as about 600 mg/vial. In certain embodiments, the formulation may be a liquid formulation and stored as about 250 mg/vial.

This present disclosure could exist in a liquid aqueous pharmaceutical formulation including a therapeutically effective amount of the protein in a buffered solution forming a formulation.

These compositions may be sterilized by conventional sterilization techniques, or may be sterile filtered. The resulting aqueous solutions may be packaged for use as-is, or lyophilized, the lyophilized preparation being combined with a sterile aqueous carrier prior to administration. The pH of the preparations typically will be between 3 and 11, more preferably between 5 and 9 or between 6 and 8, and most preferably between 7 and 8, such as 7 to 7.5. The resulting compositions in solid form may be packaged in multiple single dose units, each containing a fixed amount of the above-mentioned agent or agents. The composition in solid form can also be packaged in a container for a flexible quantity.

In certain embodiments, the present disclosure provides a formulation with an extended shelf life including the protein of the present disclosure, in combination with mannitol, citric acid monohydrate, sodium citrate, disodium phosphate dihydrate, sodium dihydrogen phosphate dihydrate, sodium chloride, polysorbate 80, water, and sodium hydroxide.

In certain embodiments, an aqueous formulation is prepared including the protein of the present disclosure in a pH-buffered solution. The buffer of this invention may have a pH ranging from about 4 to about 8, e.g., from about 4.5 to about 6.0, or from about 4.8 to about 5.5, or may have a pH of about 5.0 to about 5.2. Ranges intermediate to the above recited pH's are also intended to be part of this disclosure. For example, ranges of values using a combination of any of the above recited values as upper and/or lower limits are intended to be included. Examples of buffers that will control the pH within this range include acetate (e.g. sodium acetate), succinate (such as sodium succinate), gluconate, histidine, citrate and other organic acid buffers.

In certain embodiments, the formulation includes a buffer system which contains citrate and phosphate to maintain the pH in a range of about 4 to about 8. In certain embodiments the pH range may be from about 4.5 to about 6.0, or from about pH 4.8 to about 5.5, or in a pH range of about 5.0 to about 5.2. In certain embodiments, the buffer system includes citric acid monohydrate, sodium citrate, disodium phosphate dihydrate, and/or sodium dihydrogen phosphate dihydrate. In certain embodiments, the buffer system includes about 1.3 mg/ml of citric acid (e.g., 1.305 mg/ml), about 0.3 mg/ml of sodium citrate (e.g., 0.305 mg/ml), about 1.5 mg/ml of disodium phosphate dihydrate (e.g. 1.53 mg/ml), about 0.9 mg/ml of sodium dihydrogen phosphate dihydrate (e.g., 0.86), and about 6.2 mg/ml of sodium chloride (e.g., 6.165 mg/ml). In certain embodiments, the buffer system includes 1-1.5 mg/ml of citric acid, 0.25 to 0.5 mg/ml of sodium citrate, 1.25 to 1.75 mg/ml of disodium phosphate dihydrate, 0.7 to 1.1 mg/ml of sodium dihydrogen phosphate dihydrate, and 6.0 to 6.4 mg/ml of sodium chloride. In certain embodiments, the pH of the formulation is adjusted with sodium hydroxide.

A polyol, which acts as a tonicifier and may stabilize the antibody, may also be included in the formulation. The polyol is added to the formulation in an amount which may vary with respect to the desired isotonicity of the formulation. In certain embodiments, the aqueous formulation may be isotonic. The amount of polyol added may also be altered with respect to the molecular weight of the polyol. For example, a lower amount of a monosaccharide (e.g. mannitol) may be added, compared to a disaccharide (such as trehalose). In certain embodiments, the polyol which may be used in the formulation as a tonicity agent is mannitol. In certain embodiments, the mannitol concentration may be about 5 to about 20 mg/ml. In certain embodiments, the concentration of mannitol may be about 7.5 to 15 mg/ml. In certain embodiments, the concentration of mannitol may be about 10-14 mg/ml. In certain embodiments, the concentration of mannitol may be about 12 mg/ml. In certain embodiments, the polyol sorbitol may be included in the formulation.

A detergent or surfactant may also be added to the formulation. Exemplary detergents include nonionic detergents such as polysorbates (e.g. polysorbates 20, 80 etc.) or poloxamers (e.g., poloxamer 188). The amount of detergent added is such that it reduces aggregation of the formulated antibody and/or minimizes the formation of particulates in the formulation and/or reduces adsorption. In certain embodiments, the formulation may include a surfactant which is a polysorbate. In certain embodiments, the formulation may contain the detergent polysorbate 80 or Tween 80. Tween 80 is a term used to describe polyoxyethylene (20) sorbitanmonooleate (see Fiedler, Lexikon der Hifsstoffe, Editio Cantor Verlag Aulendorf, 4th edi., 1996). In certain embodiments, the formulation may contain between about 0.1 mg/mL and about 10 mg/mL of polysorbate 80, or between about 0.5 mg/mL and about 5 mg/mL. In certain embodiments, about 0.1% polysorbate 80 may be added in the formulation.

In embodiments, the protein product of the present disclosure is formulated as a liquid formulation. The liquid formulation may be presented at a 10 mg/mL concentration in eithera USP/Ph Eur type I 50R vial closed with a rubber stopper and sealed with an aluminum crimp seal closure. The stopper may be made of elastomer complying with USP and Ph Eur. In certain embodiments vials may be filled with 61.2 mL of the protein product solution in order to allow an extractable volume of 60 mL. In certain embodiments, the liquid formulation may be diluted with 0.9% saline solution.

In certain embodiments, the liquid formulation of the disclosure may be prepared as a 10 mg/mL concentration solution in combination with a sugar at stabilizing levels. In certain embodiments the liquid formulation may be prepared in an aqueous carrier. In certain embodiments, a stabilizer may be added in an amount no greater than that which may result in a viscosity undesirable or unsuitable for intravenous administration. In certain embodiments, the sugar may be disaccharides, e.g., sucrose. In certain embodiments, the liquid formulation may also include one or more of a buffering agent, a surfactant, and a preservative.

In certain embodiments, the pH of the liquid formulation may be set by addition of a pharmaceutically acceptable acid and/or base. In certain embodiments, the pharmaceutically acceptable acid may be hydrochloric acid. In certain embodiments, the base may be sodium hydroxide.

In addition to aggregation, deamidation is a common product variant of peptides and proteins that may occur during fermentation, harvest/cell clarification, purification, drug substance/drug product storage and during sample analysis. Deamidation is the loss of $NH_3$ from a protein forming a succinimide intermediate that can undergo hydrolysis. The succinimide intermediate results in a 17 daltons mass decrease of the parent peptide. The subsequent hydrolysis results in an 18 daltons mass increase. Isolation of the succinimide intermediate is difficult due to instability under aqueous conditions. As such, deamidation is typically detectable as a 1 dalton mass increase. Deamidation of an asparagine results in either aspartic or isoaspartic acid. The parameters affecting the rate of deamidation include pH, temperature, solvent dielectric constant, ionic strength, primary sequence, local polypeptide conformation and tertiary structure. The amino acid residues adjacent to Asn in the peptide chain affect deamidation rates. Gly and Ser following an Asn in protein sequences results in a higher susceptibility to deamidation.

In certain embodiments, the liquid formulation of the present disclosure may be preserved under conditions of pH and humidity to prevent deamination of the protein product.

The aqueous carrier of interest herein is one which is pharmaceutically acceptable (safe and non-toxic for administration to a human) and is useful for the preparation of a liquid formulation. Illustrative carriers include sterile water for injection (SWFI), bacteriostatic water for injection (BWFI), a pH buffered solution (e.g. phosphate-buffered saline), sterile saline solution, Ringer's solution or dextrose solution.

A preservative may be optionally added to the formulations herein to reduce bacterial action. The addition of a preservative may, for example, facilitate the production of a multi-use (multiple-dose) formulation.

Intravenous (IV) formulations may be the preferred administration route in particular instances, such as when a patient is in the hospital after transplantation receiving all drugs via the IV route. In certain embodiments, the liquid formulation is diluted with 0.9% Sodium Chloride solution before administration. In certain embodiments, the diluted drug product for injection is isotonic and suitable for administration by intravenous infusion.

In certain embodiments, a salt or buffer components may be added in an amount of 10 mM-200 mM. The salts and/or buffers are pharmaceutically acceptable and are derived from various known acids (inorganic and organic) with "base forming" metals or amines. In certain embodiments, the buffer may be phosphate buffer. In certain embodiments, the buffer may be glycinate, carbonate, citrate buffers, in which case, sodium, potassium or ammonium ions can serve as counterion.

A preservative may be optionally added to the formulations herein to reduce bacterial action. The addition of a preservative may, for example, facilitate the production of a multi-use (multiple-dose) formulation.

The aqueous carrier of interest herein is one which is pharmaceutically acceptable (safe and non-toxic for administration to a human) and is useful for the preparation of a liquid formulation. Illustrative carriers include sterile water for injection (SWFI), bacteriostatic water for injection (BWFI), a pH buffered solution (e.g. phosphate-buffered saline), sterile saline solution, Ringer's solution or dextrose solution.

This present disclosure could exist in a lyophilized formulation including the proteins and a lyoprotectant. The lyoprotectant may be sugar, e.g., disaccharides. In certain embodiments, the lycoprotectant may be sucrose or maltose. The lyophilized formulation may also include one or more of a buffering agent, a surfactant, a bulking agent, and/or a preservative.

The amount of sucrose or maltose useful for stabilization of the lyophilized drug product may be in a weight ratio of at least 1:2 protein to sucrose or maltose. In certain embodiments, the protein to sucrose or maltose weight ratio may be of from 1:2 to 1:5.

In certain embodiments, the pH of the formulation, prior to lyophilization, may be set by addition of a pharmaceutically acceptable acid and/or base. In certain embodiments the pharmaceutically acceptable acid may be hydrochloric acid. In certain embodiments, the pharmaceutically acceptable base may be sodium hydroxide.

Before lyophilization, the pH of the solution containing the protein of the present disclosure may be adjusted between 6 to 8. In certain embodiments, the pH range for the lyophilized drug product may be from 7 to 8.

In certain embodiments, a salt or buffer components may be added in an amount of 10 mM-200 mM. The salts and/or buffers are pharmaceutically acceptable and are derived from various known acids (inorganic and organic) with "base forming" metals or amines. In certain embodiments, the buffer may be phosphate buffer. In certain embodiments, the buffer may be glycinate, carbonate, citrate buffers, in which case, sodium, potassium or ammonium ions can serve as counterion.

In certain embodiments, a "bulking agent" may be added. A "bulking agent" is a compound which adds mass to a lyophilized mixture and contributes to the physical structure of the lyophilized cake (e.g., facilitates the production of an essentially uniform lyophilized cake which maintains an open pore structure). Illustrative bulking agents include mannitol, glycine, polyethylene glycol and sorbitol. The lyophilized formulations of the present invention may contain such bulking agents.

A preservative may be optionally added to the formulations herein to reduce bacterial action. The addition of a preservative may, for example, facilitate the production of a multi-use (multiple-dose) formulation.

In certain embodiments, the lyophilized drug product may be constituted with an aqueous carrier. The aqueous carrier of interest herein is one which is pharmaceutically acceptable (e.g., safe and non-toxic for administration to a human) and is useful for the preparation of a liquid formulation, after lyophilization. Illustrative diluents include sterile water for injection (SWFI), bacteriostatic water for injection (BWFI), a pH buffered solution (e.g. phosphate-buffered saline), sterile saline solution, Ringer's solution or dextrose solution.

In certain embodiments, the lyophilized drug product of the current disclosure is reconstituted with either Sterile Water for Injection, USP (SWFI) or 0.9% Sodium Chloride Injection, USP. During reconstitution, the lyophilized powder dissolves into a solution.

In certain embodiments, the lyophilized protein product of the instant disclosure is constituted to about 4.5 mL water for injection and diluted with 0.9% saline solution (sodium chloride solution).

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The specific dose can be a uniform dose for each patient, for example, 50-5000 mg of protein. Alternatively, a patient's dose can be tailored to the approximate body weight or surface area of the patient. Other factors in determining the appropriate dosage can include the disease or condition to be treated or prevented, the severity of the disease, the route of administration, and the age, sex and medical condition of the patient. Further refinement of the calculations necessary to determine the appropriate dosage for treatment is routinely made by those skilled in the art, especially in light of the dosage information and assays disclosed herein. The dosage can also be determined through the use of known assays for determining dosages used in conjunction with appropriate dose-response data. An individual patient's dosage can be adjusted as the progress of the disease is monitored. Blood levels of the targetable construct or complex in a patient can be measured to see if the dosage needs to be adjusted to reach or maintain an effective concentration. Pharmacogenomics may be used to determine which targetable constructs and/or complexes, and dosages thereof, are most likely to be effective for a given individual (Schmitz et al., *Clinica Chimica Acta* 308: 43-53, 2001; Steimer et al., *Clinica Chimica Acta* 308: 33-41, 2001).

In general, dosages based on body weight are from about 0.01 µg to about 100 mg per kg of body weight, such as about 0.01 µg to about 100 mg/kg of body weight, about 0.01 ng to about 50 mg/kg of body weight, about 0.01 µg to about 10 mg/kg of body weight, about 0.01 µg to about 1 mg/kg of body weight, about 0.01 µg to about 100 µg/kg of body weight, about 0.01 µg to about 50 µg/kg of body weight, about 0.01 µg to about 10 µg/kg of body weight, about 0.01 µg to about 1 µg/kg of body weight, about 0.01 µg to about 0.1 µg/kg of body weight, about 0.1 µg to about 100 mg/kg of body weight, about 0.1 µg to about 50 mg/kg of body weight, about 0.1 µg to about 10 mg/kg of body weight, about 0.1 µg to about 1 mg/kg of body weight, about 0.1 µg to about 100 µg/kg of body weight, about 0.1 µg to about 10 µg/kg of body weight, about 0.1 µg to about 1 µg/kg of body weight, about 1 µg to about 100 mg/kg of body weight, about 1 µg to about 50 mg/kg of body weight, about 1 µg to about 10 mg/kg of body weight, about 1 µg to about 1 mg/kg of body weight, about 1 µg to about 100 µg/kg of body weight, about 1 µg to about 50 µg/kg of body weight, about 1 µg to about 10 µg/kg of body weight, about 10 µg to about 100 mg/kg of body weight, about 10 µg to about 50 mg/kg of body weight, about 10 µg to about 10 mg/kg of body weight, about 10 ng to about 1 mg/kg of body weight, about 10 μg to about 100 μg/kg of body weight, about 10 μg to about 50 μg/kg of body weight, about 50 μg to about 100 mg/kg of body weight, about 50 μg to about 50 mg/kg of body weight, about 50 μg to about 10 mg/kg of body weight, about 50 μg to about 1 mg/kg of body weight, about 50 μg to about 100 μg/kg of body weight, about 100 μg to about 100 mg/kg of body weight, about 100 μg to about 50 mg/kg of body weight, about 100 μg to about 10 mg/kg of body weight, about 100 μg to about 1 mg/kg of body weight, about 1 mg to about 100 mg/kg of body weight, about 1 mg to about 50 mg/kg of body weight, about 1 mg to about 10 mg/kg of body weight, about 10 mg to about 100 mg/kg of body weight, about 10 mg to about 50 mg/kg of body weight, about 50 mg to about 100 mg/kg of body weight.

Doses may be given once or more times daily, weekly, monthly or yearly, or even once every 2 to 20 years. Persons of ordinary skill in the art can easily estimate repetition rates for dosing based on measured residence times and concentrations of the targetable construct or complex in bodily fluids or tissues. Administration of the present invention could be intravenous, intraarterial, intraperitoneal, intramuscular, subcutaneous, intrapleural, intrathecal, intracavitary, by perfusion through a catheter or by direct intralesional injection. This may be administered once or more times daily, once or more times weekly, once or more times monthly, and once or more times annually.

The description above describes multiple aspects and embodiments of the invention. The patent application specifically contemplates all combinations and permutations of the aspects and embodiments.

EXAMPLES

The invention now being generally described, will be more readily understood by reference to the following examples, which are included merely for purposes of illustration of certain aspects and embodiments of the present invention, and is not intended to limit the invention.

Example 1—NKG2D-Binding Domains Bind to NKG2D

NKG2D-Binding Domains Bind to Purified Recombinant NKG2D

The nucleic acid sequences of human, mouse or cynomolgus NKG2D ectodomains were fused with nucleic acid sequences encoding human IgG1 Fc domains and introduced into mammalian cells to be expressed. After purification, NKG2D-Fc fusion proteins were adsorbed to wells of microplates. After blocking the wells with bovine serum albumin to prevent non-specific binding, NKG2D-binding domains were titrated and added to the wells pre-adsorbed with NKG2D-Fc fusion proteins. Primary antibody binding was detected using a secondary antibody which was conjugated to horseradish peroxidase and specifically recognizes a human kappa light chain to avoid Fc cross-reactivity. 3,3', 5,5'-Tetramethylbenzidine (TMB), a substrate for horseradish peroxidase, was added to the wells to visualize the binding signal, whose absorbance was measured at 450 nM and corrected at 540 nM. An NKG2D-binding domain clone, an isotype control or a positive control (selected from SEQ ID NO: 45-48, or anti-mouse NKG2D clones MI-6 and CX-5 available at eBioscience) was added to each well.

Figure 14:
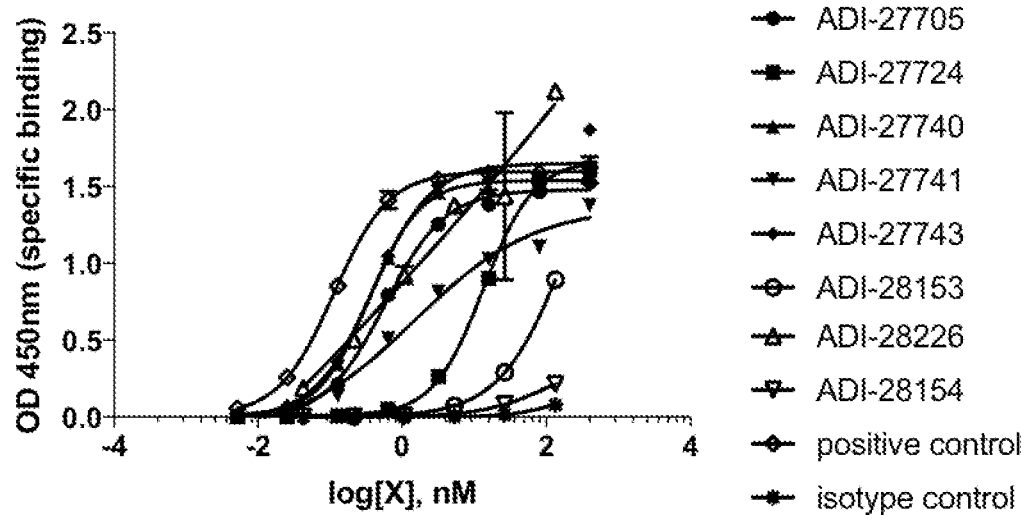
FIG. 14 is a graph demonstrating the binding affinity of NKG2D-binding domains (listed as clones) to human recombinant NKG2D in an ELISA assay.
Figure 15:
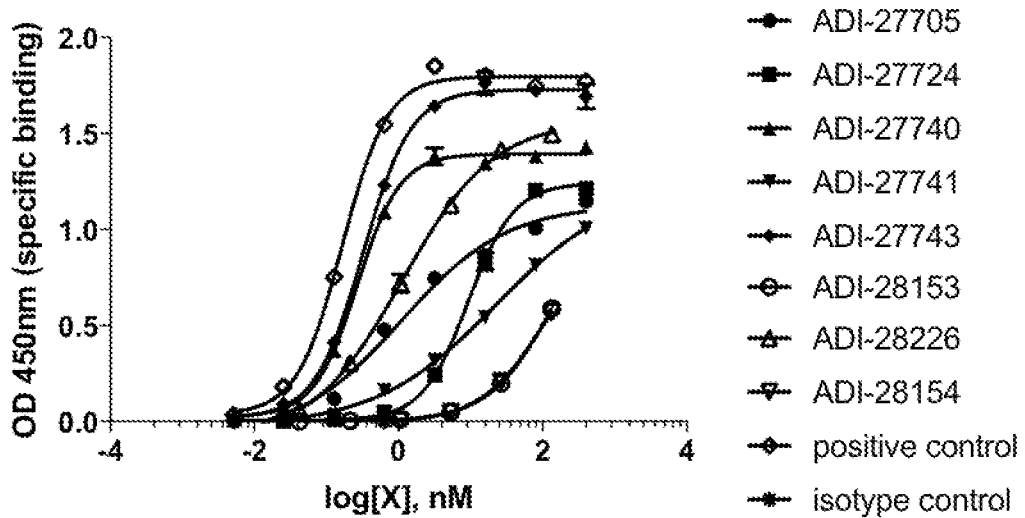
FIG. 15 is a graph demonstrating the binding affinity of NKG2D-binding domains (listed as clones) to cynomolgus recombinant NKG2D in an ELISA assay.
Figure 16:
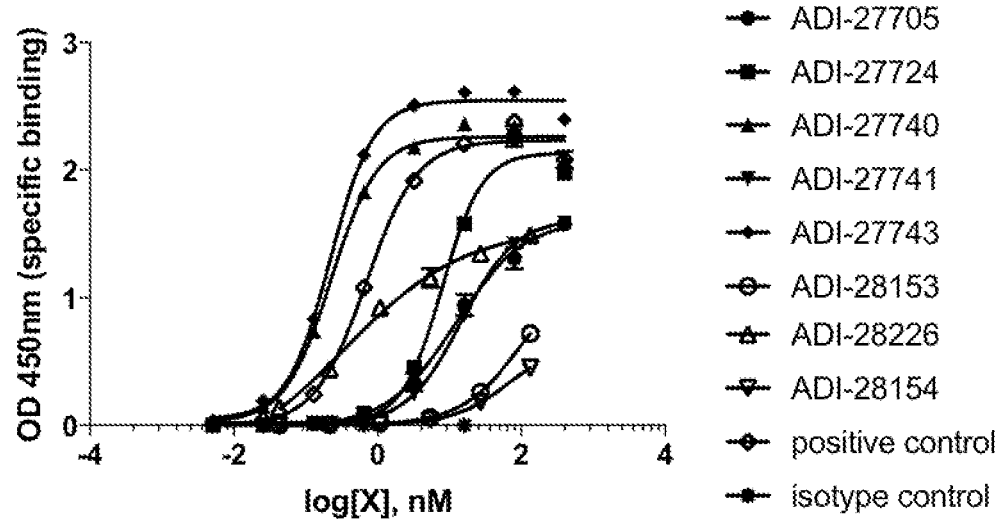
FIG. 16 is a graph demonstrating the binding affinity of NKG2D-binding domains (listed as clones) to mouse recombinant NKG2D in an ELISA assay.

The isotype control showed minimal binding to recombinant NKG2D-Fc proteins, while the positive control bound strongest to the recombinant antigens. NKG2D-binding domains produced by all clones demonstrated binding across human, mouse, and cynomolgus recombinant NKG2D-Fc proteins, although with varying affinities from clone to clone. Generally, each anti-NKG2D clone bound to human (FIG. 14) and cynomolgus (FIG. 15) recombinant NKG2D-Fc with similar affinity, but with lower affinity to mouse (FIG. 16) recombinant NKG2D-Fc.

NKG2D-Binding Domains Bind to Cells Expressing NKG2D

EL4 mouse lymphoma cell lines were engineered to express human or mouse NKG2D-CD3 zeta signaling domain chimeric antigen receptors. An NKG2D-binding clone, an isotype control or a positive control was used at a 100 nM concentration to stain extracellular NKG2D expressed on the EL4 cells. The antibody binding was detected using fluorophore-conjugated anti-human IgG secondary antibodies. Cells were analyzed by flow cytometry, and fold-over-background (FOB) was calculated using the mean fluorescence intensity (MFI) of NKG2D-expressing cells compared to parental EL4 cells.

Figure 17:
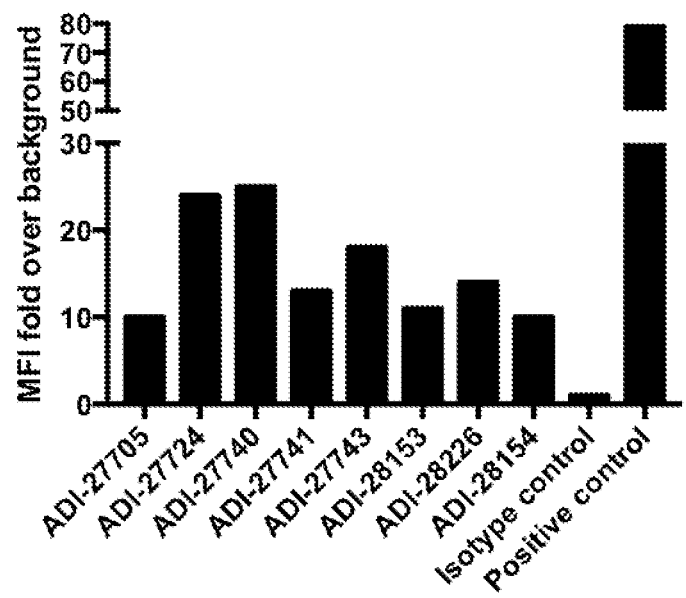
FIG. 17 is a graph demonstrating the binding of NKG2D-binding domains (listed as clones) to EL4 cells expressing human NKG2D by flow cytometry showing mean fluorescence intensity (MFI) fold over background.
Figure 18:
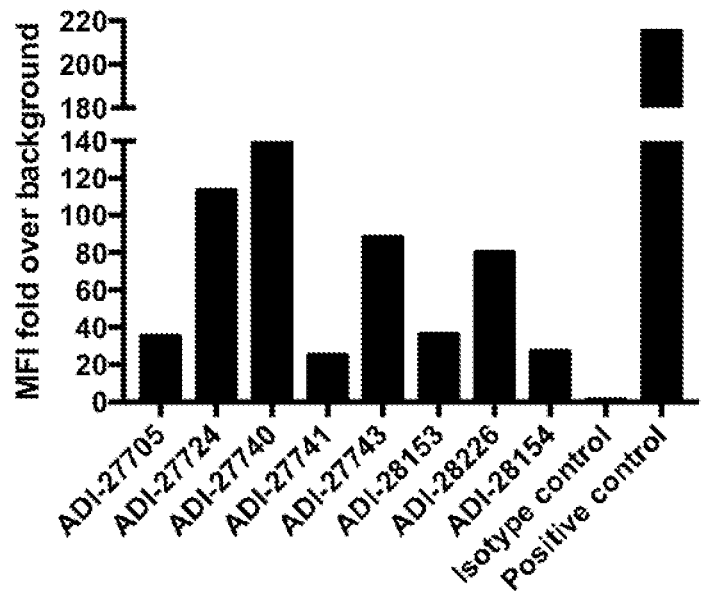
FIG. 18 is a graph demonstrating the binding of NKG2D-binding domains (listed as clones) to EL4 cells expressing mouse NKG2D by flow cytometry showing mean fluorescence intensity (MFI) fold over background.

NKG2D-binding domains produced by all clones bound to EL4 cells expressing human and mouse NKG2D. Positive control antibodies (selected from SEQ ID NO: 45-48, or anti-mouse NKG2D clones MI-6 and CX-5 available at eBioscience) gave the best FOB binding signal. The NKG2D binding affinity for each clone was similar between cells expressing human (FIG. 17) and mouse (FIG. 18) NKG2D.

Example 2—NKG2D-Binding Domains Block Natural Ligand Binding to NKG2D

Competition with ULBP-6

Figure 19:
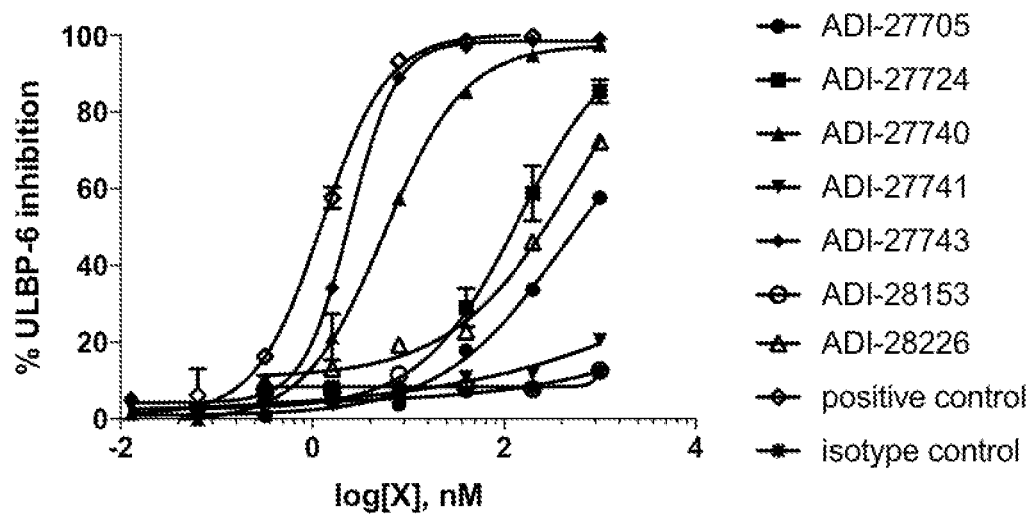
FIG. 19 is a graph demonstrating specific binding affinity of NKG2D-binding domains (listed as clones) to recombinant human NKG2D-Fc by competing with natural ligand ULBP-6.

Recombinant human NKG2D-Fc proteins were adsorbed to wells of a microplate, and the wells were blocked with bovine serum albumin reduce non-specific binding. A saturating concentration of ULBP-6-His-biotin was added to the wells, followed by addition of the NKG2D-binding domain clones. After a 2-hour incubation, wells were washed and ULBP-6-His-biotin that remained bound to the NKG2D-Fc coated wells was detected by streptavidin conjugated to horseradish peroxidase and TMB substrate. Absorbance was measured at 450 nM and corrected at 540 nM. After subtracting background, specific binding of NKG2D-binding domains to the NKG2D-Fc proteins was calculated from the percentage of ULBP-6-His-biotin that was blocked from binding to the NKG2D-Fc proteins in wells. The positive control antibody (selected from SEQ ID NO: 45-48) and various NKG2D-binding domains blocked ULBP-6 binding to NKG2D, while isotype control showed little competition with ULBP-6 (FIG. 19).

Competition With MICA

Figure 20:
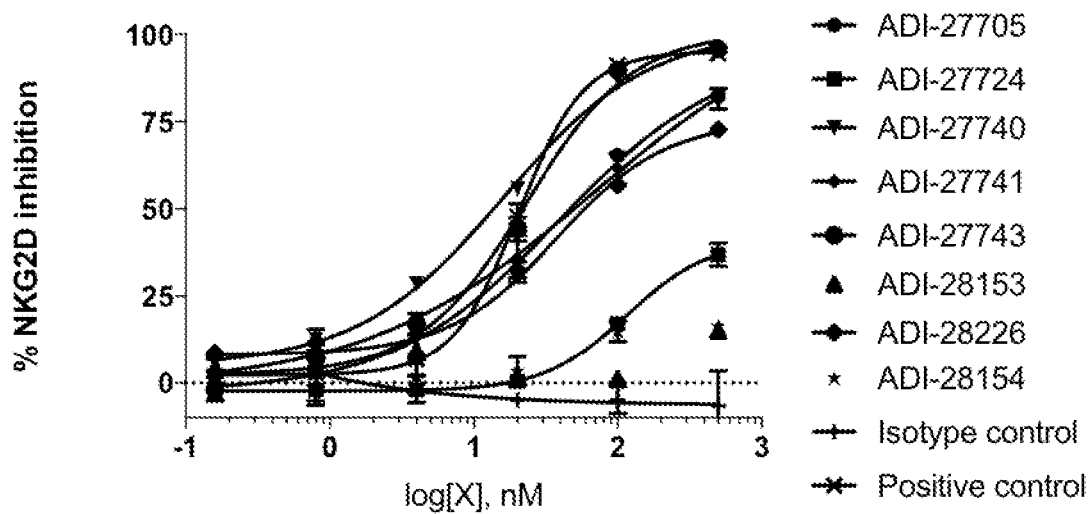
FIG. 20 is a graph demonstrating specific binding affinity of NKG2D-binding domains (listed as clones) to recombinant human NKG2D-Fc by competing with natural ligand MICA.

Recombinant human MICA-Fc proteins were adsorbed to wells of a microplate, and the wells were blocked with bovine serum albumin to reduce non-specific binding. NKG2D-Fc-biotin was added to wells followed by NKG2D-binding domains. After incubation and washing, NKG2D-Fc-biotin that remained bound to MICA-Fc coated wells was detected using streptavidin-HRP and TMB substrate. Absorbance was measured at 450 nM and corrected at 540 nM. After subtracting background, specific binding of NKG2D-binding domains to the NKG2D-Fc proteins was calculated from the percentage of NKG2D-Fc-biotin that was blocked from binding to the MICA-Fc coated wells. The positive control antibody (selected from SEQ ID NO: 45-48) and various NKG2D-binding domains blocked MICA binding to NKG2D, while isotype control showed little competition with MICA (FIG. 20).

Competition with Rae-1 Delta

Figure 21:
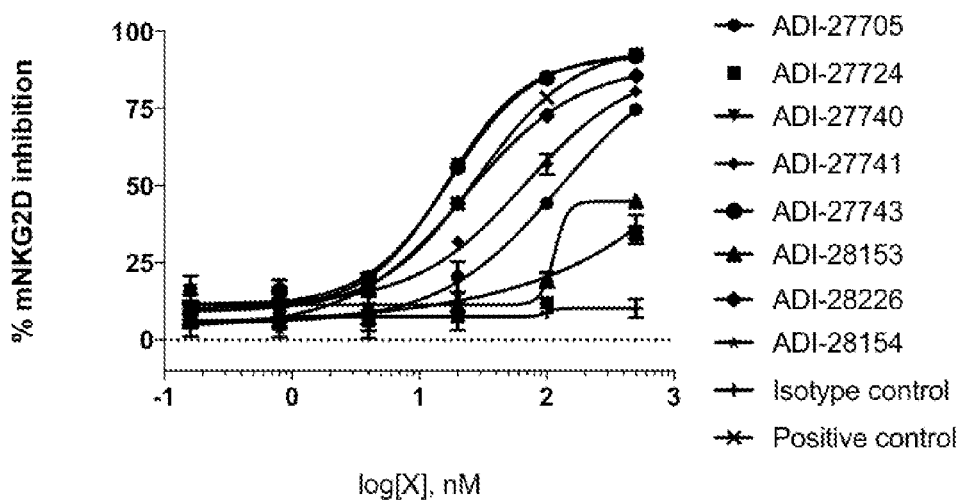
FIG. 21 is a graph demonstrating specific binding affinity of NKG2D-binding domains (listed as clones) to recombinant mouse NKG2D-Fc by competing with natural ligand Rae-1 delta.

Recombinant mouse Rae-1delta-Fc (purchased from R&D Systems) was adsorbed to wells of a microplate, and the wells were blocked with bovine serum albumin to reduce non-specific binding. Mouse NKG2D-Fc-biotin was added to the wells followed by NKG2D-binding domains. After incubation and washing, NKG2D-Fc-biotin that remained bound to Rae-1delta-Fc coated wells was detected using streptavidin-HRP and TMB substrate. Absorbance was measured at 450 nM and corrected at 540 nM. After subtracting background, specific binding of NKG2D-binding domains to the NKG2D-Fc proteins was calculated from the percentage of NKG2D-Fc-biotin that was blocked from binding to the Rae-1delta-Fc coated wells. The positive control (selected from SEQ ID NO: 45-48, or anti-mouse NKG2D clones MI-6 and CX-5 available at eBioscience) and various NKG2D-binding domain clones blocked Rae-1delta binding to mouse NKG2D, while the isotype control antibody showed little competition with Rae-1delta (FIG. 21).

Example 3—NKG2D-Binding Domain Clones Activate NKG2D

Nucleic acid sequences of human and mouse NKG2D were fused to nucleic acid sequences encoding a CD3 zeta signaling domain to obtain chimeric antigen receptor (CAR) constructs. The NKG2D-CAR constructs were then cloned into a retrovirus vector using Gibson assembly and transfected into expi293 cells for retrovirus production. EL4 cells were infected with viruses containing NKG2D-CAR together with 8 µg/mL polybrene. 24 hours after infection, the expression levels of NKG2D-CAR in the EL4 cells were analyzed by flow cytometry, and clones which express high levels of the NKG2D-CAR on the cell surface were selected.

Figure 22:
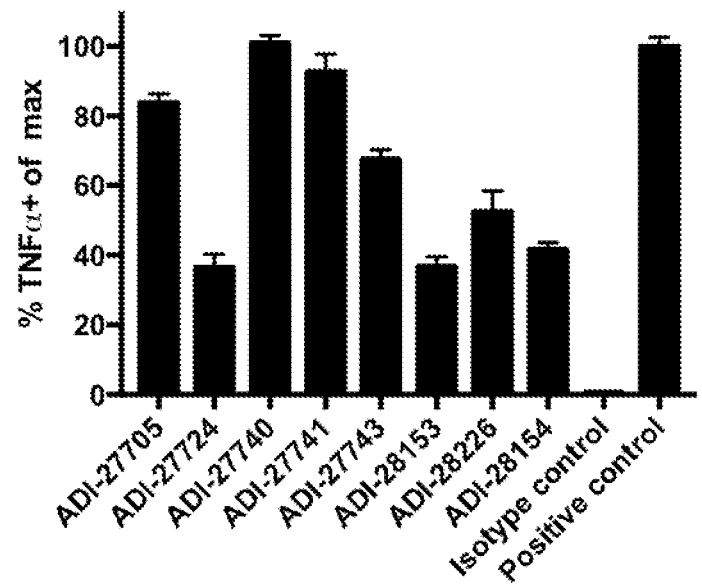
FIG. 22 is a graph showing activation of human NKG2D by NKG2D-binding domains (listed as clones) by quantifying the percentage of TNF-alpha positive cells which express human NKG2D-CD3 zeta fusion proteins.
Figure 23:
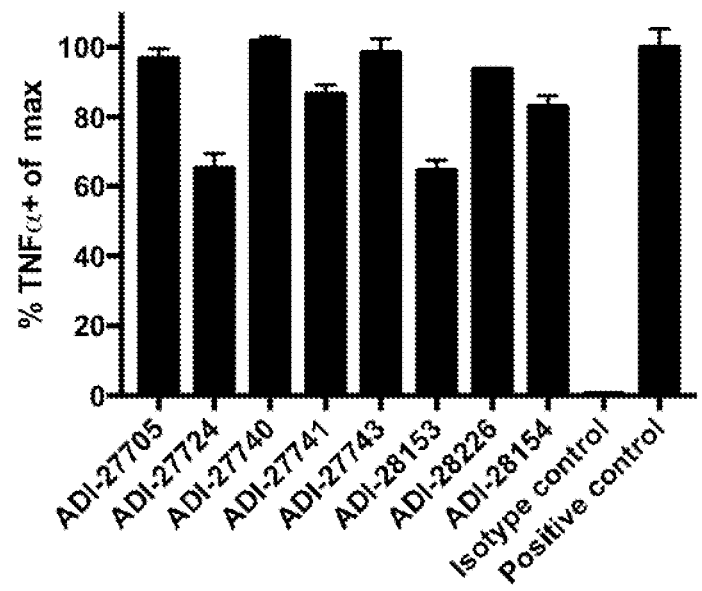
FIG. 23 is a graph showing activation of mouse NKG2D by NKG2D-binding domains (listed as clones) by quantifying the percentage of TNF-alpha positive cells which express mouse NKG2D-CD3 zeta fusion proteins.

To determine whether NKG2D-binding domains activate NKG2D, they were adsorbed to wells of a microplate, and NKG2D-CAR EL4 cells were cultured on the antibody fragment-coated wells for 4 hours in the presence of brefeldin-A and monensin. Intracellular TNF-alpha production, an indicator for NKG2D activation, was assayed by flow cytometry. The percentage of TNF-alpha positive cells was normalized to the cells treated with the positive control. All NKG2D-binding domains activated both human (FIG. 22) and mouse (FIG. 23) NKG2D.

Example 4—NKG2D-Binding Domains Activate NK Cells

Primary Human NK Cells

Figure 24:
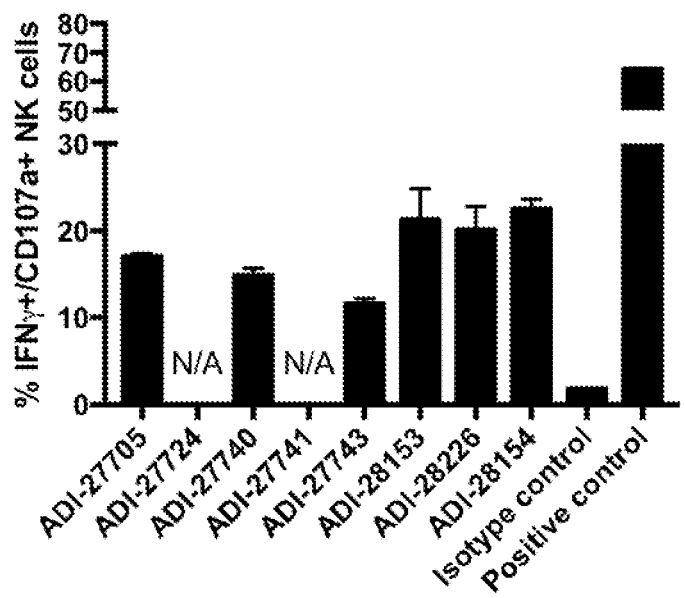
FIG. 24 is a graph showing activation of human NK cells by NKG2D-binding domains (listed as clones).
Figure 25:
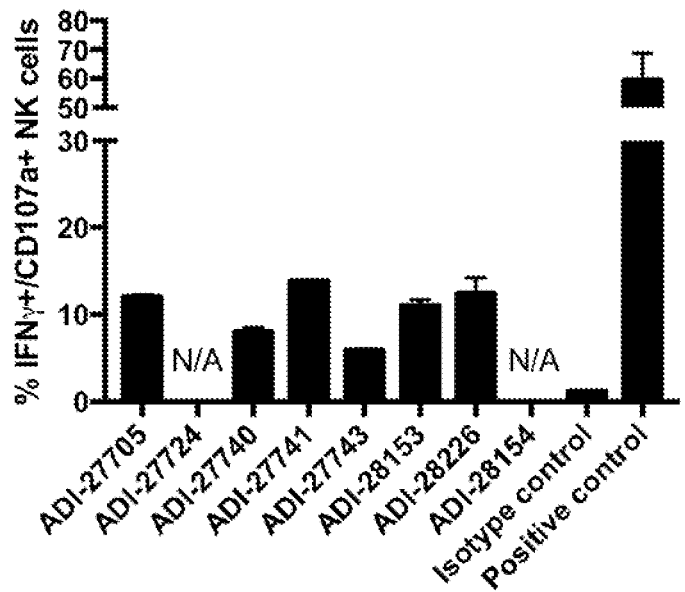
FIG. 25 is a graph showing activation of human NK cells by NKG2D-binding domains (listed as clones).

Peripheral blood mononuclear cells (PBMCs) were isolated from human peripheral blood buffy coats using density gradient centrifugation. NK cells (CD3$^-$CD56$^+$) were isolated using negative selection with magnetic beads from PBMCs, and the purity of the isolated NK cells was typically >95%. Isolated NK cells were then cultured in media containing 100 µg/mL IL-2 for 24-48 hours before they were transferred to the wells of a microplate to which the NKG2D-binding domains were adsorbed, and cultured in the media containing fluorophore-conjugated anti-CD107a antibody, brefeldin-A, and monensin. Following culture, NK cells were assayed by flow cytometry using fluorophore-conjugated antibodies against CD3, CD56 and IFN-gamma. CD107a and IFN-gamma staining were analyzed in CD3$^-$CD56$^+$ cells to assess NK cell activation. The increase in CD107a/IFN-gamma double-positive cells is indicative of better NK cell activation through engagement of two activating receptors rather than one receptor. NKG2D-binding domains and the positive control (selected from SEQ ID NO: 45-48) showed a higher percentage of NK cells becoming CD107a$^+$ and IFN-gamma$^+$ than the isotype control (FIG. 24 & FIG. 25 represent two independent experiments each using a different donor's PBMC for NK cell preparation).

Primary Mouse NK Cells

Figure 26:
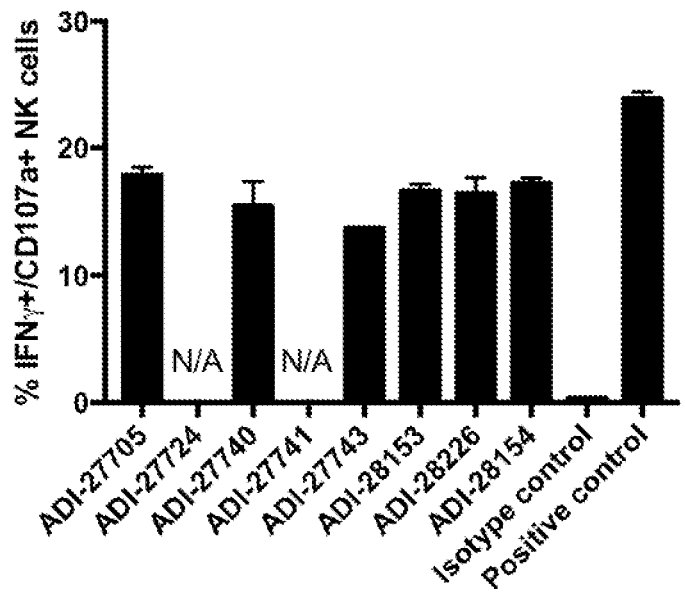
FIG. 26 is a graph showing activation of mouse NK cells by NKG2D-binding domains (listed as clones).
Figure 27:
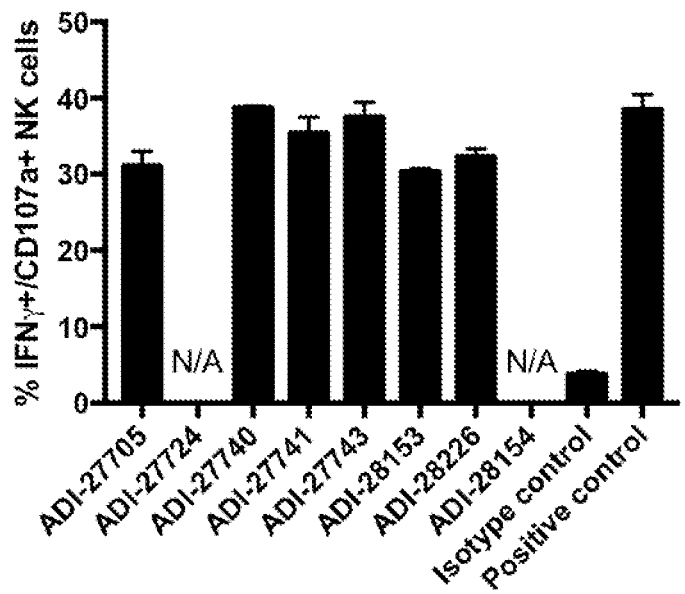
FIG. 27 is a graph showing activation of mouse NK cells by NKG2D-binding domains (listed as clones).

Spleens were obtained from C57Bl/6 mice and crushed through a 70 µm cell strainer to obtain single cell suspension. Cells were pelleted and resuspended in ACK lysis buffer (purchased from Thermo Fisher Scientific #A1049201; 155 mM ammonium chloride, 10 mM potassium bicarbonate, 0.01 mM EDTA) to remove red blood cells. The remaining cells were cultured with 100 µg/mL hIL-2 for 72 hours before being harvested and prepared for NK cell isolation. NK cells (CD3$^-$ NK1.1$^+$) were then isolated from spleen cells using a negative depletion technique with magnetic beads with typically >90% purity. Purified NK cells were cultured in media containing 100 µg/mL mIL-15 for 48 hours before they were transferred to the wells of a microplate to which the NKG2D-binding domains were adsorbed, and cultured in the media containing fluorophore-conjugated anti-CD107a antibody, brefeldin-A, and monensin. Following culture in NKG2D-binding domain-coated wells, NK cells were assayed by flow cytometry using fluorophore-conjugated antibodies against CD3, NK1.1 and IFN-gamma. CD107a and IFN-gamma staining were analyzed in CD3$^-$ NK1.1$^+$ cells to assess NK cell activation. The increase in CD107a/IFN-gamma double-positive cells is indicative of better NK cell activation through engagement of two activating receptors rather than one receptor. NKG2D-binding domains and the positive control (selected from anti-mouse NKG2D clones MI-6 and CX-5 available at eBioscience) showed a higher percentage of NK cells becoming CD107a$^+$ and IFN-gamma$^+$ than the isotype control (FIG. 26 & FIG. 27 represent two independent experiments each using a different mouse for NK cell preparation).

Example 5—NKG2D-Binding Domains Enable Cytotoxicity of Target Tumor Cells

Human and mouse primary NK cell activation assays demonstrate increased cytotoxicity markers on NK cells after incubation with NKG2D-binding domains. To address whether this translates into increased tumor cell lysis, a cell-based assay was utilized where each NKG2D-binding domain was developed into a monospecific antibody. The Fc region was used as one targeting arm, while the Fab region (NKG2D-binding domain) acted as another targeting arm to activate NK cells. THP-1 cells, which are of human origin and express high levels of Fc receptors, were used as a tumor target and a Perkin Elmer DELFIA Cytotoxicity Kit was used. THP-1 cells were labeled with BATDA reagent, and resuspended at $10^5$ cells/mL in culture media. Labeled THP-1 cells were then combined with NKG2D antibodies and isolated mouse NK cells in wells of a microtiter plate at 37° C. for 3 hours. After incubation, 20 µl of the culture supernatant was removed, mixed with 200 µl of Europium solution and incubated with shaking for 15 minutes in the dark. Fluorescence was measured over time by a PheraStar plate reader equipped with a time-resolved fluorescence module (Excitation 337 nm, Emission 620 nm) and specific lysis was calculated according to the kit instructions.

Figure 28:
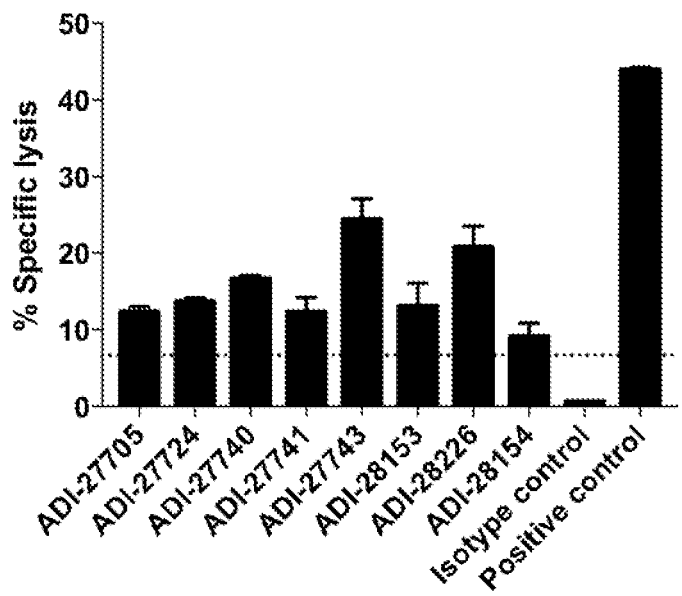
FIG. 28 is a graph showing the cytotoxic effect of NKG2D-binding domains (listed as clones) on tumor cells.

The positive control, ULBP-6—a natural ligand for NKG2D, showed increased specific lysis of THP-1 target cells by mouse NK cells. NKG2D antibodies also increased specific lysis of THP-1 target cells, while isotype control antibody showed reduced specific lysis. The dotted line indicates specific lysis of THP-1 cells by mouse NK cells without antibody added (FIG. 28).

Example 6—NKG2D Antibodies Show High Thermostability

Figure 29:
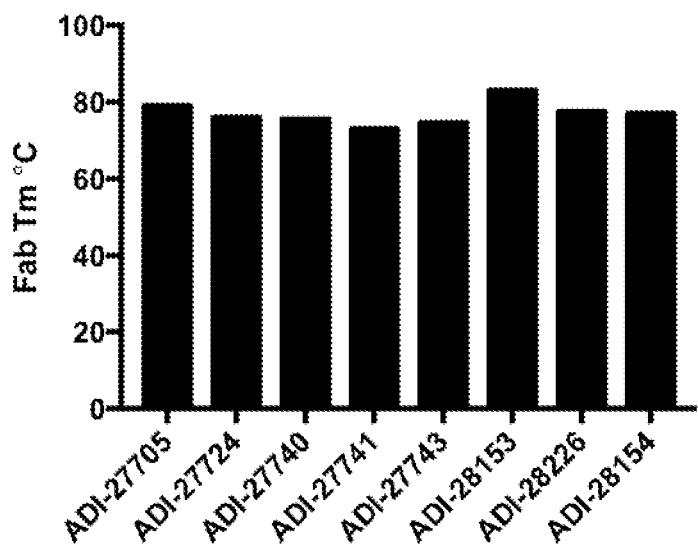
FIG. 29 is a graph showing the melting temperature of NKG2D-binding domains (listed as clones) measured by differential scanning fluorimetry.

Melting temperatures of NKG2D-binding domains were assayed using differential scanning fluorimetry. The extrapolated apparent melting temperatures are high relative to typical IgG1 antibodies (FIG. 29).

Example 7—Multi-Specific Binding Proteins Display Enhanced Ability to Activate NK Cells Peripheral blood mononuclear cells (PBMCs) were isolated from human peripheral blood buffy coats using density gradient centrifugation. NK cells (CD3$^-$CD56$^+$) were isolated using negative selection with magnetic beads from PBMCs, and the purity of the isolated NK cells was typically >95%. Isolated NK cells were then cultured in media containing 100 μg/mL IL-2 for 24-48 hours before they were transferred to the wells of a microplate to which multi-specific and bispecific binding proteins were adsorbed respectively, and cultured in the media containing fluorophore-conjugated anti-CD107a antibody, brefeldin-A, and monensin. Following culture, NK cells were assayed by flow cytometry using fluorophore-conjugated antibodies against CD3, CD56 and IFN-gamma. CD107a and IFN-gamma staining were analyzed in CD3$^-$CD56$^+$ cells to assess NK cell activation. The increase in CD107a/IFN-gamma double-positive cells is indicative of better NK cell activation. AL2.2 is a multi-specific binding protein containing HER2-binding domain (trastuzumab), NKG2D-binding domain (ULBP-6) and a human IgG1 Fc domain. It was made through a controlled Fab-arm exchange reaction (cFAE) starting from trastuzumab homodimer and ULBP-6-Fc homodimer (see Labrijn et al. Nature Protocols 9, 2450-2463). SC2.2 is single chain protein including an scFv derived from trastuzumab, and ULBP-6 (SEQ ID NO:73).

```
                                            SEQ ID NO: 73
MAAAAIPALLLCLPLLFLLFGWSRARRDDPHSLCYDITVIPKFRPGPRWC

AVQGQVDEKTFLHYDCGNKTVTPVSPLGKKLNVTMAWKAQNPVLREVVDI

LTEQLLDIQLENYTPKEPLTLQARMSCEQKAEGHSSGSWQFSIDGQTFLL

FDSEKRMWTTVHPGARKMKEKWENDKDVAMSFHYISMGDCIGWLEDFLMG

MDSTLEPSAGAPLAMSSGTTQLRATATTLILCCLLIILPCFILPGI
```

Figure 30:
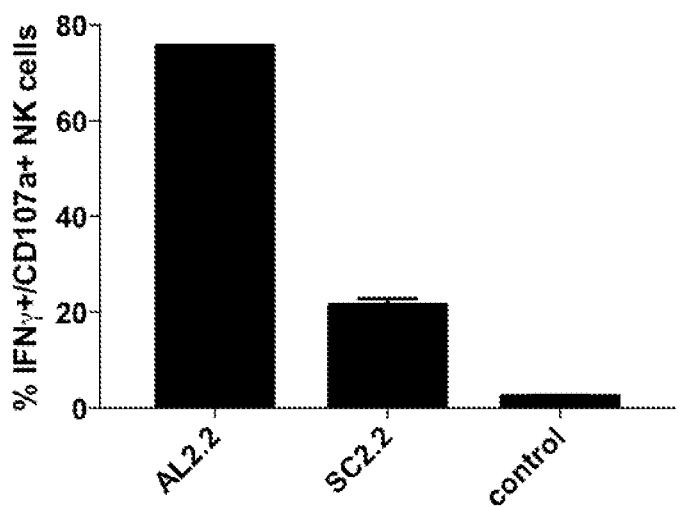
FIG. 30 is a graph showing enhanced activation of human NK cells by multi-specific binding proteins.

Analysis of CD107a and IFN-gamma staining indicated that isotype control IgG showed no activation of NK cells, while a higher percentage of NK cells becoming CD107a$^+$ and IFN-gamma$^+$ after stimulation with a multi-specific binding protein compared with a bispecific protein, demonstrating stronger NK cell activation through engagement of two activating receptors (NKG2D and CD16) rather than just one (NKG2D) (FIG. 30). This increase in NK cell activation is expected to translate into more potent tumor cell killing.

Example 8—Multi-Specific Binding Proteins Display Enhanced Cytotoxicity Towards Target Tumor Cells Primary Human NK Cell Cytotoxicity Assay Peripheral blood mononuclear cells (PBMCs) were isolated from human peripheral blood buffy coats using density gradient centrifugation. NK cells (CD3$^-$CD56$^+$) were isolated using negative selection with magnetic beads from PBMCs, and the purity of the isolated NK cells was typically >95%. NK cells were then cultured overnight in media containing 100 μg/mL IL-2 before used in cytotoxicity assays. The following day NK cells were resuspended at $5 \times 10^5$ cells/mL in fresh culture media. Human breast cancer cell SkBr-3 cells were labeled with BATDA reagent according to Perkin Elmer DELFIA Cytotoxicity Kit and resuspended at $5 \times 10^4$ cells/mL in culture media. Various dilution of the multi-specific binding proteins were made into culture media. NK cells, the labeled SkBr-3 cells and the multi-specific binding proteins were then combined in wells of a microtiter plate and incubated at 37° C. for 3 hours. After incubation, 20 μl of the culture supernatant was removed, mixed with 200 μl of Europium solution and incubated with shaking for 15 minutes in the dark. Fluorescence was measured over time by a PheraStar plate reader equipped with a time-resolved fluorescence module (Excitation 337 nm, Emission 620 nm) and specific lysis was calculated according to the kit instructions. AL0.2 is a multi-specific binding protein containing HER2-binding domain (trastuzumab), NKG2D-binding domain (selected from SEQ ID NO: 1-44)) and a human IgG1 Fc domain. It was made through a controlled Fab-arm exchange reaction (cFAE) starting from trastuzumab homodimer and anti-NKG2D homodimer. AL0.2si is based on AL0.2 and contains an additional D265A mutation in Fc domain which abrogates CD16 binding. Trastuzumab-si is based on Trastuzumab and contains an additional D265A mutation in Fc domain which abrogates CD16 binding. AL2.2 is a multi-specific binding protein containing HER2-binding domain (trastuzumab), NKG2D-binding domain (ULBP-6) and a human IgG1 Fc domain. SC2.2 is single chain protein including an scFv derived from trastuzumab, and ULBP-6.

Figure 31:
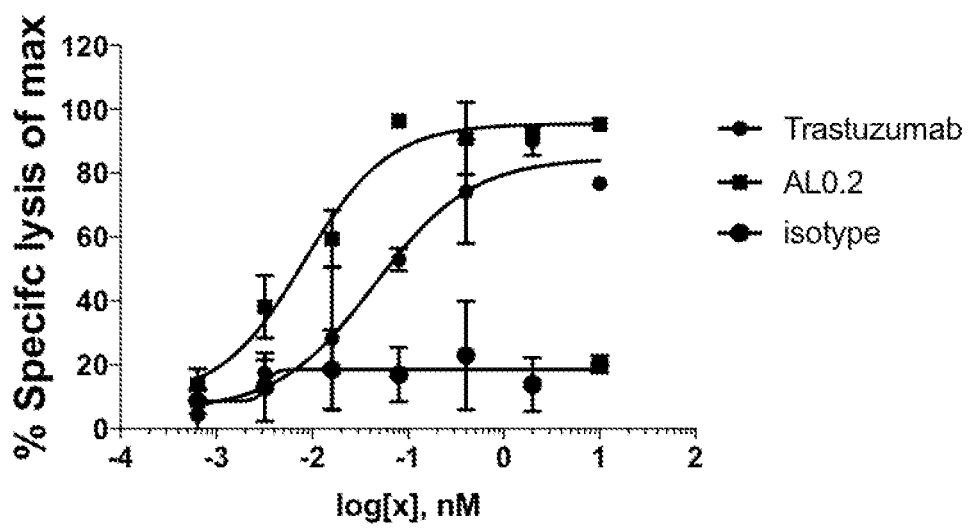
FIG. 31 is a graph showing multi-specific binding proteins induced higher levels of cytotoxicity towards tumor target cells by human NK cells.
Figure 32:
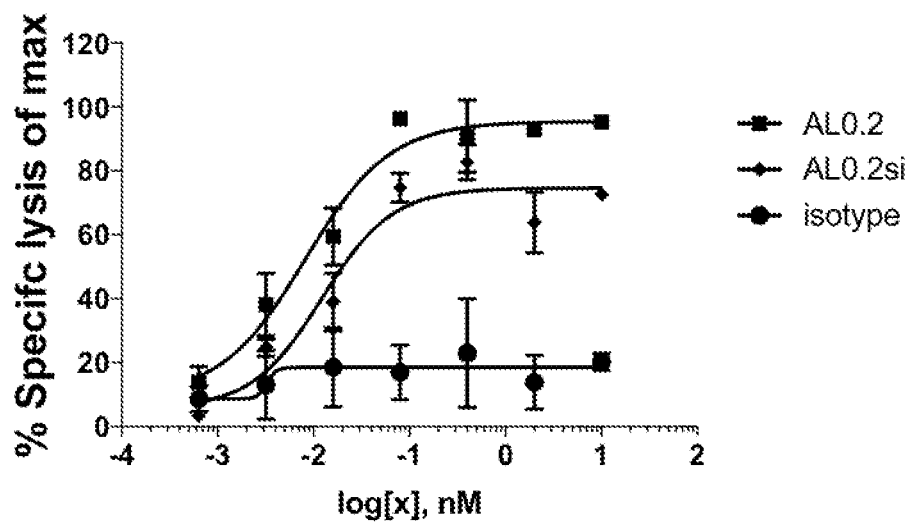
FIG. 32 is a graph showing multi-specific binding proteins induced higher levels of cytotoxicity towards tumor target cells by human NK cells.
Figure 33:
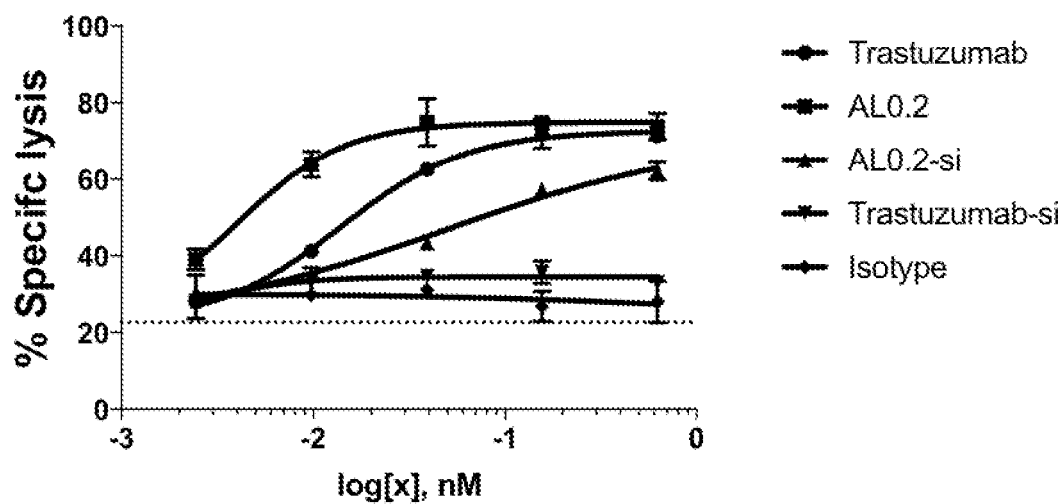
FIG. 33 is a graph showing multi-specific binding proteins induced higher levels of cytotoxicity towards tumor target cells by human NK cells.
Figure 34:
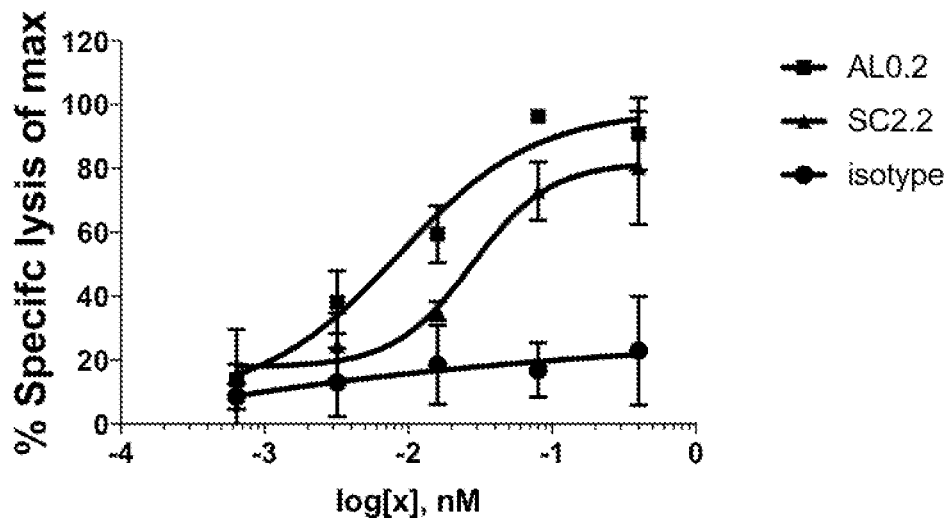
FIG. 34 is a graph showing multi-specific binding proteins induced higher levels of cytotoxicity towards tumor target cells by human NK cells.

AL0.2 showed enhanced lysis of SkBr-3 target cells by human NK cells than trastuzumab in a dose-dependent manner, with a p value of 0.0311 in EC50 (FIG. 31). AL0.2si (FIG. 32) and trastuzumab-si (FIG. 33) showed reduction in both potency and maximum specific lysis of SkBr-3 cells compared to AL0.2, with a p-value of 0.0002, and 0.0001 in EC50 respectively (FIGS. 32-33). In addition, AL0.2 showed enhanced lysis of SkBr-3 cells than SC2.2 in a dose-dependent manner (FIG. 34). Isotype control IgG showed no increase in specific lysis at any of the concentrations tested. Together the data have demonstrated that multi-specific binding proteins engaging 2 activating receptors on NK cells and one tumor antigen, induce more potent killing of tumor cells by human NK cells compared to bispecific proteins engaging one activating receptor on NK cells and one tumor antigen.

Primary Mouse NK Cell Cytotoxicity Assay

Spleens were obtained from C57Bl/6 mice and crushed through a 70 μm cell strainer to obtain single cell suspension. Cells were pelleted and resuspended in ACK lysis buffer (purchased from Thermo Fisher Scientific #A1049201; 155 mM ammonium chloride, 10 mM potassium bicarbonate, 0.01 mM EDTA) to remove red blood cells. The remaining cells were cultured with 100 μg/mL hIL-2 for 72 hours before being harvested and prepared for NK cell isolation. NK cells (CD3⁻ NK1.1⁺) were then isolated from spleen cells using a negative depletion technique with magnetic beads with typically >90% purity. Purified NK cells were cultured in media containing 100 µg/mL mIL-15 for 48 hours before resuspended in culture media at $10^6$ cells/mL for cytotoxic assays. RMA-HER2-dTomato, a mouse tumor cell line engineered to express HER2 and dTomato, and its control counterpart, RMA cells expressing zsGreen were used as targets. The cells were resuspended at $2 \times 10^5$ cells/mL in culture media and seeded into wells of a micro plate at 1:1 ratio. Dilutions of multi-specific protein were made into culture media, and added to the RMA cells together with the NK cells. After incubation overnight at 37° C. with 5% $CO_2$, the percentage of RMA-HER2-dTomato and RMA-zsGreen cells were determined by flow cytometry using the fluorescent reporter to identify the two cells types. Specific target cell death=(1−((% RMA-Ca2T-dTomato cells in treatment group*% RMA-zsGreen cells in control group)/(% RMA-Ca2T-dTomato cells in control group*% RMA-zsGreen cells in treatment group))) *100%.

Figure 35:
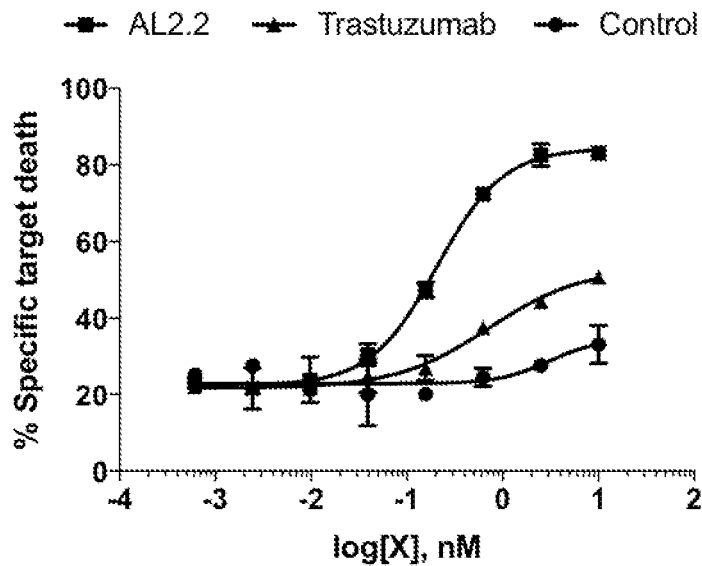
FIG. 35 is a graph showing multi-specific binding proteins induced higher levels of cytotoxicity towards tumor target cells by mouse NK cells.
Figure 36:
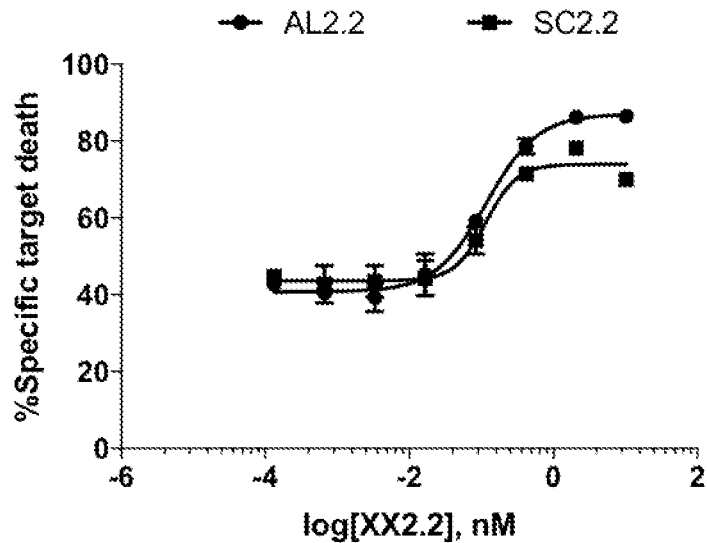
FIG. 36 is a graph showing multi-specific binding proteins induced higher levels of cytotoxicity towards tumor target cells by mouse NK cells.

AL2.2 is more potent in redirecting NK cell responses to tumor targets than SC2.2 (FIG. 36) and trastuzumab (FIG. 35). Control protein showed little impact on specific target death. These data demonstrate the multi-specific binding proteins engaging 2 activating receptors on NK cells and one tumor antigen, induce more potent killing of tumor cells by mouse NK cells compared to bispecific proteins engaging one activating receptor on NK cells and one tumor antigen.

Example 9—Multi-Specific Binding Proteins Bind to NKG2D

EL4 mouse lymphoma cell lines were engineered to express human NKG2D. Trispecific binding proteins (TriNKETs) that each contain an NKG2D-binding domain, a tumor-associated antigen binding domain (such as a CD33-, a HER2-, a CD20-, or a BCMA-binding domain), and an Fc domain that binds to CD16 as shown in FIG. 1, were tested for their affinity to extracellular NKG2D expressed on EL4 cells. The binding of the multi-specific binding proteins to NKG2D was detected using fluorophore-conjugated anti-human IgG secondary antibodies. Cells were analyzed by flow cytometry, and fold-over-background (FOB) was calculated using the mean fluorescence intensity (MFI) of NKG2D-expressing cells compared to parental EL4 cells.

TriNKETs tested include CD33-TriNKET-C26 (ADI-28226 and a CD33-binding domain), CD33-TriNKET-F04 (ADI-29404 and a CD33-binding domain), HER2-TriNKET-C26 (ADI-28226 and a HER2-binding domain), HER2-TriNKET-F04 (ADI-29404 and a HER2-binding domain), CD20-TriNKET-C26 (ADI-28226 and a CD20-binding domain), CD20-TriNKET-F04 (ADI-29404 and a CD20-binding domain), BCMA-TriNKET-C26 (ADI-28226 and a BCMA-binding domain), BCMA-TriNKET-F04 (ADI-29404 and a BCMA-binding domain), BCMA-TriNKET-F43 (ADI-29443 and a BCMA-binding domain), and BCMA-TriNKET-F47 (ADI-29447 and a BCMA-binding domain). The HER2-binding domain used in the tested molecules was composed of a heavy chain variable domain and a light chain variable domain of Trastuzumab. The CD33-binding domain was composed of a heavy chain variable domain and a light chain variable domain listed below.

```
SEQ ID NO: 74:
QVQLVQSGAEVKKPGASVKVSCKASGYTFTDYVVHWVRQAPGQGLEWMG
                            CDR1

YINPYNDGTKYNEKFKGRVTMTRDTSISTAYMELSRLRSDDTAVYYCAR
             CDR2

DYRYEVYGMDYWGQGTLVTVSS
       CDR3

SEQ ID NO: 75:
DIVLTQSPASLAVSPGQRATITCTASSSVNYIHWYQQKPGQPPKLLIY
                         CDR1

DTSKVASGVPARFSGSGSGTDFTLT1NPVEANDTANYYCQQWRSYPLT
CDR1                                     CDR3

FGQGTKLEIK
```

The CD20-binding domain used in the tested molecules was composed of a heavy chain variable domain and a light chain variable domain. The BCMA-binding domain used in the tested molecules was composed of a heavy chain variable domain and light chain variable domain as listed below.

```
EM-801 heavy chain variable domain
(SEQ ID NO: 82):
EVQLLESGGGLVQPGGSLRLSCAASGFTFSSYAMSWVRQAPGKGLEWVS
                             CDR1

AISGSGGSTYYADSVKGRFTISRDNSKNTLYLQMNSLRAEDTAVYYCAK
  CDR2

VLGWFDYWGQGTLVTVSS
    CDR3

EM-801 light chain variable domain
(SEQ ID NO: 83):
EIVLTQSPGTLSLSPGERATLSCRASQSVSSSYLAWYQQKPGQAPRLLI
                        CDR1

YGASSRATGIPDRFSGSGSGTDFTLTISRLEPEDFAVYYCQQYGYPPDFT
CDR2                                     CDR3

FGQGTKVEIK

EM-901 heavy chain variable domain (SEQ ID NO: 76)
EVQLLESGGGLVQPGGSLRLSCAASGFTFSDNAMGWVRQAPGKGLEWVS
                             CDR1

AISGPGSSTYYADSVKGRFTISRDNSKNTLYLQMNSLRAEDTAVYYCAK
  CDR2

VLGWFDYWGQGTLVTVSS
    CDR3

EM-901 light chain variable domain (SEQ ID NO: 77)
EIVLTQSPGTLSLSPGERATLSCRASQSVSDEYLSWYQQKPGQAPRLLI
                        CDR1

HSASTRATGIPDRFSGSGSGTDFTLAISRLEPEDFAVYYCQQYGYPPDFT
CDR2                                     CDR3

FGQGTKVEIK
```

The data show that a TriNKET of the present disclosure binds to NKG2D when the protein includes a tumor antigen-binding domain such as CD33, HER2, CD20, and BCMA.

Example 10—Multi-Specific Binding Proteins Bind to Human Tumor Antigens

Trispecific Binding Proteins Bind to CD33, HER2, CD20 and BCMA

Figure 41:
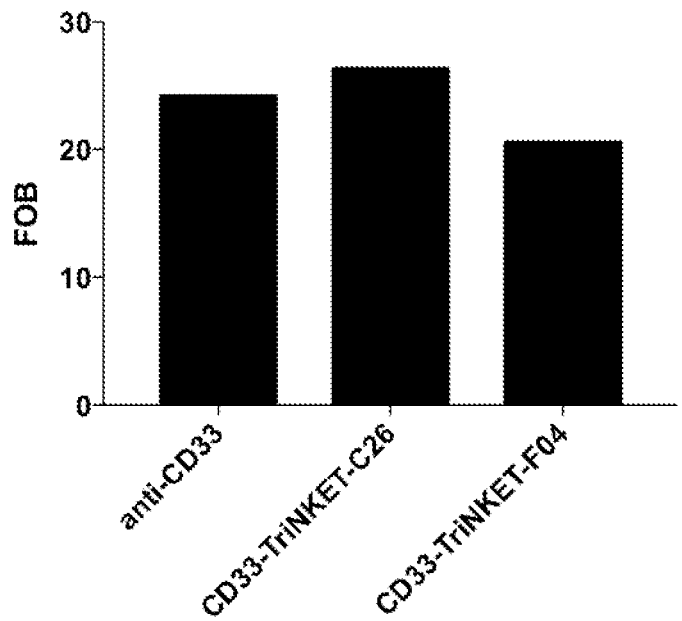
FIG. 41 is a binding profile of CD33-targeting TriNKETs to CD33 expressed on MV4-11 human AML cells.

Human AML cell line MV4-11 expressing CD33 was used to assay the binding of TriNKETs to the tumor associated antigen. TriNKETs and the parental anti-CD33 monoclonal antibody were incubated with the cells, and the binding was detected using fluorophore-conjugated anti-human IgG secondary antibodies. Cells were analyzed by flow cytometry, and fold-over-background (FOB) was calculated using the mean fluorescence intensity (MFI) from TriNKETs and the parental monoclonal anti-CD33 antibody normalized to secondary antibody controls. CD33-TriNKET-C26, and CD33-TriNKET-F04 show comparable levels of binding to CD33 as compared with the parental anti-CD33 antibody (FIG. 41).

Figure 42:
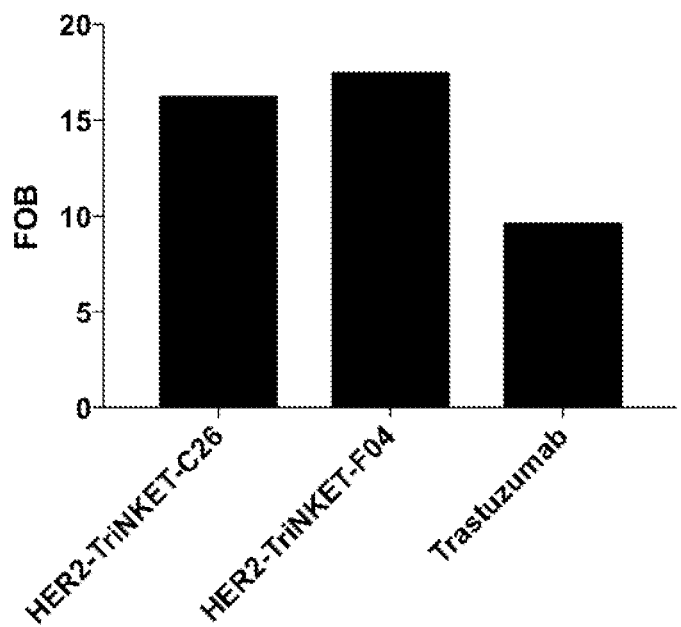
FIG. 42 is a binding profile of HER2-targeting TriNKETs to HER2 expressed on human 786-O renal cell carcinoma cells.

Human cancer cell lines expressing HER2 were used to assay the binding of TriNKETs to the tumor associated antigen. Renal cell carcinoma cell line 786-O expresses low levels of HER2. TriNKETs and optionally the parental anti-HER2 monoclonal antibody (Trastuzumab) were incubated with the cells, and the binding was detected using fluorophore-conjugated anti-human IgG secondary antibodies. Cells were analyzed by flow cytometry, and fold-over-background (FOB) was calculated using the mean fluorescence intensity (MFI) from TriNKETs and Trastuzumab normalized to secondary antibody controls. HER2-TriNKET-C26, and HER2-TriNKET-F04 show comparable levels of binding to HER2 expressed on 786-O cells as compared with Trastuzumab (FIG. 42).

Figure 43:
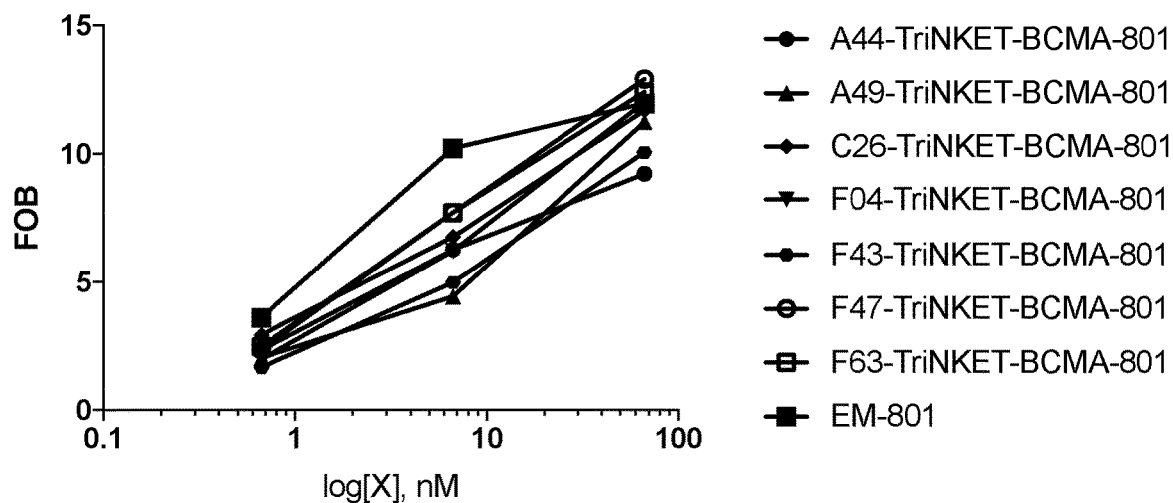
FIG. 43 is a binding profile of BCMA-targeting TriNKETs to BCMA expressed on MM.1S human myeloma cells.

MM.1S human myeloma cells expressing BCMA were used to assay the binding of TriNKETs to the tumor associated antigen BCMA. TriNKETs and optionally the parental anti-BCMA monoclonal antibody (EM-801) were incubated with the cells, and the binding was detected using fluorophore-conjugated anti-human IgG secondary antibodies. Cells were analyzed by flow cytometry, and fold-over-background (FOB) was calculated using the mean fluorescence intensity (MFI) from TriNKETs and EM-801 normalized to secondary antibody controls. C26-TriNKET-BCMA, F04-TriNKET-BCMA, F43-TriNKET-BCMA, and F47-TriNKET-BCMA show comparable levels of binding to BCMA expressed on MM.1S cells as compared with EM-801 (FIG. 43).

Figure 44:
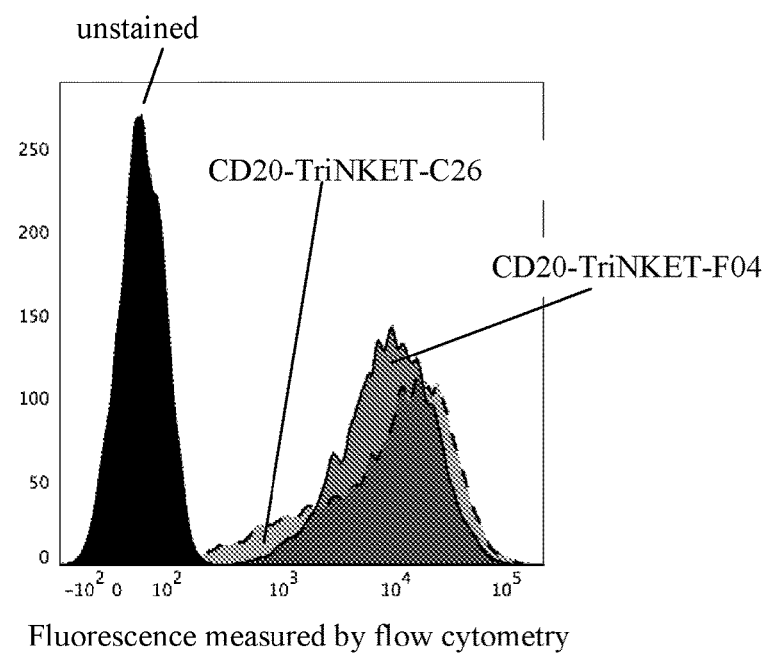
FIG. 44 is a histogram of CD20-targeting TriNKETs that bind to CD20 expressed on Raji human lymphoma cells. Unstained cells were used a negative control for fluorescence signal. Unstained: filled; CD20-TriNKET-F04: solid line; CD20-TriNKET-C26: dashed line.

Raji human lymphoma cells expressing CD20 were used to assay the binding of TriNKETs to the tumor associated antigen CD20. TriNKETs were incubated with the cells, and the binding was detected using fluorophore-conjugated anti-human IgG secondary antibodies. Cells were analyzed by flow cytometry and histogram was plot. As shown in FIG. 44, CD20-TriNKET-C26 and CD20-TriNKET-F04 bind to CD20 equally well.

Example 11—Multi-Specific Binding Proteins Activate NK Cells

Peripheral blood mononuclear cells (PBMCs) were isolated from human peripheral blood buffy coats using density gradient centrifugation. NK cells (CD3⁻CD56⁺) were isolated using negative selection with magnetic beads from PBMCs, and the purity of the isolated NK cells was typically >90%. Isolated NK cells were cultured in media containing 100 μg/mL IL-2 for activation or rested overnight without cytokine. IL-2-activated NK cells were used within 24-48 hours after activation.

Human cancer cells expressing a tumor antigen were harvested and resuspended in culture media at $2\times10^6$ cells/mL. Monoclonal antibodies or TriNKETs targeting the tumor antigen were diluted in culture media. Activated NK cells were harvested, washed, and resuspended at $2\times10^6$ cells/mL in culture media. Cancer cells were then mixed with monoclonal antibodies/TriNKETs and activated NK cells in the presence of IL-2. Brefeldin-A and monensin were also added to the mixed culture to block protein transport out of the cell for intracellular cytokine staining. Fluorophore-conjugated anti-CD107a was added to the mixed culture and the culture was incubated for 4 hours before samples were prepared for FACS analysis using fluorophore-conjugated antibodies against CD3, CD56 and IFN-gamma. CD107a and IFN-gamma staining was analyzed in CD3⁻CD56⁺ cells to assess NK cell activation. The increase in CD107a/IFN-gamma double-positive cells is indicative of better NK cell activation through engagement of two activating receptors rather than one receptor.

TriNKETs mediate activation of human NK cells co-cultured with HER2-expressing SkBr-3 cells (FIG. 47A), Colo201 cells (FIG. 47B), and HCC1954 cells (FIG. 47C) respectively as indicated by an increase of CD107a degranulation and IFN-gamma production. SkBr-3 cells and HCC1954 cells have high levels of surface HER2 expression, and Colo201 has medium HER2 expression. Compared to the monoclonal antibody trastuzumab, TriNKETs show superior activation of human NK cells in the presence of human cancer cells. NK cells alone, NK cells plus SkBr-3 cells are used as negative controls.

Figure 47A:
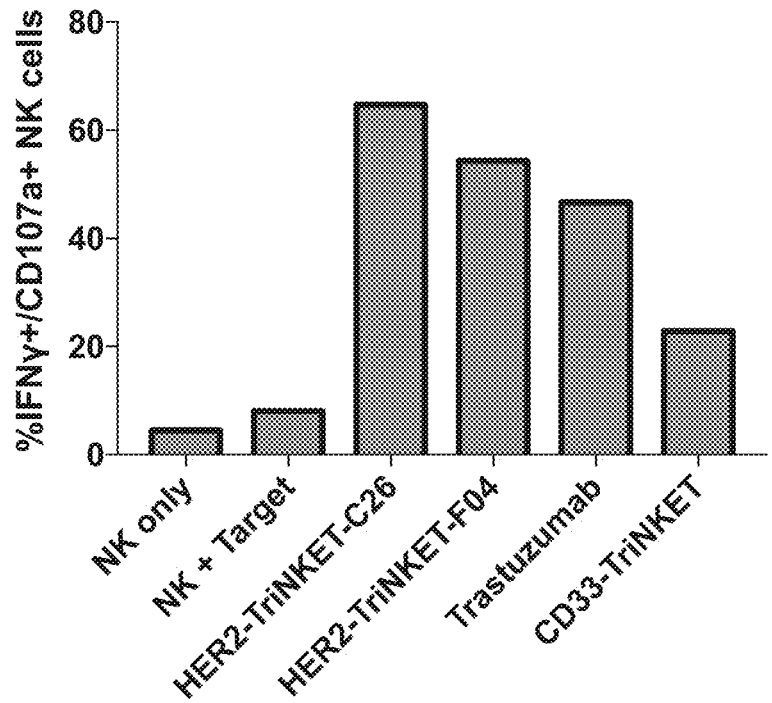
FIGS. 47A-47C are bar graphs demonstrating that TriNKETs and trastuzumab were able to activate primary human NK cells in co-culture with HER2-positive human tumor cells, indicated by an increase in CD107a degranulation and IFNγ cytokine production. Compared to the monoclonal antibody trastuzumab, both TriNKETs showed superior activation of human NK cells with a variety of human HER2 cancer cells.
Figure 47B:
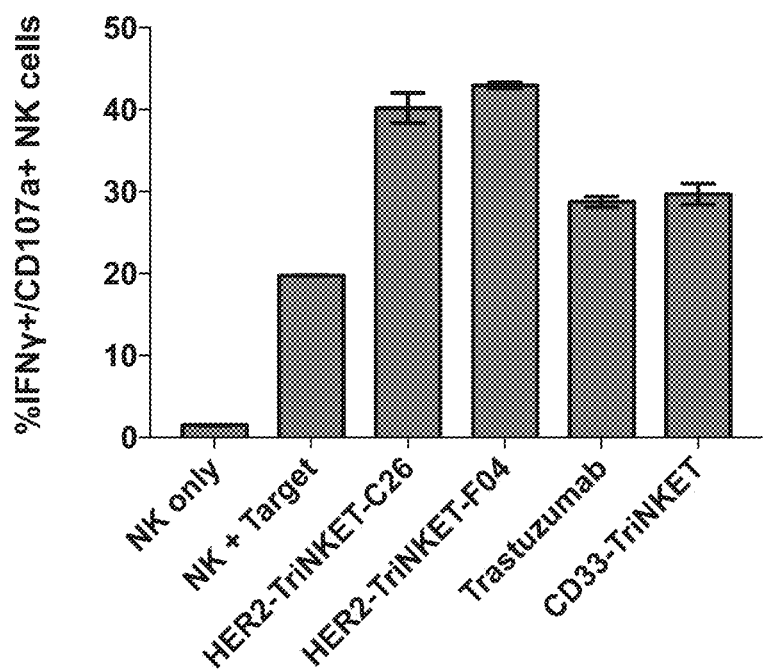
Figure 47C:
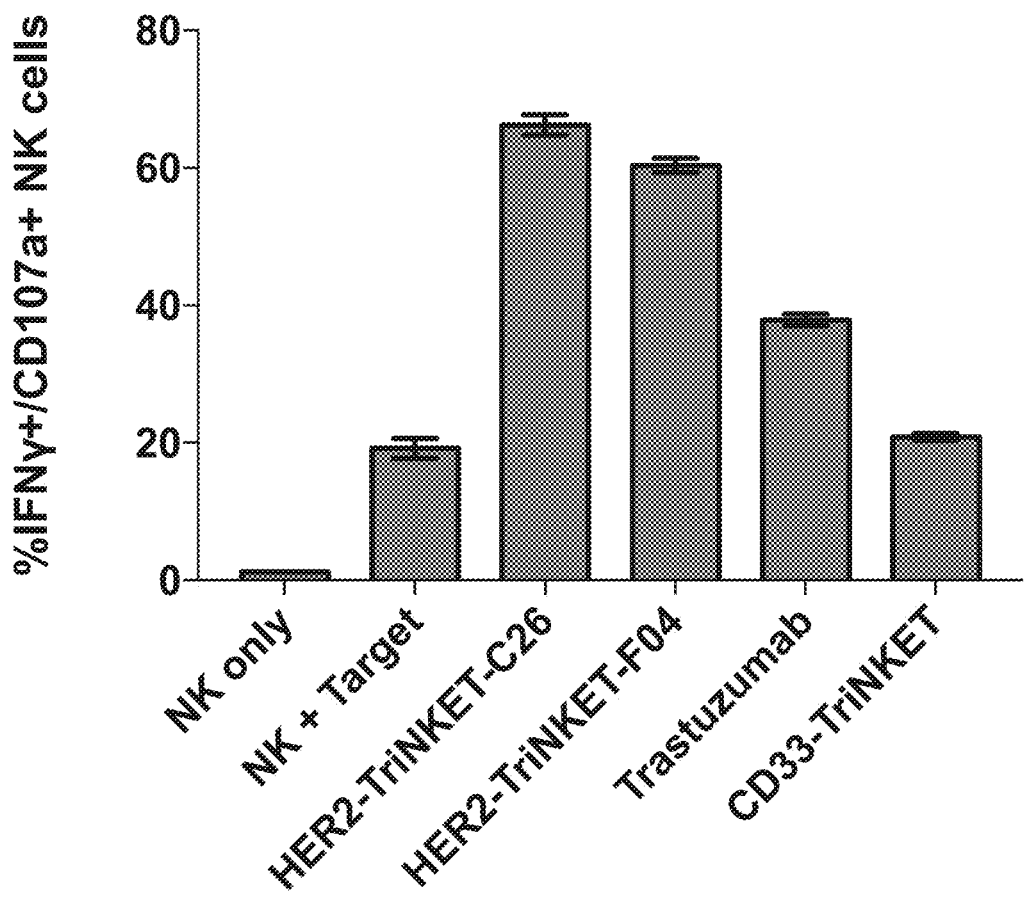

TriNKETs (C26-TriNKET-HER2 and F04-TriNKET-HER2) mediate activation of human NK cells co-cultured with CD33-expressing human AML Mv4-11 cells showed an increase of CD107a degranulation and IFN-gamma production. Compared to the monoclonal anti-CD33 antibody, TriNKETs (C26-TriNKET-HER2 and F04-TriNKET-HER2) showed superior activation of human NK cells in the presence of human cancer cells expressing HER2 (FIGS. 47A-47C).

Figure 62:
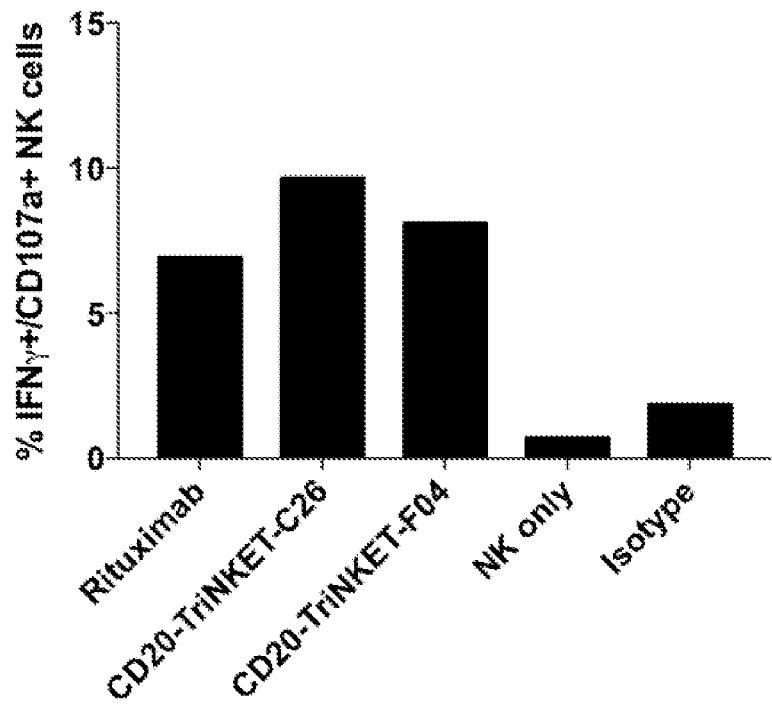
FIG. 62 is bar graph showing that human NK cells are activated by TriNKETs when cultured with CD20+ Raji cells.

Primary Human NK Cells are Activated by TriNKETs in Co-Culture with Target Expressing Human Cancer Cell Lines Co-culturing primary human NK cells with CD20-positive human cancer cells resulted in TriNKET-mediated activation of primary human NK cells (FIG. 62). TriNKETs targeting CD20 (e.g., C26-TriNKET-CD20 and F04-TriNKET-CD20), mediated activation of human NK cells co-cultured with CD20-positive Raji cells, as indicated by an increase in CD107a degranulation and IFNγ cytokine production (FIG. 62). Compared to the monoclonal antibody Rituximab, both TriNKETs (e.g., C26-TriNKET-CD20 and F04-TriNKET-CD20) showed superior activation of human NK cells (FIG. 62).

```
Rituximab_vH
                                          (SEQ ID NO: 84)
QVQLQQPGAELVKPGASVKMSCKASGYTFTSYNMHWVKQTPGRGLEWI
                              CDR1

GAIYPGNGDTSYNQKFKGKATLTADKSSSTAYMQLSSLTSEDSAVYYCAR
CDR2

STYYGGDWYFNVWGAGTTVTVSA
  CDR3

Rituximab vL
                                          (SEQ ID NO: 85)
QIVLSQSPAILSASPGEKVTMTCRASSSVSYIHWFQQKPGSSPKWI
                        CDR1

YATSNLASGVPVRFSGSGSGTSYSLTISRVEAEDAATYYCQQWTSNPPT
CDR2                                     CDR3

FGGGTKLEIK
```

Figure 63:
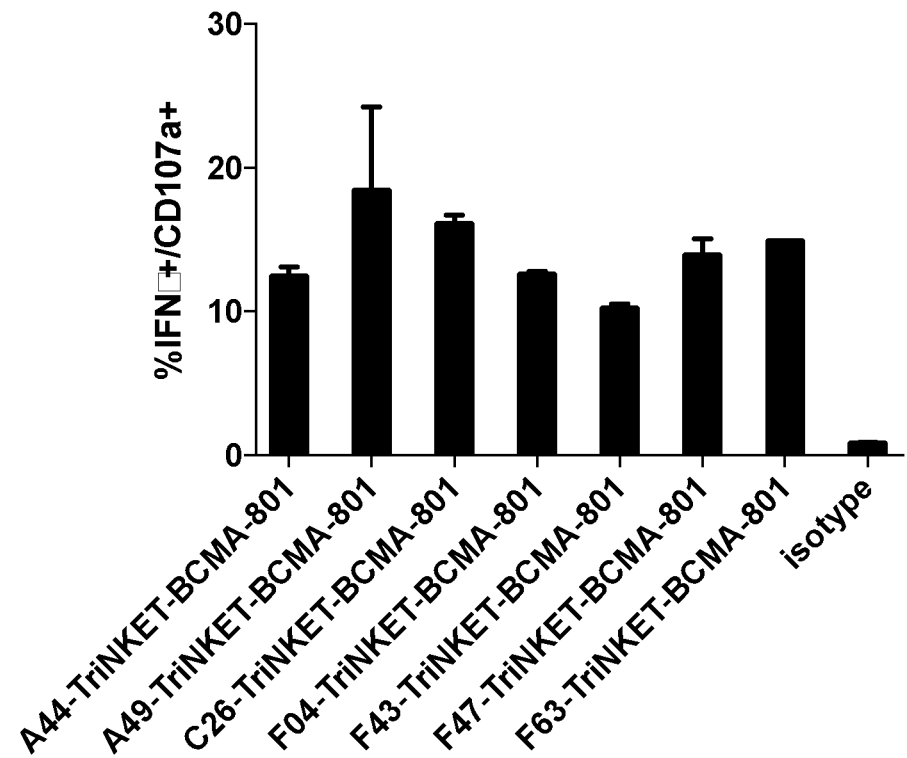
FIG. 63 is a bar graph showing that human NK activation in culture with BCMA positive MM.1S human myeloma cells.

Co-culturing primary human NK cells with BCMA-positive MM.1S myeloma cells resulted in TriNKET-mediated activation of the primary human NK cells. TriNKETs targeting BCMA (e.g., C26-TriNKET-BMCA and F04-TriN-KET-BMCA) mediated activation of human NK cells co-cultured with MM.1S myeloma cells, as indicated by an increase in CD107a degranulation and IFNγ cytokine production (FIG. 63). Compared to isotype TriNKET, TriN-KETs targeting BCMA (e.g., A44-TriNKET-BMCA, A49-TriNKET-BMCA, C26-TriNKET-BMCA, F04-TriNKET-BMCA, F43-TriNKET-BMCA, F43-TriNKET-BMCA, F47-TriNKET-BMCA, and F63-TriNKET-BMCA) showed increased NK cell activity (FIG. 63).

Example 12—Trispecific Binding Proteins Enable Cytotoxicity of Target Cancer Cells Peripheral blood mononuclear cells (PBMCs) were isolated from human peripheral blood buffy coats using density gradient centrifugation. NK cells (CD3$^-$CD56$^+$) were isolated using negative selection with magnetic beads from PBMCs, and the purity of the isolated NK cells was typically >90%. Isolated NK cells were cultured in media containing 100 µg/mL IL-2 for activation or rested overnight without cytokine. IL-2-activated or rested NK cells were used the following day in cytotoxicity assays.

In order to test the ability of human NK cells to lyse cancer cells in the presence of TriNKETs, a cyto Tox 96 non-radioactive cytotoxicity assay from Promega (G1780) was used according to the manufacturer's instructions. Briefly, human cancer cells expressing a tumor antigen were harvested, washed, and resuspended in culture media at $1-2\times10^5$/mL. Rested and/or activated NK cells were harvested, washed, and resuspended at $10^5$-$2.0\times10^6$ cells/mL in the same culture media as that of the cancer cells. In each well of a 96 well plate, 50 µl of the cancer cell suspension was mixed with 50 µl of NK cell suspension with or without TriNKETs targeting the tumor antigen expressed on the cancer cells. After incubation at 37° C. with 5% $CO_2$ for 3 hours and 15 minutes, 10× lysis buffer was added to wells containing only cancer cells, and to wells containing only media for the maximum lysis and negative reagent controls, respectively. The plate was then placed back into the incubator for an additional 45 minutes to reach a total of 4-hour incubation. Cells were then pelleted, and the culture supernatant was transferred to a new 96 well plate and mixed with a substrate for development. The new plate was incubated for 30 minutes at room temperature, and the absorbance was read at 492 nm on a SpectraMax i3x. Percentage of specific lysis of the cancer cells was calculated as follows: % Specific lysis=((experimental lysis−spontaneous lysis from NK cells alone−spontaneous lysis from cancer cells alone)/(Maximum lysis−negative reagent control))×100%.

TriNKETs mediate cytotoxicity of human NK cells against the CD33 positive Molm-13 human AML cell line. As shown in FIG. 53B, rested human NK cells were mixed with Molm-13 cancer cells, and TriNKETs (e.g., C26-TriNKET-CD33 and F04-TriNKET-CD33) are able to enhance the cytotoxic activity of rested human NK cells in a dose-responsive manner against the cancer cells. The dotted line indicates cytotoxic activity of rested NK cells without TriNKETs. Activated human NK cells were mixed with Molm-13 cancer cells, and TriNKETs enhance the cytotoxic activity of activated human NK cells even further, compared to an anti-CD33 antibody, in a dose-responsive manner against the cancer cells (FIG. 53B).

TriNKETs enhance NK cell cytotoxicity against targets with low surface expression compared to the cytotoxic activity of trastuzumab, an anti-HER2 monoclonal antibody. Rested human NK cells were mixed with high HER2-expressing SkBr tumor cells and low HER2-expressing 786-O cancer cells, and TriNKETs' ability to enhance the cytotoxic activity of rested human NK cells against the high and low HER2-expressing cancer cells in a dose-responsive manner was assayed. Dotted lines in FIG. 50A and FIG. 50B indicate the cytotoxic activity of rested NK cells against the cancer cells in the absence of TriNKETs. As shown in FIG. 50B, upon mixing activated human NK cells with low HER2-expressing 786-O cells, and TriNKET (e.g., CD26-TriNKET-HER2 and F04-TriNKET-HER2) dose-responsive cytotoxic activity of activated human NK cells against the cancer cells was observed.

Figure 64:
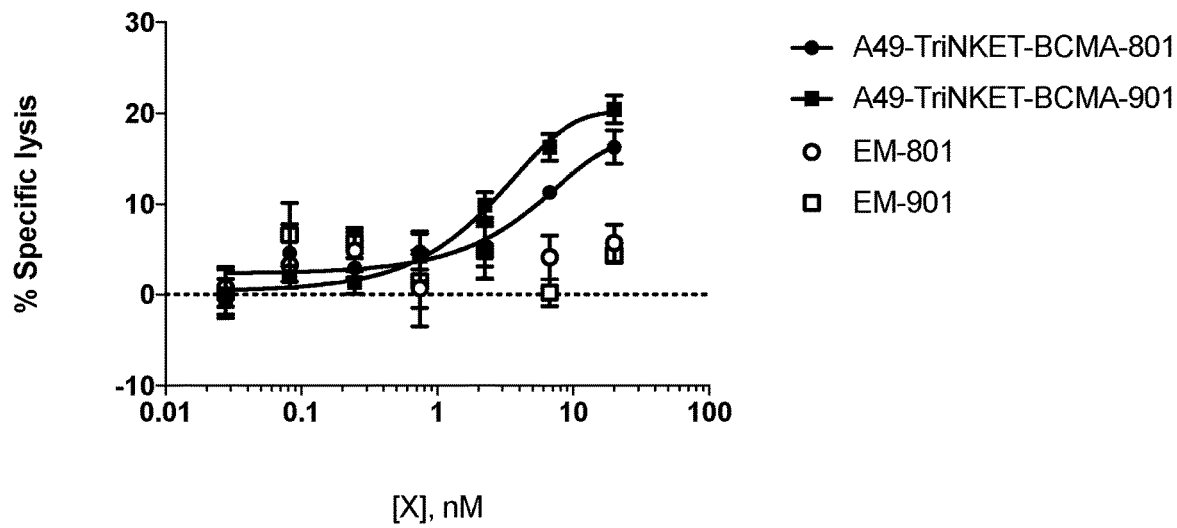
FIG. 64 is a graph showing that TriNKETs enhance human NK cell lysis of KMS12-PE myeloma cells.

TriNKET-mediated lysis of BCMA positive myeloma cells was assayed. FIG. 64 shows-TriNKET-mediated lysis of BCMA-positive KMS12-PE myeloma cells by rested human NK effector cells. Two TriNKETs (cFAE-A49.801 and cFAE-A49.901) using the same NKG2D-binding domain (A49), but different BCMA targeting domains were tested for efficacy in vitro. Both TriNKETs enhanced NK cell lysis of KMS12-PE cells to a similar extent, but TriN-KETs using the EM-901 targeting domain provided increased potency.

Figure 65:
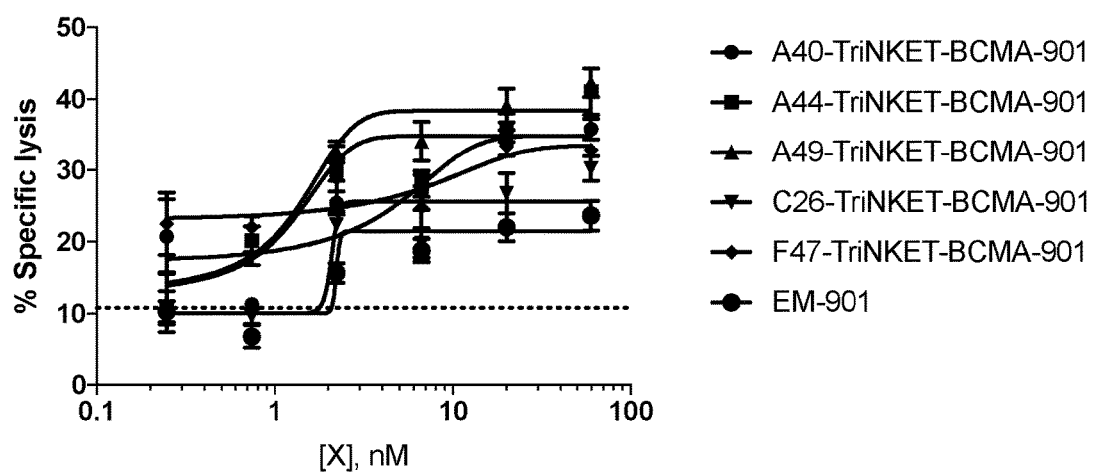
FIG. 65 is a graph showing that BCMA targeting TriN-KETs with different NKG2D-binding domains enhance human NK cell lysis of KMS12-PE myeloma cells.

FIG. 65 shows cytotoxic activity of several TriNKETs using different NKG2D-binding domains (A40, A44, A49, C26, and F47), but the same BCMA targeting domain. Changing the NKG2D-binding domain of the BCMA-targeted TriNKET produced variations in maximal killing as well as potency of the TriNKETs. All TriNKETs demonstrated increased killing of KMS12-PE target cells compared to EM-901 monoclonal antibody (FIG. 65).

Example 13

Synergistic activation of human NK cells by cross-linking NKG2D and CD 16 was investigated.
Primary Human NK Cell Activation Assay Peripheral blood mononuclear cells (PBMCs) were isolated from peripheral human blood buffy coats using density gradient centrifugation. NK cells were purified from PBMCs using negative magnetic beads (StemCell #17955). NK cells were >90% CD3$^-$CD56$^+$ as determined by flow cytometry. Cells were then expanded 48 hours in media containing 100 µg/mL hIL-2 (Peprotech #200-02) before use in activation assays. Antibodies were coated onto a 96-well flat-bottom plate at a concentration of 2 µg/ml (anti-CD16, Biolegend #302013) and 5 µg/mL (anti-NKG2D, R&D #MAB139) in 100 µl sterile PBS overnight at 4° C. followed by washing the wells thoroughly to remove excess antibody. For the assessment of degranulation IL-2-activated NK cells were resuspended at $5\times10^5$ cells/ml in culture media supplemented with 100 µg/mL hIL2 and 1 µg/mL APC-conjugated anti-CD107a mAb (Biolegend #328619). $1\times10^5$ cells/well were then added onto antibody coated plates. The protein transport inhibitors Brefeldin A (BFA, Biolegend #420601) and Monensin (Biolegend #420701) were added at a final dilution of 1:1000 and 1:270 respectively. Plated cells were incubated for 4 hours at 37° C. in 5% $CO_2$. For intracellular staining of IFN-γ NK cells were labeled with anti-CD3 (Biolegend #300452) and anti-CD56 mAb (Biolegend #318328) and subsequently fixed and permeabilized and labeled with anti-IFN-γ mAb (Biolegend #506507). NK cells were analyzed for expression of CD107a and IFN-γ by flow cytometry after gating on live CD56$^+$CD3$^-$ cells.

Figure 45C:
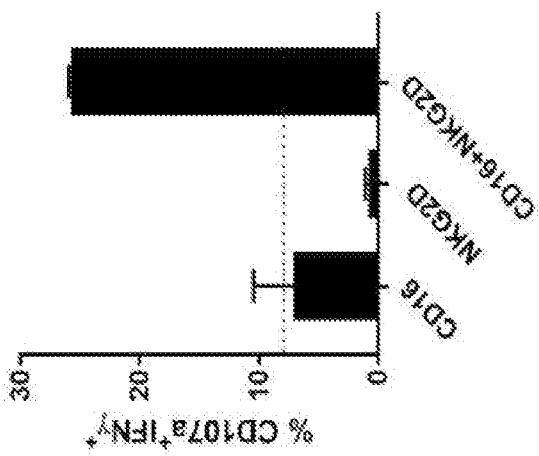
FIG. 45C demonstrates levels of CD107a. Graphs indicate the mean (n=2)±SD. Data are representative of five independent experiments using five different healthy donors.
Figure 45B:
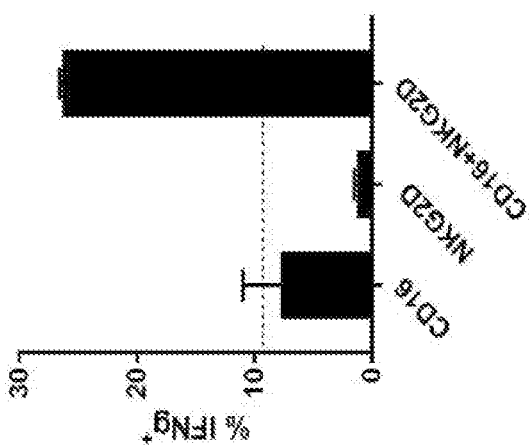
FIGS. 45A-45B are bar graphs of synergistic activation of NK cells using CD16 and NKG2D.
Figure 45A:
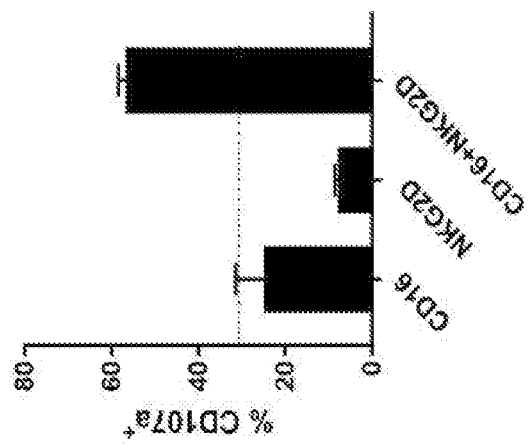

To investigate the relative potency of receptor combination, crosslinking of NKG2D or CD16 and co-crosslinking of both receptors by plate-bound stimulation was performed. As shown in FIG. 45 (FIGS. 45A-45C), combined stimulation of CD16 and NKG2D resulted in highly elevated levels of CD107a (degranulation) (FIG. 45A) and/or IFN-γ production (FIG. 45B). Dotted lines represent an additive effect of individual stimulations of each receptor.

CD107a levels and intracellular IFN-γ production of IL-2-activated NK cells were analyzed after 4 hours of plate-bound stimulation with anti-CD16, anti-NKG2D or a combination of both monoclonal antibodies. Graphs indicate the mean (n=2)±SD. FIG. 45A demonstrates levels of CD107a; FIG. 45B demonstrates levels of IFNγ; FIG. 45C demonstrates levels of CD107a and IFN-γ. Data shown in FIGS. 45A-45C are representative of five independent experiments using five different healthy donors.

Figure 46:
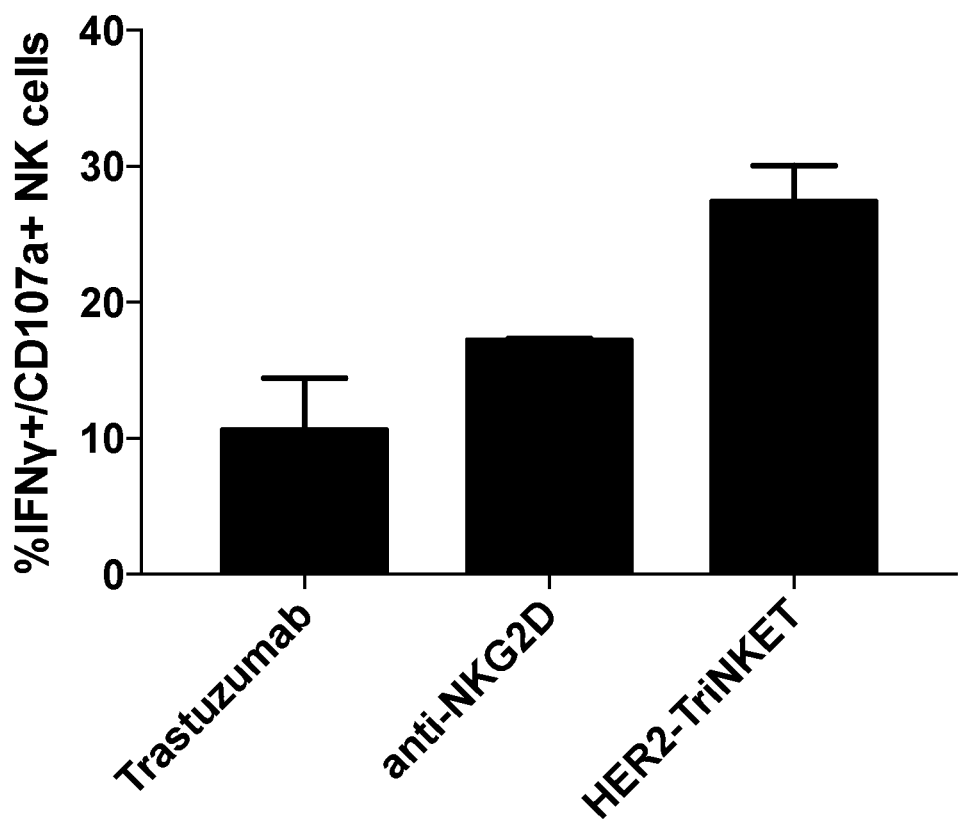
FIG. 46 is a bar graph showing activation of NK cells using TriNKETs targeting NKG2D and CD16. Antibodies tested were of human IgG1 isotypes. Graphs indicate the mean (n=2)±SD.

CD107a degranulation and intracellular IFN-γ production of IL-2-activated NK cells were analyzed after 4 hours of plate-bound stimulation with trastuzumab, anti-NKG2D, or a TriNKET derived from the binding domains of trastuzumab and the anti-NKG2D antibody (FIG. 46). In all cases antibodies tested were of the human IgG1 isotype. Graphs indicate the mean (n=2)±SD.

Example 14

Assessment of TriNKET Binding to Cell-Expressed Human NKG2D

EL4 cells transduced with human NKG2D were used to test binding to cell-expressed human NKG2D. TriNKETs were diluted to 20 µg/mL, and then diluted serially. The mAb or TriNKET dilutions were used to stain cells, and binding of the TriNKET or mAb was detected using a fluorophore-conjugated anti-human IgG secondary antibody. Cells were analyzed by flow cytometry, binding MFI was normalized to secondary antibody controls to obtain fold over background values.

Assessment of TriNKET Binding to Cell-Expressed Human Cancer Antigens

Human cancer cell lines expressing either CD33 or HER2 were used to assess tumor antigen binding of TriNKETs derived from different NKG2D targeting clones. The human AML cell line MV4-11 was used to assess binding of TriNKETs to cell-expressed CD33. The human renal cell carcinoma cell line 786-O expresses low levels of HER2 and was used to assess TriNKET binding to cell-expressed HER2. TriNKETs were diluted to 20 µg/mL, and were incubated with the respective cells. Binding of the TriNKET was detected using a fluorophore-conjugated anti-human IgG secondary antibody. Cells were analyzed by flow cytometry, binding MFI to cell expressed CD33 and HER2 was normalized to secondary antibody controls to obtain fold over background values.

Determination of Antibody Binding Capacity of Human HER2-Positive Cancer Cell Lines Antibody binding capacity (ABC) of HER2-positive human cancer cell lines was measured. The Quantum Simply Cellular kit from Bangs Lab was used (#815), and the manufacturer instructions were followed for the preparation of antibody labeled beads. Briefly, each of the four populations of beads were stained with a saturating amount of anti-HER2 antibody, and the cell populations were also stained with a saturating amount of the same antibody. Sample data was acquired for each bead population, as well as the cell populations. The QuickCal worksheet, provided with the kit, was used for the generation of a standard curve and extrapolation of ABC values for each of the cell lines.

Activation of Primary NK Cells by TriNKETs

PBMCs were isolated from human peripheral blood buffy coats using density gradient centrifugation. Isolated PBMCs were washed and prepared for NK cell isolation. NK cells were isolated using a negative selection technique with magnetic beads; the purity of isolated NK cells was typically >90% CD3-CD56+. Isolated NK cells were cultured in media containing 100 µg/mL IL-2 for activation or rested overnight without cytokine. IL-2-activated NK cells were used 24-48 hours later; rested NK cells were always used the day after purification.

Human cancer cell lines expressing a cancer target of interest were harvested from culture, and cells were adjusted to $2 \times 10^6$ cells/mL. Monoclonal antibodies or TriNKETs targeting the cancer target of interest were diluted in culture media. Rested and/or activated NK cells were harvested from culture, cells were washed, and were resuspended at $2 \times 10^6$ cells/mL in culture media. IL-2, and fluorophore-conjugated anti-CD107a were added to the NK cells for the activation culture. Brefeldin-A and monensin were diluted into culture media to block protein transport out of the cell for intracellular cytokine staining. Into a 96-well plate 50 µl of tumor targets, mAbs/TriNKETs, BFA/monensin, and NK cells were added for a total culture volume of 200 µl. The plate was cultured for 4 hours before samples were prepared for FACS analysis.

Following the 4 hour activation culture, cells were prepared for analysis by flow cytometry using fluorophore-conjugated antibodies against CD3, CD56 and IFNγ. CD107a and IFNγ staining was analyzed in CD3-CD56+ populations to assess NK cell activation.

Primary Human NK Cell Cytotoxicity Assay

PBMCs were isolated from human peripheral blood buffy coats using density gradient centrifugation. Isolated PBMCs were washed and prepared for NK cell isolation. NK cells were isolated using a negative selection technique with magnetic beads, purity of isolated NK cells was typically >90% CD3-CD56+. Isolated NK cells were cultured in media containing 100 µg/mL IL-2 or were rested overnight without cytokine. IL-2-activated or rested NK cells were used the following day in cytotoxicity assays.

Cyto Tox 96 LHD Release Assay:

The ability of human NK cells to lyse tumor cells was measured with or without the addition of TriNKETs using the cyto Tox 96 non-radioactive cytotoxicity assay from Promega (G1780). Human cancer cell lines expressing a cancer target of interest were harvested from culture, cells were washed with PBS, and were resuspended in growth media at $1-2 \times 10^5$ cells/mL for use as target cells. 50 µl of the target cell suspension were added to each well. Monoclonal antibodies or TriNKETs targeting a cancer antigen of interest were diluted in culture media, 50 µl of diluted mAb or TriNKET were added to each well. Rested and/or activated NK cells were harvested from culture, cells were washed, and were resuspended at $10^5 - 2.0 \times 10^6$ cells/mL in culture media depending on the desired E:T ratio. 50 µl of NK cells were added to each well of the plate to make a total of 150 µl culture volume. The plate was incubated at 37° C. with 5% CO2 for 3 hours and 15 minutes. After the incubation, 10× lysis buffer was added to wells of target cells alone, and to wells containing media alone, for maximum lysis and volume controls. The plate was then placed back into the incubator for an additional 45 minutes, to make to total of 4 hours of incubation before development.

After incubation, the plate was removed from the incubator and the cells were pelleted by centrifugation at 200 g for 5 minutes. 50 µl of culture supernatant were transferred to a clean microplate and 50 µl of substrate solution were added to each well. The plate was protected from the light and incubated for 30 minutes at room temperature. 50 µl of stop solution were added to each well, and absorbance was read at 492 nm on a SpectraMax i3x. % Specific lysis was calculated as follows: % Specific lysis=((Experimental release−Spontaneous release from effector−Spontaneous release from target)/(Maximum release−Spontaneous release))*100%.

DELFIA Cytotoxicity Assay:

Human cancer cell lines expressing a target of interest were harvested from culture, cells were washed with PBS, and were resuspended in growth media at $10^6$ cells/mL for labeling with BATDA reagent (Perkin Elmer AD0116). Manufacturer instructions were followed for labeling of the target cells. After labeling cells were washed 3× with PBS, and were resuspended at $0.5-1.0\times10^5$ cell s/mL in culture media. To prepare the background wells an aliquot of the labeled cells was put aside, and the cells were spun out of the media. 100 µl of the media were carefully added to wells in triplicate to avoid disturbing the pelleted cells. 100 µl of BATDA labeled cells were added to each well of the 96-well plate. Wells were saved for spontaneous release from target cells, and wells were prepared for max lysis of target cells by addition of 1% Triton-X. Monoclonal antibodies or TriNKETs against the tumor target of interest were diluted in culture media and 50 µl of diluted mAb or TriNKET were added to each well. Rested and/or activated NK cells were harvested from culture, cells were washed, and were resuspended at $10^5-2.0\times10^6$ cells/mL in culture media depending on the desired E:T ratio. 50 µl of NK cells were added to each well of the plate to make a total of 200 µl culture volume. The plate was incubated at 37° C. with 5% $CO_2$ for 2-3 hours before developing the assay.

After culturing for 2-3 hours, the plate was removed from the incubator and the cells were pelleted by centrifugation at 200 g for 5 minutes. 20 µl of culture supernatant was transferred to a clean microplate provided from the manufacturer, 200 µl of room temperature europium solution was added to each well. The plate was protected from the light and incubated on a plate shaker at 250 rpm for 15 minutes. Plate was read using either Victor 3 or SpectraMax i3X instruments. % Specific lysis was calculated as follows: % Specific lysis=((Experimental release−Spontaneous release)/(Maximum release−Spontaneous release))*100%.

Long Term Human PBMC Cytotoxicity Assay:

SkBr-3 target cells were labeled with BacMam 3.0 NucLight Green (#4622) to allow for tracking of the target cells. The manufacturer's protocol was followed for labeling of SkBr-3 target cells. Annexin V Red (Essen Bioscience #4641) was diluted and prepared according to the manufacturer's instructions. Monoclonal antibodies or TriNKETs were diluted into culture media. 50 µl of mAbs or TriNKETs, Annexin V, and rested NK cells were added to wells of a 96 well plate already containing labeled SkBr-3 cells; 50 µl of complete culture media was added for a total of 200 µl culture volume.

Image collection was setup on the IncuCyte S3. Images for the phase, green, and red channels were collected every hour, with 2 images per well. Image analysis was done using the IncuCyte S3 software. Masks for the green and red channels were created to count the number of tumor cells, and annexin V positive cells respectively. To calculate the % annexin V positive Mv4-11 target cells the following formula was used. % Annexin V positive SkBr-3 cells=((overlap object count)/(green object count))*100%.

Comparing a TriNKET that Targets HER+ Cancer Cells with SC2.2

A TriNKET targeting HER2 is more effective than Trastuzumab at reducing SkBr-3 cell number, and only 60% of the cells from time zero were left after 60 hours. A TriNKET of the present disclosure that targets HER2 expressing tumor/cancer cells is more effective than SC2.2—a single chain bispecific molecule built from an scFv derived from trastuzumab linked to ULBP-6, a ligand for NKG2D. SC2.2 binds HER2+ cancer cells and NKG2D+ NK cells simultaneously. Therefore, effectiveness of SC2.2 in reducing HER2+ cancer cell number was investigated. In vitro activation and cytotoxity assays demonstrated that SC2.2 was effective in activating and killing NK cells. However, SC2.2 failed to demonstrate efficacy in the RMA/S-HER2 subcutaneous tumor model. The efficacy of SC2.2 was also tested in vivo using an RMA/S-HER2 overexpressing syngeneic mouse model. In this mouse model, SC2.2 failed to demonstrate control of tumor growth compared to vehicle control. Thus, although SC2.2 was able to activate and kill NK cells, and binds to HER2+ cancer cells, these properties were insufficient to effectively control HER2+ tumor growth.

Assessment of SC2.2 Serum Half-Life in C57Bl/6 Mice

To determine the serum half-life of SC2.2 in C57Bl/6 mice, SC2.2 was labeled with a fluorescent tag to track its concentration in vivo. SC2.2 was labeled with IRDye 800CW (Licor #929-70020). The labeled protein was injected intravenously into 3 C57Bl/6 mice, blood was taken from each mouse at the indicated time points. After collection blood was centrifuged at 1000 g for 15 minutes and serum was collected from each sample and stored at 4° C. until all time points were collected.

Serum was imaged using an Odyssey CLx infrared imaging system, the fluorescent signal from the 800 channel was quantified using Image J software. Image intensities were normalized to the first time point, and the data was fit to a biphasic decay equation. In this experimental system the beta half-life of SC2.2 was calculated to be around 7 hours.

In Vivo Testing of SC2.2 Against RMA/S-HER2 Subcutaneous Tumors

Figure 37:
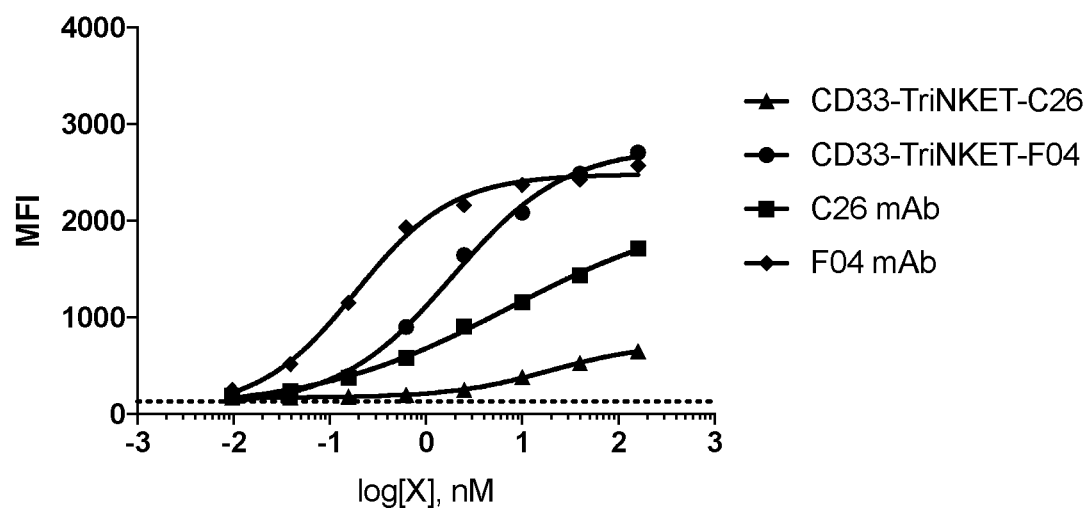
FIG. 37 is a binding profile of CD33-targeting TriNKETs to NKG2D expressed on EL4 cells.
Figure 38:
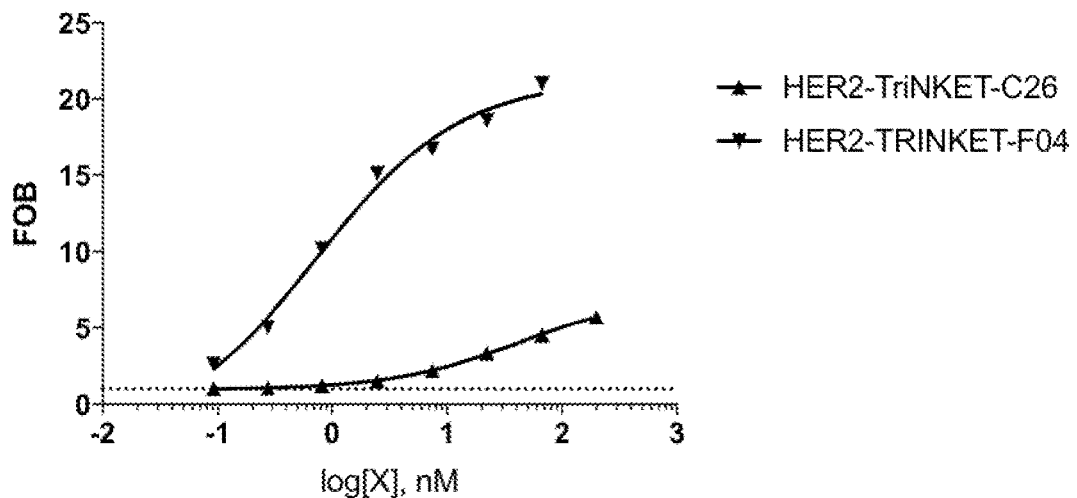
FIG. 38 is a binding profile of HER2-targeting TriNKETs to NKG2D expressed on EL4 cells.
Figure 39:
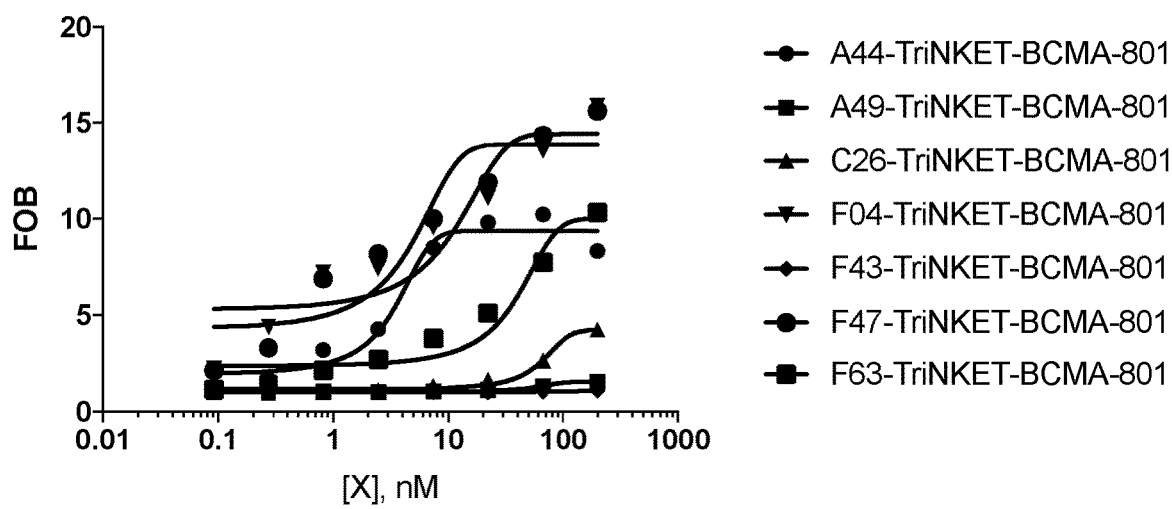
FIG. 39 is a binding profile of BCMA-targeting TriNKETs to NKG2D expressed on EL4 cells.
Figure 40:
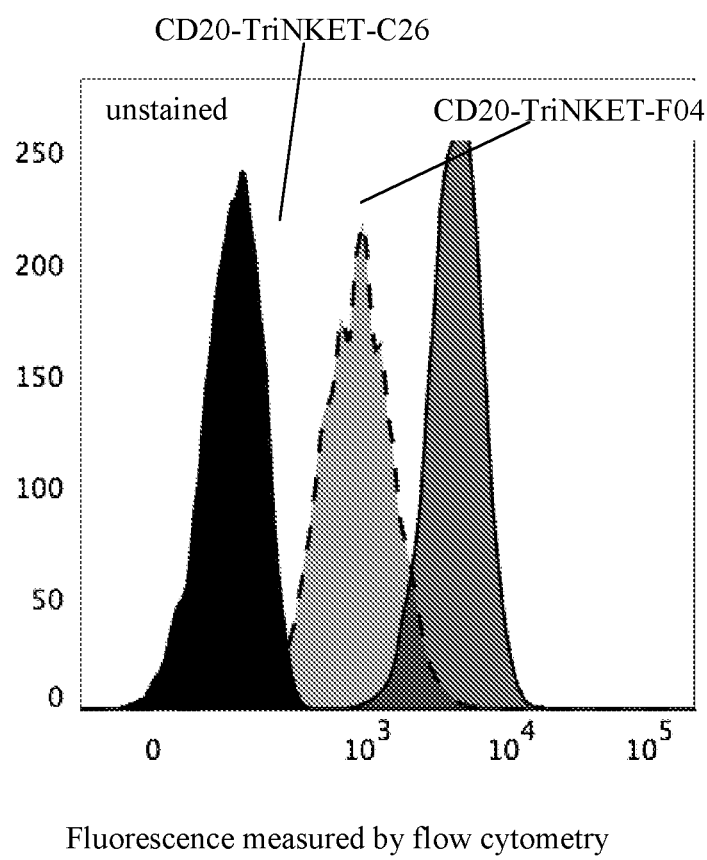
FIG. 40 is a histogram of CD20-targeting TriNKETs that bind to NKG2D expressed on EL4 cells. Unstained EL4 cells were used a negative control for fluorescence signal. Unstained: filled; CD20-TriNKET-F04: solid line; CD20-TriNKET-C26: dashed line.
Figure 56:
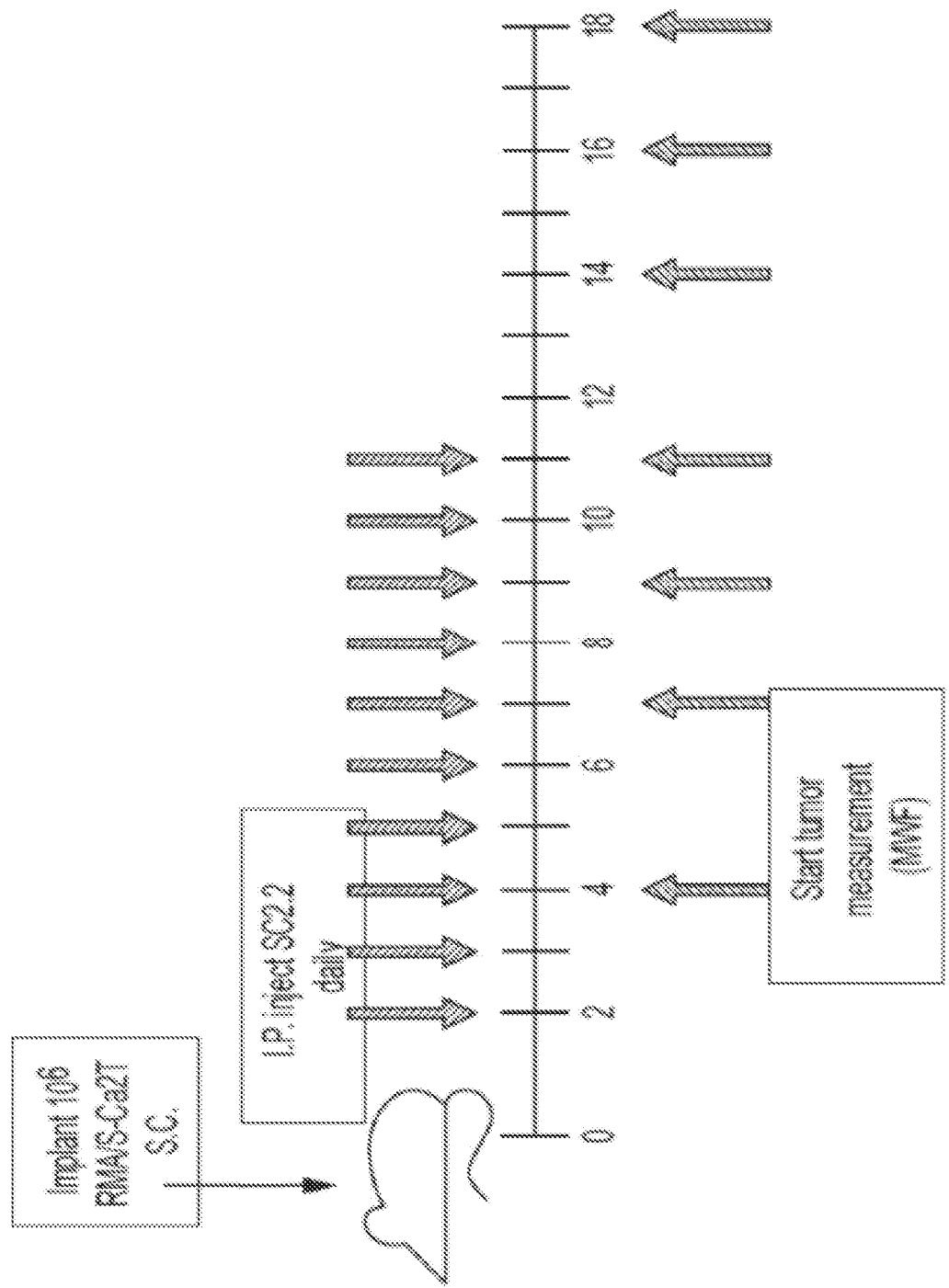
FIG. 56 is a flowchart of study design of RMA/S-HER2 subcutaneous SC2.2 efficacy.
Figure 57:
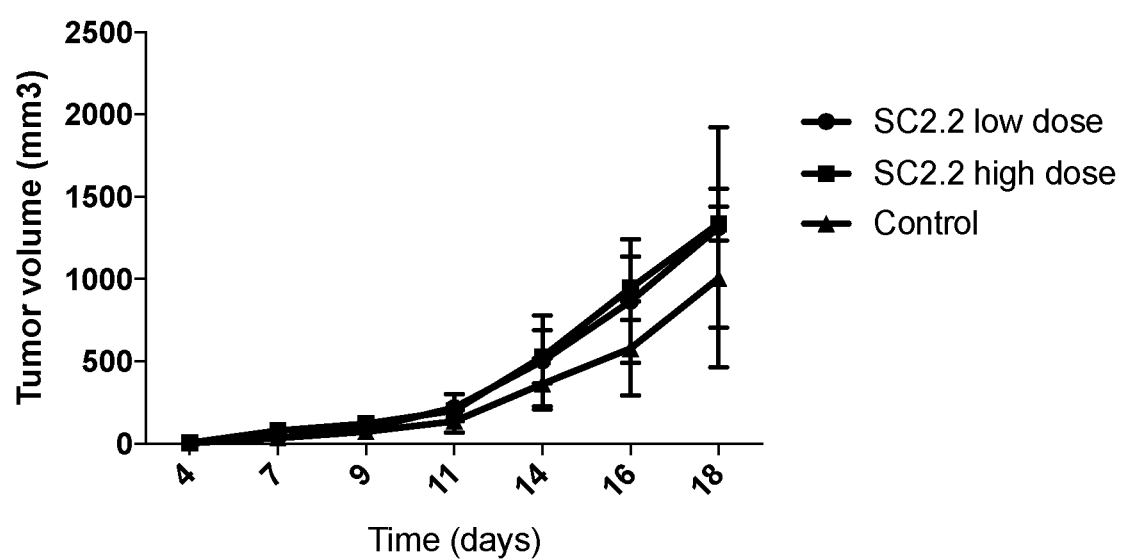
FIG. 57 are line graphs showing that SC2.2 has no effect on subcutaneous RMA/S-HER2 tumor growth.

An in vivo study was designed according to FIG. 56 to test the efficacy of SC2.2 against subcutaneous RMA/S-HER2 tumors. $10^6$ RMA/S cells transduced with human HER2 were injected subcutaneously into the flank of 20 C57Bl/6 mice. Starting day 2 after tumor innoculation SC2.2 was dosed daily via IP injection. SC2.2 was dosed at a high and a low concentrations along with a vehicle control. Starting day 4 after tumor innoculation tumors were measured Monday, Wednesday, and Friday for the duration of the study. Tumor volume was calculated using the following formula: Tumor volume=Length×width×height TriNKETs Bind to Cells Expressing Human NKG2D The ability of a TriNKET to bind cells expressing human NKG2D was determined. FIG. 37 and FIG. 38 show dose responsive binding of two TriNKETs containing different NKG2D-binding domains. FIG. 37 shows binding of the two TriNKETs when a CD33-binding domain is used as the second targeting arm. FIG. 38 shows the same two NKG2D-binding domains now paired with a HER2 second targeting arm. The six NKG2D-binding domains retain the same binding profile with both tumor targeting domains.

TriNKETs Bind to Cells Expressing Human Cancer Antigens

The ability of a TriNKET to bind cells expressing human cancer antigens was determined. FIG. 41 and FIG. 42 show binding of TriNKETs to cell-expressed CD33 (FIG. 41) and HER2 (FIG. 42). TriNKET binding to cell-expressed antigen was consistent between NKG2D-binding domains. TriNKETs bound to comparable levels as the parental monoclonal antibody.

Antibody Binding Capacity of Human HER2-Positive Cancer Cell Lines

Table 8 shows the results of HER2 surface quantification. SkBr-3 and HCC1954 cells were identified to have high (+++) levels of surface HER2. ZR-75-1 and Colo201 showed medium levels (++) of surface HER2, and 786-O showed the lowest level of HER2 (+).

TABLE 8

ABC of HER2-positive cancer cell lines

| Cell Line | HER2 expression | ABC |
|---|---|---|
| 786-0 | Low | 28,162 |
| Colo201 | Medium | 273,568 |
| ZR-75-1 | Medium | 281,026 |
| SkBr-3 | High | 6,820,532 |
| HCC1954 | High | 10,569,869 |

Primary Human NK Cells are Activated by TriNKETs in Co-Culture with Human Cancer Lines Expressing Varying Levels of HER2

FIGS. 47A-47C show that TriNKETs and trastuzumab were able to activate primary human NK cells in co-culture with HER2-positive human tumor cells, indicated by an increase in CD107a degranulation and IFNg cytokine production. Compared to the monoclonal antibody trastuzumab, both TriNKETs showed superior activation of human NK cells with a variety of human HER2 cancer cells.

FIG. 47A shows that human NK cells are activated by TriNKETs when cultured with SkBr-3 cells. FIG. 47B shows that human NK cells are activated by TriNKETs when cultured with Colo201 cells. FIG. 47C shows that human NK cell are activated by TriNKETs when cultured with HCC1954 cells.

TriNKETs Enhance Activity of Rested and IL-2-Activated Human NK Cells

Figure 48A:
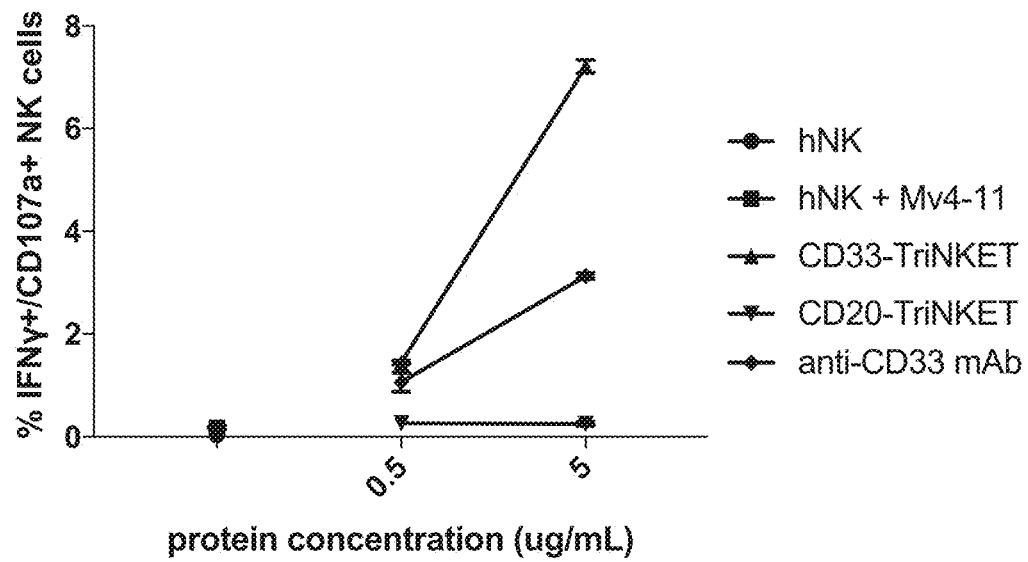
FIGS. 48A-48B are line graphs demonstrating TriNKET-mediated activation of rested or IL-2-activated human NK cells in co-culture with the CD33-expressing human AML cell line MV4-11.
Figure 48B:
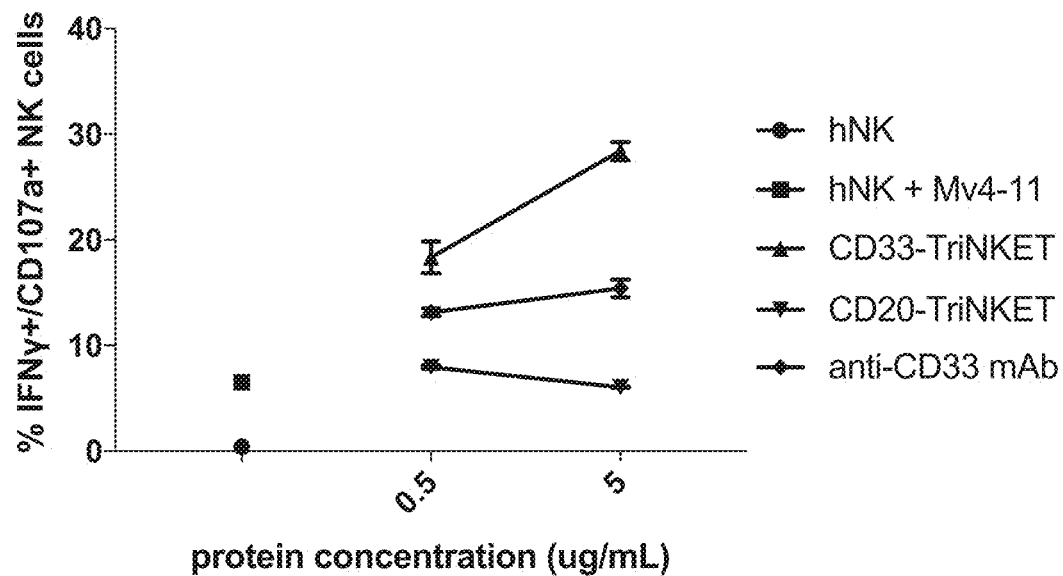

FIGS. 48A-48B show TriNKET-mediated activation of rested or IL-2-activated human NK cells in co-culture with the CD33-expressing human AML cell line MV4-11. FIG. 48 A shows TriNKET-mediated activation of resting human NK cells. FIG. 48B shows TriNKET-mediated activation of IL-2-activated human NK cells from the same donor. Rested NK cells showed less background IFNγ production and CD107a degranulation, than IL-2-activated NK cells. Rested NK cells showed a greater change in IFNγ production and CD107a degranulation compared to IL-2-activated NK cells. IL-2-activated NK cells showed a greater percentage of cells becoming IFNγ+; CD107a+ after stimulation with TriNKETs.

TriNKETs Enhance Cytotoxicity of Rested and IL-2-Activated Human NK Cells

Figure 49A:
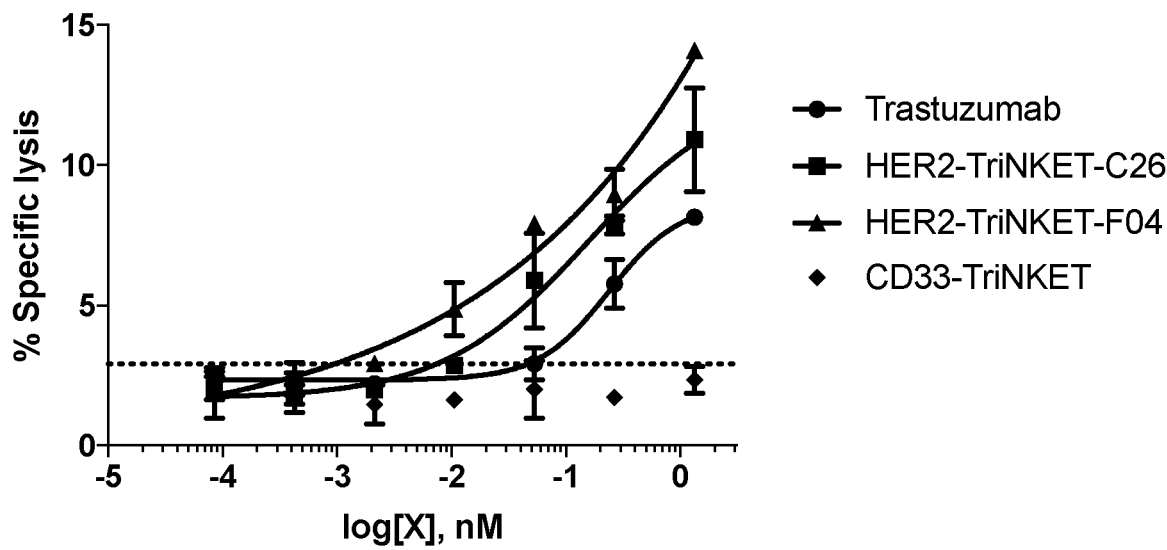
FIGS. 49A-49B are bar graphs demonstrating TriNKET enhancement of cytotoxic activity using IL-2-activated and rested human NK cells.
Figure 49B:
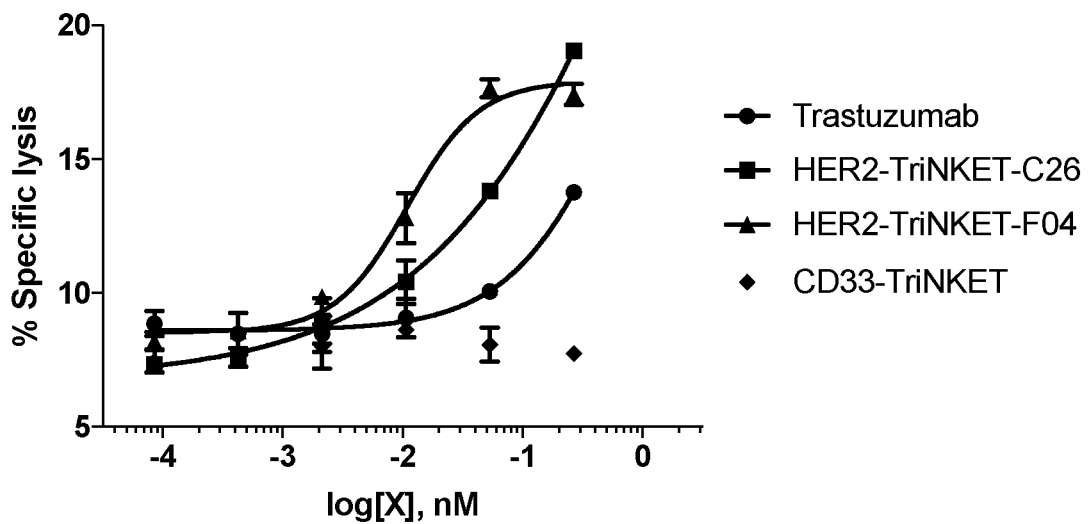

FIGS. 49A-49B show TriNKET enhancement of cytotoxic activity using IL-2-activated and rested human NK cells. FIG. 49A shows percent specific lysis of SkBr-3 tumor cells by rested human NK cells. FIG. 49B shows percent specific lysis of SkBr-3 tumor cells by IL-2-activated human NK cells. IL-2-activated and rested NK cell populations came from the same donor. Compared to trastuzumab, TriNKETs more potently direct responses against SkBr-3 cells by either activated or rested NK cell populations.

Figure 50A:
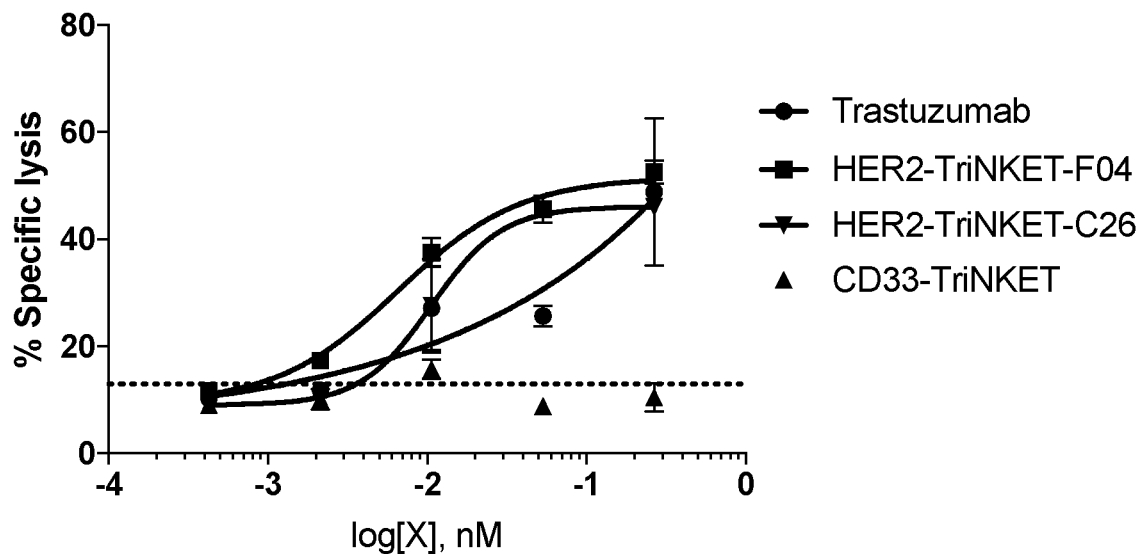
FIGS. 50A-50B are bar graphs demonstrating TriNKETs provide the greatest advantage against HER2 medium and low cancers compared to trastuzumab.
Figure 50B:
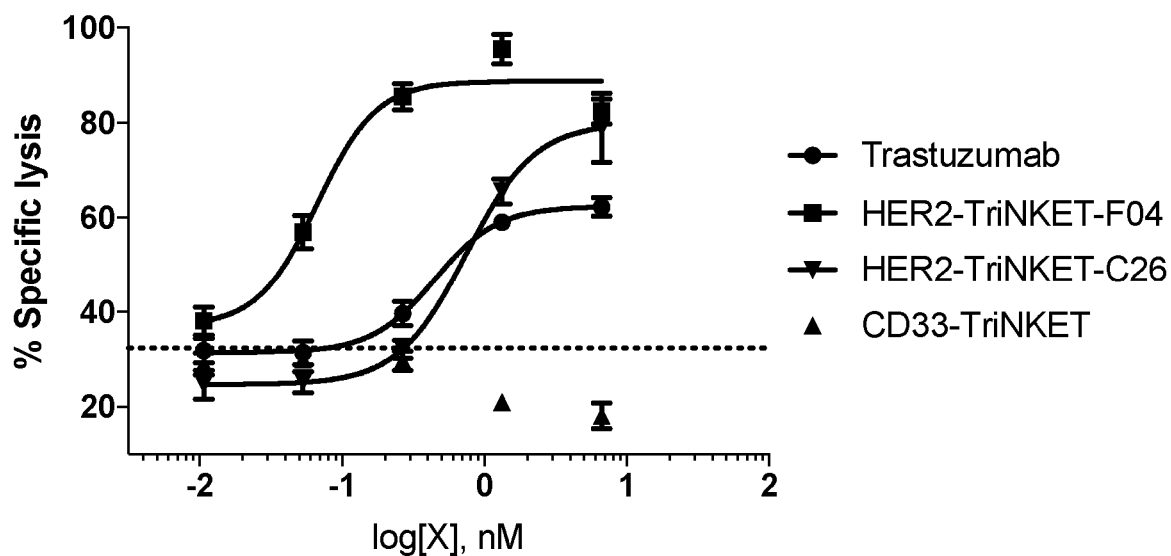

TriNKETs Enhance NK Cell Cytotoxicity Against Targets with Low Surface Expression FIGS. 50A-50B show TriNKETs provide a greater advantage against HER2-medium and low cancers compared to trastuzumab. FIG. 50A shows activated human NK cell killing of HER2-high SkBr-3 tumor cells. FIG. 50B shows human NK cell killing of HER2-low 786-O tumor cells. TriNKETs provide a greater advantage compared to trastuzumab against cancer cells with low HER2 expression. TriNKETs provide the greatest advantage against targets with low surface expression.

The advantage of TriNKETs in treating cancers with high expression of FcR, or in tumor microenvironments with high levels of FcR Monoclonal antibody therapy has been approved for the treatment of many cancer types, including both hematological and solid tumors. While the use of monoclonal antibodies in cancer treatment has improved patient outcomes, there are still limitations. Mechanistic studies have demonstrated monoclonal antibodies exert their effects on tumor growth through multiple mechanisms including ADCC, CDC, phagocytosis, and signal blockade amongst others.

Most notably, ADCC is thought to be a major mechanism through which monoclonal antibodies exert their effect. ADCC relies on antibody Fc engagement of the low-affinity FcγRIII (CD16) on the surface of natural killer cells, which mediate direct lysis of the tumor cell. Amongst FcγR, CD16 has the lowest affinity for IgG Fc, FcγRI (CD64) is the high-affinity FcR, and binds about 1000 times stronger to IgG Fc than CD16.

CD64 is normally expressed on many hematopoietic lineages such as the myeloid lineage, and can be expressed on tumors derived from these cell types, such as acute myeloid leukemia (AML). Immune cells infiltrating into the tumor, such as MDSCs and monocytes, also express CD64 and are known to infiltrate the tumor microenvironment. Expression of CD64 by the tumor or in the tumor microenvironment can have a detrimental effect on monoclonal antibody therapy. Expression of CD64 in the tumor microenvironment makes it difficult for these antibodies to engage CD16 on the surface of NK cells, as the antibodies prefer to bind the high-affinity receptor. Through targeting two activating receptors on the surface of NK cells, TriNKETs may be able to overcome the detrimental effect of CD64 expression on monoclonal antibody therapy.

FcRγI (CD64) Expression on Three AML Cell Lines

An in vitro culture system was developed to test the activity of TriNKETs and monoclonal antibodies against tumors with high and low levels of CD64 surface expression. Molm-13 and THP-1 are two human AML cell lines which have similar expression of surface CD33, but Molm-13 cells do not express CD64, while THP-1 cells express CD64 on their surface (FIGS. 51A-51C). Using monoclonal antibodies or TriNKETs directed to target CD33, the effect of CD64 expression by the tumor on monoclonal antibody or TriNKET therapy was tested. FIGS. 51A-51C show the expression of the high-affinity FcRγI (CD64) on three human AML cells lines, Molm-13 cell line (FIG. 51A), Mv4-11 cell line (FIG. 51B), and THP-1 cell line (FIG. 51C). Molm-13 cells do not express CD64, while Mv4-11 cells have a low level, and THP-1 have a high level of cell surface CD64.

Figure 52A:
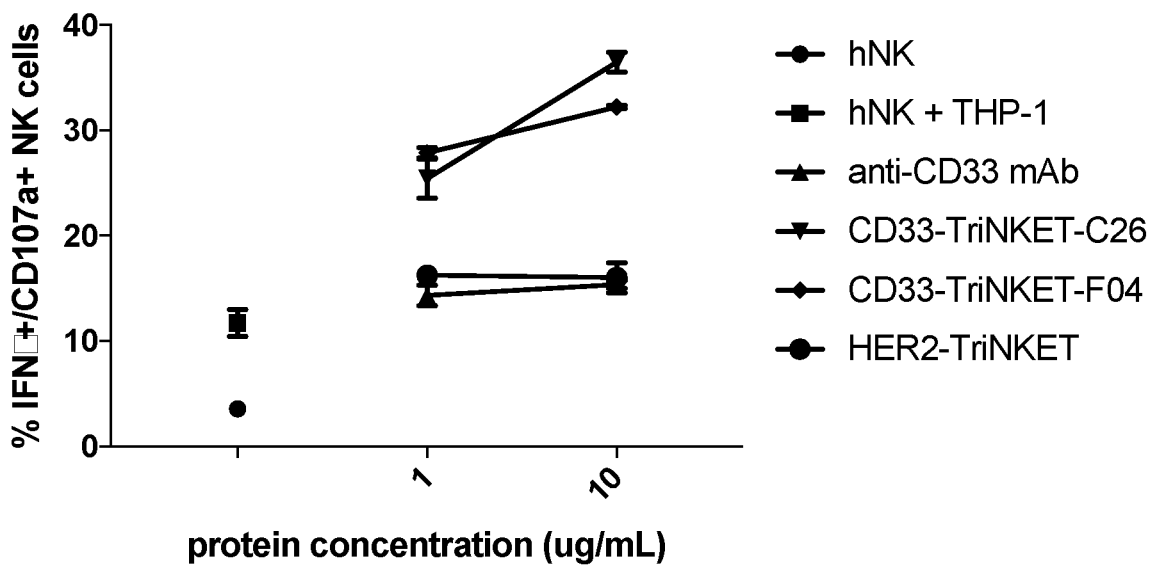
FIGS. 52A-52B are line graphs of monoclonal antibody or TriNKET mediated activation of human NK cells in co-culture with either Molm-13 (FIG. 52B) or THP-1 (FIG. 52A) cells.
Figure 52B:
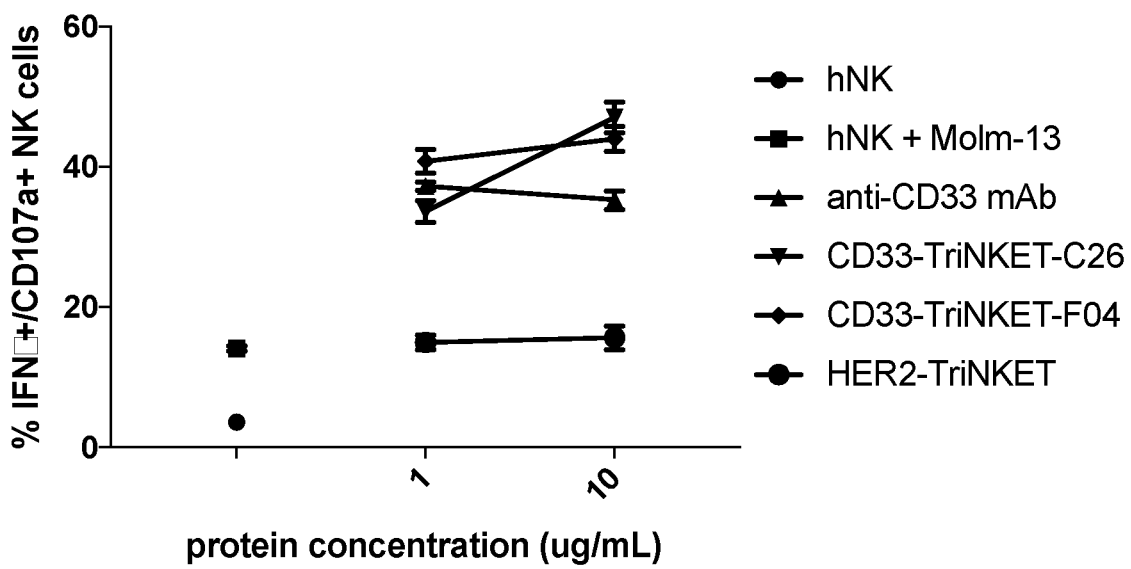

TriNKETs have an Advantage in Targeting Tumor Cells with High Surface Expression of FcRs FIGS. 52A-52B show monoclonal antibody or TriNKET mediated activation of human NK cells in co-culture with either Molm-13 (FIG. 52B) or THP-1 (FIG. 52A) cells. A monoclonal antibody against human CD33 demonstrated good activation of human NK cells, in the Molm-13 co-culture system as evidenced by increased CD107a degranulation and IFNγ production. The monoclonal antibody has no effect in the THP-1 co-culture system, where high levels of CD64 are present on the tumor. Interestingly, TriNKETs were effective against both Molm-13 (FIG. 52B) and THP-1 (FIG. 52A) cells, while monoclonal antibodies fail to activate NK cells in culture with FcR-Hi THP-1 cells, indicating TriNKETs are able to overcome binding to CD64 on the tumor, and effectively target NK cells for activation. Dual targeting of two activating receptors on NK cells provided stronger specific binding to NK cells. Monoclonal antibodies, which only target CD16 on NK cells, can be bound by other high-affinity FcRs, and prevent engagement of CD16 on NK cells.

Human NK cell cytotoxicity assays using the Molm-13 and THP-1 co-culture systems provide additional evidence to support the efficacy of TriNKETs in the presence of high-levels of CD64. In these cytotoxicity assays a third human AML cell line was used, Mv4-11. Mv4-11 cells express low levels of CD64, and fall in between THP-1 and Molm-13 cells for the levels of CD64 on their surface (FIGS. 51A-51C).

TriNKETs Demonstrate Efficacy on AML Cell Lines Regardless of FcγRI Expression

Figure 53A:
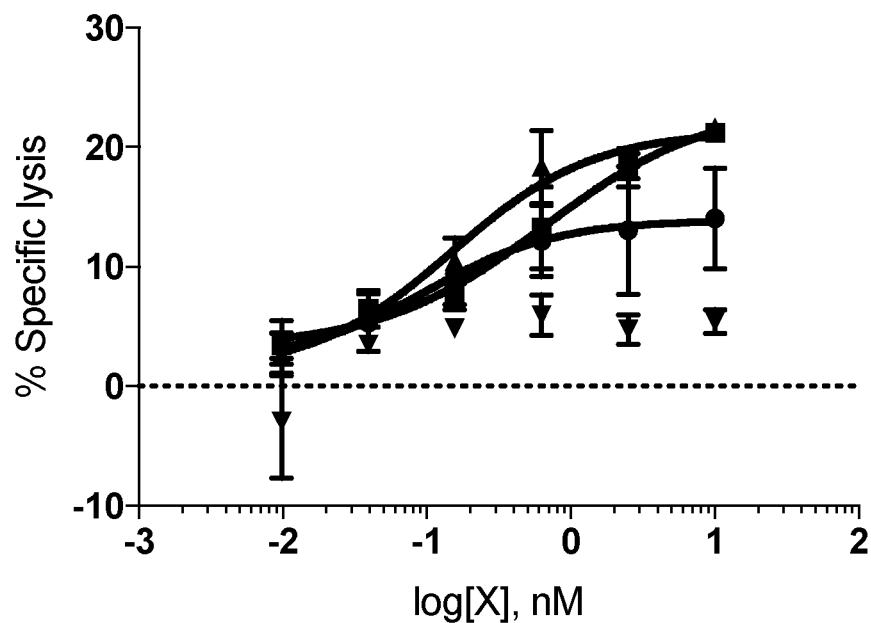
FIGS. 53A-53C are line graphs of human NK cytotoxicity assays using the three human AML cell lines as targets.
Figure 53B:
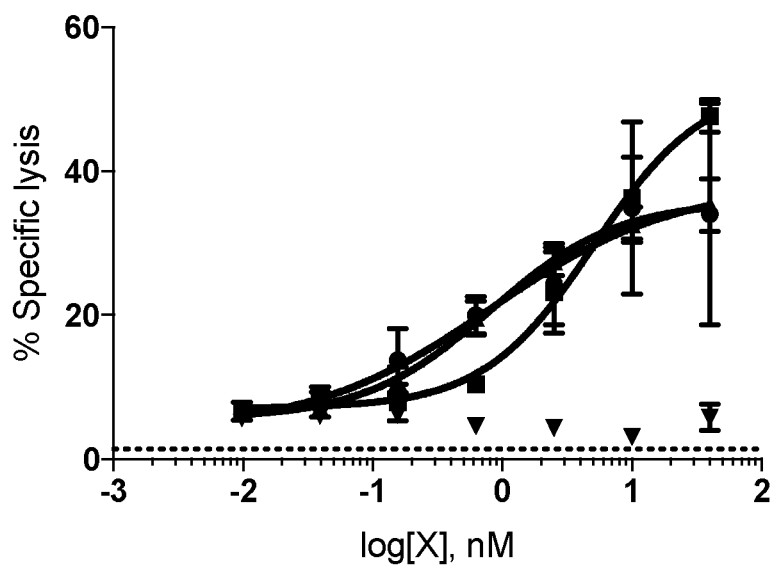
Figure 53C:
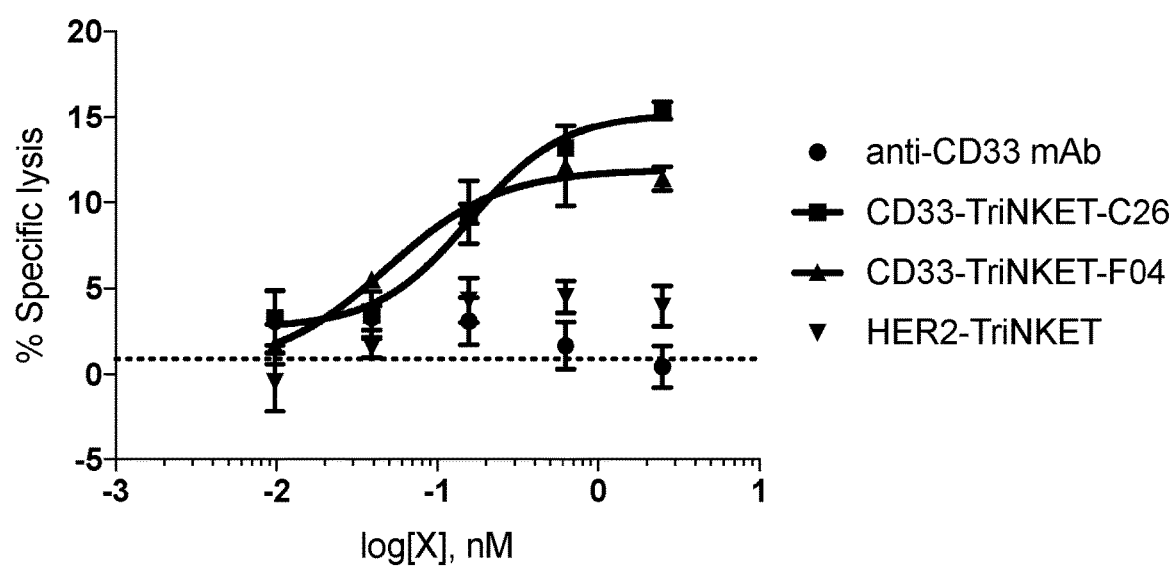

FIGS. 53A-53C show human NK cytotoxicity assays using the three human AML cell lines as targets. A monoclonal antibody against CD33 shows good efficacy against Molm-13 cells (FIG. 53B), which do not express CD64. Mv4-11 cells (FIG. 53A), which express CD64, but at a lower level than THP-1, showed reduced efficacy with the monoclonal anti-CD33. THP-1 cells (FIG. 53C) showed no effect with monoclonal anti-CD33 alone. Regardless of CD64 expression on the tumor cells, TriNKETs were able to mediate human NK cell responses against all tumor cells tested here.

FIGS. 53A-53C show that THP-1 cells were protected against monoclonal antibody therapy, due to high levels of high-affinity FcR expression on their surface. TriNKETs circumvented this protection by targeting two activating receptors on the surface of NK cells. Cytotoxicity data correlated directly to what was seen in the co-culture activation experiments. TriNKETs were able to circumvent protection from mAb therapy seen with THP-1 cells, and induce NK cell mediated lysis despite high levels of FcR.

Killing of Normal Myeloid and Normal B Cells in PBMC Cultures: TriNKETs Provide Better Safety Profile Through Less On-Target Off-Tumor Side Effects Natural killer cells and CD8 T cells are both able to directly lyse tumor cells, although the mechanisms through which NK cells and CD8 T cell recognize normal self from tumor cells differ. The activity of NK cells is regulated by the balance of signals from activating (NCRs, NKG2D, CD16, etc.) and inhibitory (KIRs, NKG2A, etc.) receptors. The balance of these activating and inhibitory signals allow NK cells to determine healthy self-cells from stressed, virally infected, or transformed self-cells. This 'built-in' mechanism of self-tolerance, will help protect normal heathy tissue from NK cell responses. To extend this principle, the self-tolerance of NK cells will allow TriNKETs to target antigens expressed both on self and tumor without off tumor side effects, or with an increased therapeutic window.

Unlike natural killer cells, T cells require recognition of a specific peptide presented by MEW molecules for activation and effector functions. T cells have been the primary target of immunotherapy, and many strategies have been developed to redirect T cell responses against the tumor. T cell bispecifics, checkpoint inhibitors, and CAR-T cells have all been approved by the FDA, but often suffer from dose-limiting toxicities. T cell bispecifics and CAR-T cells work around the TCR-MHC recognition system by using binding domains to target antigens on the surface of tumor cells, and using engineered signaling domains to transduce the activation signals into the effector cell. Although effective at eliciting an anti-tumor immune response these therapies are often coupled with cytokine release syndrome (CRS), and on-target off-tumor side effects. TriNKETs are unique in this context as they will not 'override' the natural systems of NK cell activation and inhibition. Instead, TriNKETs are designed to sway the balance, and provide additional activation signals to the NK cells, while maintaining NK tolerance to healthy self PBMCs were isolated from whole blood by density gradient centrifugation. Any contaminating red blood cells were lysed by incubation in ACK lysis buffer. PBMCs were washed 3x in PBS, and total PBMCs were counted. PBMCs were adjusted to $10^6$ cells/mL in primary cell culture media. 1 mL of PBMCs were seeded into wells of a 24 well plate, the indicated TriNKETs or mAbs were added to the PBMC cultures at 10 µg/mL. Cells were cultured overnight at 37° C. with 5% CO2. The following day (24 hrs later) PBMCs were harvested from culture and prepared for FACS analysis. The percentage of CD45+; CD19+ B cells and CD45+; CD33+; CD11b+ myeloid cells was analyzed over the different treatment groups.

Figure 54A:
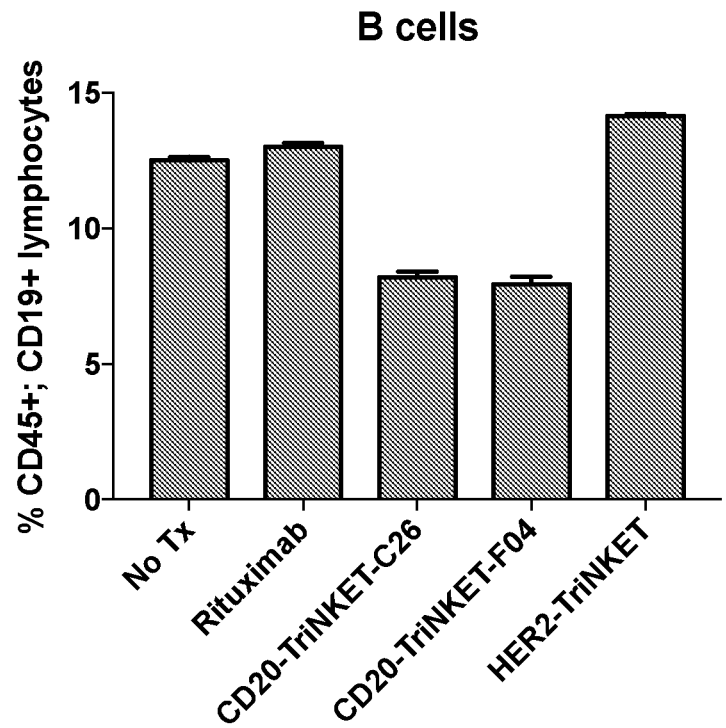
FIGS. 54A & 54B are bar graphs showing B cells from a health donor are sensitive to TriNKET-mediated lysis.
Figure 54B:
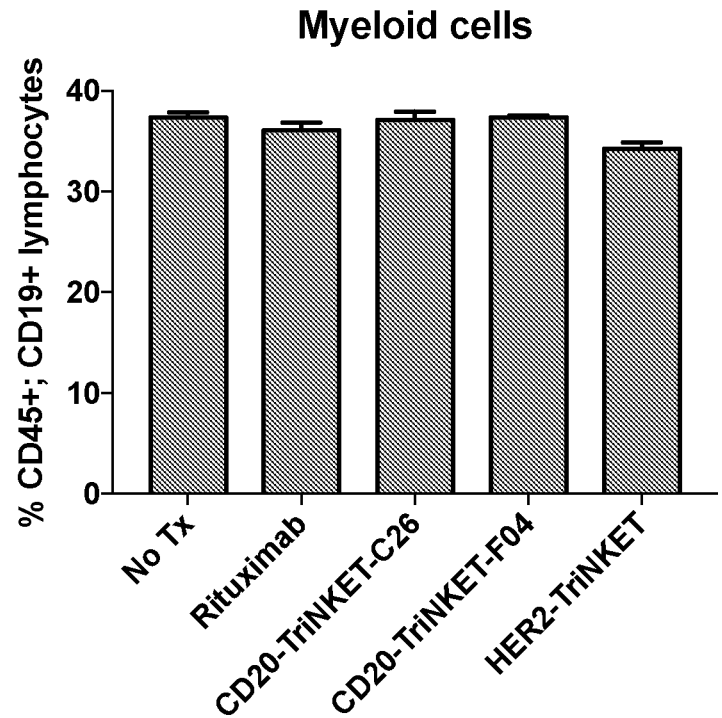
Figure 54C:
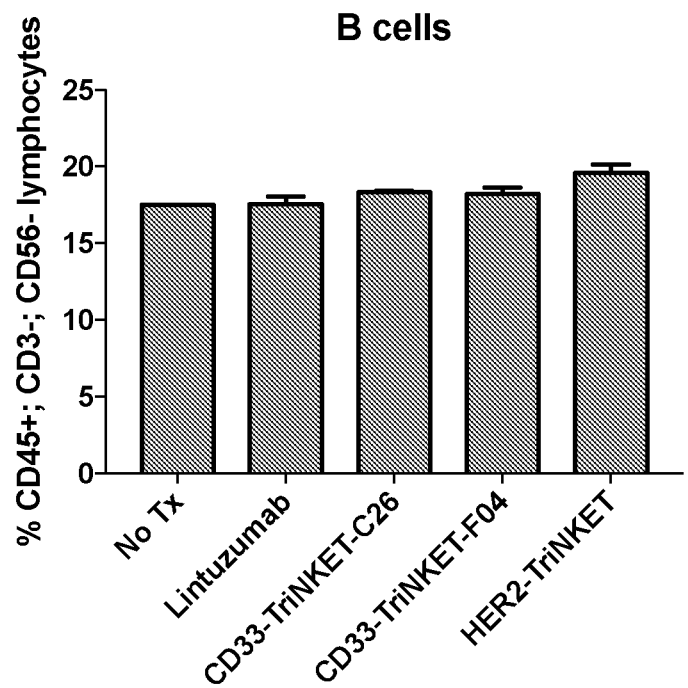
FIGS. 54C & 54D are bar graphs showing myeloid cells are resistant to TriNKET-mediated lysis.
Figure 54D:
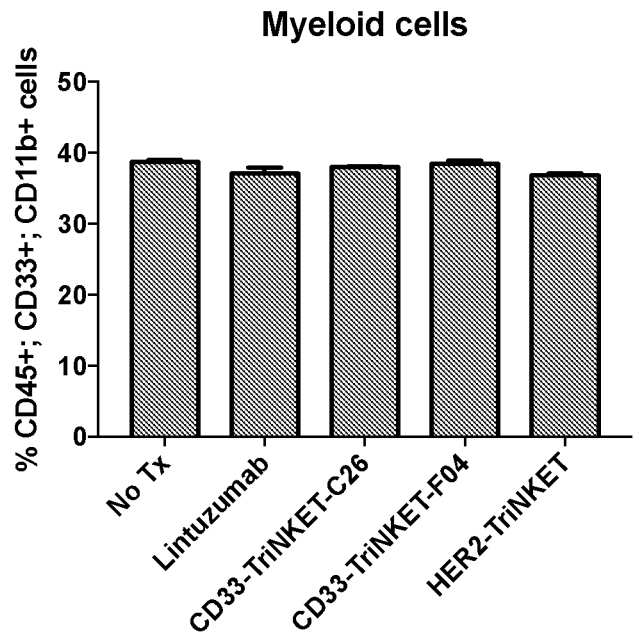

FIGS. 54B & 54D show that autologous myeloid cells are protected from TriNKET mediated NK cell responses. FIGS. 54A & 54B shows B cells from a health donor are sensitive to TriNKET mediated lysis, while myeloid cells are resistant to TriNKET lysis. PBMCs treated with TriNKETs targeting CD20 showed reduced frequency of CD19+ B cells with the CD45+ lymphocyte population (FIG. 54A), but no effect in CD45+, CDD3−, CD56− lymphocyte population (FIG. 54C). In these cultures the frequency of CD45+, CD19+ myeloid cells (FIG. 54B), or the frequency of CD33+, CD 33+, CD11b+ myeloid cells (FIG. 54D) were unchanged.

TriNKETs Mediate hPBMC Killing of SkBr-3 Tumor Cells in Long-Term Co-Cultures

Primary Human PBMC Cytotoxicity Assay

Figure 55:
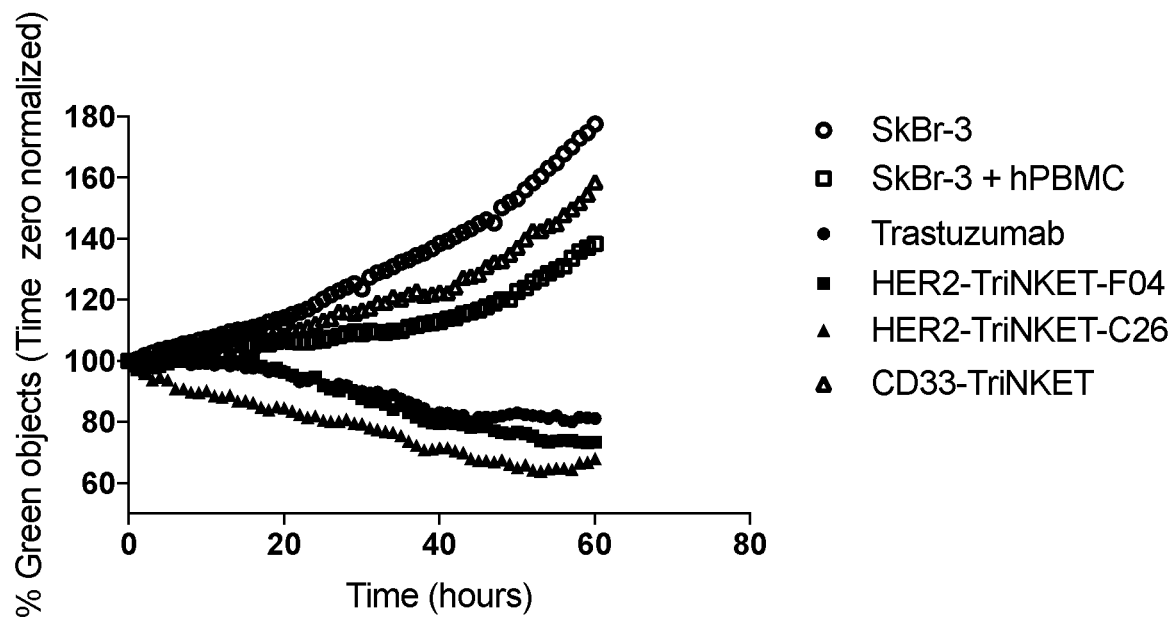
FIG. 55 are line graphs of TriNKETs-mediated hPBMC killing of SkBr-3 tumor cells in long-term co-cultures.

FIG. 55 shows long term killing of SkBr-3 cells in culture with human PBMCs. When cultured alone SkBr-3 cells proliferate and almost double in 60 hours. When human PBMCs are added to SkBr-3 cells in culture the rate of proliferation is slowed, and when an isotype control TriNKET targeting CD33 is added proliferation is also slowed, but to a lesser extent. When cultures are treated with Trastuzumab SkBr-3 no longer proliferate, and after 60 hours only 80% of the cells from time zero are left. Since SkBr-3 cells are sensitive to HER2 signal blockade the effect on SkBr-3 cell growth could be mediated by HER2 signal blockade or through Fc effector functions such as ADCC.

Example 15

Anti-Tumor Efficacy of mcFAE-C26.99 TriNKETs In Vitro

Figure 58B:
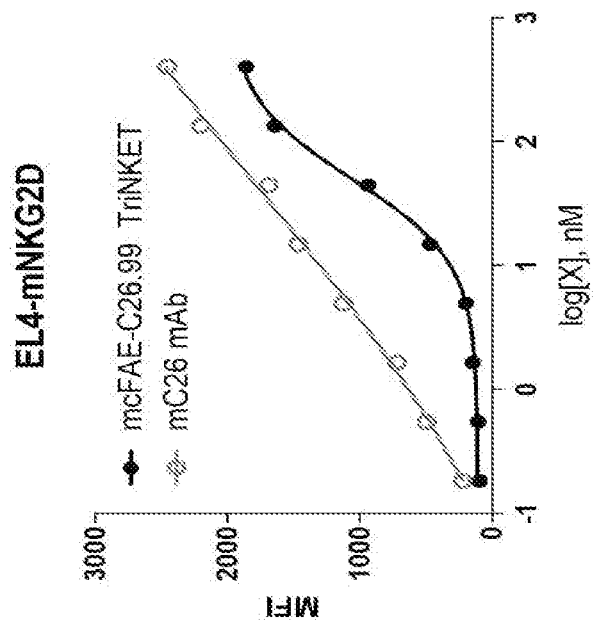
FIGS. 58A-58B are graphs showing in vitro binding by mcFAE-C26.99 TriNKET. 60 µg/mL of indicated antibodies with four-fold dilutions were added to $2 \times 10^5$ B16F10 tumor cells (FIG. 58A) or EL4-mNKG2D cells (FIG. 58B). Binding was assessed using a goat anti-mouse PE secondary antibody followed by flow cytometric analysis.
Figure 58A:
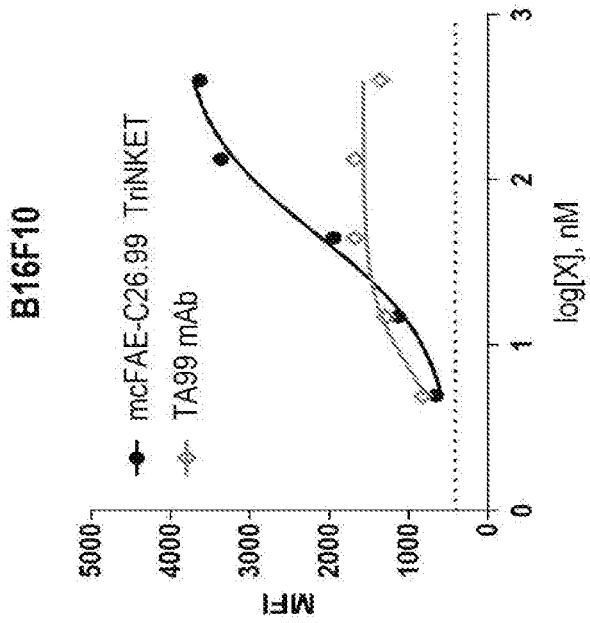

To verify binding activities of the murine cFAE-C26.99 TriNKET, direct binding was measured in comparison to its monoclonal antibodies by flow cytometry assays against Tyrp-1-positive B16F10 melanoma cells (FIG. 58A) and the EL4 line overexpressing murine NKG2D (EL4-mNKG2D, FIG. 58B).

Figure 59:
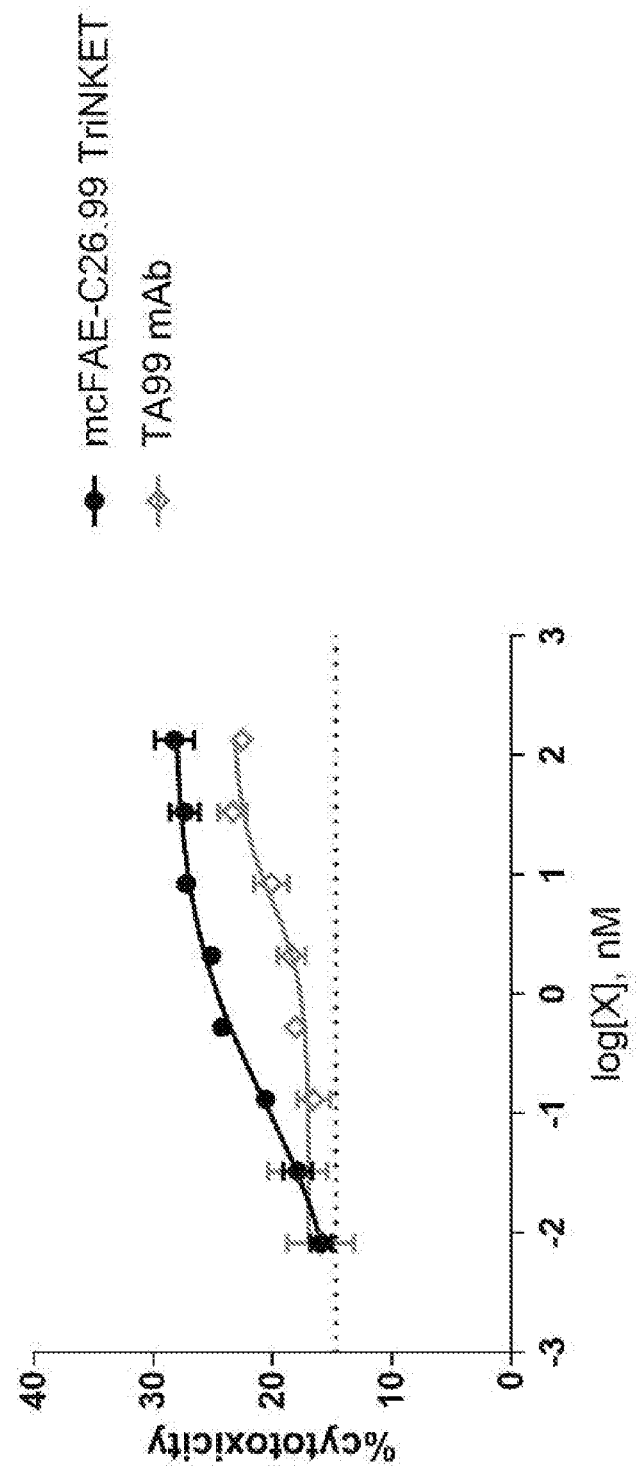
FIG. 59 is a graph showing increased NK cytotoxicity mediated by mcFAE-C26.99 TriNKET.

To test whether mcFAE-C26.99 TriNKETs retained the ability to mediate cytotoxicity, killing of Tyrp-1-positive B16F10 tumor targets by murine IL-2-activated NK cells was measured. As shown in FIG. 59, murine NK cells increased their cytotoxic activity in the presence of mcFAE-C26.99. Importantly, the anti-Tyrp-1 monoclonal antibody TA99 exhibited only marginal effects.

Increased NK Cytotoxicity Mediated by mcFAE-C26.99 TriNKET

About 5×10³ Bl6F10 melanoma cells per well were seeded two days prior to assay. On the day of the experiment 5×10⁴ murine IL-2-activated NK cells were added in the presence of TA99 monoclonal antibody or mcFAE-C26.99 TriNKET (mcFAE-C26.99 is a heterodimer of mC26 and TA99 with mouse IgG2c as the Fc. Gm mutations refer to heterodimerization mutations used to generate heterodimer). 20 µg/mL of antibodies with four-fold dilutions were used. After 4 hours of co-culture, percentage of cytotoxicity was assessed using CytoTox96 kit for LDH release. Dotted line represents baseline cytotoxicity in the absence of antibodies.

```
mC26_hvL_mCL (bolded section) (italicized
underlined amino acids are the heterodimerization
mutations used to generate heterodimer):
                                (SEQ ID NO: 86)
DIQMTQSPSTLSASVGDRVTITCRASQSISSWLAWYQQKPGKAPKLLIYK

ASSLESGVPSRFSGSGSGTEFTLTISSLQPDDFATYYCQQYGSFPITFGG

GTKVEIKRADAAPTVSIFPPSSEQLTSGGASVVCFLNNFYPKDINVKWKI

DGSERQNGVLNSWTDQDSKDSTYSMSSTLTLTKDEYERHNSYTCEATHKT

STSPIVKSFNRNEC mC26_hvH_IgG2cGmB
                                (SEQ ID NO: 87)
QVQLQQWGAGLLKPSETLSLTCAVYGGSFSGYYWSWIRQPPGKGLEWIGE

IDHSGSTNYNPSLKSRVTISVDTSKNQFSLKLSSVTAADTAVYYCARARG

PWSFDPWGQGTLVTVSSAKTTAPSVYPLAPVCGGTTGSSVTLGCLVKGYF

PEPVTLTWNSGSLSSGVHTFPALLQSGLYTLSSSVTVTSNTWPSQTITCN

VAHPASSTKVDKKIEPRVPITQNPCPPLKECPPCAAPDLLGGPSVFIFPP

KIKDVLMISLSPMVTCVVVDVSEDDPDVQISWFVNNVEVHTAQTQTHRED

YNSTLRVVSALPIQHQDWMSGKEFKCKVNNRALPSPIEKTISKPRGPVRA

PQVYVLPPPAEEMTKKEFSLTCMIKGFLPAEIAVDWTSNGRTEQNYKNTA

TVLDSDGSYFMYSRLRVQKSTWERGSLFACSVVHEGLHNHLTTKTISRSL

GK

TA99_mvL_mCL
                                (SEQ ID NO: 88)
DIQMSQSPASLSASVGETVTITCRASGNIYNYLAWYQQKQGKSPHLLVYD

AKTLADGVPSRFSGSGSGTQYSLKISSLQTEDSGNYYCQHFWSLPFTFGS

GTKLEIKRADAAPTVSIFPPSSEQLTSGGASVVCFLNNFYPKDINVKWKI

DGSERQNGVLNSWTDQDSKDSTYSMSSTLTLTKDEYERHNSYTCEATHKT

STSPIVKSFNRNEC

TA99_mvH_IgG2cGmA
                                (SEQ ID NO: 89)
EVQLQQSGAELVRPGALVKLSCKTSGFNIKDYFLHWVRQRPDQGLEWIGW

INPDNGNTVYDPKFQGTASLTADTSSNTVYLQLSGLTSEDTAVYFCTRRD

YTYEKAALDYWGQGASVIVSSAKTTAPSVYPLAPVCGGTTGSSVTLGCLV

KGYFPEPVTLTWNSGSLSSGVHTFPALLQSGLYTLSSSVTVTSNTWPSQT

ITCNVAHPASSTKVDKKIEPRVPITQNPCPPLKECPPCAAPDLLGGPSVF

IFPPKIKDVLMISLSPMVTCVVVDVSEDDPDVQISWFVNNVEVHTAQTQT

HREDYNSTLRVVSALPIQHQDWMSGKEFKCKVNNRALPSPIEKTISKPRG

PVRAPQVYVLPPPAEEMTKKEFSLTCMITGFLPAEIAVDWTSNGRTEQNY

KNTATVLDSDGSYLMYSKLTVQKSTWERGSLFACSVVHEGLHNHLTTKTI

SRSLGK
```

Example 16

Anti-Tumor Efficacy of mcFAE-C26.99 TriNKETs In Vivo

Figure 60A:
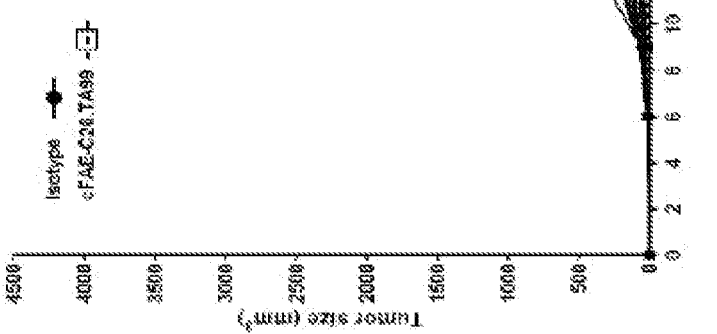
FIGS. 60A-60B show the anti-tumor efficacy of mcFAE-C26.99 TriNKET in B16F10 s.c. models. Mice were treated intraperitoneally with (FIG. 60A) isotype control mouse IgG2a monoclonal antibody C1.18.4 and mouse anti-Tyrp-1 monoclonal antibody or (FIG. 60B) isotype control mouse IgG2a monoclonal antibody C1.18.4 and mcFAE-C26.99 TriNKET, injected at a dose of 150 µg (days 6, 8, 10, 12, 14, 16, and 21). Tumor growth was assessed for 28 days. Graphs show tumor growth curves of individual mice.
Figure 60B:
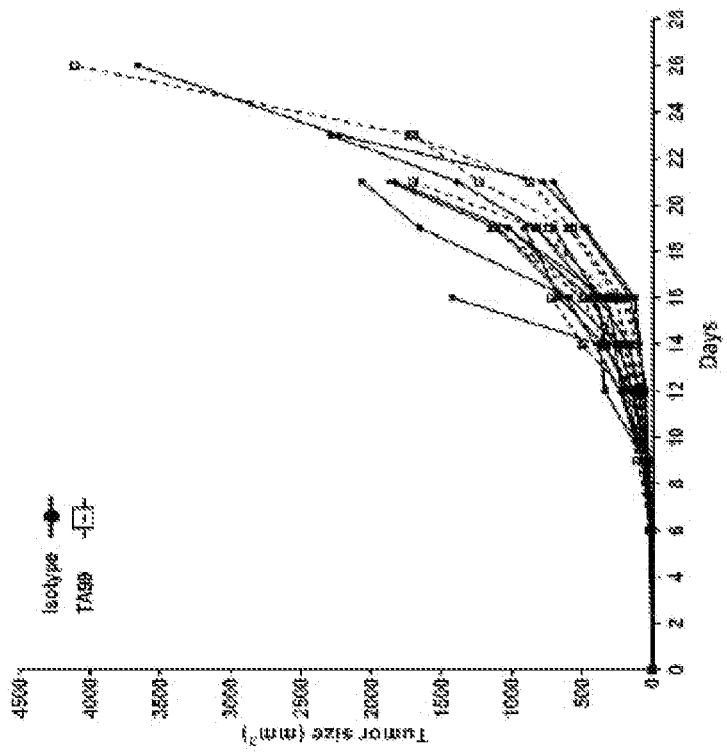

To test whether mcFAE-C26.99 elicits antitumor functions in vivo, C57BL/6 mice were injected subcutaneously with 2×10⁵ B16F10 tumor cells. Mice were treated either with the isotype control, monoclonal TA99 antibody or with the mcFAE-C26.99 TriNKET. Treatment with the monoclonal TA99 antibody showed similar tumor progression as in the control group treated with the isotype. However, administration of the mcFAE-C26.99 TriNKET resulted in delayed tumor progression compared to the isotype-treated group. About 2×10⁵ B16F10 melanoma cells were injected subcutaneously into the flank of C57BL/6 mice. On Day 6 after tumor inoculation mice were randomized (n=10 per group). Mice were treated intraperitoneally with (FIG. 60A) isotype control mouse IgG2a monoclonal antibody C1.18.4 and mouse anti-Tyrp-1 monoclonal antibody or (FIG. 60B) isotype control mouse IgG2a monoclonal antibody C1.18.4 and mcFAE-C26.99 TriNKET, injected at a dose of 150 µg (days 6, 8, 10, 12, 14, 16, and 21). Tumor growth was assessed for 28 days. Graphs show tumor growth curves of individual mice.

Figure 61B:
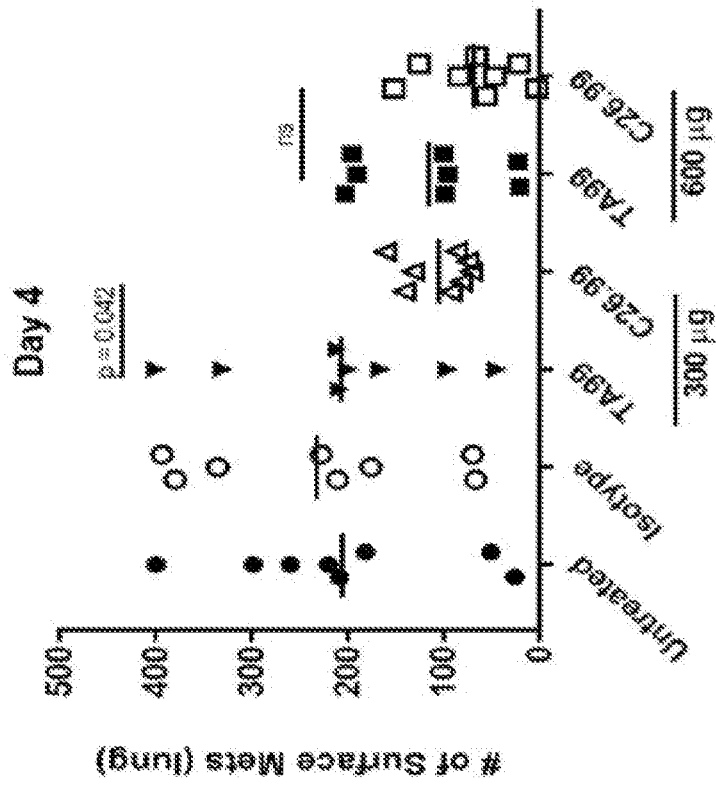
FIGS. 61A-61B show anti-tumor efficacy of mcFAE-C26.99 TriNKET in B16F10 i.v. models.
Figure 61A:
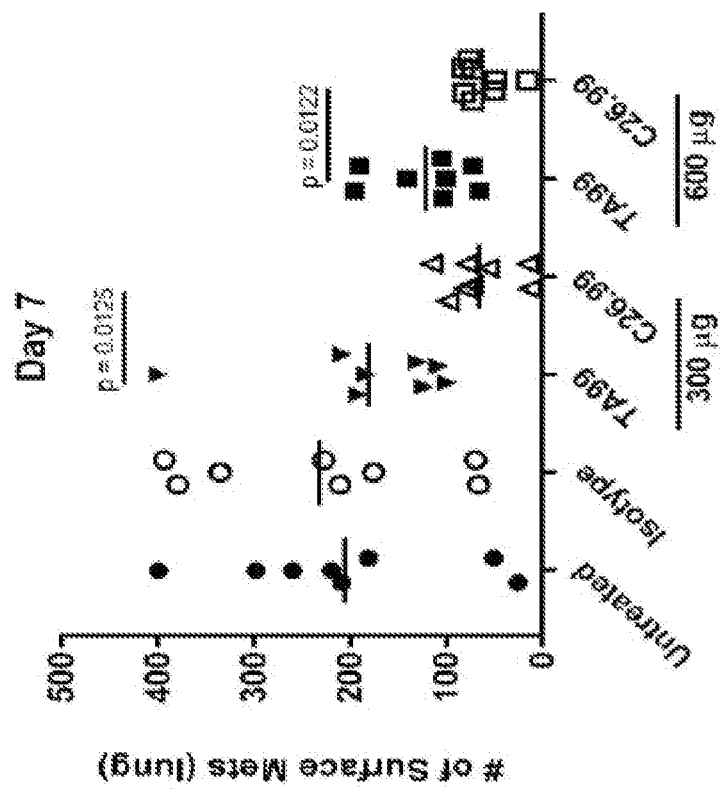

In addition to the subcutaneous Bl6F10 tumor model, the mcFAE-C26.99 TriNKET was also tested for its tumor efficacy in a disseminated tumor setting. 1×10⁵ Bl6F10 cells were intravenously injected into mice. Treatment started either on day 4 or day 7 with a low (300 µg/injection) and high (600 µg/injection) antibody dose. On day 18 after tumor inoculation, lung metastases were counted. Treatment started at day 4 and 7 after tumor inoculation resulted in reduced numbers of lung metastases when TA99 monoclonal antibody or mcFAE-C26.99 TriNKET was used at high concentration compared to the isotype-treated control group. At low concentrations only mcFAE-C26.99 TriNKET diminished tumor burden (FIG. 61A). Similar effects were seen when antibodies were administered starting on day 7 after tumor inoculation. Overall, mcFAE-C26.99 TriNKET therapy resulted in lower numbers of lung metastases compared to the monoclonal TA99 antibody in all tested conditions. About 1×10⁵ B16F10 melanoma cells were injected intravenously into the tail vein of C57BL/6 mice (n=8 per group). Mice were either left untreated or treated intraperitoneally with control monoclonal antibody (isotype, clone C1.18.4), monoclonal TA99 antibody or TA99 TriNKET (mcFAE-C26.99). FIG. 61A represents tumor burden when antibodies were administered at a 150-µg dose (days 4, 6, 8, 11, 13, 15). FIG. 61B represents tumor burden when antibodies were administered at a 150-µg dose (days 7, 9, 11, 13, 15). 18 days after tumor challenge, mice were euthanized and surface lung metastases were scored (FIG. 61B).

Example 17

Combination Therapies with mcFAE-C26.99 TriNKETs In Vivo

The levels of anti-tumor response of multi-specific proteins of the present disclosure when combined with another anti-tumor agent was determined. To determine whether anti-tumor immune responses mediated by the mcFAE-C26.99 can be amplified, combination studies using anti-PD-1 antibodies or IL-2 cytokines were performed. C57BL/6 mice were injected subcutaneously with $2\times10^5$ B16F10 tumor cells. Mice were treated with the isotype control, mcFAE-C26.99 TriNKET, an anti-PD-1 monoclonal antibody, or the combination of mcFAE-C26.99 and anti-PD-1 monoclonal antibody. Monotherapy with either mcFAE-C26.99 or anti-PD-1 resulted in 10% responder mice. However, combination therapy of mcFAE-C26.99 and anti-PD-1 monoclonal antibody delayed tumor progression and led to 40% responder mice compared to the isotype-treated group.

Figure 66A:
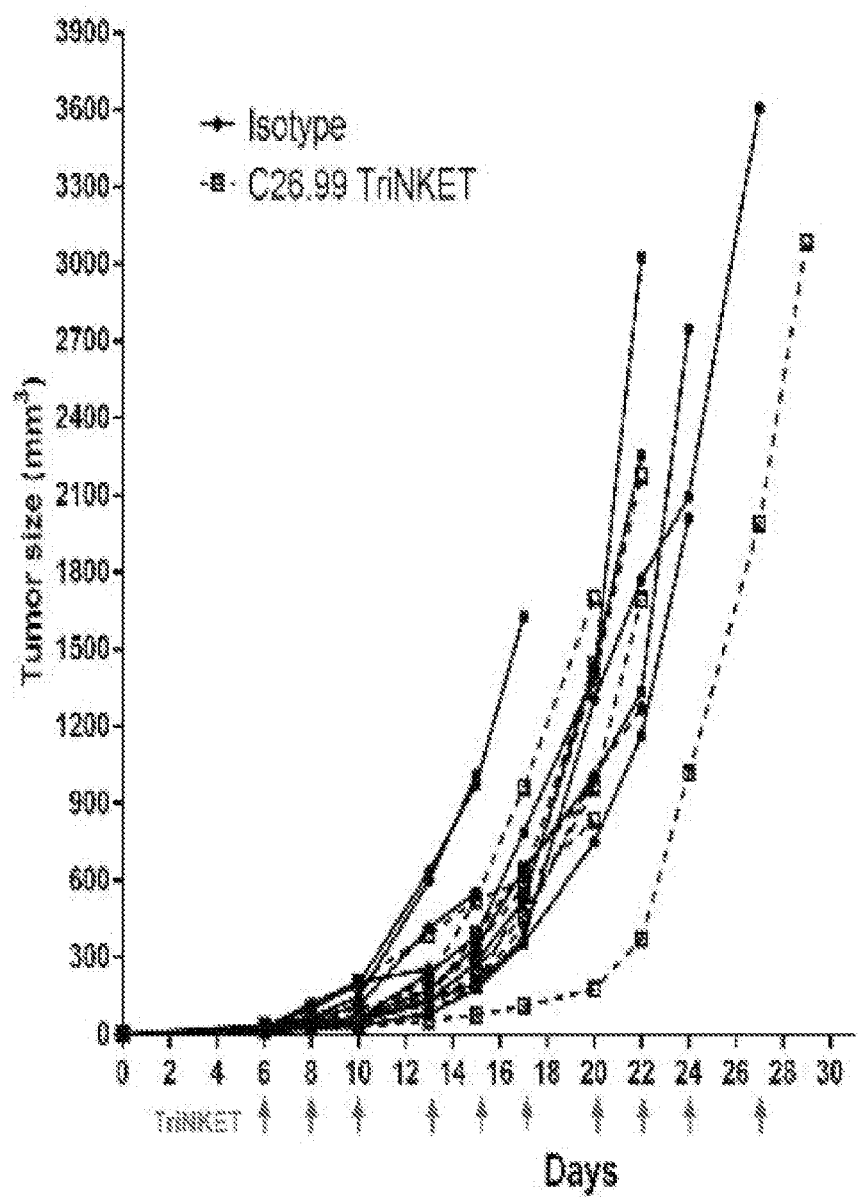
FIGS. 66A-66C are line graphs showing effects of combination therapy using mcFAE-C26.99 TriNKET and anti-PD-1 antibodies in B16F10 s.c. models.
Figure 66B:
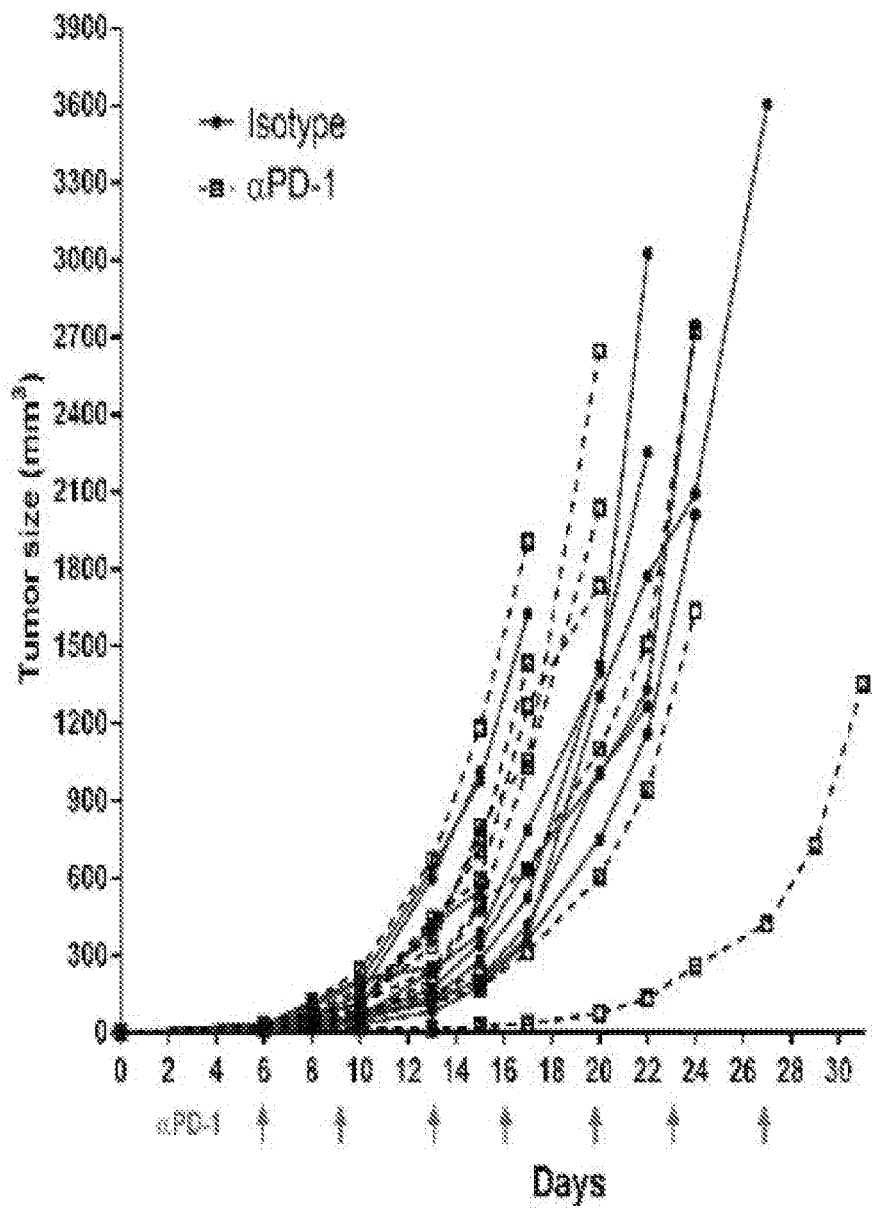
Figure 66C:
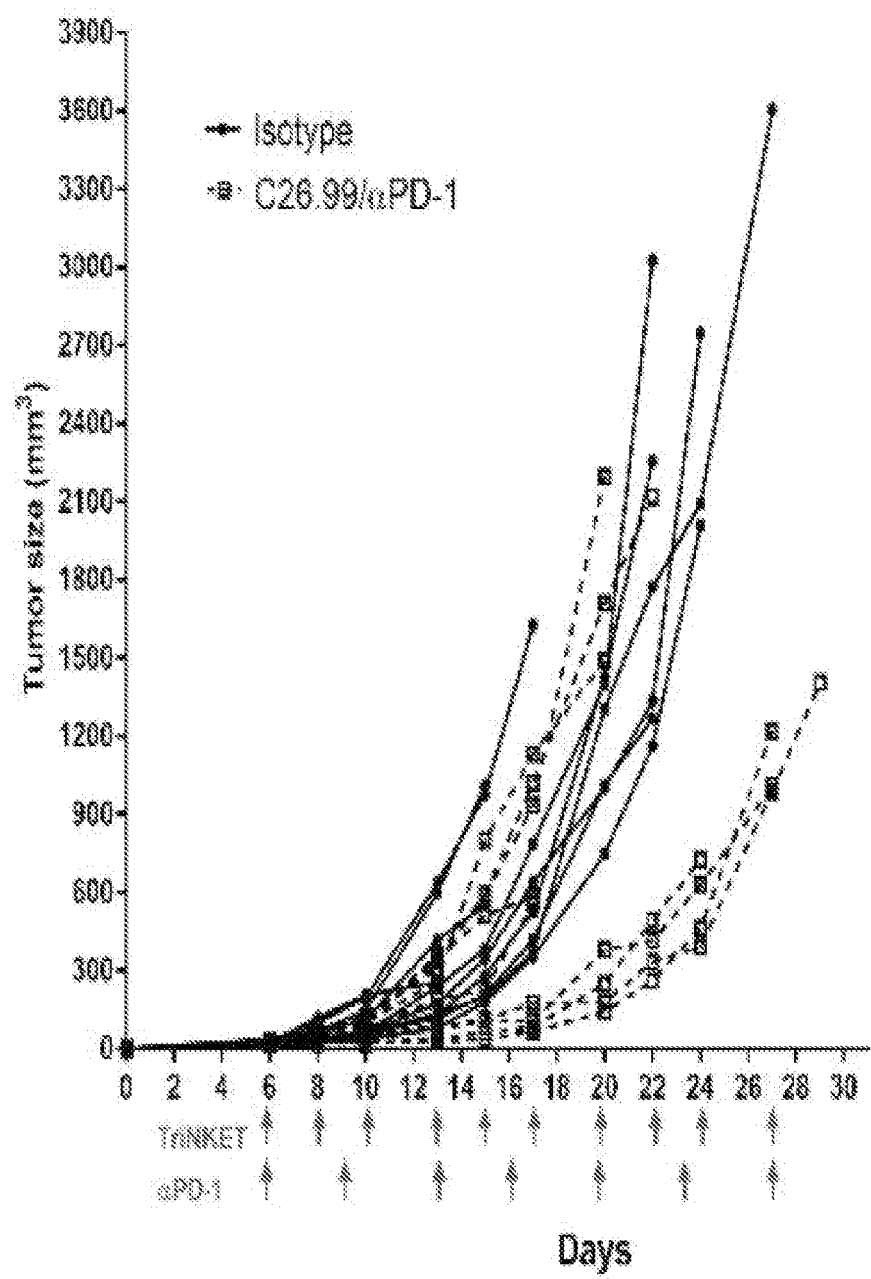

Combination Therapy with Anti-PD-1 Monoclonal Antibody $2\times10^5$ B16F10 melanoma cells were injected subcutaneously into the flank of C57BL/6 mice. On Day 6 after tumor, inoculated mice were randomized (n=10 per group). Mice were treated intraperitoneally with isotype controls mouse IgG2a monoclonal antibody C1.18.4 with rat IgG2a monoclonal antibody 2A3 and mcFAE-C26.99; with isotype controls and anti-PD-1 monoclonal antibody clone RPM1-14; or combination of mcFAE-C26.99 and anti-PD-1 monoclonal antibody. Animals were injected as indicated above with single doses of 150 µg (mcFAE-C26.99 and C1.18.4) and 200 µg (anti-PD-1 monoclonal antibody and 2A3). Tumor growth was assessed for 30 days. Graphs in FIGS. 66A-66C show tumor growth curves of individual mice. FIG. 66A are line graphs showing tumor size (mm³) in mice treated intraperitoneally with isotype controls mouse IgG2a monoclonal antibody C1.18.4 with rat IgG2a monoclonal antibody 2A3, or with mcFAE-C26.99. FIG. 66B are line graphs showing tumor size (mm³) in mice treated intraperitoneally with isotype controls or anti-PD-1 monoclonal antibody clone RPM1-14. FIG. 66C are line graphs showing tumor size (mm³) in mice treated intraperitoneally with combination of mcFAE-C26.99 and anti-PD-1 monoclonal antibody.

Combination Therapy with IL-2

Effects on tumor size upon administration of a combination of mcFAE-C26.99 and recombinant human IL-2 was also evaluated. C57BL/6 mice were injected subcutaneously with $2\times10^5$ B16F10 tumor cells. These mice were treated with the isotype control, mcFAE-C26.99 TriNKET, or IL-2 individually, or treated with a combination of mcFAE-C26.99 and IL-2. Monotherapy with either mcFAE-C26.99 (FIG. 67A) or IL-2 (FIG. 67B) resulted in 10% responder mice. However, combination therapy (FIG. 67C) delayed tumor progression and led to 70-90% responder mice compared to the isotype-treated group.

For this experiment, $2\times10^5$ B16F10 melanoma cells were injected subcutaneously into the flank of C57BL/6 mice. On Day 6 after tumor, inoculated mice were randomized (n=10 per group). Mice were treated intraperitoneally with isotype control mouse IgG2a monoclonal antibody C1.18.4 or mcFAE-C26.99; with isotype control or IL-2; or with a combination of mcFAE-C26.99 and IL-2. Animals were injected as indicated above with single doses of 150 µg (mcFAE-C26.99 and C1.18.4) and 100,000 IU (IL-2, twice a day). Tumor growth was assessed for 40 days with 3 mice from the combination group remaining tumor-free. Graphs show tumor growth curves of individual mice.

Figure 67A:
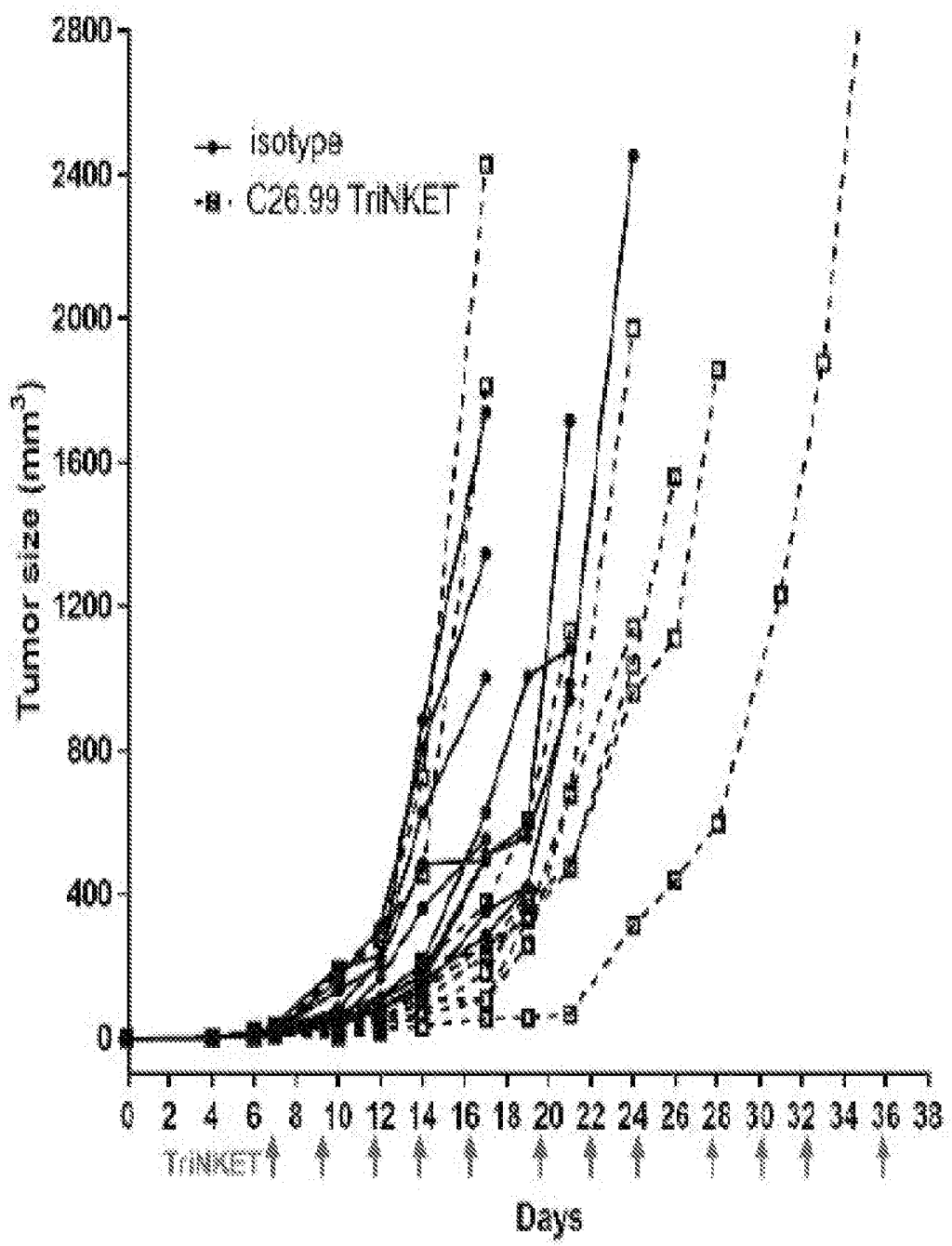
FIGS. 67A-67C are line graphs showing effects of combination therapy using mcFAE-C26.99 TriNKET and recombinant human IL-2 in B16F10 s.c. models.
Figure 67B:
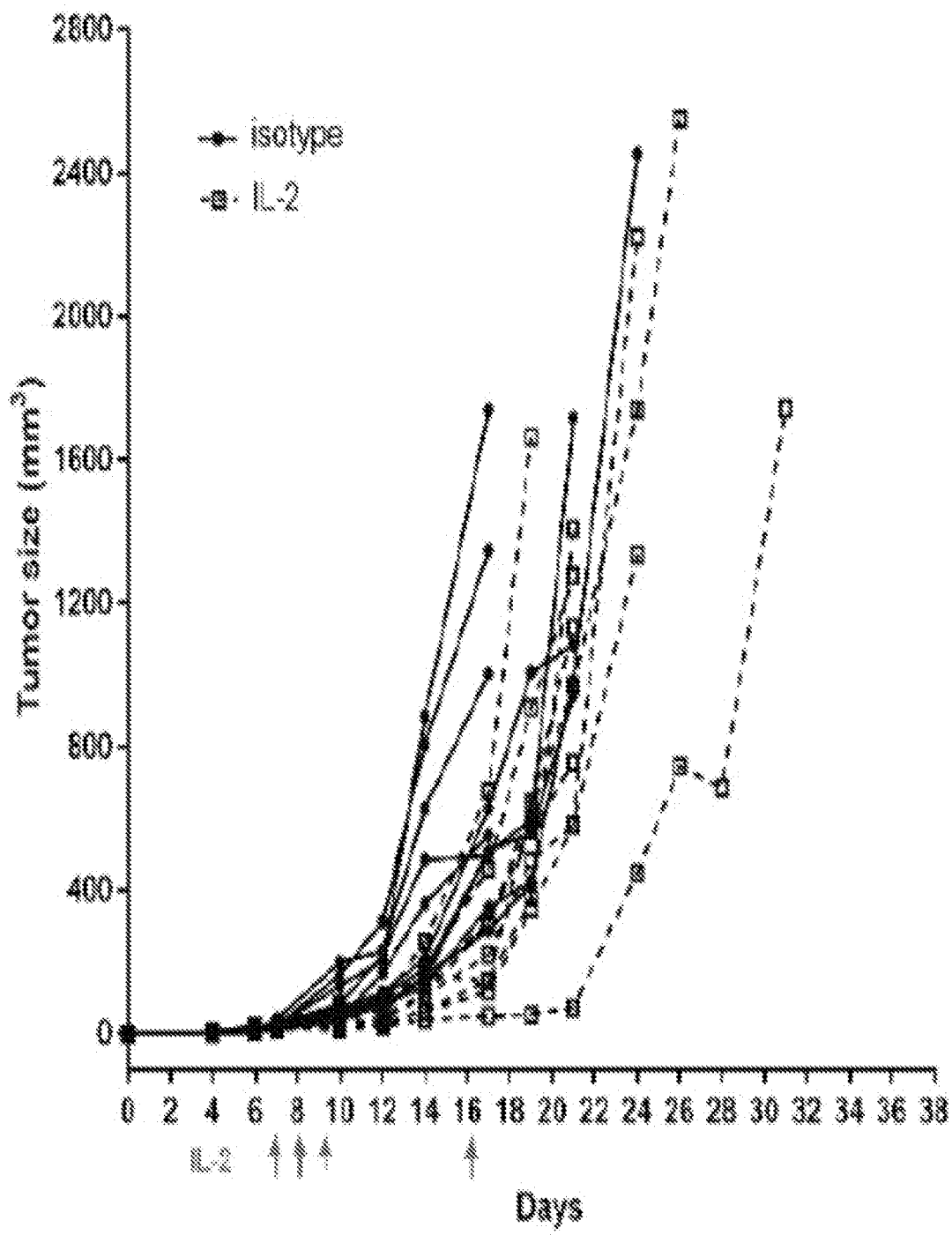
Figure 67C:
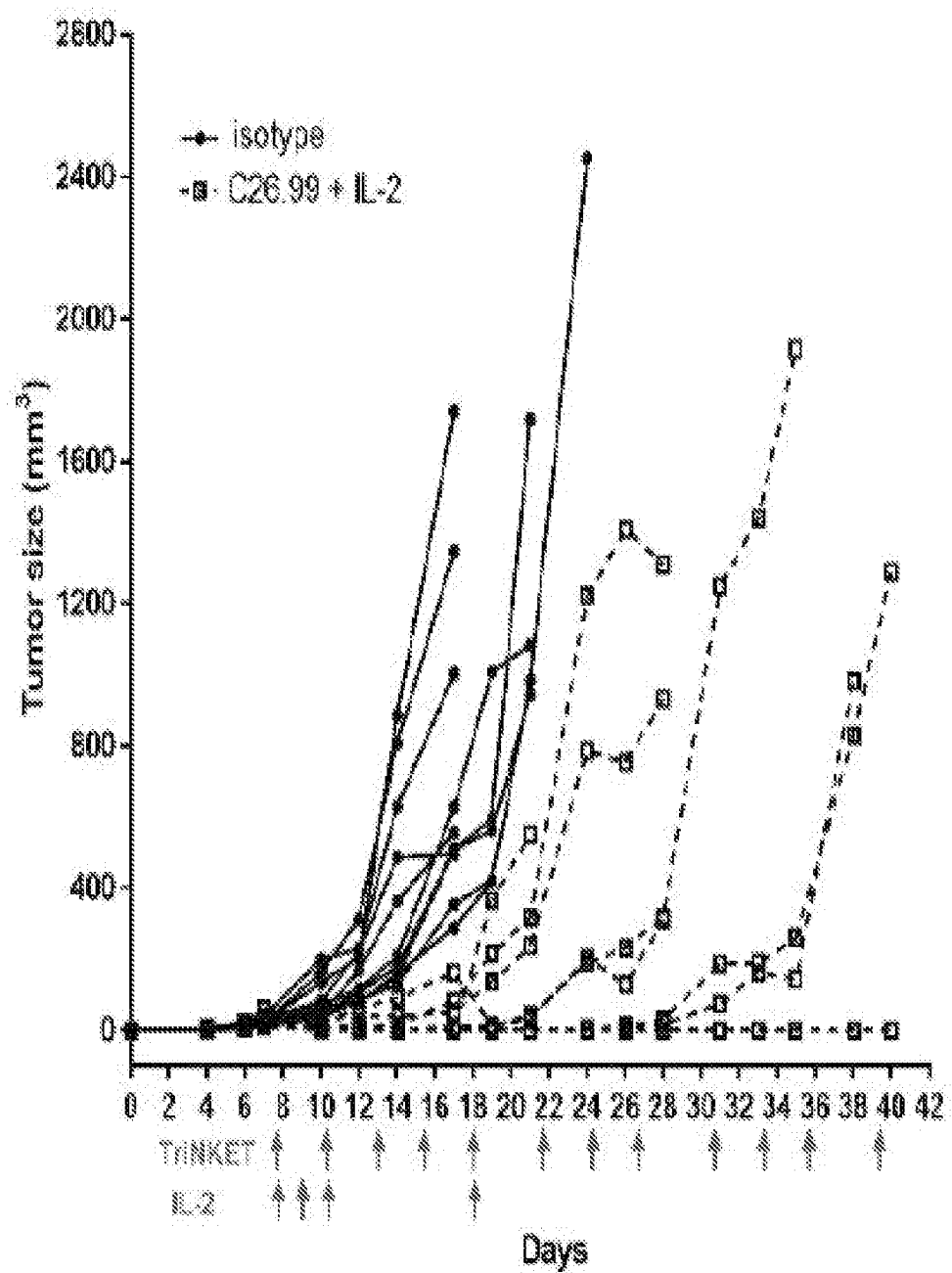

FIG. 67A are line graphs showing tumor size (mm³) in mice treated intraperitoneally with isotype control mouse IgG2a monoclonal antibody C1.18.4 or with mcFAE-C26.99. FIG. 67B are line graphs showing tumor size (mm³) in mice treated intraperitoneally with isotype control or with IL-2. FIG. 67C are line graphs showing tumor size (mm³) in mice treated intraperitoneally with a combination of mcFAE-C26.99 and IL-2.

Example 18

Cytotoxic Activity of Rested Human NK Cells Mediated by TriNKETs, Monoclonal Antibodies, or Bispecific Antibodies Against HER2-Positive Cells PBMCs were isolated from human peripheral blood buffy coats using density gradient centrifugation. Isolated PBMCs were washed and prepared for NK cell isolation. NK cells were isolated using a negative selection technique with magnetic beads; the purity of the isolated NK cells was typically >90% CD3-CD56+. Isolated NK cells were cultured in media containing 100 µg/mL IL-2 or were rested overnight without cytokine. IL-2-activated or rested NK cells were used the following day in cytotoxicity assays.

DELFIA Cytotoxicity Assay:

Human cancer cell lines expressing a target of interest were harvested from culture, cells were washed with HBS, and were resuspended in growth media at $10^6$ cells/mL for labeling with BATDA reagent (Perkin Elmer AD0116). Manufacturer instructions were followed for labeling of the target cells. After labeling, cells were washed 3x with HBS, and were resuspended at $0.5-1.0\times10^5$ cells/mL in culture media. To prepare the background wells an aliquot of the labeled cells was put aside, and the cells were spun out of the media. 100 µl of the media was carefully added to wells in triplicate to avoid disturbing the pelleted cells. 100 µl of BATDA labeled cells were added to each well of the 96-well plate. Wells were saved for spontaneous release from target cells, and wells were prepared for maximal lysis of target cells by addition of 1% Triton-X. Monoclonal antibodies or TriNKETs against the tumor target of interest were diluted in culture media and 50 µl of diluted mAb or TriNKET was added to each well. Rested and/or activated NK cells were harvested from culture, the cells were washed and were resuspended at $10^5-2.0\times10^6$ cells/mL in culture media depending on the desired E:T ratio. 50 µl of NK cells were added to each well of the plate to make a total 200 µl culture volume. The plate was incubated at 37° C. with 5% CO2 for 2-3 hours before developing the assay.

After culturing for 2-3 hours, the plate was removed from the incubator and the cells were pelleted by centrifugation at 200 g for 5 minutes. 20 µl of culture supernatant was transferred to a clean microplate provided from the manufacturer and 200 µl of room temperature europium solution was added to each well. The plate was protected from the light and incubated on a plate shaker at 250 rpm for 15 minutes. The plate was read using either Victor 3 or SpectraMax i3X instruments. % Specific lysis was calculated as follows: % Specific lysis=((Experimental release−Spontaneous release)/(Maximum release−Spontaneous release))*100%.

Figure 68:
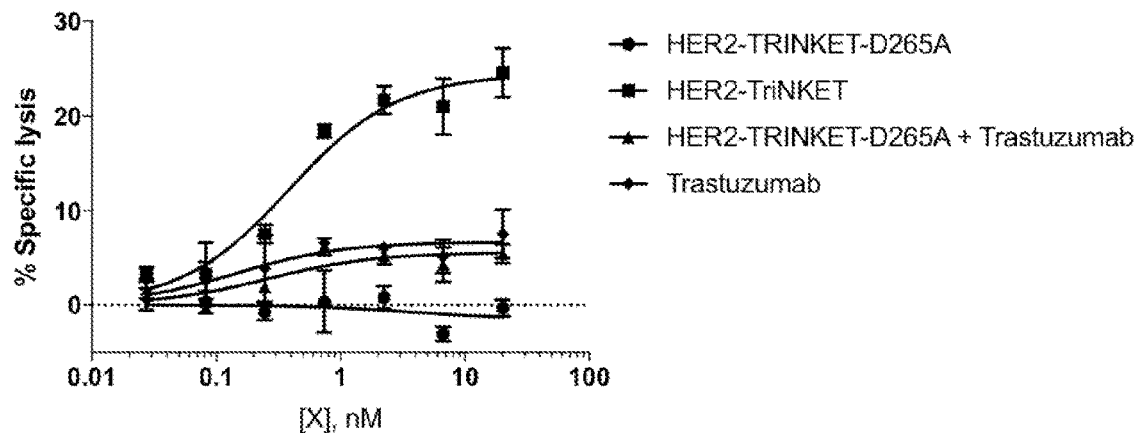
FIG. 68 is a line graph showing that tri-specific binding in one molecule is important for maximal NK cell activity.
Figure 69:
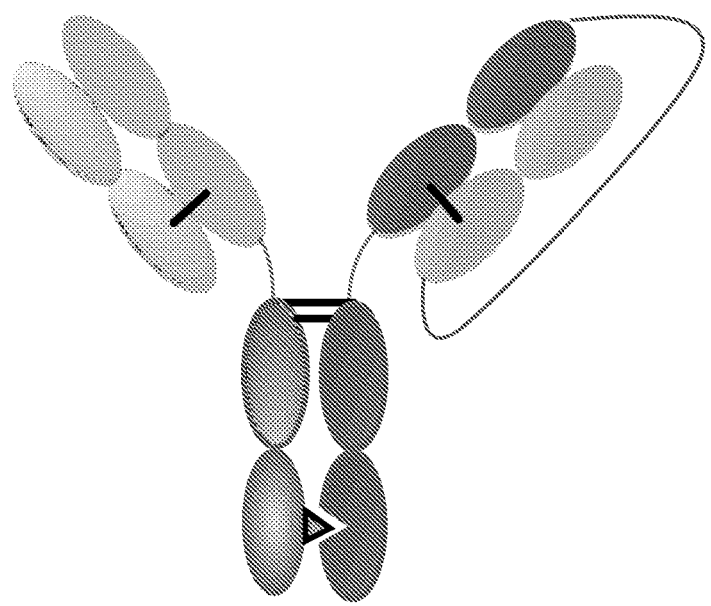
FIG. 69 is an Oasc-Fab heterodimeric construct that includes Fab binding to target 1 and scFab binding to target 2 fused to $F_C$. Heterodimerization is ensured by mutations in the $F_C$.
Figure 70:
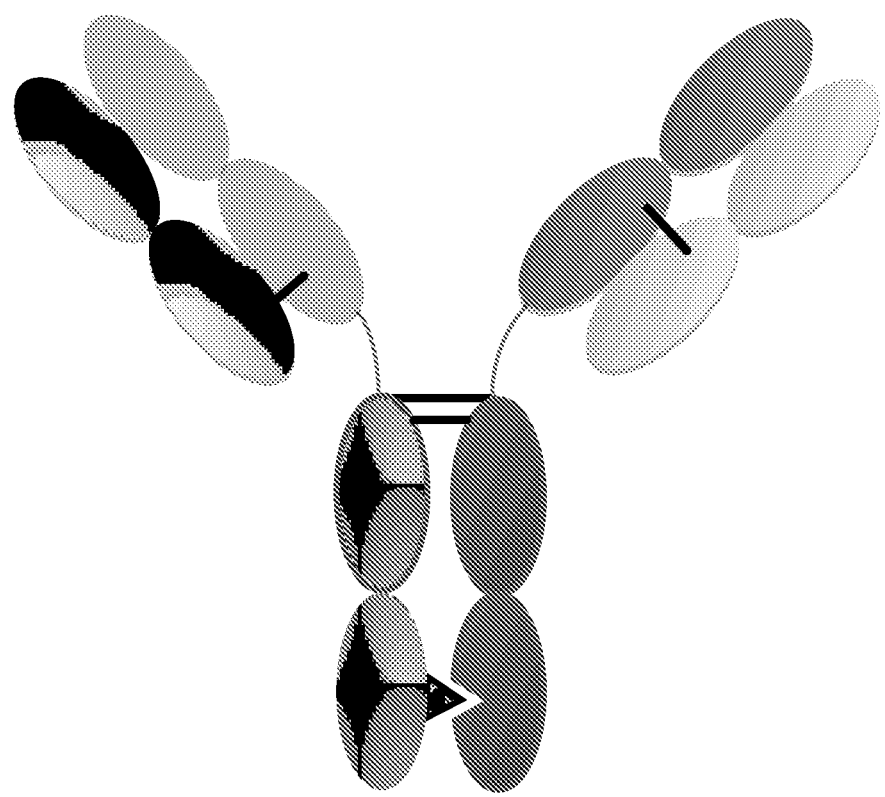
FIG. 70 is a DuetMab, which is an heterodimeric construct containing 2 different Fabs binding to antigen 1 and 2 and $F_C$ stabilized by heterodimerization mutations. Fab 1 and 2 contain differential S-S bridges that ensure correct LC and HC pairing.
Figure 71:
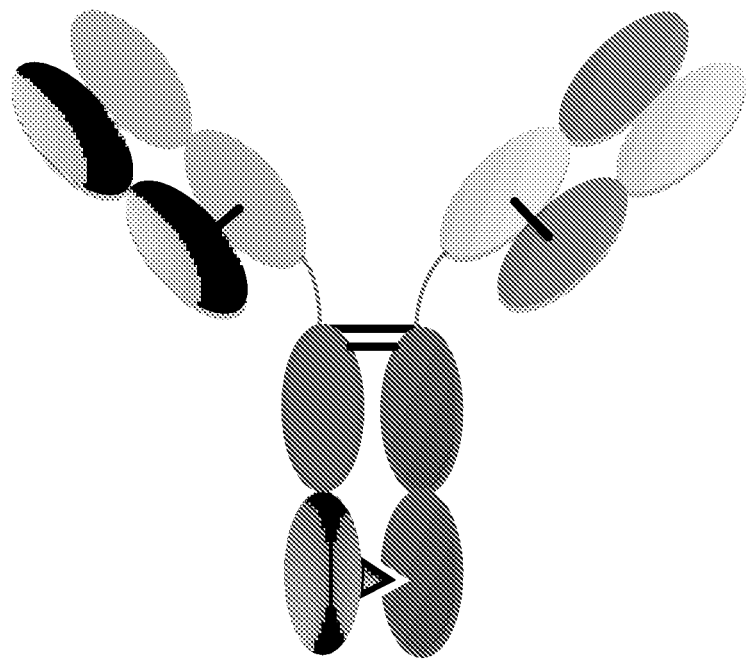
FIG. 71 is a CrossmAb, which is an heterodimeric construct with 2 different Fabs binding to target 1 and 2 fused to Fc stabilized by heterodimerization. CL and CH1 domains and VH and VL domains are switched, e.g., CH1 is fused in-line with VL, while CL is fused in-line with VH.
Figure 72:
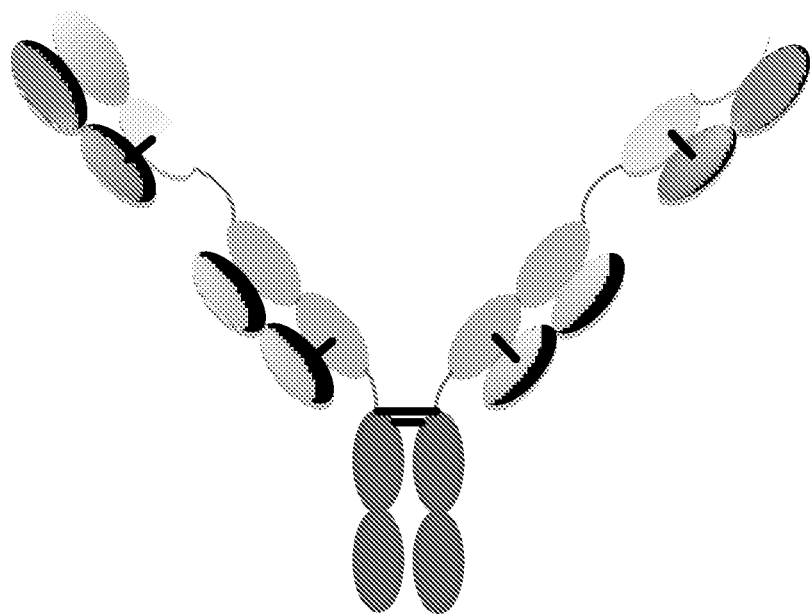
FIG. 72 is a Fit-Ig, which is an homodimeric constructs where Fab binding to antigen 2 is fused to the N terminus of HC of Fab that binds to antigen 1. The construct contains wild-type $F_C$.

Combination of Monoclonal Antibody and Bispecifc NK Cell Engager does not Recapitulate TriNKET Activity FIG. 68 shows the cytotoxic activity of rested human NK cells mediated by TriNKETs, monoclonal antibodies, or bispecific antibodies against the HER2-positive Colo-201 cell line. A TriNKET (ADI-29404 (F04)) targeting HER2 induced maximum lysis of Colo-201 cells by rested human NK cells. The D265A mutation was introduced into the CH2 domain of the TriNKET to abrogate FcR binding. The HER2-TriNKET (ADI-29404 (F04))-D265A fails to mediate lysis of Colo-201 cells, demonstrating the importance of dual targeting of CD16 and NKG2D on NK cells. To further demonstrate the importance of dual targeting on NK cells the monoclonal antibody Trastuzumab was used to target HER2 and mediate ADCC by NK cells, Trastuzumab alone was able to increase NK cell lysis of Colo-201 cells, but maximum lysis achieved by Trastuzumab alone was about 4x lower compared to the TriNKET. To understand the importance of having CD16 and NKG2D targeting on the same molecule, TriNKET (ADI-29404 (F04)) activity was compared to the activity of a bispecific antibody targeting HER2 and NKG2D combined with Trastuzumab. When used at equimolar concentrations the combination of bispecific and Trastuzumab was not able to mediate maximal lysis of Colo-201 cells by rested human NK cells. The failure of Trastuzumab+ bispecific combination demonstrates the importance of containing the trispecific-binding of TriNKETs in one molecule.

Example 19

Example 14 demonstrates that HER2-, CD33-, and BCMA-TriNKETs enhanced cytotoxicity of rested and IL-2-activated human NK cells. This example further characterizes the effects of the TriNKETs on IL-12- and IL-15-activated human NK cells. The cytotoxicity was measured in the context of three different tumor-associated antigens, HER2, CD33, and BCMA, with NK cells isolated from human PBMC using the DELFIA cytotoxicity assay as described in Example 14.

Figure 73A:
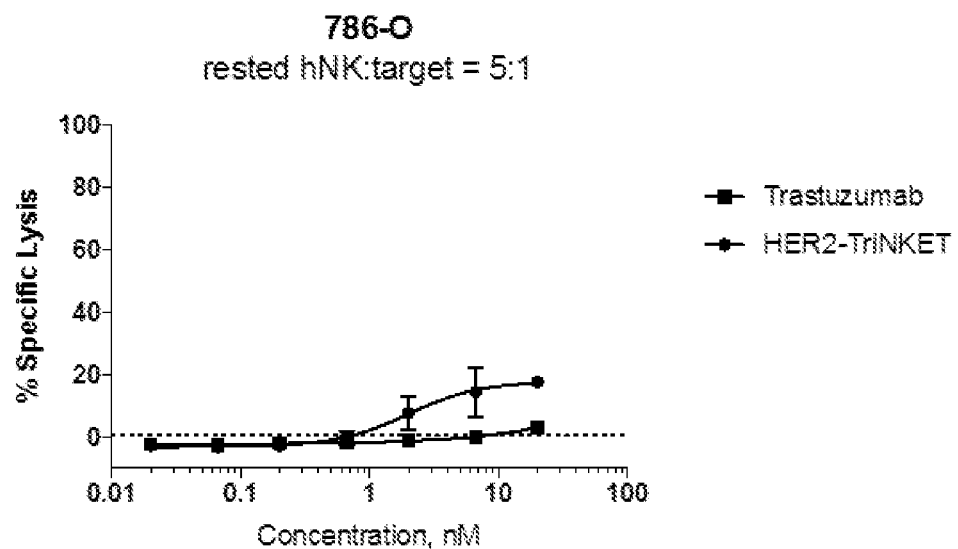
FIGS. 73A-73D are line graphs showing the percentage lysis of 786-O target cells by rested NK cells (FIG. 73A) or NK cells activated by IL-2 (FIG. 73B), IL-12 (FIG. 73C), or IL-15 (FIG. 73D) in the presence of trastuzumab or a HER2-TriNKET.
Figure 73B:
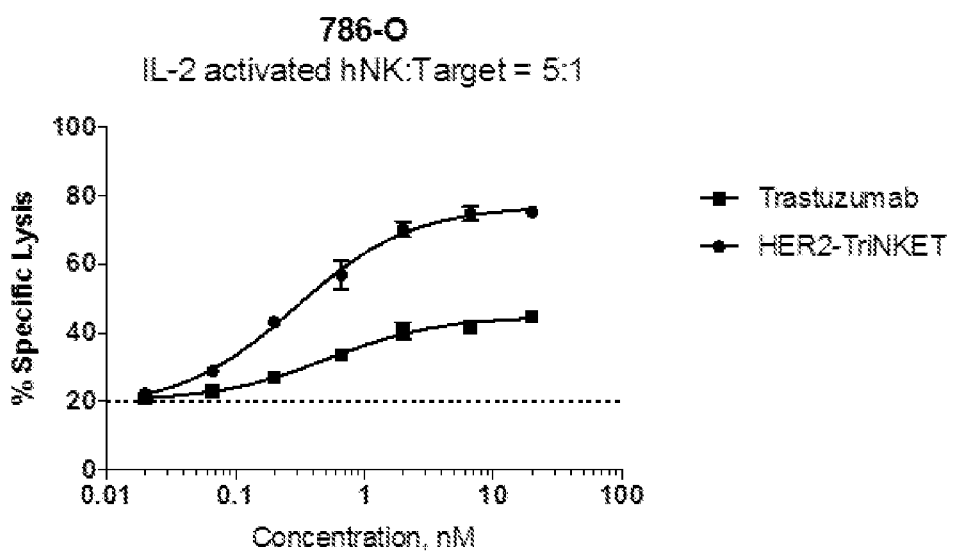
Figure 73C:
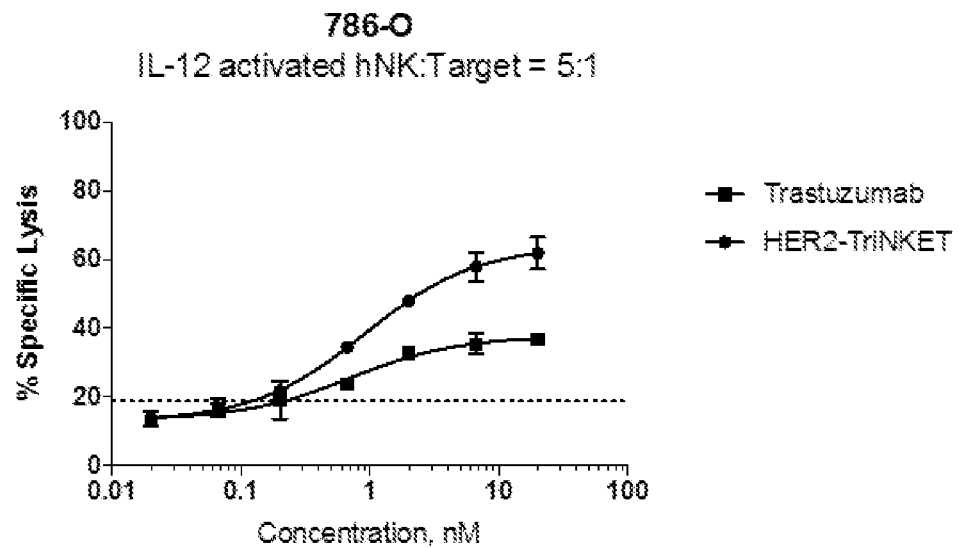
Figure 73D:
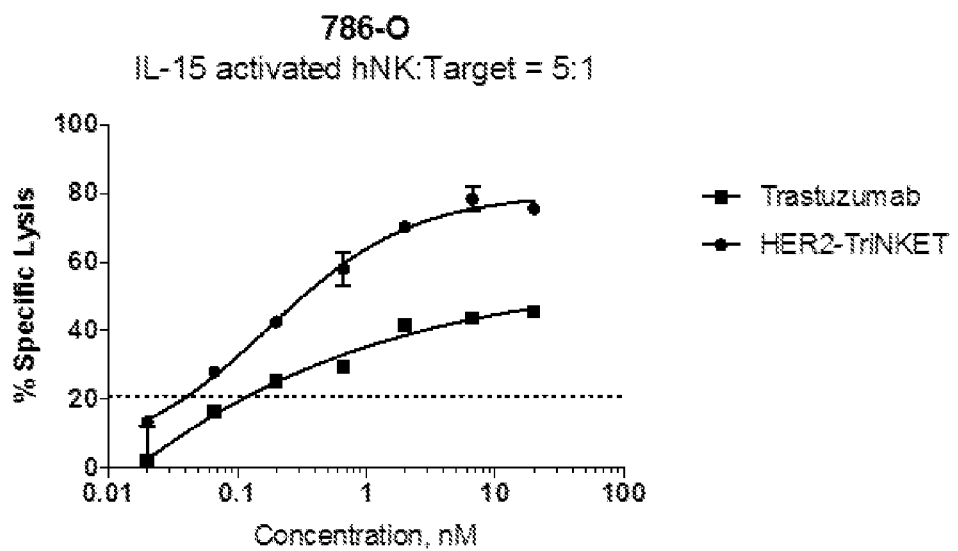

To measure the cytotoxicity against HER2-expressing cells, human NK cells were cultured with IL-2, IL-12, or IL-15, or were rested overnight without cytokines. Rested or cytokine-activated NK cells were co-cultured with HER2-low 786-O tumor cells in the presence of serially diluted trastuzumab or a trastuzumab-derived HER2-TriNKET. As shown in FIG. 73A, rested human NK cells showed no killing of 786-O target cells, and trastuzumab was unable to increase lysis of 786-O target cells. The HER2-TriNKET was able to increase rested NK cells lysis of 786-O target cells, but lysis only reached about 20%. As shown in FIGS. 73B-D, cytokine-activated NK cells showed about 20% of specific lysis when co-cultured with 786-O target cells. Unlike with rested NK cells, trastuzumab was able to increase the activity of cytokine-activated NK cells to about 40% of specific lysis. The HER2-TriNKET more potently enhanced cytotoxicity-activated NK cell lysis of 786-O target cells. Specific lysis also reached a higher maximum value with the HER2-TriNKET compared to trastuzumab with cytokine-activated NK effector cells.

Figure 74A:
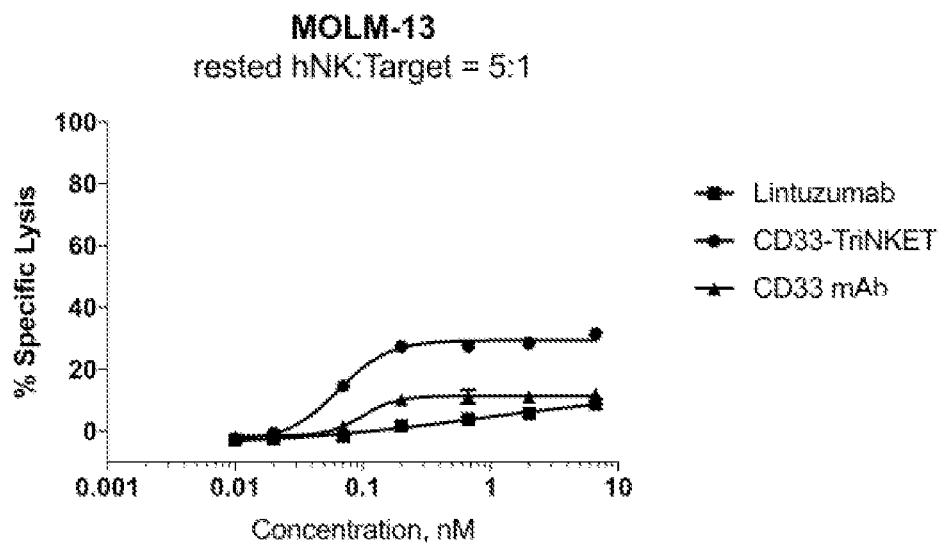
FIGS. 74A-74D are line graphs showing the percentage lysis of Molm-13 target cells by rested NK cells (FIG. 74A) or NK cells activated by IL-2 (FIG. 74B), IL-12 (FIG. 74C), or IL-15 (FIG. 74D) in the presence of lintuzumab, a proprietary anti-CD33 monoclonal antibody, or a CD33-TriNKET.
Figure 74B:
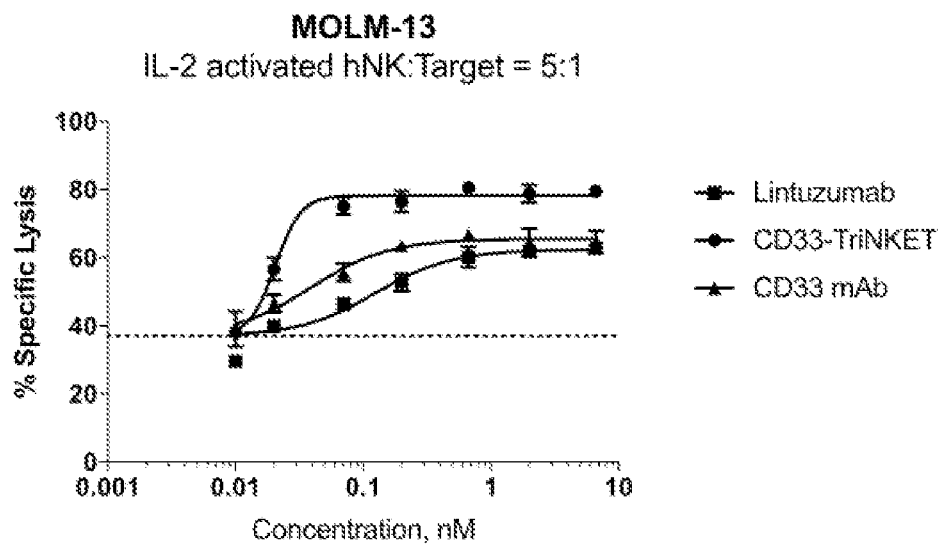
Figure 74C:
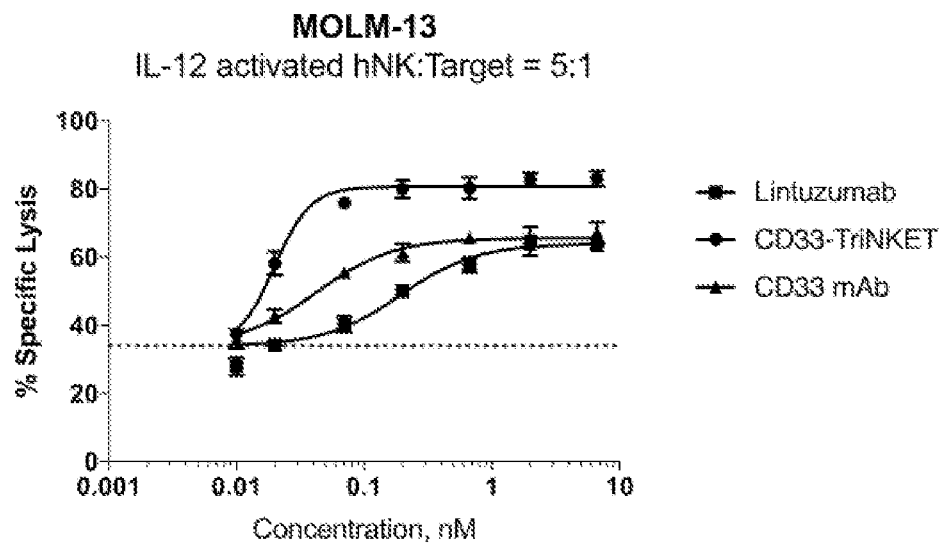
Figure 74D:
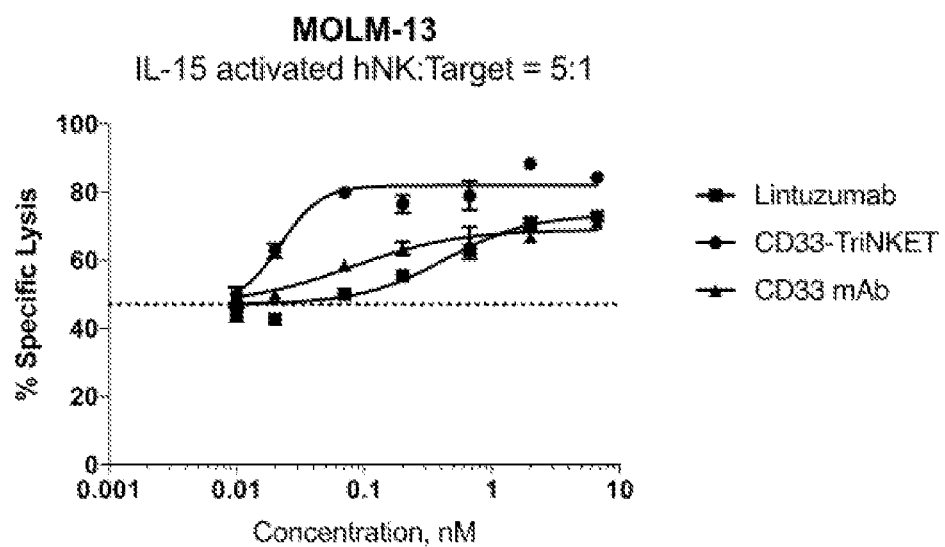

To measure the cytotoxicity against CD33-expressing cells, human NK cells were cultured with IL-2, IL-12, or IL-15, or were rested overnight without cytokines. Rested or cytokine-activated NK cells were co-cultured with CD33-positive Molm-13 tumor cells in the presence of serially diluted lintuzumab, a proprietary anti-CD33 monoclonal antibody, or a CD33-TriNKET derived from the proprietary anti-CD33 antibody. As shown in FIG. 74A, rested human NK cells showed no killing of Molm-13 target cells, and both monoclonal antibodies led to only a small increase in NK cell lysis of Molm-13 target cells. As shown in FIGS. 74B-D, the CD33-TriNKET was able to increase rested NK cell lysis of Molm-13 target cells to about 30% of specific lysis. Cytokine-activated NK cells showed about 35-55% lysis when co-cultured with Molm-13 target cells. Unlike with rested NK cells, both monoclonal antibodies were able to increase the activity of cytokine-activated NK cells to about 60-70% of specific lysis. The CD33-TriNKET more potently enhanced cytokine-activated NK cell lysis of Molm-13 target cells. Specific lysis also reached a higher maximum value with the CD33-TriNKET compared to either monoclonal antibody with cytokine-activated NK effector cells.

Figure 75A:
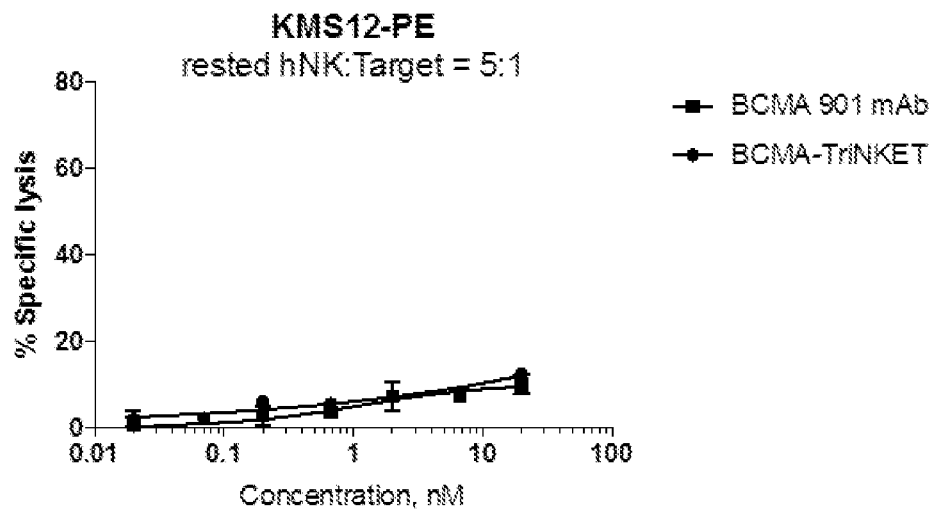
FIGS. 75A-75D are line graphs showing the percentage lysis of KMS12-PE target cells by rested NK cells (FIG. 75A) or NK cells activated by IL-2 (FIG. 75B), IL-12 (FIG. 75C), or IL-15 (FIG. 75D) in the presence of BCMA monoclonal antibody EM-901 or a BCMA-TriNKET.
Figure 75B:
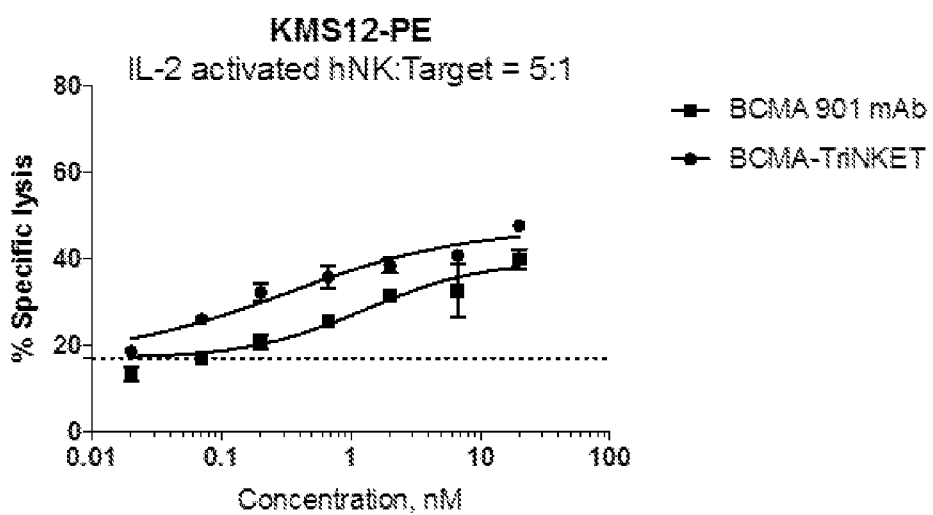
Figure 75C:
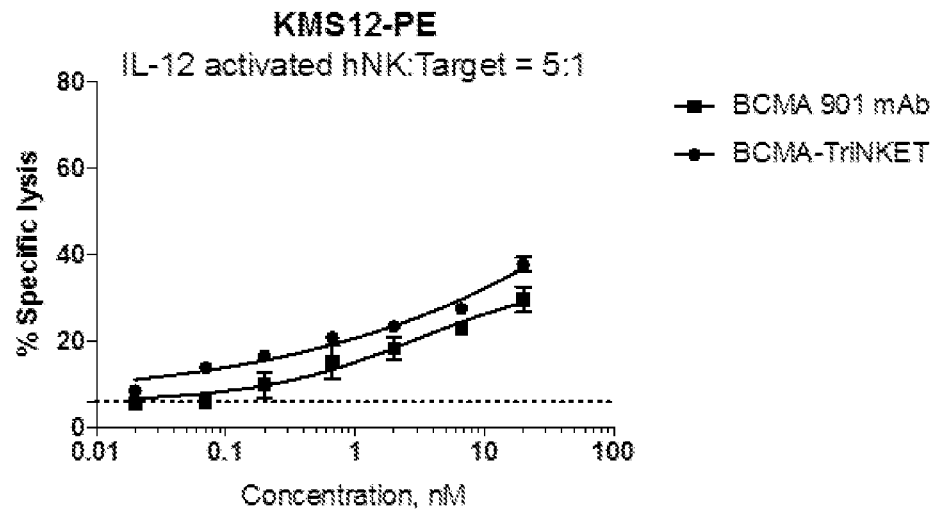
Figure 75D:
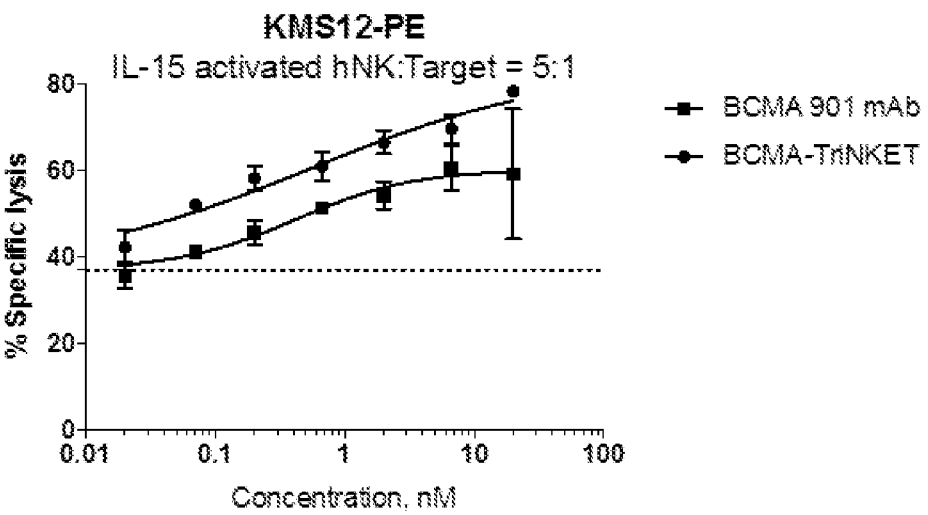

To measure the cytotoxicity against BCMA-expressing cells, human NK cells were cultured with IL-2, IL-12, or IL-15, or were rested overnight without cytokines. Rested or cytokine-activated NK cells were co-cultured with BCMA-positive KMS12-PE tumor cells in the presence of serially diluted EM-901 anti-BCMA antibody or a EM-901-derived BCMA-TriNKET. As shown in FIG. 75A, rested human NK cells showed no killing of KMS12-PE target cells, and EM-901 and BCMA-TriNKET showed only a small increase in NK cell lysis of KMS12-PE target cells. As shown in FIGS. 75B-D, cytokine-activated NK cells showed about 10-40% lysis when co-cultured with KMS12-PE target cells, the degree of lysis varying for NK cells treated with the different cytokines. Unlike with rested NK cells, EM-901 was able to increase the activity of cytokine-activated NK cells to about 40-80% of specific lysis depending on the cytokine used. The BCMA-TriNKET more potently enhanced cytokine activated NK cell lysis of KMS12-PE target cells. Specific lysis also reached a higher maximum value with the BCMA-TriNKET compared to the parental monoclonal antibody with cytokine activated NK effector cells.

Figure 76A:
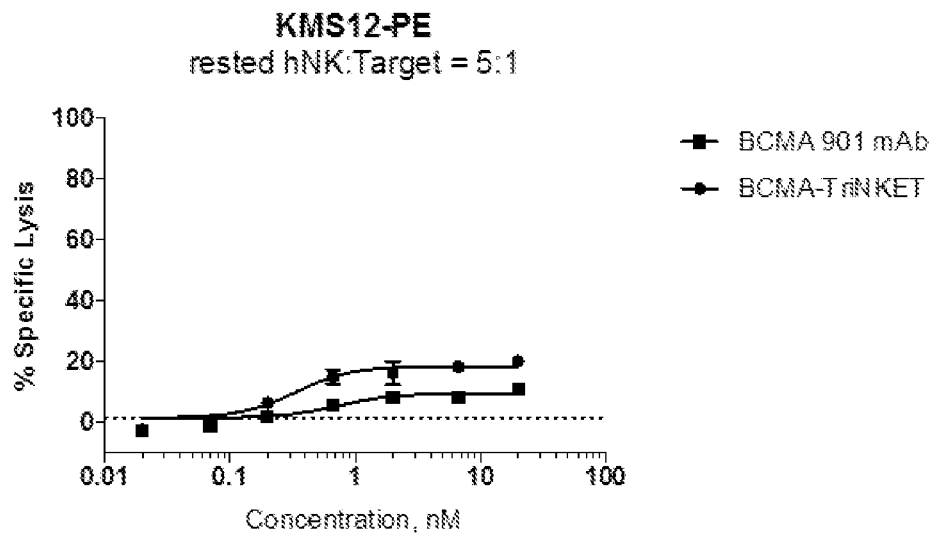
FIGS. 76A-76D are line graphs showing the percentage lysis of KMS12-PE target cells by rested NK cells (FIG. 76A) or NK cells activated by pomalidomide (FIG. 76B), IL-2 (FIG. 76C), or a combination of IL-2 and pomalidomide (FIG. 76D) in the presence of BCMA monoclonal antibody EM-901 or a BCMA-TriNKET.
Figure 76B:
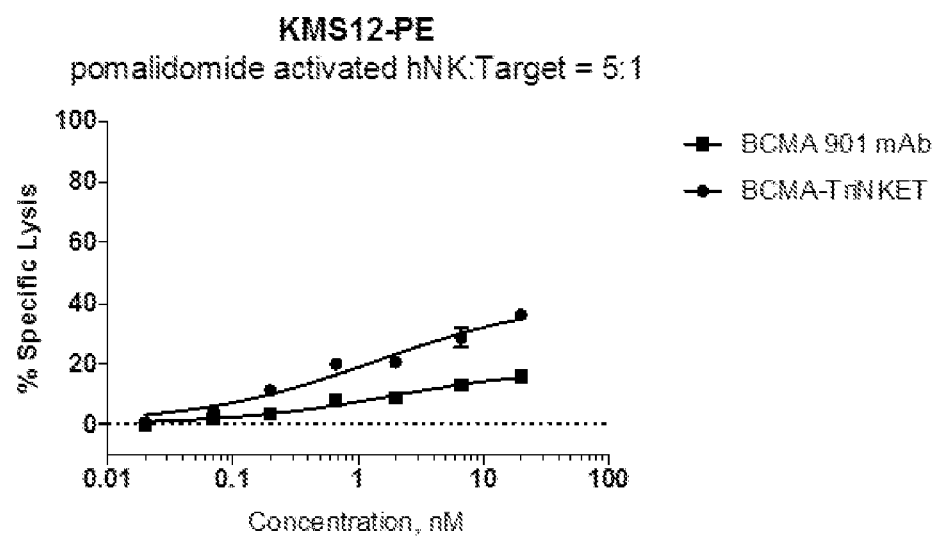
Figure 76C:
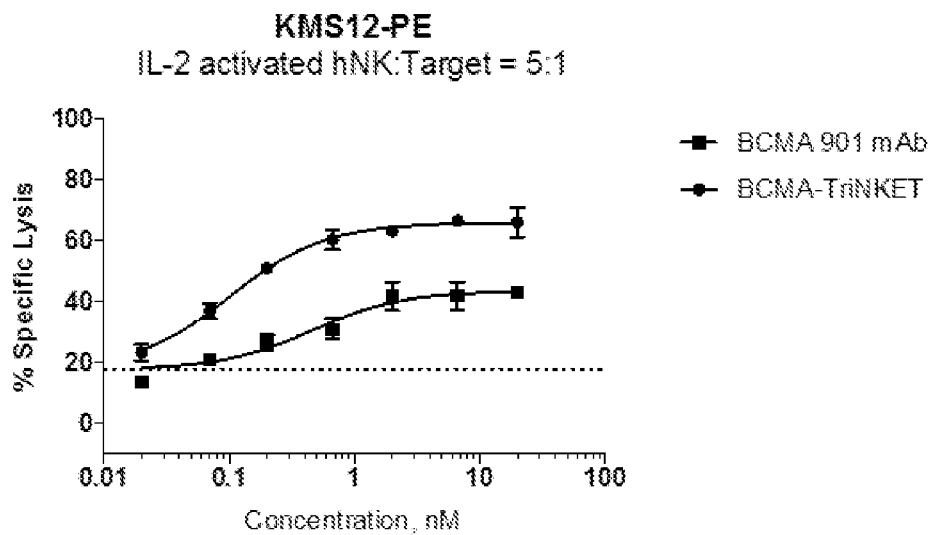
Figure 76D:
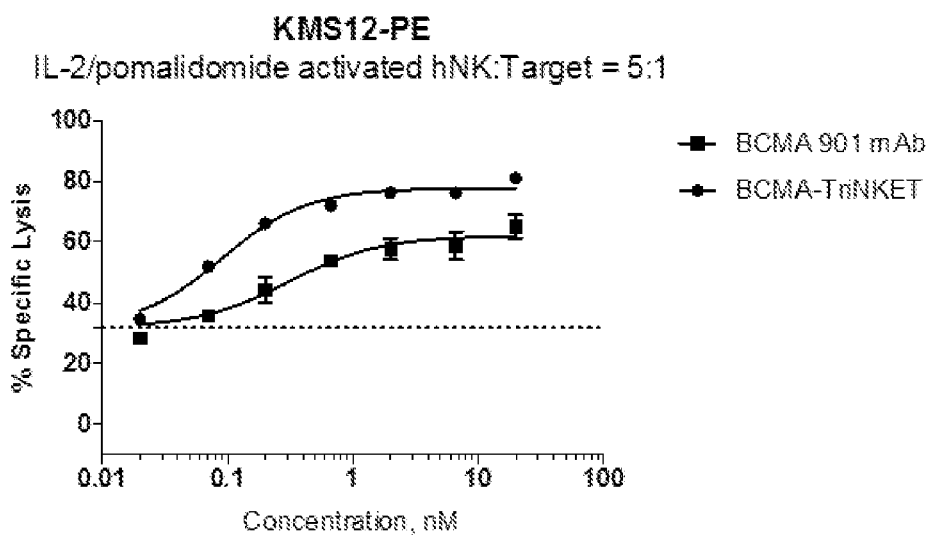

Pomalidomide is a compound reported to have an immunomodulatory activity. To assess the effect of pomalidomide and/or IL-2 on the cytotoxicity of NK cells against BCMA-expressing cells, human NK cells were rested or cultured with IL-2, pomalidomide, or combination of IL-2 and pomalidomide overnight. Rested or activated NK cells were co-cultured with KMS12-PE target cells in the presence of serially diluted EM-901 or a EM-901-derived BCMA-TriNKET. As shown in FIG. 76A, rested human NK cells showed no killing of KMS12-PE target cells. EM-901 showed only a small increase in NK cell lysis of KMS12-PE target cells, while the BCMA-TriNKET demonstrated higher and more potent specific lysis. As shown in FIG. 76B, pomalidomide activated NK cells showed similar lysis of KMS12-PE target cells as rested NK cells. The BCMA-TriNKET increased lysis of target cells by pomalidomide-activated NK cells to a greater degree than the increase of lysis by rested NK cells. As shown in FIG. 76C, IL-2-activated NK cells lysed about 20% of target cells in the co-culture. EM-901 increased NK cell lysis of KMS12-PE target cells to about 40%, while the BCMA-TriNKET increased specific lysis to about 60%. Therefore, NK cells were more active after treatment with IL-2 compared to treatment with pomalidomide. When IL-2 and pomalidomide are combined for NK cell activation, the NK cells demonstrated even higher activity of about 30% of specific lysis. EM-901 increased lysis by IL-2/pomalidomide-activated NK cells to about 60%, and the BCMA-TriNKET increased lysis to about 80%. This result demonstrated greater potency of a TriNKET compared to its parental antibody and is consistent with the other conditions tested in this example.

Example 20

This example shows the cytotoxicity of human CD8$^+$ T cells against HER2-expressing target cells in the presence of a HER2-TriNKET and anti-PD-1 antibody pembrolizumab.

Briefly, human PBMCs were isolated from human peripheral blood buffy coats using density gradient centrifugation. Isolated PBMCs were stimulated with 1 µg/ml Concanavalin A (ConA) at 37° C. for 18 hours. Then ConA was removed, and the PBMCs were cultured with 25 U/ml IL-2 at 37° C. for 4 days. CD8+ T cells were purified using a negative selection method with magnetic beads. The purified CD8+ T cells were cultured in media containing 10 µg/ml IL-15 at 37° C. for 3-14 days.

Figure 77A:
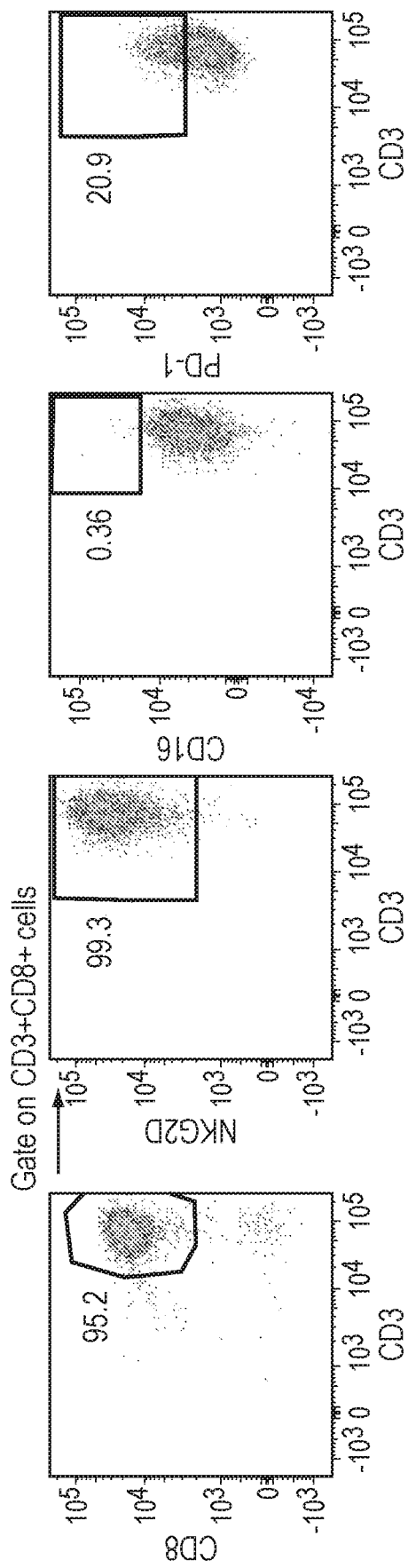
FIGS. 77A-77B are graphs showing flow cytometry analysis of purified CD8⁺ T cells and HCC1954 target cells.

The purity of cell population, as well as the expression of NKG2D, CD16 and PD-1, was assessed. Briefly, the cells were stained with fluorophore conjugated antibodies against CD3, CD8, CD56, CD4, NKG2D, and CD16, and analyzed by flow cytometry. As shown in FIG. 77A, the CD8+ T cells were of high purity. The CD3+CD8+ T cells were uniformly positive for NKG2D and negative for CD16. About 20% of the CD3+CD8+ T cells expressed PD-1.

Figure 77B:
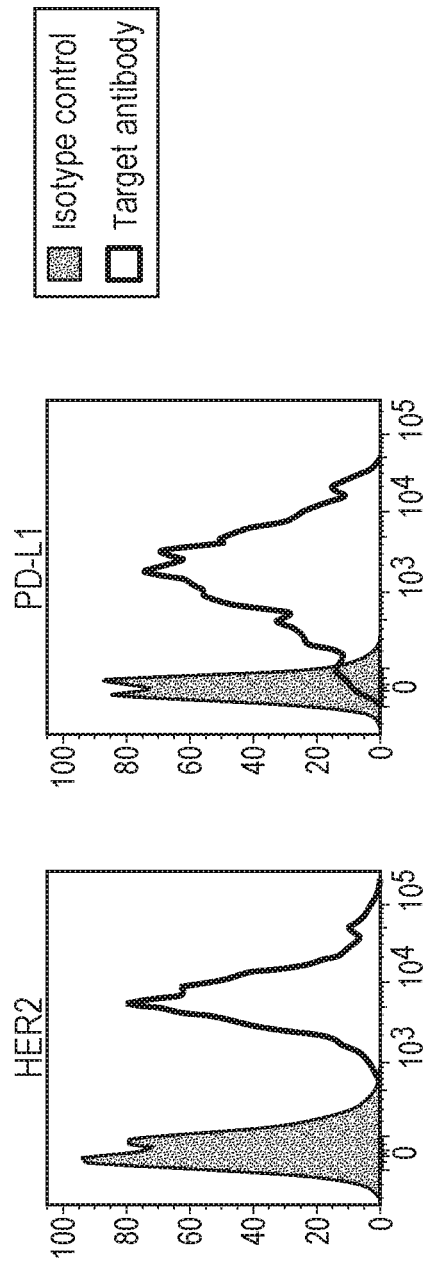

Human cancer cell line HCC1954 that expressed HER2, transduced with BacMam 3.0 NucLight Green (#4622) to allow for tracking of the cells, was used as target cells. The cells were stained with fluorophore-conjugated antibodies against HER2 and PD-L1, and expression of HER2 and PD-L1 was analyzed by flow cytometry. As shown in FIG. 77B, HER2 and PD-L1 expression was detected on the HCC1954 cells.

The effect of a HER2-TriNKET, pembrolizumab, and a combination thereof on T cell cytotoxicity was assessed using a long-term CD8+ T cell cytotoxicity assay. Briefly, HCC1954 target cells were harvested from culture, washed, resuspended in growth media, and plate at 5,000 cells/well in a 96-well plate. The plate was incubated at 37° C. with 5% CO2 overnight. The HER2-TriNKET, pembrolizumab, and their respective isotype controls were diluted in culture media. 50 µl of antibodies and TriNKETs combined was added to each well. CD8+ effector T cells were harvested from culture, washed, and resuspended at $1\times10^6$ cells/mL (for E:T ratio of 10:1) or $2.5\times10^6$ cells/mL (for E:T ratio of 25:1) in culture media. 50 µl of CD8+ T cells were added to each well of the plate to make a total of 200 µl culture volume in each well. The plate was incubated at 37° C. with 5% $CO_2$ for up to 7 days. Images in the phase and green channels were collected every hour, with 2 images per well, using an IncuCyte S3 instrument. The images were analyzed using the IncuCyte S3 software. The numbers of live tumor cells in the wells were represented by the counts of green objects.

Figure 78A:
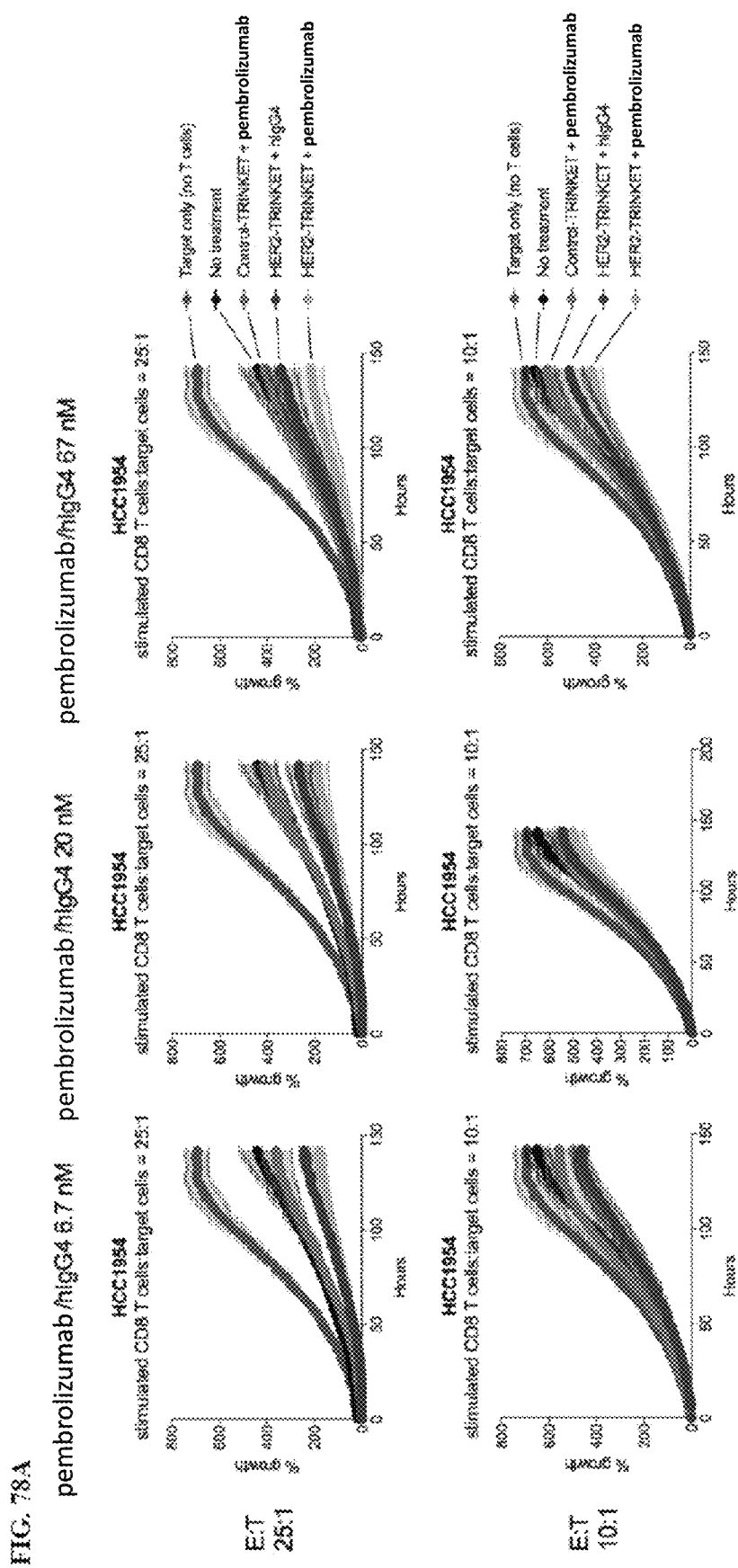
FIGS. 78A-78B are line graphs showing growth of HCC1954 target cells in the presence of CD8⁺ T cells and a HER2-TriNKET, pembrolizumab ("Keytruda"), or a combination thereof. The CD8⁺ T cells used in FIG. 78A and FIG. 78B were isolated from different donors.
Figure 78B:
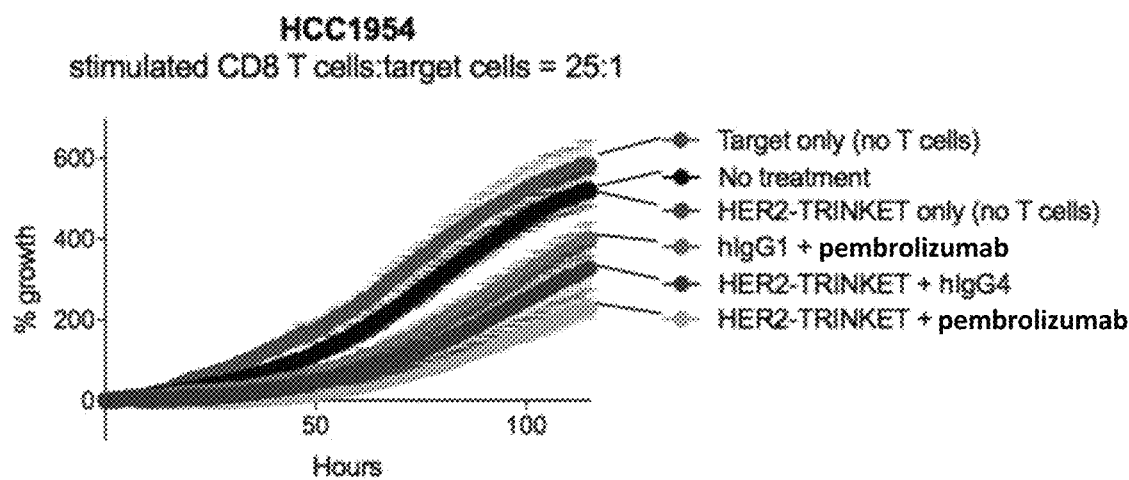

As shown in FIG. 78A, the combination of 20 nM HER2-TriNKET and 6.7 nM, 20 nM, or 67 nM pembrolizumab showed stronger tumor killing effect than the HER2-TriNKET or pembrolizumab alone. The combination effect was more substantial with higher E:T ratio and increased pembrolizumab concentration. A similar combination effect was observed with CD8+ effector T cells isolated from a different donor, when the HER2-TriNKET was used at a low dose of 0.04 nM and pembrolizumab was used at 67 nM (FIG. 78B).

Example 21

This example shows the cytotoxicity of human PBMCs against a HER2-expressing human breast cancer cell line Skbr-3 in the presence of a HER2-TriNKET and a TLR agonist (Invivogen TL8-506).

Briefly, Skbr-3 cells were transduced to stably express NucLight Green (Essen BioScience 4475). After puromycin selection, the cells were harvested from culture and resuspended in culture media. $3\times10^3$ target cells were added to each well of a flat-bottom 96-well plate in 100 µl medium. The plate was incubated at 37° C. with 5% CO2 for 20 hours.

50 µl of the HER2-TriNKET and/or the TLR agonist diluted in culture media were added at final assay concentrations of 10 µg/ml and 50 µg/ml, respectively. Freshly processed human PBMCs were resuspended at $1.2\times10^6$ cells/mL in culture media, and 50 µl of the PBMCs were added to all wells except for the target-only control group (which received 50 µl of the culture media). The plate was placed into the Incucyte instrument (Essen BioScience) for the duration of the assay, with phase and green fluorescent images acquired hourly for four days. Cell counts were obtained using green event masks with minimum area restrictions to exclude debris. The cell count at each time point was normalized to that of the starting SKBR-3 green cell count to obtain percent growth.

Figure 79:
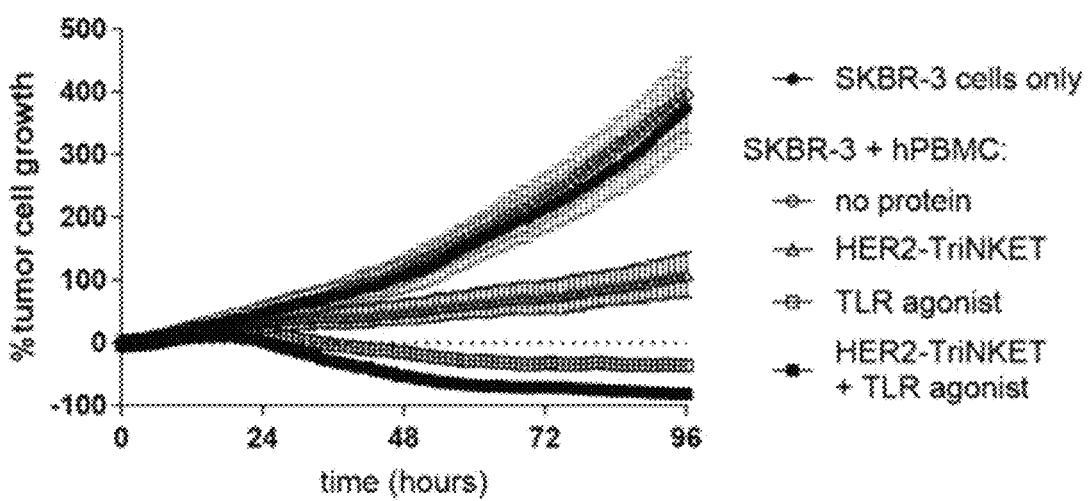
FIG. 79 is a line graph showing growth of Skbr-3 target cells in the presence of PBMCs and a HER2-TriNKET, a TLR agonist, or a combination thereof.

As shown in FIG. 79, addition of human PBMCs alone exerted no effect on the proliferation of SKBR-3 target cells, but simultaneous inclusion of the HER2-TriNKET in the culture enabled the PBMCs to substantially inhibit the tumor cell growth. At the tested dose, the TLR agonist stimulated the PBMCs to slowly reduce the population of SKBR-3 cells from the initial count. The combination of HER2-TriNKET and TLR agonist was the most potent, facilitating killing of almost all target cells within 4 days.

Example 22

Example 17 demonstrates that mcFAE-C26.99 TriNKET suppressed tumor growth alone or in combination with IL-2 or with an anti-PD-1 monoclonal antibody in the B16F10 tumor cell xenograft mouse model. This example further characterizes the combination of mcFAE-C26.99 TriNKET with IL-12.

Briefly, $2\times10^5$ B16F10 melanoma cells were injected subcutaneously into the flank of C57BL/6 mice. On Day 5 after tumor, the inoculated mice were randomized (n=10 per group). The mice were injected intraperitoneally with (A) 7.5 mg/kg mcFAE-C26.99 TriNKET or 7.5 mg/kg isotype control mouse IgG2a monoclonal antibody C1.18.4, (B) 1 recombinant murine IL-12 (rmIL-12) or 7.5 mg/kg isotype control mouse IgG2a monoclonal antibody C1.18.4, or (C) a combination of 7.5 mg/kg mcFAE-C26.99 TriNKET and 1 rmIL-12. Tumor growth was assessed for 61 days, and survival of the mice was monitored.

Figure 80A:
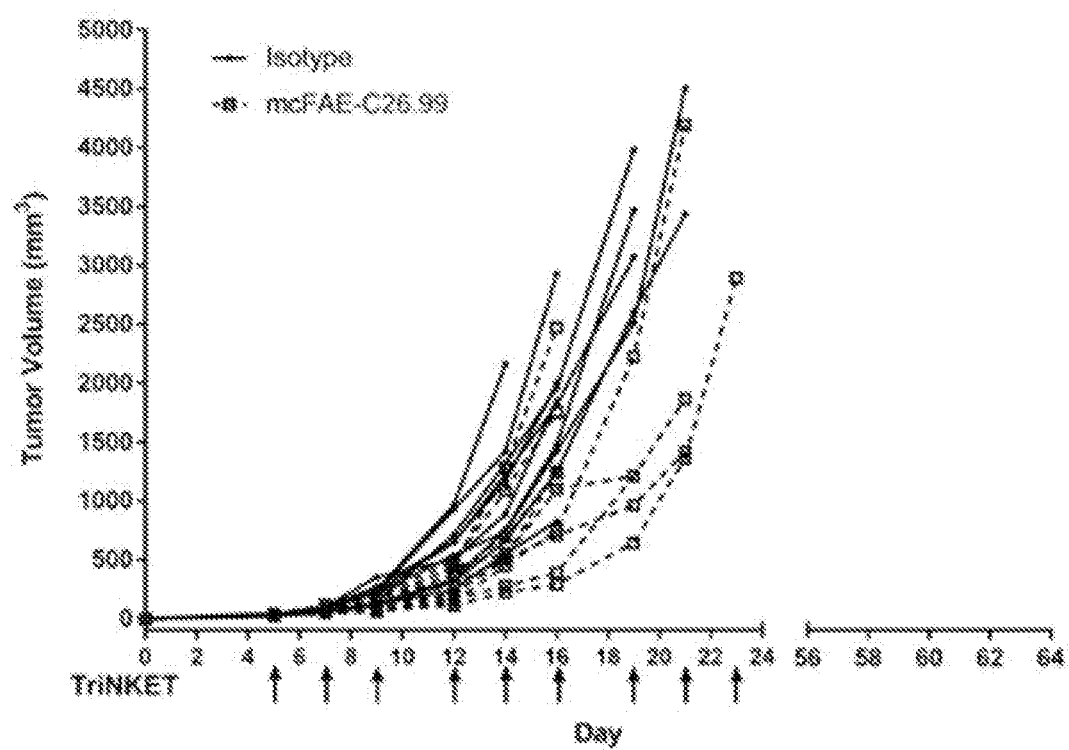
Figure 81:
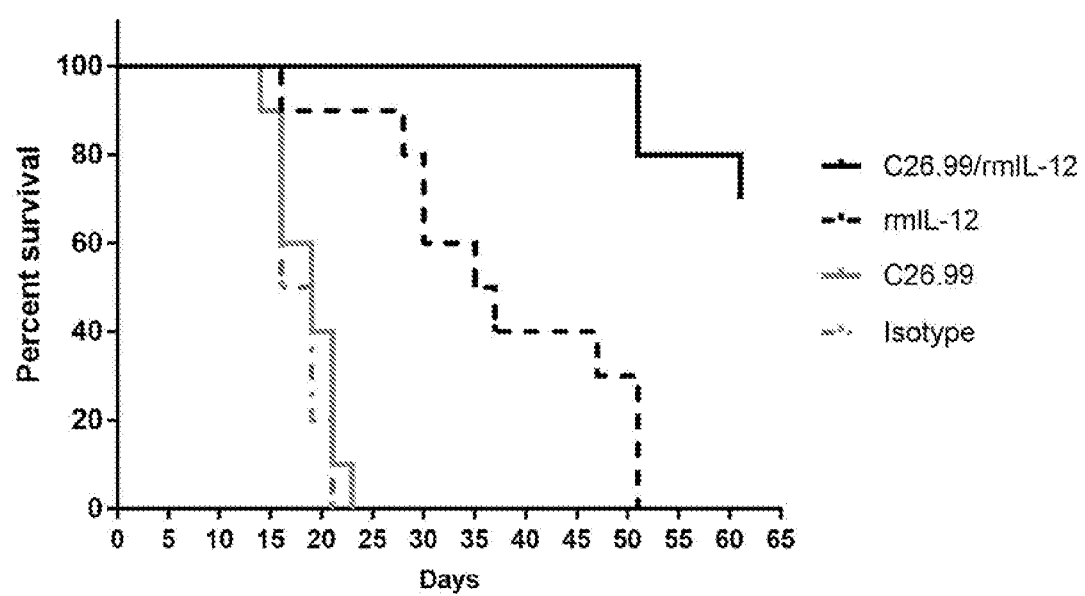
FIG. 81 is a Kaplan-Meier curve showing the percentage of animals that survived after the B16F10 tumor cell inoculation and the treatments of 7.5 mg/kg isotype control mouse IgG2a monoclonal antibody C1.18.4, 7.5 mg/kg mcFAE-C26.99 TriNKET, 1 µg rmIL-12, or a combination of 7.5 mg/kg mcFAE-C26.99 TriNKET and 1 µg rmIL-12.

As shown in FIGS. 80A-C, monotherapy of mcFAE-C26.99 TriNKET (FIG. 80A) or murine IL-12 (FIG. 80B) was effective by itself in suppressing Bl6F10 tumor growth, but the combination therapy of mcFAE-C26.99 TriNKET and IL-12 (FIG. 80C) had a more substantial effect, leading to full tumor regression in 40% of the treated mice. As shown in FIG. 81, overall survival was significantly extended by the combination therapy: 70% of the mice treated with the combination therapy were still alive at day 61, whereas the median survival time was only 20 days in the control group and the TriNKET-treated group, and 37 days in the IL-12 single agent treatment group.

INCORPORATION BY REFERENCE

The entire disclosure of each of the patent documents and scientific articles referred to herein is incorporated by reference for all purposes.

EQUIVALENTS

The invention may be embodied in other specific forms without departing from the spirit or essential characteristics thereof. The foregoing embodiments are therefore to be considered in all respects illustrative rather than limiting the invention described herein. Scope of the invention is thus indicated by the appended claims rather than by the foregoing description, and all changes that come within the meaning and range of equivalency of the claims are intended to be embraced therein.

What is claimed is:

1. A method of enhancing tumor cell death directly or indirectly, the method comprising exposing a tumor cell and a natural killer cell to a multi-specific binding protein comprising:
 (a) a first antigen-binding site that binds and activates human NKG2D;
 (b) a second antigen-binding site that binds a tumor-associated antigen; and
 (c) a first antibody Fc domain of human IgG1 and a second antibody Fc domain of human IgG1 that together bind CD16, wherein the first and second antibody Fc domains comprise different amino acid mutations to promote heterodimerization, and the first and second antibody Fc domains each comprise an N-terminus,
 wherein the first antigen-binding site is linked to the N-terminus of the first antibody Fc domain, and the second antigen-binding site is linked to the N-terminus of the second antibody Fc domain,
 wherein the tumor cell is also contacted with a second therapeutic agent comprising a checkpoint blocker that is an anti-PD-1 antibody, and
 wherein the tumor cell expresses the tumor-associated antigen on its surface.

2. The method of claim 1, wherein the anti-PD-1 antibody is nivolumab.

3. The method of claim 1, wherein the anti-PD-1 antibody is pembrolizumab.

4. The method of claim 1, wherein the first antigen-binding site of the multi-specific binding protein binds to NKG2D in humans and non-human primates.

5. The method of claim 1, wherein the second antigen-binding site comprises a heavy chain variable domain and a light chain variable domain.

6. The method of claim 1, wherein the multi-specific binding protein is administered in a formulation that further comprises a pharmaceutically acceptable carrier.

7. The method of claim 1, wherein the first antigen binding site comprises a heavy chain variable domain comprising a CDR1 amino acid sequence of SEQ ID NO:57, a CDR2 amino acid sequence of SEQ ID NO:58, and a CDR3 amino acid sequence of SEQ ID NO:59; and a light chain variable domain comprising a CDR1 amino acid sequence of SEQ ID NO:60, a CDR2 amino acid sequence of SEQ ID NO:61, and a CDR3 amino acid sequence of SEQ ID NO:62.

8. The method of claim 7, wherein the first antigen-binding site comprises a heavy chain variable domain comprising an amino acid sequence at least 90% identical to SEQ ID NO:47 and a light chain variable domain comprising an amino acid sequence at least 90% identical to SEQ ID NO:48.

9. A method of treating a solid tumor, the method comprising administering an effective amount of a multi-specific binding protein to a subject in need thereof who also receives an effective amount of a second therapeutic agent comprising a checkpoint blocker that is an anti-PD-1 antibody, wherein the multi-specific binding protein comprises:
 (a) a first antigen-binding site that binds and activates human NKG2D;
 (b) a second antigen-binding site that binds a tumor-associated antigen; and
 (c) a first antibody Fc domain of human IgG1 and a second antibody Fc domain of human IgG1 that together bind CD16, wherein the first and second antibody Fc domains comprise different amino acid mutations to promote heterodimerization, and the first and second antibody Fc domains each comprise an N-terminus,
 wherein the first antigen-binding site is linked to the N-terminus of the first antibody Fc domain, and the second antigen-binding site is linked to the N-terminus of the second antibody Fc domain, and
 wherein the solid tumor expresses the tumor-associated antigen on its surface.

10. The method of claim 9, wherein the solid tumor is selected from the group consisting of B cell lymphoma, bladder cancer, breast cancer, colorectal cancer, diffuse large B cell lymphoma, esophageal cancer, follicular lymphoma, gastric cancer, gastrointestinal cancer, gastrointestinal stromal tumors, glioblastoma, head and neck cancer, melanoma, mesothelioma, multiple myeloma, myelodysplastic syndrome, renal cell carcinoma, neuroblastoma, non-small cell lung cancer, neuroendocrine tumors, ovarian cancer, pancreatic cancer, prostate cancer, sarcomas, including Ewing's sarcoma, small cell lung cancer, T cell lymphoma, testicular cancer, thymic carcinoma, thyroid cancer, urothelial cancer, cancers infiltrated by myeloid-derived suppressor cells, cancers with extracellular matrix deposition, cancers with high levels of reactive stroma, and cancers with neoangiogenesis.

11. The method of claim 9, wherein the anti-PD-1 antibody is nivolumab.

12. The method of claim 9, wherein the anti-PD-1 antibody is pembrolizumab.

13. The method of claim 9, wherein the first antigen-binding site of the multi-specific binding protein binds to NKG2D in humans and non-human primates.

14. The method of claim 9, wherein the first antigen-binding site comprises a heavy chain variable domain and a light chain variable domain present on the same polypeptide.

15. The method of claim 9, wherein the second antigen-binding site comprises a heavy chain variable domain and a light chain variable domain.

16. The method of claim 9, wherein the multi-specific binding protein is administered in a formulation that further comprises a pharmaceutically acceptable carrier.

17. The method of claim 9, wherein the first antigen binding site comprises a heavy chain variable domain comprising a CDR1 amino acid sequence of SEQ ID NO:57, a CDR2 amino acid sequence of SEQ ID NO:58, and a CDR3 amino acid sequence of SEQ ID NO:59; and a light chain variable domain comprising a CDR1 amino acid sequence of SEQ ID NO:60, a CDR2 amino acid sequence of SEQ ID NO:61, and a CDR3 amino acid sequence of SEQ ID NO:62.

18. The method of claim 17, wherein the first antigen-binding site comprises a heavy chain variable domain comprising an amino acid sequence at least 90% identical to SEQ ID NO:47 and a light chain variable domain comprising an amino acid sequence at least 90% identical to SEQ ID NO:48.

19. The method of claim 9, wherein the first antigen binding site comprises:
(a) a heavy chain variable domain comprising a CDR1 amino acid sequence of SEQ ID NO:90, a CDR2 amino acid sequence of SEQ ID NO:52, and a CDR3 amino acid sequence of SEQ ID NO:91; and a light chain variable domain comprising a CDR1 amino acid sequence of SEQ ID NO:54, a CDR2 amino acid sequence of SEQ ID NO:55, and a CDR3 amino acid sequence of SEQ ID NO:56;
(b) a heavy chain variable domain comprising a CDR1 amino acid sequence of SEQ ID NO:94, a CDR2 amino acid sequence of SEQ ID NO:64, and a CDR3 amino acid sequence of SEQ ID NO:95; and a light chain variable domain comprising a CDR1 amino acid sequence of SEQ ID NO:66, a CDR2 amino acid sequence of SEQ ID NO:67, and a CDR3 amino acid sequence of SEQ ID NO:68;
(c) a heavy chain variable domain comprising a CDR1 amino acid sequence of SEQ ID NO:122, a CDR2 amino acid sequence of SEQ ID NO:117, and a CDR3 amino acid sequence of SEQ ID NO:123; and a light chain variable domain comprising a CDR1 amino acid sequence of SEQ ID NO:119, a CDR2 amino acid sequence of SEQ ID NO:120, and a CDR3 acid sequence of SEQ ID NO:121; or
(d) a heavy chain variable domain comprising a CDR1 amino acid sequence of SEQ ID NO:122, a CDR2 amino acid sequence of SEQ ID NO:117, and a CDR3 amino acid sequence of SEQ ID NO:130; and a light chain variable domain comprising a CDR1 amino acid sequence of SEQ ID NO:127, a CDR2 amino acid sequence of SEQ ID NO:128, and a CDR3 amino acid sequence of SEQ ID NO:129.

20. The method of claim 19, wherein the first antigen-binding site comprises:
(a) a heavy chain variable domain comprising an amino acid sequence at least 90% identical to SEQ ID NO:45 and a light chain variable domain comprising an amino acid sequence at least 90% identical to SEQ ID NO:46, wherein the heavy chain variable domain comprises a CDR1 amino acid sequence of SEQ ID NO:90, a CDR2 amino acid sequence of SEQ ID NO:52, and a CDR3 amino acid sequence of SEQ ID NO:91; and the light chain variable domain comprises a CDR1 amino acid sequence of SEQ ID NO:54, a CDR2 amino acid sequence of SEQ ID NO:55, and a CDR3 amino acid sequence of SEQ ID NO:56;
(b) a heavy chain variable domain comprising an amino acid sequence at least 90% identical to SEQ ID NO:49 and a light chain variable domain comprising an amino acid sequence at least 90% identical to SEQ ID NO:50, wherein the heavy chain variable domain comprises a CDR1 amino acid sequence of SEQ ID NO:94, a CDR2 amino acid sequence of SEQ ID NO:64, and a CDR3 amino acid sequence of SEQ ID NO:95; and the light chain variable domain comprises a CDR1 amino acid sequence of SEQ ID NO:66, a CDR2 amino acid sequence of SEQ ID NO:67, and a CDR3 amino acid sequence of SEQ ID NO:68;
(c) a heavy chain variable domain comprising an amino acid sequence at least 90% identical to SEQ ID NO:114 and a light chain variable domain comprising an amino acid sequence at least 90% identical to SEQ ID NO:115, wherein the heavy chain variable domain comprises a CDR1 amino acid sequence of SEQ ID NO:122, a CDR2 amino acid sequence of SEQ ID NO:117, and a CDR3 amino acid sequence of SEQ ID NO:123; and the light chain variable domain comprises a CDR1 amino acid sequence of SEQ ID NO:119, a CDR2 amino acid sequence of SEQ ID NO:120, and a CDR3 acid sequence of SEQ ID NO:121; or
(d) a heavy chain variable domain comprising an amino acid sequence at least 90% identical to SEQ ID NO:124 and a light chain variable domain comprising an amino acid sequence at least 90% identical to SEQ ID NO:125, wherein the heavy chain variable domain comprises a CDR1 amino acid sequence of SEQ ID NO:122, a CDR2 amino acid sequence of SEQ ID NO:117, and a CDR3 amino acid sequence of SEQ ID NO:130; and the light chain variable domain comprises a CDR1 amino acid sequence of SEQ ID NO:127, a CDR2 amino acid sequence of SEQ ID NO:128, and a CDR3 amino acid sequence of SEQ ID NO:129.

* * * * *

```
                            SEQUENCE LISTING

<160> NUMBER OF SEQ ID NOS: 130

<210> SEQ ID NO 1
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asp His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ala Arg Gly Pro Trp Ser Phe Asp Pro Trp Gly Gln Gly Thr Leu
            100                 105                 110

Val Thr Val Ser Ser
        115

<210> SEQ ID NO 2
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Tyr Pro Ile
                85                  90                  95

Thr Phe Gly Gly Gly Thr Lys Val Glu Ile Lys
            100                 105

<210> SEQ ID NO 3
<211> LENGTH: 117
<212> TYPE: PRT
<213> ORGANISM: Artificial Sequence
```

```
-continued

<220> FEATURE:
<223> OTHER INFORMATION: Description of Artificial Sequence: Synthetic
      polypeptide

<400> SEQUENCE: 3

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asp His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ala Arg Gly Pro Trp Ser Phe Asp Pro Trp Gly Gln Gly Thr Leu
            100                 105                 110

Val Thr Val Ser Ser
        115

<210> SEQ ID NO 4
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Ile Thr Phe Gly Gly Gly Thr Lys Val Glu Ile Lys
            100                 105

<210> SEQ ID NO 5
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30
```

```
Tyr Trp Ser Trp Ile Arg Gln Pro Pro Gly Lys Gly Leu Glu Trp Ile
            35                  40                  45

Gly Glu Ile Asp His Ser Gly Ser Thr Asn Tyr Asn Pro Ser Leu Lys
 50                  55                  60

Ser Arg Val Thr Ile Ser Val Asp Thr Ser Lys Asn Gln Phe Ser Leu
 65                  70                  75                  80

Lys Leu Ser Ser Val Thr Ala Ala Asp Thr Ala Val Tyr Tyr Cys Ala
                 85                  90                  95

Arg Ala Arg Gly Pro Trp Ser Phe Asp Pro Trp Gly Gln Gly Thr Leu
            100                 105                 110

Val Thr Val Ser Ser
            115

<210> SEQ ID NO 6
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Asp Ile Gln Met Thr Gln Ser Pro Ser Thr Leu Ser Ala Ser Val Gly
 1               5                  10                  15

Asp Arg Val Thr Ile Thr Cys Arg Ala Ser Gln Ser Ile Gly Ser Trp
            20                  25                  30

Leu Ala Trp Tyr Gln Gln Lys Pro Gly Lys Ala Pro Lys Leu Leu Ile
            35                  40                  45

Tyr Lys Ala Ser Ser Leu Glu Ser Gly Val Pro Ser Arg Phe Ser Gly
 50                  55                  60

Ser Gly Ser Gly Thr Glu Phe Thr Leu Thr Ile Ser Ser Leu Gln Pro
 65                  70                  75                  80

Asp Asp Phe Ala Thr Tyr Tyr Cys Gln Gln Tyr His Ser Phe Tyr Thr
                 85                  90                  95

Phe Gly Gly Gly Thr Lys Val Glu Ile Lys
            100                 105

<210> SEQ ID NO 7
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Gln Val Gln Leu Gln Gln Trp Gly Ala Gly Leu Leu Lys Pro Ser Glu
 1               5                  10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
            35                  40                  45

Gly Glu Ile Asp His Ser Gly Ser Thr Asn Tyr Asn Pro Ser Leu Lys
 50                  55                  60

Ser Arg Val Thr Ile Ser Val Asp Thr Ser Lys Asn Gln Phe Ser Leu
 65                  70                  75                  80

Lys Leu Ser Ser Val Thr Ala Ala Asp Thr Ala Val Tyr Tyr Cys Ala
                 85                  90                  95
```

Arg Ala Arg Gly Pro Trp Ser Phe Asp Pro Trp Gly Gln Gly Thr Leu
            100                 105                 110

Val Thr Val Ser Ser
        115

<210> SEQ ID NO 8
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Gly Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Ser Asn Ser Tyr Tyr Thr
                85                  90                  95

Phe Gly Gly Gly Thr Lys Val Glu Ile Lys
            100                 105

<210> SEQ ID NO 9
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asp His Ser Gly Ser Thr Asn Tyr Asn Pro Ser Leu Lys
50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ala Arg Gly Pro Trp Ser Phe Asp Pro Trp Gly Gln Gly Thr Leu
            100                 105                 110

Val Thr Val Ser Ser
        115

<210> SEQ ID NO 10
<211> LENGTH: 106
<212> TYPE: PRT
<213> ORGANISM: Artificial Sequence
<220> FEATURE:

<223> OTHER INFORMATION: Description of Artificial Sequence: Synthetic
      polypeptide

<400> SEQUENCE: 10

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Tyr Pro Thr
                85                  90                  95

Phe Gly Gly Gly Thr Lys Val Glu Ile Lys
            100                 105

<210> SEQ ID NO 11
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asp His Ser Gly Ser Thr Asn Tyr Asn Pro Ser Leu Lys
50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ala Arg Gly Pro Trp Gly Phe Asp Pro Trp Gly Gln Gly Thr Leu
            100                 105                 110

Val Thr Val Ser Ser
        115

<210> SEQ ID NO 12
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Glu Leu Gln Met Thr Gln Ser Pro Ser Ser Leu Ser Ala Ser Val Gly
1               5                   10                  15

Asp Arg Val Thr Ile Thr Cys Arg Thr Ser Gln Ser Ile Ser Ser Tyr
            20                  25                  30

Leu Asn Trp Tyr Gln Gln Lys Pro Gly Gln Pro Pro Lys Leu Leu Ile

```
                35                  40                  45
Tyr Trp Ala Ser Thr Arg Glu Ser Gly Val Pro Asp Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Ser Ala Thr Tyr Tyr Cys Gln Gln Ser Tyr Asp Ile Pro Tyr
                 85                  90                  95

Thr Phe Gly Gln Gly Thr Lys Leu Glu Ile Lys
            100                 105

<210> SEQ ID NO 13
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Gln Val Gln Leu Gln Gln Trp Gly Ala Gly Leu Leu Lys Pro Ser Glu
 1               5                  10                  15

Thr Leu Ser Leu Thr Cys Ala Val Tyr Gly Gly Ser Phe Ser Gly Tyr
                 20                  25                  30

Tyr Trp Ser Trp Ile Arg Gln Pro Pro Gly Lys Gly Leu Glu Trp Ile
             35                  40                  45

Gly Glu Ile Asp His Ser Gly Ser Thr Asn Tyr Asn Pro Ser Leu Lys
 50                  55                  60

Ser Arg Val Thr Ile Ser Val Asp Thr Ser Lys Asn Gln Phe Ser Leu
 65                  70                  75                  80

Lys Leu Ser Ser Val Thr Ala Ala Asp Thr Ala Val Tyr Tyr Cys Ala
                 85                  90                  95

Arg Ala Arg Gly Pro Trp Ser Phe Asp Pro Trp Gly Gln Gly Thr Leu
            100                 105                 110

Val Thr Val Ser Ser
            115

<210> SEQ ID NO 14
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Asp Ile Gln Met Thr Gln Ser Pro Ser Thr Leu Ser Ala Ser Val Gly
 1               5                  10                  15

Asp Arg Val Thr Ile Thr Cys Arg Ala Ser Gln Ser Ile Ser Ser Trp
                 20                  25                  30

Leu Ala Trp Tyr Gln Gln Lys Pro Gly Lys Ala Pro Lys Leu Leu Ile
             35                  40                  45

Tyr Lys Ala Ser Ser Leu Glu Ser Gly Val Pro Ser Arg Phe Ser Gly
 50                  55                  60

Ser Gly Ser Gly Thr Glu Phe Thr Leu Thr Ile Ser Ser Leu Gln Pro
 65                  70                  75                  80

Asp Asp Phe Ala Thr Tyr Tyr Cys Gln Gln Tyr Gly Ser Phe Pro Ile
                 85                  90                  95

Thr Phe Gly Gly Gly Thr Lys Val Glu Ile Lys
```

<210> SEQ ID NO 15
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asp His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ala Arg Gly Pro Trp Ser Phe Asp Pro Trp Gly Gln Gly Thr Leu
            100                 105                 110

Val Thr Val Ser Ser
        115

<210> SEQ ID NO 16
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Asp Asp Phe Ala Thr Tyr Tyr Cys Gln Gln Ser Lys Glu Val Pro Trp
                85                  90                  95

Thr Phe Gly Gln Gly Thr Lys Val Glu Ile Lys
            100                 105

<210> SEQ ID NO 17
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

```
Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asp His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ala Arg Gly Pro Trp Ser Phe Asp Pro Trp Gly Gln Gly Thr Leu
            100                 105                 110

Val Thr Val Ser Ser
        115

<210> SEQ ID NO 18
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Phe Pro Thr
                85                  90                  95

Phe Gly Gly Gly Thr Lys Val Glu Ile Lys
            100                 105

<210> SEQ ID NO 19
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asp His Ser Gly Ser Thr Asn Tyr Asn Pro Ser Leu Lys
    50                  55                  60
```

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ala Arg Gly Pro Trp Ser Phe Asp Pro Trp Gly Gln Gly Thr Leu
            100                 105                 110

Val Thr Val Ser Ser
        115

<210> SEQ ID NO 20
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Gly Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asp Ile Tyr Pro Thr
                85                  90                  95

Phe Gly Gly Gly Thr Lys Val Glu Ile Lys
            100                 105

<210> SEQ ID NO 21
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asp His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ala Arg Gly Pro Trp Ser Phe Asp Pro Trp Gly Gln Gly Thr Leu
            100                 105                 110

Val Thr Val Ser Ser
        115

```
<210> SEQ ID NO 22
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asp Ser Tyr Pro Thr
                85                  90                  95

Phe Gly Gly Gly Thr Lys Val Glu Ile Lys
            100                 105

<210> SEQ ID NO 23
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asp His Ser Gly Ser Thr Asn Tyr Asn Pro Ser Leu Lys
50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ala Arg Gly Pro Trp Ser Phe Asp Pro Trp Gly Gln Gly Thr Leu
            100                 105                 110

Val Thr Val Ser Ser
        115

<210> SEQ ID NO 24
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24
```

```
Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Gly Ser Phe Pro Thr
                85                  90                  95

Phe Gly Gly Gly Thr Lys Val Glu Ile Lys
            100                 105
```

<210> SEQ ID NO 25
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

```
Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asp His Ser Gly Ser Thr Asn Tyr Asn Pro Ser Leu Lys
50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ala Arg Gly Pro Trp Ser Phe Asp Pro Trp Gly Gln Gly Thr Leu
            100                 105                 110

Val Thr Val Ser Ser
        115
```

<210> SEQ ID NO 26
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

```
Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
50                  55                  60
```

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Gln Ser Phe Pro Thr
            85                  90                  95

Phe Gly Gly Gly Thr Lys Val Glu Ile Lys
        100                 105

<210> SEQ ID NO 27
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asp His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
            85                  90                  95

Arg Ala Arg Gly Pro Trp Ser Phe Asp Pro Trp Gly Gln Gly Thr Leu
        100                 105                 110

Val Thr Val Ser Ser
        115

<210> SEQ ID NO 28
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Ser Ser Phe Ser Thr
            85                  90                  95

Phe Gly Gly Gly Thr Lys Val Glu Ile Lys
        100                 105

<210> SEQ ID NO 29
<211> LENGTH: 117

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asp His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ala Arg Gly Pro Trp Ser Phe Asp Pro Trp Gly Gln Gly Thr Leu
            100                 105                 110

Val Thr Val Ser Ser
        115

<210> SEQ ID NO 30
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Glu Ser Tyr Ser Thr
                85                  90                  95

Phe Gly Gly Gly Thr Lys Val Glu Ile Lys
            100                 105

<210> SEQ ID NO 31
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
```

```
                    20                  25                  30

Tyr Trp Ser Trp Ile Arg Gln Pro Pro Gly Lys Gly Leu Glu Trp Ile
            35                  40                  45

Gly Glu Ile Asp His Ser Gly Ser Thr Asn Tyr Asn Pro Ser Leu Lys
        50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ala Arg Gly Pro Trp Ser Phe Asp Pro Trp Gly Gln Gly Thr Leu
            100                 105                 110

Val Thr Val Ser Ser
        115

<210> SEQ ID NO 32
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asp Ser Phe Ile Thr
                85                  90                  95

Phe Gly Gly Gly Thr Lys Val Glu Ile Lys
            100                 105

<210> SEQ ID NO 33
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asp His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
```

```
                85                  90                  95
Arg Ala Arg Gly Pro Trp Ser Phe Asp Pro Trp Gly Gln Gly Thr Leu
            100                 105                 110

Val Thr Val Ser Ser
        115

<210> SEQ ID NO 34
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Gln Ser Tyr Pro Thr
                85                  90                  95

Phe Gly Gly Gly Thr Lys Val Glu Ile Lys
            100                 105

<210> SEQ ID NO 35
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asp His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ala Arg Gly Pro Trp Ser Phe Asp Pro Trp Gly Gln Gly Thr Leu
            100                 105                 110

Val Thr Val Ser Ser
        115

<210> SEQ ID NO 36
<211> LENGTH: 106
<212> TYPE: PRT
```

<213> ORGANISM: Artificial Sequence
<220> FEATURE:
<223> OTHER INFORMATION: Description of Artificial Sequence: Synthetic
      polypeptide

<400> SEQUENCE: 36

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Gly Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr His Ser Phe Pro Thr
                85                  90                  95

Phe Gly Gly Gly Thr Lys Val Glu Ile Lys
            100                 105

<210> SEQ ID NO 37
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asp His Ser Gly Ser Thr Asn Tyr Asn Pro Ser Leu Lys
50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ala Arg Gly Pro Trp Ser Phe Asp Pro Trp Gly Gln Gly Thr Leu
            100                 105                 110

Val Thr Val Ser Ser
        115

<210> SEQ ID NO 38
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Gly Ser Trp
            20                  25                  30

```
Leu Ala Trp Tyr Gln Gln Lys Pro Gly Lys Ala Pro Lys Leu Leu Ile
            35                  40                  45

Tyr Lys Ala Ser Ser Leu Glu Ser Gly Val Pro Ser Arg Phe Ser Gly
 50                  55                  60

Ser Gly Ser Gly Thr Glu Phe Thr Leu Thr Ile Ser Ser Leu Gln Pro
 65                  70                  75                  80

Asp Asp Phe Ala Thr Tyr Tyr Cys Gln Gln Tyr Glu Leu Tyr Ser Tyr
                 85                  90                  95

Thr Phe Gly Gly Gly Thr Lys Val Glu Ile Lys
                100                 105

<210> SEQ ID NO 39
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Gln Val Gln Leu Gln Gln Trp Gly Ala Gly Leu Leu Lys Pro Ser Glu
 1               5                  10                  15

Thr Leu Ser Leu Thr Cys Ala Val Tyr Gly Gly Ser Phe Ser Gly Tyr
             20                  25                  30

Tyr Trp Ser Trp Ile Arg Gln Pro Pro Gly Lys Gly Leu Glu Trp Ile
            35                  40                  45

Gly Glu Ile Asp His Ser Gly Ser Thr Asn Tyr Asn Pro Ser Leu Lys
 50                  55                  60

Ser Arg Val Thr Ile Ser Val Asp Thr Ser Lys Asn Gln Phe Ser Leu
 65                  70                  75                  80

Lys Leu Ser Ser Val Thr Ala Ala Asp Thr Ala Val Tyr Tyr Cys Ala
                 85                  90                  95

Arg Ala Arg Gly Pro Trp Ser Phe Asp Pro Trp Gly Gln Gly Thr Leu
                100                 105                 110

Val Thr Val Ser Ser
            115

<210> SEQ ID NO 40
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

Asp Ile Gln Met Thr Gln Ser Pro Ser Thr Leu Ser Ala Ser Val Gly
 1               5                  10                  15

Asp Arg Val Thr Ile Thr Cys Arg Ala Ser Gln Ser Ile Ser Ser Trp
             20                  25                  30

Leu Ala Trp Tyr Gln Gln Lys Pro Gly Lys Ala Pro Lys Leu Leu Ile
            35                  40                  45

Tyr Lys Ala Ser Ser Leu Glu Ser Gly Val Pro Ser Arg Phe Ser Gly
 50                  55                  60

Ser Gly Ser Gly Thr Glu Phe Thr Leu Thr Ile Ser Ser Leu Gln Pro
 65                  70                  75                  80

Asp Asp Phe Ala Thr Tyr Tyr Cys Gln Gln Tyr Asp Thr Phe Ile Thr
                 85                  90                  95
```

```
Phe Gly Gly Gly Thr Lys Val Glu Ile Lys
            100                 105
```

<210> SEQ ID NO 41
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Asp Ser Ser Ile Arg His Ala Tyr Tyr Tyr Gly Met
            100                 105                 110

Asp Val Trp Gly Gln Gly Thr Thr Val Thr Val Ser Ser
        115                 120                 125
```

<210> SEQ ID NO 42
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

```
Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Thr Pro Ile Thr Phe Gly Gly Gly Thr Lys Val Glu Ile
            100                 105                 110

Lys
```

<210> SEQ ID NO 43
<211> LENGTH: 121
<212> TYPE: PRT
<213> ORGANISM: Artificial Sequence
<220> FEATURE:

<223> OTHER INFORMATION: Description of Artificial Sequence: Synthetic
      polypeptide

<400> SEQUENCE: 43

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Tyr Trp Gly Trp Ile Arg Gln Pro Pro Gly Lys Gly Leu Glu
        35                  40                  45

Trp Ile Gly Ser Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Gly Ser Asp Arg Phe His Pro Tyr Phe Asp Tyr Trp Gly
            100                 105                 110

Gln Gly Thr Leu Val Thr Val Ser Ser
        115                 120

<210> SEQ ID NO 44
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Arg Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Phe Asp Thr Trp Pro Pro
                85                  90                  95

Thr Phe Gly Gly Gly Thr Lys Val Glu Ile Lys
            100                 105

<210> SEQ ID NO 45
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val

```
            35                  40                  45
Ser Ala Ile Ser Gly Ser Gly Gly Ser Thr Tyr Tyr Ala Asp Ser Val
 50                  55                  60
Lys Gly Arg Phe Thr Ile Ser Arg Asp Asn Ser Lys Asn Thr Leu Tyr
 65                  70                  75                  80
Leu Gln Met Asn Ser Leu Arg Ala Glu Asp Thr Ala Val Tyr Tyr Cys
                 85                  90                  95
Ala Lys Asp Gly Gly Tyr Tyr Asp Ser Gly Ala Gly Asp Tyr Trp Gly
                100                 105                 110
Gln Gly Thr Leu Val Thr Val Ser Ser
            115                 120
```

<210> SEQ ID NO 46
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 46

```
Asp Ile Gln Met Thr Gln Ser Pro Ser Ser Val Ser Ala Ser Val Gly
  1               5                  10                  15
Asp Arg Val Thr Ile Thr Cys Arg Ala Ser Gln Gly Ile Asp Ser Trp
             20                  25                  30
Leu Ala Trp Tyr Gln Gln Lys Pro Gly Lys Ala Pro Lys Leu Leu Ile
         35                  40                  45
Tyr Ala Ala Ser Ser Leu Gln Ser Gly Val Pro Ser Arg Phe Ser Gly
 50                  55                  60
Ser Gly Ser Gly Thr Asp Phe Thr Leu Thr Ile Ser Ser Leu Gln Pro
 65                  70                  75                  80
Glu Asp Phe Ala Thr Tyr Tyr Cys Gln Gln Gly Val Ser Tyr Pro Arg
                 85                  90                  95
Thr Phe Gly Gly Gly Thr Lys Val Glu Ile Lys
                100                 105
```

<210> SEQ ID NO 47
<211> LENGTH: 122
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 47

```
Glu Val Gln Leu Val Glu Ser Gly Gly Gly Leu Val Lys Pro Gly Gly
  1               5                  10                  15
Ser Leu Arg Leu Ser Cys Ala Ala Ser Gly Phe Thr Phe Ser Ser Tyr
             20                  25                  30
Ser Met Asn Trp Val Arg Gln Ala Pro Gly Lys Gly Leu Glu Trp Val
         35                  40                  45
Ser Ser Ile Ser Ser Ser Ser Tyr Ile Tyr Tyr Ala Asp Ser Val
 50                  55                  60
Lys Gly Arg Phe Thr Ile Ser Arg Asp Asn Ala Lys Asn Ser Leu Tyr
 65                  70                  75                  80
Leu Gln Met Asn Ser Leu Arg Ala Glu Asp Thr Ala Val Tyr Tyr Cys
                 85                  90                  95
Ala Arg Gly Ala Pro Met Gly Ala Ala Ala Gly Trp Phe Asp Pro Trp
```

Gly Gln Gly Thr Leu Val Thr Val Ser Ser
        115                 120

<210> SEQ ID NO 48
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Val Ser Phe Pro Arg
                85                  90                  95

Thr Phe Gly Gly Gly Thr Lys Val Glu Ile Lys
            100                 105

<210> SEQ ID NO 49
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Asp Thr Gly Glu Tyr Tyr Asp Thr Asp His Gly Met Asp
            100                 105                 110

Val Trp Gly Gln Gly Thr Thr Val Thr Val Ser Ser
        115                 120

<210> SEQ ID NO 50
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 50

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Asp Asp Tyr Trp Pro Pro
                85                  90                  95

Thr Phe Gly Gly Gly Thr Lys Val Glu Ile Lys
            100                 105

<210> SEQ ID NO 51
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Phe Thr Phe Ser Ser Tyr Ala Met Ser
1               5

<210> SEQ ID NO 52
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Ala Ile Ser Gly Ser Gly Gly Ser Thr Tyr Tyr Ala Asp Ser Val Lys
1               5                   10                  15

Gly

<210> SEQ ID NO 53
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Ala Lys Asp Gly Gly Tyr Tyr Asp Ser Gly Ala Gly Asp Tyr
1               5                   10

<210> SEQ ID NO 54
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Arg Ala Ser Gln Gly Ile Asp Ser Trp Leu Ala
1               5                   10

<210> SEQ ID NO 55
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Ala Ala Ser Ser Leu Gln Ser
1               5

<210> SEQ ID NO 56
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Gln Gln Gly Val Ser Tyr Pro Arg Thr
1               5

<210> SEQ ID NO 57
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Phe Thr Phe Ser Ser Tyr Ser Met Asn
1               5

<210> SEQ ID NO 58
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Ser Ile Ser Ser Ser Ser Ser Tyr Ile Tyr Tyr Ala Asp Ser Val Lys
1               5                   10                  15

Gly

<210> SEQ ID NO 59
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Ala Arg Gly Ala Pro Met Gly Ala Ala Ala Gly Trp Phe Asp Pro
1               5                   10                  15

<210> SEQ ID NO 60
<211> LENGTH: 11

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Arg Ala Ser Gln Gly Ile Ser Ser Trp Leu Ala
1               5                   10

<210> SEQ ID NO 61
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Ala Ala Ser Ser Leu Gln Ser
1               5

<210> SEQ ID NO 62
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Gln Gln Gly Val Ser Phe Pro Arg Thr
1               5

<210> SEQ ID NO 63
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Tyr Thr Phe Thr Gly Tyr Tyr Met His
1               5

<210> SEQ ID NO 64
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Trp Ile Asn Pro Asn Ser Gly Gly Thr Asn Tyr Ala Gln Lys Phe Gln
1               5                   10                  15

Gly

<210> SEQ ID NO 65
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65
```

```
Ala Arg Asp Thr Gly Glu Tyr Tyr Asp Thr Asp Asp His Gly Met Asp
1               5                   10                  15

Val

<210> SEQ ID NO 66
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Arg Ala Ser Gln Ser Val Ser Ser Asn Leu Ala
1               5                   10

<210> SEQ ID NO 67
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Gly Ala Ser Thr Arg Ala Thr
1               5

<210> SEQ ID NO 68
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Gln Gln Asp Asp Tyr Trp Pro Pro Thr
1               5

<210> SEQ ID NO 69
<211> LENGTH: 121
<212> TYPE: PRT
<213> ORGANISM: Artificial Sequence
<220> FEATURE:
<223> OTHER INFORMATION: Synthetic peptide

<400> SEQUENCE: 69

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Phe Ile Arg Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Arg Gly Leu Gly Asp Gly Thr Tyr Phe Asp Tyr Trp Gly
            100                 105                 110
```

Gln Gly Thr Thr Val Thr Val Ser Ser
          115                 120

<210> SEQ ID NO 70
<211> LENGTH: 110
<212> TYPE: PRT
<213> ORGANISM: Artificial Sequence
<220> FEATURE:
<223> OTHER INFORMATION: Synthetic peptide

<400> SEQUENCE: 70

Gln Ser Ala Leu Thr Gln Pro Ala Ser Val Ser Gly Ser Pro Gly Gln
1               5                   10                  15

Ser Ile Thr Ile Ser Cys Ser Gly Ser Ser Ser Asn Ile Gly Asn Asn
            20                  25                  30

Ala Val Asn Trp Tyr Gln Gln Leu Pro Gly Lys Ala Pro Lys Leu Leu
        35                  40                  45

Ile Tyr Tyr Asp Asp Leu Leu Pro Ser Gly Val Ser Asp Arg Phe Ser
50                  55                  60

Gly Ser Lys Ser Gly Thr Ser Ala Phe Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly Pro Val Phe Gly Gly Gly Thr Lys Leu Thr Val Leu
            100                 105                 110

<210> SEQ ID NO 71
<211> LENGTH: 115
<212> TYPE: PRT
<213> ORGANISM: Artificial Sequence
<220> FEATURE:
<223> OTHER INFORMATION: Synthetic peptide

<400> SEQUENCE: 71

Gln Val His Leu Gln Glu Ser Gly Pro Gly Leu Val Lys Pro Ser Glu
1               5                   10                  15

Thr Leu Ser Leu Thr Cys Thr Val Ser Asp Asp Ser Ile Ser Ser Tyr
            20                  25                  30

Tyr Trp Ser Trp Ile Arg Gln Pro Pro Gly Lys Gly Leu Glu Trp Ile
        35                  40                  45

Gly His Ile Ser Tyr Ser Gly Ser Ala Asn Tyr Asn Pro Ser Leu Lys
50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Asn Trp Asp Asp Ala Phe Asn Ile Trp Gly Gln Gly Thr Met Val Thr
            100                 105                 110

Val Ser Ser
        115

<210> SEQ ID NO 72
<211> LENGTH: 108
<212> TYPE: PRT
<213> ORGANISM: Artificial Sequence
<220> FEATURE:
<223> OTHER INFORMATION: Synthetic peptide

<400> SEQUENCE: 72

Glu Ile Val Leu Thr Gln Ser Pro Gly Thr Leu Ser Leu Ser Pro Gly

```
                1               5                   10                  15
           Glu Arg Ala Thr Leu Ser Cys Arg Ala Ser Gln Ser Val Ser Ser Ser
                             20                  25                  30

Tyr Leu Ala Trp Tyr Gln Gln Lys Pro Gly Gln Ala Pro Arg Leu Leu
                             35                  40                  45

Ile Tyr Gly Ala Ser Ser Arg Ala Thr Gly Ile Pro Asp Arg Phe Ser
                        50                  55                  60

Gly Ser Gly Ser Gly Thr Asp Phe Thr Leu Thr Ile Ser Arg Leu Glu
           65                  70                  75                  80

Pro Glu Asp Phe Ala Val Tyr Tyr Cys Gln Gln Tyr Gly Ser Ser Pro
                             85                  90                  95

Trp Thr Phe Gly Gln Gly Thr Lys Val Glu Ile Lys
                            100                 105

<210> SEQ ID NO 73
<211> LENGTH: 246
<212> TYPE: PRT
<213> ORGANISM: Artificial Sequence
<220> FEATURE:
<223> OTHER INFORMATION: Synthetic peptide

<400> SEQUENCE: 73

Met Ala Ala Ala Ile Pro Ala Leu Leu Cys Leu Pro Leu Leu
1               5                   10                  15

Phe Leu Leu Phe Gly Trp Ser Arg Ala Arg Arg Asp Asp Pro His Ser
                20                  25                  30

Leu Cys Tyr Asp Ile Thr Val Ile Pro Lys Phe Arg Pro Gly Pro Arg
            35                  40                  45

Trp Cys Ala Val Gln Gly Gln Val Asp Glu Lys Thr Phe Leu His Tyr
        50                  55                  60

Asp Cys Gly Asn Lys Thr Val Thr Pro Val Ser Pro Leu Gly Lys Lys
65                  70                  75                  80

Leu Asn Val Thr Met Ala Trp Lys Ala Gln Asn Pro Val Leu Arg Glu
                85                  90                  95

Val Val Asp Ile Leu Thr Glu Gln Leu Leu Asp Ile Gln Leu Glu Asn
            100                 105                 110

Tyr Thr Pro Lys Glu Pro Leu Thr Leu Gln Ala Arg Met Ser Cys Glu
        115                 120                 125

Gln Lys Ala Glu Gly His Ser Ser Gly Ser Trp Gln Phe Ser Ile Asp
    130                 135                 140

Gly Gln Thr Phe Leu Leu Phe Asp Ser Glu Lys Arg Met Trp Thr Thr
145                 150                 155                 160

Val His Pro Gly Ala Arg Lys Met Lys Glu Lys Trp Glu Asn Asp Lys
                165                 170                 175

Asp Val Ala Met Ser Phe His Tyr Ile Ser Met Gly Asp Cys Ile Gly
            180                 185                 190

Trp Leu Glu Asp Phe Leu Met Gly Met Asp Ser Thr Leu Glu Pro Ser
        195                 200                 205

Ala Gly Ala Pro Leu Ala Met Ser Ser Gly Thr Thr Gln Leu Arg Ala
    210                 215                 220

Thr Ala Thr Thr Leu Ile Leu Cys Cys Leu Leu Ile Ile Leu Pro Cys
225                 230                 235                 240

Phe Ile Leu Pro Gly Ile
                245
```

```
<210> SEQ ID NO 74
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 74

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Val Val His Trp Val Arg Gln Ala Pro Gly Gln Gly Leu Glu Trp Met
        35                  40                  45

Gly Tyr Ile Asn Pro Tyr Asn Asp Gly Thr Lys Tyr Asn Glu Lys Phe
    50                  55                  60

Lys Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Asp Tyr Arg Tyr Glu Val Tyr Gly Met Asp Tyr Trp Gly Gln
            100                 105                 110

Gly Thr Leu Val Thr Val Ser Ser
        115                 120

<210> SEQ ID NO 75
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 75

Asp Ile Val Leu Thr Gln Ser Pro Ala Ser Leu Ala Val Ser Pro Gly
1               5                   10                  15

Gln Arg Ala Thr Ile Thr Cys Thr Ala Ser Ser Ser Val Asn Tyr Ile
            20                  25                  30

His Trp Tyr Gln Gln Lys Pro Gly Gln Pro Pro Lys Leu Leu Ile Tyr
        35                  40                  45

Asp Thr Ser Lys Val Ala Ser Gly Val Pro Ala Arg Phe Ser Gly Ser
    50                  55                  60

Gly Ser Gly Thr Asp Phe Thr Leu Thr Ile Asn Pro Val Glu Ala Asn
65                  70                  75                  80

Asp Thr Ala Asn Tyr Tyr Cys Gln Gln Trp Arg Ser Tyr Pro Leu Thr
                85                  90                  95

Phe Gly Gln Gly Thr Lys Leu Glu Ile Lys
            100                 105

<210> SEQ ID NO 76
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 76

Glu Val Gln Leu Leu Glu Ser Gly Gly Gly Leu Val Gln Pro Gly Gly
1               5                   10                  15
```

Ser Leu Arg Leu Ser Cys Ala Ala Ser Gly Phe Thr Phe Ser Asp Asn
            20                  25                  30

Ala Met Gly Trp Val Arg Gln Ala Pro Gly Lys Gly Leu Glu Trp Val
        35                  40                  45

Ser Ala Ile Ser Gly Pro Gly Ser Ser Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Val Leu Gly Trp Phe Asp Tyr Trp Gly Gln Gly Thr Leu Val
            100                 105                 110

Thr Val Ser Ser
        115

<210> SEQ ID NO 77
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 77

Glu Ile Val Leu Thr Gln Ser Pro Gly Thr Leu Ser Leu Ser Pro Gly
 1               5                  10                  15

Glu Arg Ala Thr Leu Ser Cys Arg Ala Ser Gln Ser Val Ser Asp Glu
            20                  25                  30

Tyr Leu Ser Trp Tyr Gln Gln Lys Pro Gly Gln Ala Pro Arg Leu Leu
        35                  40                  45

Ile His Ser Ala Ser Thr Arg Ala Thr Gly Ile Pro Asp Arg Phe Ser
 50                  55                  60

Gly Ser Gly Ser Gly Thr Asp Phe Thr Leu Ala Ile Ser Arg Leu Glu
 65                  70                  75                  80

Pro Glu Asp Phe Ala Val Tyr Tyr Cys Gln Gln Tyr Gly Tyr Pro Pro
                 85                  90                  95

Asp Phe Thr Phe Gly Gln Gly Thr Lys Val Glu Ile Lys
            100                 105

<210> SEQ ID NO 78
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 78

Gln Val Gln Leu Gln Gln Trp Gly Ala Gly Leu Leu Lys Pro Ser Glu
 1               5                  10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asp His Ser Gly Ser Thr Asn Tyr Asn Pro Ser Leu Lys
 50                  55                  60

Ser Arg Val Thr Ile Ser Val Asp Thr Ser Lys Asn Gln Phe Ser Leu
 65                  70                  75                  80

```
Lys Leu Ser Ser Val Thr Ala Ala Asp Thr Ala Val Tyr Tyr Cys Ala
                85                  90                  95

Arg Ala Arg Gly Pro Trp Ser Phe Asp Pro Trp Gly Gln Gly Thr Leu
            100                 105                 110

Val Thr Val Ser Ser
        115

<210> SEQ ID NO 79
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 79

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Glu Gln Tyr Asp Ser Tyr Pro Thr
                85                  90                  95

Phe Gly Gly Gly Thr Lys Val Glu Ile Lys
            100                 105

<210> SEQ ID NO 80
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 80

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Gly Arg Lys Ala Ser Gly Ser Tyr Tyr Tyr Tyr Gly
            100                 105                 110

Met Asp Val Trp Gly Gln Gly Thr Thr Val Thr Val Ser Ser
        115                 120                 125

<210> SEQ ID NO 81
```

-continued

```
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 81

Asp Ile Val Met Thr Gln Ser Pro Asp Ser Leu Ala Val Ser Leu Gly
1               5                   10                  15

Glu Arg Ala Thr Ile Asn Cys Glu Ser Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Pro Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Asn
                85                  90                  95

Asp Tyr Ser Tyr Pro Tyr Thr Phe Gly Gln Gly Thr Lys Leu Glu Ile
            100                 105                 110

Lys

<210> SEQ ID NO 82
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 82

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Val Leu Gly Trp Phe Asp Tyr Trp Gly Gln Gly Thr Leu Val
            100                 105                 110

Thr Val Ser Ser
        115

<210> SEQ ID NO 83
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 83

Glu Ile Val Leu Thr Gln Ser Pro Gly Thr Leu Ser Leu Ser Pro Gly
```

```
            1               5                  10                 15
          Glu Arg Ala Thr Leu Ser Cys Arg Ala Ser Gln Ser Val Ser Ser
                          20                  25                  30

Tyr Leu Ala Trp Tyr Gln Gln Lys Pro Gly Gln Ala Pro Arg Leu Leu
                          35                  40                  45

Ile Tyr Gly Ala Ser Ser Arg Ala Thr Gly Ile Pro Asp Arg Phe Ser
           50                  55                  60

Gly Ser Gly Ser Gly Thr Asp Phe Thr Leu Thr Ile Ser Arg Leu Glu
          65                  70                  75                  80

Pro Glu Asp Phe Ala Val Tyr Tyr Cys Gln Gln Tyr Gly Tyr Pro Pro
                              85                  90                  95

Asp Phe Thr Phe Gly Gln Gly Thr Lys Val Glu Ile Lys
                          100                 105

<210> SEQ ID NO 84
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 84

Gln Val Gln Leu Gln Gln Pro Gly Ala Glu Leu Val Lys Pro Gly Ala
          1               5                  10                  15

Ser Val Lys Met Ser Cys Lys Ala Ser Gly Tyr Thr Phe Thr Ser Tyr
                          20                  25                  30

Asn Met His Trp Val Lys Gln Thr Pro Gly Arg Gly Leu Glu Trp Ile
                          35                  40                  45

Gly Ala Ile Tyr Pro Gly Asn Gly Asp Thr Ser Tyr Asn Gln Lys Phe
           50                  55                  60

Lys Gly Lys Ala Thr Leu Thr Ala Asp Lys Ser Ser Ser Thr Ala Tyr
          65                  70                  75                  80

Met Gln Leu Ser Ser Leu Thr Ser Glu Asp Ser Ala Val Tyr Tyr Cys
                              85                  90                  95

Ala Arg Ser Thr Tyr Tyr Gly Gly Asp Trp Tyr Phe Asn Val Trp Gly
                          100                 105                 110

Ala Gly Thr Thr Val Thr Val Ser Ala
                  115                 120

<210> SEQ ID NO 85
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 85

Gln Ile Val Leu Ser Gln Ser Pro Ala Ile Leu Ser Ala Ser Pro Gly
          1               5                  10                  15

Glu Lys Val Thr Met Thr Cys Arg Ala Ser Ser Ser Val Ser Tyr Ile
                          20                  25                  30

His Trp Phe Gln Gln Lys Pro Gly Ser Ser Pro Lys Pro Trp Ile Tyr
                          35                  40                  45

Ala Thr Ser Asn Leu Ala Ser Gly Val Pro Val Arg Phe Ser Gly Ser
           50                  55                  60

Gly Ser Gly Thr Ser Tyr Ser Leu Thr Ile Ser Arg Val Glu Ala Glu
```

```
                65                  70                  75                  80
Asp Ala Ala Thr Tyr Tyr Cys Gln Gln Trp Thr Ser Asn Pro Pro Thr
                    85                  90                  95

Phe Gly Gly Gly Thr Lys Leu Glu Ile Lys
            100                 105

<210> SEQ ID NO 86
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 86

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Gly Ser Phe Pro Ile
                85                  90                  95

Thr Phe Gly Gly Gly Thr Lys Val Glu Ile Lys Arg Ala Asp Ala Ala
            100                 105                 110

Pro Thr Val Ser Ile Phe Pro Pro Ser Ser Glu Gln Leu Thr Ser Gly
        115                 120                 125

Gly Ala Ser Val Val Cys Phe Leu Asn Asn Phe Tyr Pro Lys Asp Ile
    130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
            180                 185                 190

Thr Cys Glu Ala Thr His Lys Thr Ser Thr Ser Pro Ile Val Lys Ser
        195                 200                 205

Phe Asn Arg Asn Glu Cys
    210

<210> SEQ ID NO 87
<211> LENGTH: 452
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 87

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
```

-continued

```
                35                  40                  45
Gly Glu Ile Asp His Ser Gly Ser Thr Asn Tyr Asn Pro Ser Leu Lys
         50                  55                  60
Ser Arg Val Thr Ile Ser Val Asp Thr Ser Lys Asn Gln Phe Ser Leu
 65                  70                  75                  80
Lys Leu Ser Ser Val Thr Ala Ala Asp Thr Ala Val Tyr Tyr Cys Ala
                 85                  90                  95
Arg Ala Arg Gly Pro Trp Ser Phe Asp Pro Trp Gly Gln Gly Thr Leu
            100                 105                 110
Val Thr Val Ser Ser Ala Lys Thr Thr Ala Pro Ser Val Tyr Pro Leu
        115                 120                 125
Ala Pro Val Cys Gly Gly Thr Thr Gly Ser Ser Val Thr Leu Gly Cys
    130                 135                 140
Leu Val Lys Gly Tyr Phe Pro Glu Pro Val Thr Leu Thr Trp Asn Ser
145                 150                 155                 160
Gly Ser Leu Ser Ser Gly Val His Thr Phe Pro Ala Leu Leu Gln Ser
                165                 170                 175
Gly Leu Tyr Thr Leu Ser Ser Ser Val Thr Val Thr Ser Asn Thr Trp
            180                 185                 190
Pro Ser Gln Thr Ile Thr Cys Asn Val Ala His Pro Ala Ser Ser Thr
        195                 200                 205
Lys Val Asp Lys Lys Ile Glu Pro Arg Val Pro Ile Thr Gln Asn Pro
    210                 215                 220
Cys Pro Pro Leu Lys Glu Cys Pro Pro Cys Ala Ala Pro Asp Leu Leu
225                 230                 235                 240
Gly Gly Pro Ser Val Phe Ile Phe Pro Pro Lys Ile Lys Asp Val Leu
                245                 250                 255
Met Ile Ser Leu Ser Pro Met Val Thr Cys Val Val Asp Val Ser
            260                 265                 270
Glu Asp Asp Pro Asp Val Gln Ile Ser Trp Phe Val Asn Asn Val Glu
        275                 280                 285
Val His Thr Ala Gln Thr Gln Thr His Arg Glu Asp Tyr Asn Ser Thr
    290                 295                 300
Leu Arg Val Val Ser Ala Leu Pro Ile Gln His Gln Asp Trp Met Ser
305                 310                 315                 320
Gly Lys Glu Phe Lys Cys Lys Val Asn Asn Arg Ala Leu Pro Ser Pro
                325                 330                 335
Ile Glu Lys Thr Ile Ser Lys Pro Arg Gly Pro Val Arg Ala Pro Gln
            340                 345                 350
Val Tyr Val Leu Pro Pro Pro Ala Glu Glu Met Thr Lys Lys Glu Phe
        355                 360                 365
Ser Leu Thr Cys Met Ile Lys Gly Phe Leu Pro Ala Glu Ile Ala Val
    370                 375                 380
Asp Trp Thr Ser Asn Gly Arg Thr Glu Gln Asn Tyr Lys Asn Thr Ala
385                 390                 395                 400
Thr Val Leu Asp Ser Asp Gly Ser Tyr Phe Met Tyr Ser Arg Leu Arg
                405                 410                 415
Val Gln Lys Ser Thr Trp Glu Arg Gly Ser Leu Phe Ala Cys Ser Val
            420                 425                 430
Val His Glu Gly Leu His Asn His Leu Thr Thr Lys Thr Ile Ser Arg
        435                 440                 445
Ser Leu Gly Lys
    450
```

<210> SEQ ID NO 88
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 88

Asp Ile Gln Met Ser Gln Ser Pro Ala Ser Leu Ser Ala Ser Val Gly
1               5                   10                  15

Glu Thr Val Thr Ile Thr Cys Arg Ala Ser Gly Asn Ile Tyr Asn Tyr
            20                  25                  30

Leu Ala Trp Tyr Gln Gln Lys Gln Gly Lys Ser Pro His Leu Leu Val
        35                  40                  45

Tyr Asp Ala Lys Thr Leu Ala Asp Gly Val Pro Ser Arg Phe Ser Gly
    50                  55                  60

Ser Gly Ser Gly Thr Gln Tyr Ser Leu Lys Ile Ser Ser Leu Gln Thr
65                  70                  75                  80

Glu Asp Ser Gly Asn Tyr Tyr Cys Gln His Phe Trp Ser Leu Pro Phe
                85                  90                  95

Thr Phe Gly Ser Gly Thr Lys Leu Glu Ile Lys Arg Ala Asp Ala Ala
            100                 105                 110

Pro Thr Val Ser Ile Phe Pro Pro Ser Ser Glu Gln Leu Thr Ser Gly
        115                 120                 125

Gly Ala Ser Val Val Cys Phe Leu Asn Asn Phe Tyr Pro Lys Asp Ile
    130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
            180                 185                 190

Thr Cys Glu Ala Thr His Lys Thr Ser Thr Ser Pro Ile Val Lys Ser
        195                 200                 205

Phe Asn Arg Asn Glu Cys
    210

<210> SEQ ID NO 89
<211> LENGTH: 456
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 89

Glu Val Gln Leu Gln Gln Ser Gly Ala Glu Leu Val Arg Pro Gly Ala
1               5                   10                  15

Leu Val Lys Leu Ser Cys Lys Thr Ser Gly Phe Asn Ile Lys Asp Tyr
            20                  25                  30

Phe Leu His Trp Val Arg Gln Arg Pro Asp Gln Gly Leu Glu Trp Ile
        35                  40                  45

Gly Trp Ile Asn Pro Asp Asn Gly Asn Thr Val Tyr Asp Pro Lys Phe
    50                  55                  60

Gln Gly Thr Ala Ser Leu Thr Ala Asp Thr Ser Ser Asn Thr Val Tyr
65                  70                  75                  80

Leu Gln Leu Ser Gly Leu Thr Glu Asp Thr Ala Val Tyr Phe Cys
                 85                  90                  95

Thr Arg Arg Asp Tyr Thr Tyr Glu Lys Ala Ala Leu Asp Tyr Trp Gly
                100                 105                 110

Gln Gly Ala Ser Val Ile Val Ser Ser Ala Lys Thr Thr Ala Pro Ser
            115                 120                 125

Val Tyr Pro Leu Ala Pro Val Cys Gly Gly Thr Thr Gly Ser Ser Val
        130                 135                 140

Thr Leu Gly Cys Leu Val Lys Gly Tyr Phe Pro Glu Pro Val Thr Leu
145                 150                 155                 160

Thr Trp Asn Ser Gly Ser Leu Ser Ser Gly Val His Thr Phe Pro Ala
                165                 170                 175

Leu Leu Gln Ser Gly Leu Tyr Thr Leu Ser Ser Val Thr Val Thr
            180                 185                 190

Ser Asn Thr Trp Pro Ser Gln Thr Ile Thr Cys Asn Val Ala His Pro
            195                 200                 205

Ala Ser Ser Thr Lys Val Asp Lys Lys Ile Glu Pro Arg Val Pro Ile
        210                 215                 220

Thr Gln Asn Pro Cys Pro Pro Leu Lys Glu Cys Pro Pro Cys Ala Ala
225                 230                 235                 240

Pro Asp Leu Leu Gly Gly Pro Ser Val Phe Ile Phe Pro Pro Lys Ile
                245                 250                 255

Lys Asp Val Leu Met Ile Ser Leu Ser Pro Met Val Thr Cys Val Val
                260                 265                 270

Val Asp Val Ser Glu Asp Asp Pro Asp Val Gln Ile Ser Trp Phe Val
            275                 280                 285

Asn Asn Val Glu Val His Thr Ala Gln Thr Gln Thr His Arg Glu Asp
        290                 295                 300

Tyr Asn Ser Thr Leu Arg Val Val Ser Ala Leu Pro Ile Gln His Gln
305                 310                 315                 320

Asp Trp Met Ser Gly Lys Glu Phe Lys Cys Lys Val Asn Asn Arg Ala
                325                 330                 335

Leu Pro Ser Pro Ile Glu Lys Thr Ile Ser Lys Pro Arg Gly Pro Val
                340                 345                 350

Arg Ala Pro Gln Val Tyr Val Leu Pro Pro Pro Ala Glu Glu Met Thr
            355                 360                 365

Lys Lys Glu Phe Ser Leu Thr Cys Met Ile Thr Gly Phe Leu Pro Ala
370                 375                 380

Glu Ile Ala Val Asp Trp Thr Ser Asn Gly Arg Thr Glu Gln Asn Tyr
385                 390                 395                 400

Lys Asn Thr Ala Thr Val Leu Asp Ser Asp Gly Ser Tyr Leu Met Tyr
                405                 410                 415

Ser Lys Leu Thr Val Gln Lys Ser Thr Trp Glu Arg Gly Ser Leu Phe
            420                 425                 430

Ala Cys Ser Val Val His Glu Gly Leu His Asn His Leu Thr Thr Lys
        435                 440                 445

Thr Ile Ser Arg Ser Leu Gly Lys
    450                 455

<210> SEQ ID NO 90
<211> LENGTH: 5
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 90

Ser Tyr Ala Met Ser
1               5

<210> SEQ ID NO 91
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Asp Gly Gly Tyr Tyr Asp Ser Gly Ala Gly Asp Tyr
1               5                   10

<210> SEQ ID NO 92
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Ser Tyr Ser Met Asn
1               5

<210> SEQ ID NO 93
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Gly Ala Pro Met Gly Ala Ala Ala Gly Trp Phe Asp Pro
1               5                   10

<210> SEQ ID NO 94
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Gly Tyr Tyr Met His
1               5

<210> SEQ ID NO 95
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Asp Thr Gly Glu Tyr Tyr Asp Thr Asp Asp His Gly Met Asp Val
1               5                   10                  15
```

```
<210> SEQ ID NO 96
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 96

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Ala Pro Gln Gly Ala Ala Ala Gly Trp Phe Asp Pro Trp
            100                 105                 110

Gly Gln Gly Thr Leu Val Thr Val Ser Ser
        115                 120

<210> SEQ ID NO 97
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Ala Arg Gly Ala Pro Gln Gly Ala Ala Ala Gly Trp Phe Asp Pro
1               5                   10                  15

<210> SEQ ID NO 98
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Gly Ala Pro Gln Gly Ala Ala Ala Gly Trp Phe Asp Pro
1               5                   10

<210> SEQ ID NO 99
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 99

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30
```

```
Ser Met Asn Trp Val Arg Gln Ala Pro Gly Lys Gly Leu Glu Trp Val
            35                  40                  45

Ser Ser Ile Ser Ser Ser Ser Tyr Ile Tyr Tyr Ala Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Ala Pro Leu Gly Ala Ala Ala Gly Trp Phe Asp Pro Trp
            100                 105                 110

Gly Gln Gly Thr Leu Val Thr Val Ser Ser
            115                 120

<210> SEQ ID NO 100
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

Ala Arg Gly Ala Pro Leu Gly Ala Ala Ala Gly Trp Phe Asp Pro
1               5                   10                  15

<210> SEQ ID NO 101
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Gly Ala Pro Leu Gly Ala Ala Ala Gly Trp Phe Asp Pro
1               5                   10

<210> SEQ ID NO 102
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 102

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
            35                  40                  45

Ser Ser Ile Ser Ser Ser Ser Tyr Ile Tyr Tyr Ala Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Ala Pro Ile Gly Ala Ala Ala Gly Trp Phe Asp Pro Trp
            100                 105                 110

Gly Gln Gly Thr Leu Val Thr Val Ser Ser
```

```
<210> SEQ ID NO 103
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103

Ala Arg Gly Ala Pro Ile Gly Ala Ala Ala Gly Trp Phe Asp Pro
1               5                   10                  15

<210> SEQ ID NO 104
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

Gly Ala Pro Ile Gly Ala Ala Ala Gly Trp Phe Asp Pro
1               5                   10

<210> SEQ ID NO 105
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 105

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Ala Pro Phe Gly Ala Ala Ala Gly Trp Phe Asp Pro Trp
            100                 105                 110

Gly Gln Gly Thr Leu Val Thr Val Ser Ser
        115                 120

<210> SEQ ID NO 106
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 106

Ala Arg Gly Ala Pro Phe Gly Ala Ala Ala Gly Trp Phe Asp Pro
1               5                   10                  15
```

<210> SEQ ID NO 107
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

Gly Ala Pro Phe Gly Ala Ala Ala Gly Trp Phe Asp Pro
1               5                   10

<210> SEQ ID NO 108
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 108

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Ala Pro Val Gly Ala Ala Ala Gly Trp Phe Asp Pro Trp
            100                 105                 110

Gly Gln Gly Thr Leu Val Thr Val Ser Ser
        115                 120

<210> SEQ ID NO 109
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 109

Ala Arg Gly Ala Pro Val Gly Ala Ala Ala Gly Trp Phe Asp Pro
1               5                   10                  15

<210> SEQ ID NO 110
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 110

Gly Ala Pro Val Gly Ala Ala Ala Gly Trp Phe Asp Pro
1               5                   10

<210> SEQ ID NO 111

-continued

```
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: VARIANT
<222> LOCATION: (102)..(102)
<223> OTHER INFORMATION: Met, Leu, Ile, Val, Gln, or Phe

<400> SEQUENCE: 111

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Ala Pro Xaa Gly Ala Ala Ala Gly Trp Phe Asp Pro Trp
            100                 105                 110

Gly Gln Gly Thr Leu Val Thr Val Ser Ser
        115                 120

<210> SEQ ID NO 112
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: VARIANT
<222> LOCATION: (6)..(6)
<223> OTHER INFORMATION: Met, Leu, Ile, Val, Gln, or Phe

<400> SEQUENCE: 112

Ala Arg Gly Ala Pro Xaa Gly Ala Ala Ala Gly Trp Phe Asp Pro
1               5                   10                  15

<210> SEQ ID NO 113
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: VARIANT
<222> LOCATION: (4)..(4)
<223> OTHER INFORMATION: Met, Leu, Ile, Val, Gln, or Phe

<400> SEQUENCE: 113

Gly Ala Pro Xaa Gly Ala Ala Ala Gly Trp Phe Asp Pro
1               5                   10

<210> SEQ ID NO 114
<211> LENGTH: 125
<212> TYPE: PRT
<213> ORGANISM: Artificial Sequence
<220> FEATURE:
```

<223> OTHER INFORMATION: Description of Artificial Sequence: Synthetic
    polypeptide

<400> SEQUENCE: 114

Gln Val Gln Leu Val Gln Ser Gly Ala Glu Val Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Glu Gly Ala Gly Phe Ala Tyr Gly Met Asp Tyr Tyr Tyr Met
            100                 105                 110

Asp Val Trp Gly Lys Gly Thr Thr Val Thr Val Ser Ser
        115                 120                 125

<210> SEQ ID NO 115
<211> LENGTH: 107
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 115

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Asp Asn Trp Pro Phe
                85                  90                  95

Thr Phe Gly Gly Gly Thr Lys Val Glu Ile Lys
            100                 105

<210> SEQ ID NO 116
<211> LENGTH: 9
<212> TYPE: PRT
<213> ORGANISM: Artificial Sequence
<220> FEATURE:
<223> OTHER INFORMATION: Description of Artificial Sequence: Synthetic
    peptide

<400> SEQUENCE: 116

Tyr Thr Phe Thr Ser Tyr Tyr Met His
1               5

<210> SEQ ID NO 117
<211> LENGTH: 17
<212> TYPE: PRT

```
<213> ORGANISM: Artificial Sequence
<220> FEATURE:
<223> OTHER INFORMATION: Description of Artificial Sequence: Synthetic
      peptide

<400> SEQUENCE: 117

Ile Ile Asn Pro Ser Gly Gly Ser Thr Ser Tyr Ala Gln Lys Phe Gln
1               5                   10                  15

Gly

<210> SEQ ID NO 118
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 118

Ala Arg Glu Gly Ala Gly Phe Ala Tyr Gly Met Asp Tyr Tyr Tyr Met
1               5                   10                  15

Asp Val

<210> SEQ ID NO 119
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 119

Arg Ala Ser Gln Ser Val Ser Ser Tyr Leu Ala
1               5                   10

<210> SEQ ID NO 120
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 120

Asp Ala Ser Asn Arg Ala Thr
1               5

<210> SEQ ID NO 121
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 121

Gln Gln Ser Asp Asn Trp Pro Phe Thr
1               5

<210> SEQ ID NO 122
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 122

Ser Tyr Tyr Met His
1               5

<210> SEQ ID NO 123
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 123

Glu Gly Ala Gly Phe Ala Tyr Gly Met Asp Tyr Tyr Met Asp Val
1               5                   10                  15

<210> SEQ ID NO 124
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 124

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Tyr Met His Trp Val Arg Gln Ala Pro Gly Gln Gly Leu Glu Trp Met
            35                  40                  45

Gly Ile Ile Asn Pro Ser Gly Gly Ser Thr Ser Tyr Ala Gln Lys Phe
        50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Ala Pro Asn Tyr Gly Asp Thr Thr His Asp Tyr Tyr Tyr
            100                 105                 110

Met Asp Val Trp Gly Lys Gly Thr Thr Val Thr Val Ser Ser
        115                 120                 125

<210> SEQ ID NO 125
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 125

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
                20                  25                  30

Leu Ala Trp Tyr Gln Gln Lys Pro Gly Gln Ala Pro Arg Leu Leu Ile
            35                  40                  45

Tyr Gly Ala Ser Thr Arg Ala Thr Gly Ile Pro Ala Arg Phe Ser Gly
        50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asp Asp Trp Pro Phe
                85                  90                  95

Thr Phe Gly Gly Gly Thr Lys Val Glu Ile Lys
            100                 105

<210> SEQ ID NO 126
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 126

Ala Arg Gly Ala Pro Asn Tyr Gly Asp Thr Thr His Asp Tyr Tyr Tyr
1               5                   10                  15

Met Asp Val

<210> SEQ ID NO 127
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 127

Arg Ala Ser Gln Ser Val Ser Ser Asn Leu Ala
1               5                   10

<210> SEQ ID NO 128
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 128

Gly Ala Ser Thr Arg Ala Thr
1               5

<210> SEQ ID NO 129
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 129

Gln Gln Tyr Asp Asp Trp Pro Phe Thr
1               5

<210> SEQ ID NO 130
<211> LENGTH: 17
<212> TYPE: PRT

```
<213> ORGANISM: Artificial Sequence
<220> FEATURE:
<223> OTHER INFORMATION: Description of Artificial Sequence: Synthetic
      peptide

<400> SEQUENCE: 130

Gly Ala Pro Asn Tyr Gly Asp Thr Thr His Asp Tyr Tyr Tyr Met Asp
1               5                   10                  15

Val
```